(12) United States Patent
Makings et al.

(10) Patent No.: US 7,858,635 B2
(45) Date of Patent: *Dec. 28, 2010

(54) SPIRO COMPOUNDS AS MODULATORS OF MUSCARINIC RECEPTORS

(75) Inventors: Lewis R. Makings, Encinitas, CA (US); Miguel Garcia-Guzman Blanco, San Diego, CA (US); Dennis J. Hurley, San Marcos, CA (US); Ioana Drutu, La Jolla, CA (US); Gabriel Raffai, Temecula, CA (US); Daniele M. Bergeron, La Mesa, CA (US); Akiko Nakatani, San Diego, CA (US); Andreas P. Termin, Encinitas, CA (US); Alina Silina, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 40 days.

This patent is subject to a terminal disclaimer.

(21) Appl. No.: 11/644,124

(22) Filed: Dec. 22, 2006

(65) Prior Publication Data

US 2008/0015179 A1    Jan. 17, 2008

Related U.S. Application Data

(60) Provisional application No. 60/753,187, filed on Dec. 22, 2005.

(51) Int. Cl.
*A61K 31/438* (2006.01)
*A61K 31/497* (2006.01)
*C07D 487/00* (2006.01)
*C07D 487/10* (2006.01)

(52) U.S. Cl. ............. 514/278; 514/212.02; 514/255.05; 540/543; 544/230; 544/238; 544/278; 544/358; 546/17

(58) Field of Classification Search ............ 514/212.02, 514/255.05, 278; 540/543; 544/230, 238, 544/278, 356; 546/17
See application file for complete search history.

(56) References Cited

U.S. PATENT DOCUMENTS

| | | | |
|---|---|---|---|
| 3,654,287 A | 4/1972 | Dykstra | |
| 3,666,764 A | 5/1972 | Campbell et al. | |
| 3,959,475 A | 5/1976 | Bauer et al. | |
| 3,962,259 A | 6/1976 | Bauer et al. | |
| 4,233,307 A | 11/1980 | Ono et al. | |
| 4,349,549 A | 9/1982 | Roszkowski et al. | |
| 4,558,049 A | 12/1985 | Bernardi et al. | |
| 5,091,387 A | 2/1992 | Evans et al. | |
| 5,219,860 A | 6/1993 | Chambers et al. | |
| 5,536,716 A | 7/1996 | Chen et al. | |
| 5,576,321 A | 11/1996 | Krushinski et al. | |
| 5,578,593 A | 11/1996 | Chen et al. | |
| 5,614,523 A | 3/1997 | Audia et al. | |
| 5,627,196 A | 5/1997 | Audia et al. | |
| 5,652,235 A | 7/1997 | Chen et al. | |
| 5,658,921 A | 8/1997 | Perregaard et al. | |
| 5,741,789 A | 4/1998 | Hibschman et al. | |
| 5,789,402 A | 8/1998 | Audia et al. | |
| 5,817,679 A * | 10/1998 | Shen et al. ................. 514/339 |
| 5,885,999 A | 3/1999 | Elliott et al. | |
| 6,013,652 A | 1/2000 | Maccoss et al. | |
| 6,130,217 A | 10/2000 | Arnold et al. | |
| 6,166,040 A | 12/2000 | Fairhurst et al. | |
| 6,326,375 B1 | 12/2001 | Fukami | |
| 6,436,962 B1 | 8/2002 | Hoffman et al. | |
| 6,566,367 B2 | 5/2003 | Bakthavatchalam et al. | |
| 6,720,324 B2 | 4/2004 | Marzabadi et al. | |
| 6,828,440 B2 | 12/2004 | Goehring et al. | |
| 6,869,960 B2 | 3/2005 | Ito et al. | |
| 6,943,199 B2 | 9/2005 | deLombaert et al. | |
| 7,045,527 B2 | 5/2006 | Chen et al. | |
| 7,205,417 B2 | 4/2007 | Fukami et al. | |
| 7,279,471 B2 | 10/2007 | Mueller et al. | |
| 7,351,706 B2 | 4/2008 | Bissantz et al. | |
| 2002/0188124 A1 | 12/2002 | Fukami et al. | |
| 2003/0036652 A1 | 2/2003 | Bakthavatchalam et al. | |

(Continued)

FOREIGN PATENT DOCUMENTS

CN            1535967           10/2004

(Continued)

OTHER PUBLICATIONS

Bignan et al, "Preparation of 3-spirocyclic indolin-2-ones as ligands for the ORL-1 receptor", Bioorganic & Medicinal Chemistry Letters 15 (2005) 5022-5026.*

(Continued)

*Primary Examiner*—Sreeni Padmanabhan
*Assistant Examiner*—Sahar Javanmard
(74) *Attorney, Agent, or Firm*—Honigman Miller Schwartz and Cohn LLP; Jonathan P. O'Brien; Christopher C. Forbes

(57) ABSTRACT

The present invention relates to spiro compounds of formula XX as modulators of muscarinic receptors, wherein $R_1$, $R_2$, $R_3$, $Z_1$, $Z_2$, L, G, n, m, t and p are defined herein. The present invention also provides compositions comprising such modulators, and methods therewith for treating muscarinic receptor mediated diseases.

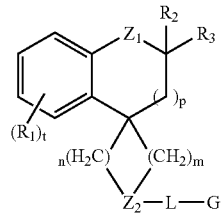

(XX)

19 Claims, No Drawings

U.S. PATENT DOCUMENTS

| | | |
|---|---|---|
| 2003/0158219 A1 | 8/2003 | Ito et al. |
| 2004/0054177 A1 | 3/2004 | Otake et al. |
| 2004/0072847 A1 | 4/2004 | Bakthavatchalam et al. |
| 2004/0122074 A1 | 6/2004 | Dow et al. |
| 2004/0142956 A1 | 7/2004 | Chen et al. |
| 2004/0204397 A1 | 10/2004 | Chaturvedula et al. |
| 2005/0033048 A1 | 2/2005 | Bakthavatchalam et al. |
| 2005/0143372 A1 | 6/2005 | Ghosh et al. |
| 2005/0153998 A1 | 7/2005 | Ito et al. |
| 2005/0176703 A1 | 8/2005 | Gabriel et al. |
| 2005/0215576 A1 | 9/2005 | Degnan et al. |
| 2005/0261332 A1 | 11/2005 | Distefano et al. |
| 2006/0019962 A1 | 1/2006 | Makings et al. |
| 2006/0040964 A1 | 2/2006 | Bakthavatchalam et al. |
| 2006/0106045 A1 | 5/2006 | Huges et al. |
| 2006/0111380 A1 | 5/2006 | Otake et al. |
| 2006/0173027 A1 | 8/2006 | Marzabadi et al. |
| 2006/0183904 A1 | 8/2006 | Guo et al. |
| 2006/0211722 A1 | 9/2006 | Jiao et al. |
| 2006/0217372 A1 | 9/2006 | Blanco-Pillado et al. |
| 2007/0043023 A1 | 2/2007 | Makings et al. |
| 2007/0254903 A1 | 11/2007 | Boatman et al. |

FOREIGN PATENT DOCUMENTS

| | | |
|---|---|---|
| DE | 2444728 | 4/1975 |
| DE | 3342164 | 5/1984 |
| EP | 0065864 | 12/1982 |
| EP | 0070171 | 1/1983 |
| EP | 0128886 | 12/1984 |
| EP | 0414289 | 2/1991 |
| EP | 0444945 | 9/1991 |
| EP | 0445974 | 9/1991 |
| EP | 0486280 | 5/1992 |
| EP | 0518805 | 12/1992 |
| EP | 0533243 | 3/1993 |
| EP | 0615977 | 9/1994 |
| EP | 0722941 | 11/1997 |
| EP | 1 415 986 | 5/2004 |
| GB | 1575800 | 10/1980 |
| GB | 2131021 | 6/1984 |
| GB | 2308064 | 6/1997 |
| GB | 2355264 | 4/2001 |
| GB | 2355456 | 4/2001 |
| JP | 59059685 | 4/1984 |
| JP | 2001/278886 | 10/2001 |
| JP | 2002/316987 | 10/2002 |
| WO | WO 94/19367 | 9/1994 |
| WO | WO 94/22846 | 10/1994 |
| WO | WO 95/09631 | 4/1995 |
| WO | WO 95/11029 | 4/1995 |
| WO | WO 95/14025 | 5/1995 |
| WO | WO 95/28389 | 10/1995 |
| WO | WO 97/41878 | 11/1997 |
| WO | WO 97/41879 | 11/1997 |
| WO | WO 99/06434 | 2/1999 |
| WO | WO 99/09984 | 3/1999 |
| WO | WO 99/32489 | 7/1999 |
| WO | WO 99/64002 | 12/1999 |
| WO | WO 00/06146 | 2/2000 |
| WO | WO 00/06153 | 2/2000 |
| WO | WO 00/06545 | 2/2000 |
| WO | WO 00/38720 | 7/2000 |
| WO | WO 01/02386 | 1/2001 |
| WO | WO 01/22919 | 4/2001 |
| WO | WO 01/29027 | 4/2001 |
| WO | WO 01/45707 | 6/2001 |
| WO | WO 01/64213 | 9/2001 |
| WO | WO 02/48152 | 6/2002 |
| WO | WO 02/070511 | 9/2002 |
| WO | WO 02/085354 | 10/2002 |
| WO | WO 02/094825 | 11/2002 |
| WO | WO 03/014083 | 2/2003 |
| WO | WO 03/064425 | 8/2003 |
| WO | WO 03/095427 | 11/2003 |
| WO | WO 03/106457 | 12/2003 |
| WO | WO 2004/004714 | 1/2004 |
| WO | WO 2004/010942 | 2/2004 |
| WO | WO 2004/010943 | 2/2004 |
| WO | WO 2004/011427 | 2/2004 |
| WO | WO 2004/028459 | 4/2004 |
| WO | WO 2004/050652 | 6/2004 |
| WO | WO 2004/074273 | 9/2004 |
| WO | WO 2004/089307 | 10/2004 |
| WO | WO 2005/016913 | 2/2005 |
| WO | WO 2005/063254 | 7/2005 |
| WO | WO 2005/063745 | 7/2005 |
| WO | WO 2006/001958 | 1/2006 |
| WO | WO-2006/023852 | 3/2006 |
| WO | WO 2006/058303 | 3/2006 |
| WO | WO 2006/058303 | 6/2006 |

OTHER PUBLICATIONS

Chambers, Mark S., et al., "Spiropiperidines as high-affinity, selective σ ligands," Journal of Medicinal Chemistry (1992), 35(11), 2033-9.

Dhar, T.G. Murali, "Design and synthesis of novel α1a adrenoceptor-selective antagonists," Journal of Medicinal Chemistry (1999), 42 (23), 4778-4793.

Efange, S.M.N., et al., "Spirovesamicols: Conformationally restricted analogs of 2-(4-Phenylpiperidino) cyclohexanol (Vesamicol, AH5183) as potential modulators of presynaptic cholinergic function," Journal of Medicinal Chemistry (1994), 37 (16), 2574-82.

Efange, Simon, et al, "Vesamicol analogs as sigma ligands. Molecular determinants of selectivity at the vesamicol," Biochem. Pharm. (1995), 49(6), 791-7.

Efange, S.M.N., et al., "Comparative tissue distribution of conformationally restricted radioiodinated vesamicol receptor ligands," Nuclear Medicine and Biology (1995), 22(4), 437-44.

Efange, Simon M.N., et al.; "N-Hydroxyalkyl Derivatives of 3β-Phenyltropane and Methylspiro[1H-indoline-3,4'-piperidine]: Vesamicol Analogues with Affinity or Monoamine Transporters," J. Med. Chem. (1997) vol. 40, pp. 3905-3914.

Evans, Ben E., et al., "Orally active, nonpeptide oxytocin antagonists," Journal of Medicinal Chemistry (1992) 35(21), 3919-3927.

Moltzen, Ejner K., et al., "σ Ligands with Subnanomolar affinity and preference for the σ2 binding site," Journal of Medicinal Chemistry (1995), 38(11), 2009-17.

Yang, Lihu, et al., "Potent 3-spiropiperidine growth hormone secretagogues," Bioorganic & Medicinal Chemistry Letters (1998), 8(1), 107-112.

Yang, Lihu, et al., "The design and synthesis o fnon-peptide somatostatin receptor agonists," Peptides for the New Millennium, Proceedings of the American Peptide Symposium, 16th, Minneapolis, MN, Jun. 26-Jul. 1, 1999 (2000), Meeting Date 1999, 250-252.

International Search Report and Written Opinion of the International Searching Authority for International Application No. PCT/US2005/029780, filed Aug. 19, 2005. Forms PCT/ISA/210 & PCT/ISA/237.

Partial International Search from the European Patent Office issued in a corresponding PCT application PCT/US2005/029780 with International Filing Date Aug. 19, 2005 (Form PCT/ISA/206).

PCT International Search Report for International Application No. PCT/US2006/049412.

Dooseop, Kim, et al, Discovery of human CCR5 antagonists containing hydantoins for the treatment of HIV-1 infection, *Bioorganic and Medicinal Chemistry Letters*, vol. 11, No. 24, Dec. 17, 2001, pp. 3099-3102; Elsevier Science Ltd.

Abdel-Magid, A., "Reductive Amination of Aldehydes and Ketones with Sodium Triacetoxyborohydride. Studies on Direct and Indirect Reductive Amination Procedures1", J. Org. Chem., 61 (1996), pp. 3849-3862.

Freireich, et al., "Quantitative Comparison of Toxicity of Anticancer Agents in Mouse, Rat, Hamster, Dog, Monkey and Man," Cancer Chemother. Rep., 50: 219 (1966).

Butera, J., "Recent Approaches to the Treatment of Urinary Incontinence: A Survey of Patent Activity from 1995 to 1998", Expert Opinion on Therapeutic Patents, 8(8) (1998), pp. 1017-1035.

Bymaster, F., "Xanomeline: A Selective Muscarinic Agonist for the Treatment of Alzheimer's Disease", Drug Development Research, 40 (1997), pp. 158-170.

Caufield, M.P., "International Union of Pharmacology. XVII. Classification of Muscarinic Acetylcholine Receptors", Pharmacol. Rev., 50 (1998), pp. 279-290.

Caufield, M.P., "Muscarinic Receptors-Characterization, Coupling and function", Pharmac. Ther., vol. 58 (1998), pp. 319-379.

Williams, P., "1-(((7,7-Dimethyl-2(S)-(2(S)-amino-4-(methylsulfonyl)butyramido)bicyclo[2.2.1]-heptan-1(S)-yl)methyl)sulfonyl)-4-2(2-methylphenyl)piperazine (L-368,899): An Orally Bioavailable, Non-Peptide Oxytocin Antagonist with Potential Utility for Managing Preterm Labor", J. Med. Chem, 37 (1994), pp. 555-571.

Chiaverelli, S., "Ricerche nella serle della 4-feniipiperidina. Nota v. Derivati della 4,4'-spiro-(1"metilpiperidin)-1,2,3,4,-tetraidroisochinolina", Gazzetta Chimica Italiana, 90, 189 (1960), CN1535967.

Custers, F., "Vesamicol and Some of its Derivatives: Questionable Ligands for Selectively Labelling Acetylcholine Transporters in Rat Brain", Eur. Jour. of Pharm., 338 (1997), pp. 177-183.

deLaszlo, S., "A Nonpeptidic Agonist Ligand of the Human C5A Receptor: Synthesis, Bidning Affinity Optimization and functional Characterization", Bioorganic and Medicinal Chem. Lett., 7(2) (1997), pp. 213-218.

Tata, J., "The Synthesis and Activity of Spiroindane Growth Hormone Secretagogues", Bioorganic and Medicinal Chem. Lett, 7(6) (1997), pp. 663-668.

Takemoto, T., "Asymmetric Synthesis of Enantiomerically Pure Spiro[((2S)-hydroxy)indane-1,4'-piperidine]", Tetrahedron Asymmetry, 10 (1999), pp. 1787-1793.

Reimann, E., "Synthese und pharmakologische Prüfung Homologer und hydroxylierter 3,4-Dihydro-1'-methylspiro [naphthalin-(2H),4'-piperidine]", Archiv. Der. Pharmazie, VCH Verlagsgesellschaft MBH, Weinheim, DE, 323 (1990), pp. 35-39.

Pettibone, D.J., "Identification of an Orally Active, Nonpeptidyl Oxytocin Antagonist", Journal of Pharm. and Experimental Therap., 264(1) (1993), pp. 308-314.

Efange, S., "(+)-p-([18F]Fluorobenzyl)Spirotrozamicol {(+)-[18F]Spiro-FBT}: Synthesis and Biological Evaluation of a High-Affinity Ligand for the Vesicular Acetylcholine Transporter (VAChT)", Nuclear Medicine and Biology, vol. 26 (1999), pp. 189-192.

Patchett, A.A., "The Synthesis of 17β-Amino-17 α-(2'-carboxyethyl)androstane Lacatama1", J. Org. Chem, 27 (1962), pp. 3822-3828.

Pasternak, A., "Potent, Orally Bioavailable Somatostatin Agonists: Good Absorption Achieved by Urea Backbone Cyclization", Bioorganic and Medicinal Chem. Lett., 9 (1999), pp. 491-496.

Felder, C., "Therapeutic Opportunities for Muscarinic Receptors in the Central Nervous System", J. Med. Chem., 43 (23) (2000), pp. 4333-4353.

Hulme, E.C., "Muscarinic Receptor Subtypes", Annu. Rev. Pharmacol. Toxicol., 30 (1990), pp. 633-673.

Oprea, T., "Is There a Difference between Leads and Drugs? A Historical Perspective", J. Chem. Inf. Comput. Sci., 41 (2001), pp. 1308-1315.

Malmstrom, R., "Pharmacology of H 394/84, a dihydropyridine neuropeptide Y Y1 Receptor Antagonist, in Vivo", Eur. Jour. of Pharm., 418 (2001), pp. 95-104.

Matier, W., "Novel Cyclizations and Ring-Opening Reactions of 3-Phenylindene Derivatives", J. Org. Chem., vol. 36, No. 5 (1971), pp. 650-654.

Nargund, R., "Synthesis and Biological Activities of Camphor-Based Non-Peptide Growth Hormone Secretagogues", Bioorganic and Medicinal Chem. Lett., vol. 6, No. 11 (1996), pp. 1265-1270.

Morrow, D., "Synthesis of Some New 17-Spiro-Substituted Steroids", J. Med. Chem., 10(2) (1967), pp. 133-138.

Nargund, R., "Peptidomimetic Growth Hormone Secretagogues: Synthesis and Biological Activites of Analogs Varied at the Indole Nucleus of the Prototypical Spiropiperidine L-162,752", Bioorganic and Medicinal Chem. Lett., vol. 6, No. 14 (1996), pp. 1731-1736.

Cheng, Y., "Solid Phase Synthesis of Spiroindoline", Tet. Lett., 38 (1997), pp. 1497-1500.

Maligres, P. E., "Synthesis of the Orally Active Spiroindoline-Based Growth Hormone Secretagogue, MK-677", Tetrahedron, 53 (1997), pp. 10983-10992.

* cited by examiner

SPIRO COMPOUNDS AS MODULATORS OF MUSCARINIC RECEPTORS

CLAIM OF PRIORITY

This patent application claims the benefit of U.S. Provisional Patent Application Ser. No. 60/753,187, filed on Dec. 22, 2005, which is hereby incorporated by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43(23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors—Characterization, Coupling, and Function," Pharmacol. Ther., 58, pp. 319-379 (1993); Caulfield, M. P. et al., International Union of Pharmacology. XVII. Classification of Muscarinic Acetylcholine Receptors," Pharmacol. Rev., 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides compounds of formula XX and methods of modulating activity of a muscarinic receptor with a compound of the formula XX

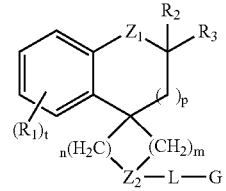

(XX)

or pharmaceutically acceptable salts thereof, wherein

Each of $R_1$, $R_2$, $R_3$ is independently $Q_1$ or $Q_2$, or $R_2$ and $R_3$ together form oxo;

$Z_1$ is —$C(Q_1)_2$-, —$C(H)(Q_5)$-, —$C(H)(Q_5)$-, —C(O)—, —$CH_2$—, —$N(Q_1)$-, —$N(Q_2)$-, or O;

$Z_2$ is N;

L is a bond, an aliphatic group, $C_3$-$C_6$ cycloaliphatic, —O—, —S(O)$_z$—, —S(O)$_z$—($C_1$-$C_4$)alkyl-, —C(O)N($Q_2$)-, or —S(O)$_z$N($Q_2$)-, in which the aliphatic group is optionally substituted with 1-3 of oxo, $Q_1$, or $Q_2$;

G is a monocycloaliphatic, a monocycloheteroaliphatic group, adamantyl, or a bicyclic or a tricyclic group of the formula (XXIII)

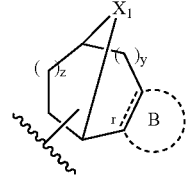

(XXIII)

in which the monocycloaliphatic group, the monocycloheteroaliphatic group, the adamantyl, and the bicyclic or tricyclic group are connected to L via any ring atom including those in $X_1$ and ring B, and the monocycloaliphatic, the monocycloheteroaliphatic, the bicyclic, and the tricyclic groups are substituted with aryl or heteroaryl in which the aryl and heteroaryl are optionally substituted with 1-3 substituents independently selected from $Q_2$ and $Q_3$;

Bond r is a single or double bond and when ring B is present, bond r is fused with B;

Ring B, when present, is a 5-6 membered cycloaliphatic or heterocycloaliphatic ring, and is optionally substituted with 1-3 of oxo, $Q_1$, or $Q_2$;

$X_1$ is —($CH_2$)$_i$—, —O—, or —S—, or $X_1$ is —N— and the nitrogen atom is bound to the aryl or the heteroaryl substituted on G;

Each $Q_1$ is independently halo, —CN, —$NO_2$, —$OQ_2$, —S(O)$_z$$Q_2$, —S(O)$_z$N($Q_2$)$_2$, —N($Q_2$)$_2$, —C(O)$OQ_2$, —C(O)-$Q_2$, —C(O)N($Q_2$)$_2$, —C(O)N($Q_2$)($OQ_2$), —N($Q_2$)C(O)-$Q_2$, —N($Q_2$)C(O)N($Q_2$)$_2$, —N($Q_2$)C(O)O-$Q_2$, —N($Q_2$)S(O)$_z$-$Q_2$ or aliphatic optionally including 1-3 substituents independently selected from $Q_2$ or $Q_3$;

Each $Q_2$ is independently H, aliphatic, cycloaliphatic, aryl, arylalkyl, heterocyclic, or heteroaryl ring, each optionally including 1-3 substituents independently selected from $Q_3$;

Each $Q_3$ is halo, oxo, —CN, —$NO_2$, —$CF_3$, —$OCF_3$, —OH, —$S(O)_zQ_4$, —$N(Q_4)_2$, —$COOQ_4$, —$C(O)Q_4$, —$OQ_4$, or $C_{1-4}$ alkyl optionally substituted with halo, oxo, —CN, —$NO_2$, —$CF_3$, —$OCF_3$, —OH, —SH, —$S(O)_zH$, —$NH_2$, or —COOH;

Each $Q_4$ is aliphatic, cycloaliphatic, aryl, aralkyl, heterocycloaliphatic, heteroaralky, or heteroaryl, each optionally including 1-3 substituents selected from halo, oxo, —CN, —$NO_2$, —$CF_3$, —$OCF_3$, —OH, —SH, —$S(O)_zH$, —$NH_2$, or —COOH;

Each $Q_5$ is a heterocyclic ring optionally including 1-3 substituents selected from halo, $C_{1-4}$ alkyl, oxo, —CN, —$NO_2$, —$CF_3$, —$OCF_3$, —OH, —SH, —$S(O)_zH$, —$NH_2$, —COOH;

Each i is independently 1, 2, or 3;

Each m and n is independently 1, 2, 3, or 4 provided that m+n is at least 4;

Each p is 0 or 1;

Each y is independently 0 or 1;

Each t is 1 to 4; and

Each z is independently 0, 1, or 2.

Additional aspects of the present invention provide compounds as described herein, pharmaceutical compositions that are useful modulators of muscarinic receptors, and methods of treating muscarinic receptor mediated diseases using compounds described herein.

Advantageously, the compounds of the invention are generally selective for $M_1$ and $M_4$ muscarinic receptors. Unexpectedly, the compounds of the invention exhibit increased activity and/or efficacy for $M_1$ and/or $M_4$ muscarinic receptors relative to other muscarinic receptors.

DETAILED DESCRIPTION OF THE INVENTION

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

As described herein, compounds of the invention may optionally be substituted with one or more substituents, such as are illustrated or as exemplified by particular classes, subclasses, and species of the invention described herein.

As used herein the term "aliphatic" encompasses the terms alkyl, alkenyl, alkynyl. An aliphatic group can be optionally substituted with one or more of halo, hydroxy, cyano, nitro, cycloaliphatic, heterocycloaliphatic, aryl, heteroaryl, alkylcarbonyl, alkoxy, alkylsulfonyl, alkylsulfanyl, alkylsulfinyl, amino, alkylamino, alkoxycarbonyl, alkylaminocarbonyl, combinations thereof, or the like.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, isobutyl, n-pentyl, n-heptyl, or 2-ethylhexyl. An alkyl group can be optionally substituted with one or more substituents as described above.

As used herein, an "alkenyl" group refers to an aliphatic carbon group that contains 2-10 (e.g., 2, 3, 4, 5, 6, 7, 8, 9 or 10) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents as described above.

As used herein, an "alkynyl" group refers to an aliphatic carbon group that contains 2-8 (e.g., 2-6 or 2-4) carbon atoms and at least one triple bond. Like an alkyl group, an alkynyl group can be straight or branched. An alkynyl group can be optionally substituted with one or more substituents as described above.

As used herein, an "amino" group refers to —$NR^XR^Y$ wherein each of $R^X$ and $R^Y$ is independently hydrogen, alkyl, cycloalkyl, sulfonyl, (cycloalkyl)alkyl, aryl, aralkyl, heterocycloalkyl, (heterocycloalkyl)alkyl, heteroaryl, or heteroaralkyl each of which are defined herein and are optionally substituted. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); tricyclic (e.g., fluorenyl, tetrahydrofluorenyl, anthracenyl, or tetrahydroanthracenyl); or a benzofused group having 3 rings.

For example, a benzofused group includes phenyl fused with two or more $C_{4-8}$ carbocyclic moieties. An aryl can be optionally substituted with one or more substituents. Without limitation, an aryl can be optionally substituted with halo, hydroxy, cyano, nitro, aliphatic, cycloaliphatic, aryl, heterocycloaliphatic, heteroaryl, alkylsulfonyl, aliphaticaminocarbonyl, alkoxy, aminocarbonyl, alkoxycarbonyl, heteroarylcarbonyl, (heterocycloaliphatic)carbonyl, (heteroarylamino)carbonyl, cycloalkylcarbonyl, alkylcarbonylamino, cycloaliphaticsulfonyl, heterocycloaliphaticsulfonyl, alkylsulfanyl, alkylsulfonyl, (alkoxyalkyl)aminocarbony, combinations thereof, or the like.

As used herein, an "araliphatic" group refers to an aliphatic group (e.g., a $C_{1-4}$ alkyl group, a $C_{1-4}$ alkenyl group, or a $C_{1-4}$ alkynyl group) that is substituted with an aryl group. Both "aliphatic" and "aryl" have been defined above.

As used herein, an "aralkyl" group refers to an alkyl group (e.g., a $C_{1-4}$ alkyl group) that is substituted with an aryl group. Both "alkyl" and "aryl" are defined herein. An example of an aralkyl group is benzyl.

As used herein, a "bicyclic ring system" includes 5-12 (e.g., 7, 8, 9, 10, or 11) membered structures that form two rings, wherein the two rings have at least one atom in common (e.g., 2 atoms in common). Bicyclic ring structures include bicycloaliphatics (e.g., bicycloalkyl or bicycloalkenyl), bicycloheteroaliphatics (e.g., bicycloheteroalkyl or bicycloheteroalkenyl), bicyclic aryls, and bicyclic heteroaryls. Bicyclic ring systems also include bridged bicyclic rings and fused bicyclic rings (e.g., benzo fused).

The term "cycloaliphatic" means a saturated or partially unsaturated monocyclic, bicyclic, or tricyclic hydrocarbon ring that has a single point of attachment to the rest of the molecule. Cycloaliphatic rings are 3-8 membered monocyclic rings (e.g., 3-6 membered rings). Cycloaliphatic rings also include 5-12 membered bicyclic rings. Bicyclic cycloaliphatic (i.e., bicycloaliphatic rings) include bridged bicyclic cycloaliphatic rings and cycloaliphatic fused bicyclic rings. A cycloaliphatic group also encompasses a "cycloalkyl" group and a "cycloalkenyl" group.

Examples of substituents on a cycloaliphatic group include, without limitation, halo, hydroxy, cyano, nitro, aliphatic, alkoxy, alkoxyimino, alkoxyamino, oxo, aryloxyimmino, As used herein, a "cycloalkyl" group refers to a saturated carbocyclic mono-, bi-, or tri-, or multicyclic (fused or bridged) ring of 3-10 (e.g., 5-10) carbon atoms. Without limitation, examples of monocyclic cycloalkyl groups include cyclopropyl, cyclobutyl, cyclopentyl, cyclohexyl, cycloheptyl, or the like. Examples of bicyclic cycloalkyl groups include bridged bicyclic cycloalkyls and fused bicyclic cycloalkyls. Without limitation, bicyclic cycloalkyls include octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, bicycle[2.2.1]heptanyl, bicycle[3.1.1]heptanyl, or the like. Without limitation, multicyclic groups include adamantyl, cubyl, norbornyl, or the like. Cycloalkyl rings can be optionally substituted at any chemically viable ring position.

As used herein, a "cycloalkenyl" group refers to a partially unsaturated carbocyclic mono-, bi-, or tri-, or multicyclic (fused or bridged) ring of 3-10 (e.g., 5-10) carbon atoms. Without limitation, examples of monocyclic cycloalkenyl groups include cyclopropenyl, cyclobutenyl, cyclopentenyl, cyclohexenyl, cycloheptenyl, or the like. Without limitation, bicyclic cycloalkenyl groups include, for example, bicyclo[3.2.1]octenyl, bicyclo[2.2.2]octenyl, bicyclo[3.3.1]nonenyl, bicyclo[3.3.2.]decenyl, bicycle[2.2.1]heptenyl, or bicycle[3.1.1]heptenyl.

As used herein, the term "heterocycloaliphatic" and "heterocyclic" encompasses a heterocycloalkyl group and a heterocycloalkenyl group. Heterocycloaliphatic groups include 3-10 membered monocyclic ring structures having 1-3 heteroatoms. Heterocycloaliphatic groups also include 5-10 membered bicyclic heterocycloaliphatics (i.e., bicycloheterocycloaliphatics). Bicycloheteroaliphatic groups include bridged bicyclic structures, and fused bicyclic structures. Fused bicyclic structures can include a monocyclic heterocycloaliphatic fused to a monocyclic cycloaliphatic ring or a monocyclic heterocycloaliphatic ring.

As used herein, a "heterocycloalkyl" group refers to a 3-10 membered mono or bicyclic (fused or bridged) (e.g., 5 to 10 membered mono or bicyclic) saturated ring structure, in which one or more of the ring atoms is a heteroatom (e.g., N, O, S, or combinations thereof). Bicyclic heterocycloalkyls include bridged and fused bicyclic heterocycloalkyls. Non-limiting examples of heterocycloalkyls include optionally substituted piperidinyl, piperazinyl, tetrahydropyranyl, tetrahydrofuranyl, 1,4-dioxolanyl, 1,4-dithianyl, 1,3-dioxolanyl, oxazolidyl, isoxazolidyl, morpholinyl, thiomorpholinyl, octahydro-benzofuranyl, octahydro-chromenyl, octahydro-thiochromenyl, octahydro-indolyl, octahydro-pyrindinyl, decahydro-quinolinyl, octahydro-benzo[b]thiopheneyl, 2-oxa-bicyclo[2.2.2]octyl, 1-aza-bicyclo[2.2.2]octyl, 3-aza-bicyclo[3.2.1]octanyl, 2,6-dioxa-tricyclo[3.3.1.0$^{3,7}$]nonyl, or tropane. A monocyclic heterocycloalkyl group may be fused with a phenyl moiety such as tetrahydroisoquinoline. Heterocycloalkyl ring structures can be optionally substituted at any chemically viable position on the ring or rings.

A heterocycloalkyl group can be substituted at any chemically feasible position. Heterocycloalkyl substituents, without limitation, include halo, hydroxy, cyano, alkoxy, alkoxycarbonyl, aliphatic (e.g., alkyl, alkenyl, or alkynyl), cycloaliphatic, heterocycloaliphatic, aryl, heteroaryl, heterocycloaliphatic, arylcarbonyl, combinations thereof, or the like.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Bicyclic heterocycloalkenyls include bridged and fused bicyclic heterocycloalkenyls. Examples of heterocycloalkenyls include 2-pyrrolyl, 3-pyrrolyl, 2-imidazolyl, or 2-pyrazolyl. Monocyclic heterocycloaliphatics are numbered according to standard chemical nomenclature. Heterocycloalkenyl substituents, without limitation, include halo, hydroxy, cyano, alkoxy, alkoxycarbonyl, aliphatic (e.g., alkyl, alkenyl, or alkynyl), cycloaliphatic, heterocycloaliphatic, aryl, heteroaryl, heterocycloaliphatic, arylcarbonyl, combinations thereof, or the like.

A "heteroaryl" group, as used herein, refers to a monocyclic, bicyclic, or tricyclic ring systems having 4 to 15 ring atoms wherein one or more of the ring atoms is a heteroatom (e.g., N, O, S, or combinations thereof) and wherein one or more rings of the bicyclic or tricyclic ring structure is aromatic. A heteroaryl group includes a benzofused ring system having 2 to 3 rings. For example, a benzofused group includes benzo fused with one or two $C_{4-8}$ heterocyclic moieties (e.g., indolizyl, indolyl, isoindolyl, 3H-indolyl, indolinyl, benzo[b]furyl, benzo[b]thiopheneyl, quinolinyl, or isoquinolinyl). Some examples of heteroaryl are azetidinyl, pyridinyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiopheneyl, indazolyl, benzimidazolyl, benzthiazolyl, puryl, cinnolinyl, quinolinyl, cinnolinyl, phthalazyl, quinazolinyl, quinoxalinyl, isoquinolinyl, 4H-quinolizyl, benzo-1,2,5-thiadiazolyl, or 1,8-naphthyridyl. A heteroaryl can be optionally substituted at any chemically feasible position.

Without limitation, monocyclic heteroaryls include furyl, thiopheneyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, or 1,3,5-triazyl.

Without limitation, bicyclic heteroaryls include indolizyl, indolyl, isoindolyl, 3H-indolyl, indolinyl, benzo[b]furyl, benzo[b]thiopheneyl, quinolinyl, isoquinolinyl, indolizyl, isoindolyl, indazolyl, benzimidazolyl, benzthiazolyl, purinyl, 4H-quinolizyl, quinolinyl, isoquinolinyl, cinnolinyl, phthalazyl, quinazolinyl, quinoxalinyl, 1,8-naphthyridyl, or pteridyl.

Without limitation, a heteroaryl can be substituted with halo, hydroxy, cyano, aliphatic, cycloaliphatic, heterocycloaliphatic, aryl, heteroaryl, arylcarbonyl, arylcarbonylamino, aliphaticaminocarbonyl, alkoxy, combinations thereof, or the like.

A "heteroaraliphatic" group, as used herein, refers to an aliphatic group (e.g., $C_{1-4}$ alkyl group, $C_{1-4}$ alkenyl group, or $C_{1-4}$ alkynyl group) that is substituted with a heteroaryl group. Both "aliphatic" and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic group" includes mono-, bi-, and tri-cyclic structures including cycloaliphatic, heterocycloaliphatic, aryl, or heteroaryl, each of which has been previously defined.

As used herein, an "acyl" group refers to a formyl group or alkyl-C(=O)— (also referred to as "alkylcarbonyl") where "alkyl" has been defined previously. Acetyl and pivaloyl are examples of acyl groups.

As used herein, a "carbonyl" group, when used alone or as part of another structure refers to the structure —C(O)—.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ can be alkyl, aryl, aralkyl, cycloalkyl, heterocycloalkyl, heteroaryl, or heteroaralkyl.

As used herein, a "carboxy" and a "sulfo" group refer to —C(O)OH or —C(O)OR$^X$ and —SO$_3$H or —SO$_3$R$^X$, respectively.

As used herein, an "alkoxy" group refers to an alkyl-O— group where "alkyl" has been defined previously. Moreover an alkoxy group includes structures comprising two alkoxy groups on the same atom or adjacent atoms that form a ring together with the atom(s) to which they are bound.

As used herein, an "alkoxycarbonyl" group refers to the structure —C(O)O-alkyl.

As used herein, a "nitro" group refers to —N$^+$(O)O$^-$.

As used herein, a "sulfoxy" group refers to —O—SO—R$^X$ or —SO—O—R$^X$, where R$^X$ has been defined above.

As used herein, a "mercapto" group refers to —SH.

As used herein, a "sulfonyl" group refers to —S(O)$_2$—.

As used herein a "sulfinyl" group refers to —S(O)—.

As used herein a "sulfanyl" group refers to —S—.

As used herein, a "halogen" or "halo" group refers to fluorine, chlorine, bromine or iodine.

As used herein, a "haloaliphatic" group refers to an aliphatic group substituted with 1-3 halogen. For instance, the term haloalkyl includes the group —CF$_3$.

As used herein, a "sulfamoyl" group refers to the structure —S(O)$_2$—NR$^X$R$^Y$ or —NR$^X$—S(O)$_2$—R$^Z$ wherein R$^X$, R$^Y$, and R$^Z$ have been defined above.

As used herein, a "sulfamide" group refers to the structure —NR$^X$—S(O)$_2$—NR$^Y$R$^Z$ wherein R$^X$, R$^Y$, and R$^Z$ have been defined above.

As used herein, a "carbonylamino" group used alone or in connection with another group refers to an amido group such as R$^X$—C(O)—NR$^X$—. For instance an alkylcarbonylamino includes alkyl-C(O)—NR$^X$—, wherein R$^X$ has been defined above.

As used herein, a "aminocarbonyl" group used alone or in connection with another group refers to an amido group such as N(R$^X$)$_2$—C(O)—.

As used herein, an "alkoxycarbonyl" used alone or in connection with another group refers to a carbonyl group such as alkyl-O—C(O)—.

As used herein, an "alkoxyalkyl" refers to an alkyl group such as alkyl-O-alkyl-, wherein alkyl has been defined above.

As used herein, an "aminocarbonyl" refers to an amido group such as —NR$^X$—C(O)—, wherein R$^X$ has been defined above.

As used herein, an "aminosulfonyl" refers to the structure —N(R$^X$)$_2$—S(O)$_2$—, wherein R$^X$ has been defined above.

As used herein, an "oxo" refers to =O.

As used herein, an "aminoalkyl" refers to the structure N(R$^X$)$_2$-alkyl-.

As used herein, a "cyanoalkyl" refers to the structure (CN)-alkyl-.

As used herein, an "alkylsulfonyl" group refers to the structure alkyl-S(O)$_2$—.

As used herein, a "sulfonylamino" group refers to the structure R$^X$—S(O)$_2$—N(R$^X$)$_2$—, wherein R$^X$ has been defined above.

As used herein, an "imino" group refers to the functional group =N— and covers the structure =N—R$^X$ and oximes having the structure =N—OR$^X$ wherein R$^X$ is defined above.

As used herein, a "hydroxy" group refers to the structure —OH.

As used herein, a "guanidinyl" group refers to the structure NH$_2$C(NH)NH—.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$— where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

As used herein, a "urea" group refers to the structure —NR$^X$—CO—NR$^Y$R$^Z$ and a "thiourea" group refers to the structure —NR$^X$—CS—NR$^Y$R$^Z$. R$^X$, R$^Y$, and R$^Z$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase: "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. Such compounds are useful, for example, as analytical tools or probes in biological assays.

II. Compounds

The present invention provides methods of modulating muscarinic receptor activity using compounds of formulae (I and II), described above, that are useful in modulating activity of a muscarinic receptor.

Methods of modulating muscarinic receptors according to one aspect of the present invention involve compounds of formula (I):

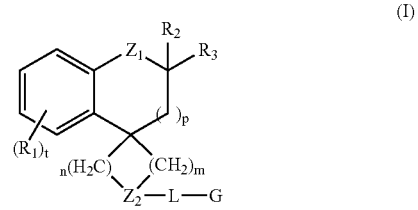

(I)

or pharmaceutically acceptable salts thereof.

Each of $R_1$, $R_2$, $R_3$ is independently $Q_1$ or $Q_2$, or $R_2$ and $R_3$ together form oxo.

$Z_1$ is —C($Q_1$)$_2$-, —C(H)($Q_1$)-, —C(H)($Q_5$)-, —C(O)—, —CH$_2$—, —N($Q_1$)-, —N($Q_2$)-, or —O—.

$Z_2$ is —N—.

L is a bond, an aliphatic group, $C_{3-6}$ cycloaliphatic, —O—, —S(O)$_z$—, —S(O)$_z$—(C$_{1-4}$)alkyl-, —C(O)N($Q_2$)-, or —S(O)$_z$N($Q_2$)-, in which the aliphatic group is optionally substituted with 1-3 of oxo, $Q_1$, or $Q_2$.

G is a monocycloaliphatic group, a monocycloheteroaliphatic group, adamantyl, or a bicyclic or a tricyclic group of the formula (III)

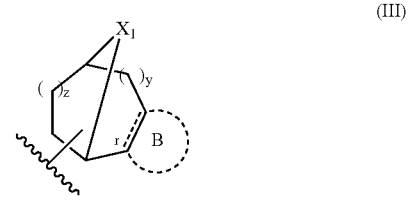

(III)

in which the monocycloaliphatic group, the monocycloheteroaliphatic group, the adamantyl, and the bicyclic or tricyclic group are connected to L via any ring atom including those in $X_1$ and ring B, and the monocycloaliphatic, the monocycloheteroaliphatic, the bicyclic, and the tricyclic groups are optionally substituted with 1-3 of oxo, =N-O$Q_4$, fluorine, $Q_2$, —C(O)—$X_2$-aliphatic in which $X_2$ is absent, —O—, —NH—, —N$Q_2$-, or —S(O)$_z$— and the aliphatic group is optionally substituted with 1-3 substituents independently selected from $Q_3$, or 2 occurrences of $Q_2$ are taken together with the carbon atom to which they are attached to form a 5-6 membered optionally substituted heterocycloaliphatic or 5-6 membered optionally substituted cycloaliphatic. Bond r is a single or double bond and when ring B is present, bond r is fused with B; Ring B, when present, is a 5-6 membered cycloaliphatic or heterocycloaliphatic ring, and is optionally substituted with 1-3 of oxo, $Q_1$, or $Q_2$ $X_1$ is —(CH$_2$)$_i$—, —O—, —S—, —N($Q_2$)-, —N(C(O)—$X_2$-aliphatic)- in which $X_2$ is absent, —O—, —NH—, —NQ$_2$-, or —S(O)$_z$— and the aliphatic group is optionally substituted with 1-3 substituents independently selected from Q$_3$.

Each Q$_1$ is independently halo, —CN, —NO$_2$, —OQ$_2$, —S(O)$_z$Q$_2$, —S(O)$_z$N(Q$_2$)$_2$, —N(Q$_2$)$_2$, —C(O)OQ$_2$, —C(O)Q$_2$, —C(O)N(Q$_2$)$_2$, —C(O)N(Q$_2$)(OQ$_2$), —N(Q$_2$)C(O)-Q$_2$, —N(Q$_2$)C(O)N(Q$_2$)$_2$, —N(Q$_2$)C(O)O-Q$_2$, —N(Q$_2$)S(O)$_z$-Q$_2$, or aliphatic optionally including 1-3 substituents independently selected from Q$_2$ or Q$_3$.

Each Q$_2$ is independently H, aliphatic, cycloaliphatic, aryl, arylalkyl, heterocyclic, or heteroaryl ring, each optionally including 1-3 substituents independently selected from Q$_3$.

Each Q$_3$ is halo, oxo, —CN, —NO$_2$, —CF$_3$, —OCF$_3$, —OH, —S(O)$_z$Q$_4$, —N(Q$_4$)$_2$, —COOQ$_4$, —C(O)Q$_4$, —OQ$_4$, or C$_{1-4}$ alkyl optionally substituted with 1-3 of halo, oxo, —CN, —NO$_2$, —CF$_3$, —OCF$_3$, —OH, —SH, —S(O)$_z$H, —NH$_2$, or —COOH.

Each Q$_4$ is aliphatic, cycloaliphatic, aryl, aralkyl, heterocyclic, heteroaralyl, or heteroaryl ring, each optionally substituted with 1-3 substituents selected from halo, oxo, —CN, —NO$_2$, —CF$_3$, —OCF$_3$, —OH, —SH, —S(O)$_z$H, —NH$_2$, —COOH.

Each Q$_5$ is a heterocyclic ring optionally substituted with 1-3 substituents selected from halo, C$_{1-4}$ alkyl, oxo, —CN, —NO$_2$, —CF$_3$, —OCF$_3$, —OH, —SH, —S(O)$_z$H, —NH$_2$, —COOH; and each i is independently 1, 2, or 3.

Each m and n is independently 1, 2, 3, or 4 provided that m+n is at least 4.

Each p is 0 or 1.

Each y is independently 0 or 1; each t is 1 to 4; and each z is independently 0, 1, or 2.

Another aspect of the invention provides compounds of formula (II) including:

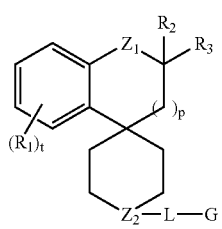

(II)

or pharmaceutically acceptable salts thereof.

Each of R$_1$, R$_2$, R$_3$ is independently Q$_1$ or Q$_2$, or R$_2$ and R$_3$ together form oxo.

Z$_1$ is —C(Q$_1$)$_2$-, —C(H)(Q$_1$)-, —C(H)(Q$_5$)-, —C(O)—, —CH$_2$—, —N(Q$_1$)-, —N(Q$_2$)-, or O.

Z$_2$ is N.

L is a bond, an aliphatic group, C$_{3-6}$ cycloaliphatic, —O—, —S(O)$_z$—, —S(O)$_z$—(C$_{1-4}$) alkyl-, —-C(O)N(Q$_2$)-, or —S(O)$_z$N(Q$_2$)-, in which the aliphatic group is optionally substituted with 1-3 of oxo, Q$_1$, or Q$_2$.

G is a monocycloaliphatic group, a monocycloheteroaliphatic group, adamantyl, or a bicyclic or a tricyclic group of formula (III)

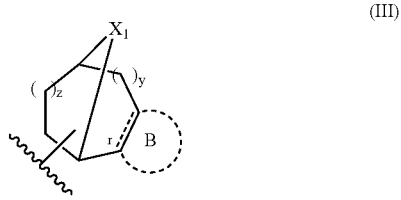

(III)

in which the monocycloaliphatic group, the monocycloheteroaliphatic group, the adamantyl, and the bicyclic or tricyclic group are connected to L via any ring atom including those in X$_1$ and ring B, and the monocycloaliphatic, the monocycloheteroaliphatic, the bicyclic, and the tricyclic groups are optionally substituted with 1-3 of oxo, =N-OQ$_4$, fluorine, Q$_2$, —C(O)—X$_2$-aliphatic in which X$_2$ is absent, —O—, —NH—, —NQ$_2$-, or —S(O)$_z$— and the aliphatic group is optionally substituted with 1-3 substituents independently selected from Q$_3$, or 2 occurrences of Q$_2$ are taken together with the carbon atom to which they are attached to form a 5-6 membered optionally substituted heterocycloaliphatic or 5-6 membered optionally substituted cycloaliphatic; bond r is a single or double bond and when ring B is present, bond r is fused with B; ring B, when present, is a 5-6 membered cycloaliphatic or heterocyclic ring, and is optionally substituted with 1-3 of oxo, Q$_1$, or Q$_2$.

X$_1$ is —(CH$_2$)$_i$—, —O—, —S—, —N(Q$_2$)-, —N(C(O)—X$_2$-aliphatic)- in which X$_2$ is absent, —O—, —NH—, —NQ$_2$-, or S(O)$_z$— and the aliphatic group is optionally substituted with 1-3 substituents independently selected from Q$_3$.

Each Q$_1$ is independently halo, —CN, —NO$_2$, —OQ$_2$, —S(O)$_z$Q$_2$, —S(O)$_z$N(Q$_2$)$_2$, —N(Q$_2$)$_2$, —C(O)OQ$_2$, —C(O)-Q$_2$, —C(O)N(Q$_2$)$_2$, —C(O)N(Q$_2$)(OQ$_2$), —N(Q$_2$)C(O)-Q$_2$, —N(Q$_2$)C(O)N(Q$_2$)$_2$, —N(Q$_2$)C(O)O-Q$_2$, —N(Q$_2$)S(O)$_z$-Q$_2$, or aliphatic optionally including 1-3 substituents independently selected from Q$_2$ or Q$_3$.

Each Q$_2$ is independently H, aliphatic, cycloaliphatic, aryl, arylalkyl, heterocyclic, or heteroaryl ring, each optionally substituted with 1-3 substituents independently selected from Q$_3$.

Each Q$_3$ is halo, oxo, —CN, —NO$_2$, —CF$_3$, —OCF$_3$, —OH, —S(O)$_z$Q$_4$, —N(Q$_4$)$_2$, —COOQ$_4$, —C(O)Q$_4$, —OQ$_4$, or —C$_{1-4}$ alkyl optionally substituted with 1-3 halo, oxo, —CN, —NO$_2$, —CF$_3$, —OCF$_3$, —OH, —SH, —S(O)$_z$H, —NH$_2$, or —COOH.

Each Q$_4$ is aliphatic, cycloaliphatic, aryl, aralkyl, heterocycloaliphatic, heteroaralky, or heteroaryl, each optionally including 1-3 substituents selected from halo, oxo, CN, NO$_2$, CF$_3$, OCF$_3$, OH, SH, —S(O)$_z$H, —NH$_2$, or COOH.

Each Q$_5$ is a heterocyclic ring optionally substituted with 1-3 substituents selected from halo, oxo, C$_{1-4}$ alkyl, —CN, —NO$_2$, —CF$_3$, —OCF$_3$, —OH, —SH, —S(O)$_z$H, —NH$_2$, and —COOH.

Each i is independently 1, 2, or 3.

Each p is 0 or 1.

Each y is independently 0 or 1.

Each z is independently 0, 1, or 2.

In yet another aspect, the invention features

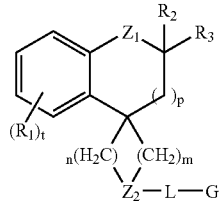

(XX)

or pharmaceutically acceptable salts thereof, wherein

Each of $R_1$, $R_2$, $R_3$ is independently $Q_1$ or $Q_2$, or $R_2$ and $R_3$ together form oxo;

$Z_1$ is —$C(Q_1)_2$-, —$C(H)(Q_1)$-, —$C(H)(Q_5)$-, —C(O)—, —$CH_2$—, —$N(Q_1)$-, —$N(Q_2)$-, or O;

$Z_2$ is N;

L is a bond, an aliphatic group, $C_3$-$C_6$ cycloaliphatic, —O—, —$S(O)_z$—, —$S(O)_z$—($C_1$-$C_4$)alkyl-, —$C(O)N(Q_2)$-, or —$S(O)_zN(Q_2)$-, in which the aliphatic group is optionally substituted with 1-3 of oxo, $Q_1$, or $Q_2$;

G is a monocycloaliphatic, a monocycloheteroaliphatic group, adamantyl, or a bicyclic or a tricyclic group of the formula (XXIII)

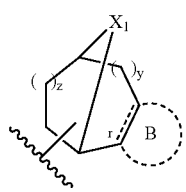

(XXIII)

in which the monocycloaliphatic group, the monocycloheteroaliphatic group, the adamantyl, and the bicyclic or tricyclic group are connected to L via any ring atom including those in $X_1$ and ring B, and the monocycloaliphatic, the monocycloheteroaliphatic, the bicyclic, and the tricyclic groups are substituted with aryl or heteroaryl in which the aryl and heteroaryl are optionally substituted with 1-3 substituents independently selected from $Q_2$ and $Q_3$;

Bond r is a single or double bond and when ring B is present, bond r is fused with B;

Ring B, when present, is a 5-6 membered cycloaliphatic or heterocycloaliphatic ring, and is optionally substituted with 1-3 of oxo, $Q_1$, or $Q_2$;

$X_1$ is —$(CH_2)_i$—, —O—, or —S—, or $X_1$ is —N— and the nitrogen atom is bound to the aryl or the heteroaryl substituted on G;

Each $Q_1$ is independently halo, —CN, —$NO_2$, —$OQ_2$, —$S(O)_zQ_2$, —$S(O)_zN(Q_2)_2$, —$N(Q_2)_2$, —$C(O)OQ_2$, —C(O)-$Q_2$, —$C(O)N(Q_2)_2$, —$C(O)N(Q_2)(OQ_2)$, —$N(Q_2)C(O)$-$Q_2$, —$N(Q_2)C(O)N(Q_2)_2$, —$N(Q_2)C(O)O$-$Q_2$, —$N(Q_2)S(O)_z$-$Q_2$ or aliphatic optionally including 1-3 substituents independently selected from $Q_2$ or $Q_3$;

Each $Q_2$ is independently H, aliphatic, cycloaliphatic, aryl, arylalkyl, heterocyclic, or heteroaryl ring, each optionally including 1-3 substituents independently selected from $Q_3$;

Each $Q_3$ is halo, oxo, —CN, —$NO_2$, —$CF_3$, —$OCF_3$, —OH, —$S(O)_zQ_4$, —$N(Q_4)_2$, —$COOQ_4$, —$C(O)Q_4$, —$OQ_4$, or $C_{1-4}$ alkyl optionally substituted with halo, oxo, —CN, —$NO_2$, —$CF_3$, —$OCF_3$, —OH, —SH, —$S(O)_zH$, —$NH_2$, or —COOH;

Each $Q_4$ is aliphatic, cycloaliphatic, aryl, aralkyl, heterocycloaliphatic, heteroaralky, or heteroaryl, each optionally including 1-3 substituents selected from halo, oxo, —CN, —$NO_2$, —$CF_3$, —$OCF_3$, —OH, —SH, —$S(O)_zH$, —$NH_2$, or —COOH;

Each $Q_5$ is a heterocyclic ring optionally including 1-3 substituents selected from halo, $C_{1-4}$ alkyl, oxo, —CN, —$NO_2$, —$CF_3$, —$OCF_3$, —OH, —SH, —$S(O)_zH$, —$NH_2$, —COOH;

Each i is independently 1, 2, or 3;

Each m and n is independently 1, 2, 3, or 4 provided that m+n is at least 4;

Each p is 0 or 1;

Each y is independently 0 or 1;

Each t is 1 to 4; and

Each z is independently 0, 1, or 2.

III. Specific Embodiments

A. Substituent G

G is a monocycloaliphatic group, a monocycloheteroaliphatic group, adamantyl, or a bicyclic or a tricyclic group of formula (III)

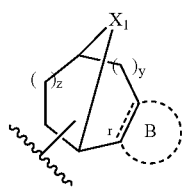

(III)

in which the monocycloaliphatic group, the monocycloheteroaliphatic group, the adamantyl, and the bicyclic or tricyclic group are connected to L via any ring atom including those in $X_1$ and ring B, and the monocycloaliphatic, the monocycloheteroaliphatic, the bicyclic, and the tricyclic groups are optionally substituted with 1-3 of oxo, =N-$OQ_4$, fluorine, $Q_2$, —C(O)—$X_2$-aliphatic in which $X_2$ is absent, —O—, —NH—, —$NQ_2$-, or —$S(O)_z$— and the aliphatic group is optionally substituted with 1-3 substituents independently selected from $Q_3$, or 2 occurrences of $Q_2$ are taken together with the carbon atom to which they are attached to form a 5-6 membered optionally substituted heterocycloaliphatic or 5-6 membered optionally substituted cycloaliphatic; bond r is a single or double bond and when ring B is present, bond r is fused with B; ring B, when present, is a 5-6 membered cycloaliphatic or heterocyclic ring, and is optionally substituted with 1-3 of oxo, $Q_1$, or $Q_2$.

In other aspects, G is a monocycloaliphatic, a monocycloheteroaliphatic group, adamantyl, or a bicyclic or a tricyclic group of the formula (XXIII)

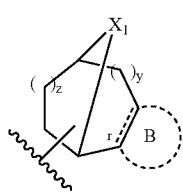

(XXIII)

in which the monocycloaliphatic group, the monocycloheteroaliphatic group, and the bicyclic or tricyclic group are connected to L via any ring atom including those in $X_1$ and ring B, and the monocycloaliphatic, the monocycloheteroaliphatic, the bicyclic, and the tricyclic groups are substituted with aryl or heteroaryl in which the aryl and heteroaryl are optionally substituted with 1-3 substituents independently selected from $Q_2$ and $Q_3$.

In certain embodiments, G is an optionally substituted monocycloaliphatic group.

In several embodiments, G is an optionally substituted cycloaliphatic. In examples of this embodiment, G is an optionally substituted monocycloaliphatic. Specific examples of G include, but are not limited to, 5 to 8 membered monocycloalkyls or a 5 to 8 membered monocycloalkenyls. In other examples, G can be an optionally substituted cyclopentyl, cyclopentenyl, cyclohexyl, cyclohexenyl, cycloheptyl, or cyclooctyl.

In several embodiments, G is optionally substituted with $Q_2$, or —C(O)—$X_2$-aliphatic, where $X_2$ is absent, —O—, —NH—, or —$NQ_2$-, and the aliphatic group is optionally substituted with 1-3 substituents independently selected from $Q_3$. In examples of these embodiments, G can be substituted with carbonyl, sulfonyl, alkoxy, combinations thereof, or the like.

In several embodiments, G is optionally substituted with 1 to 3 of carbonyl, sulfonyl, or combinations thereof. Examples of G include, but are not limited to, alkoxycarbonyl, aliphaticcarbonyl (e.g., alkylcarbonyl, alkenylcarbonyl, or alkynylcarbonyl), aliphatic, alkoxyalkoxycarbonyl, cycloalkoxycarbonyl, heterocycloalkoxycarbonyl, aminoaliphatic, aliphaticamino, arylcarbonyl, or heteroarylcarbonyl, each of which is optionally substituted.

In several embodiments, G is substituted with alkyl, aryl, heteroaryl, haloalkyl, alkoxycarbonyl, or alkoxyamino.

In several embodiments, G is substituted with an optionally substituted aryl. For example, G is substituted with an optionally substituted phenyl. In other examples, G is substituted with a phenyl that is substituted with 1-3 of halo, aliphatic, alkoxy, or combinations thereof. In other examples, G is an unsubstituted phenyl.

In several embodiments, G is substituted with an optionally substituted heteroaryl. For example, G is substituted with furanyl, thiophenyl, pyridinyl, pyranyl, pyridazinyl, pyrimidinyl, pyrazinyl, or combinations thereof. In other examples, G is a heteroaryl optionally substituted with 1-3 of halo, aliphatic, alkoxy, alkylcarbonyl, alkylaminocarbonyl, or combinations thereof. In several examples, G is substituted with an unsubstituted heteroaryl.

In several embodiments, G is optionally substituted with 2 occurrences of $Q_2$. For example, G is substituted by two occurrences of $Q_2$ that are attached to the same carbon atom. In other examples, two occurrences of $Q_2$ taken together with the carbon atom to which they are attached form a 5-6 membered optionally substituted cycloaliphatic or heterocycloaliphatic. In several alternative embodiments, two occurrences of $Q_2$ taken together with the carbon atom to which they are attached form 4,5-dihydroisoxazolyl, isoxazolidinyl, piperidinyl, pyrrolidinyl, or tetrahydropyran, each of which is optionally substituted.

In several embodiments, G is selected from:

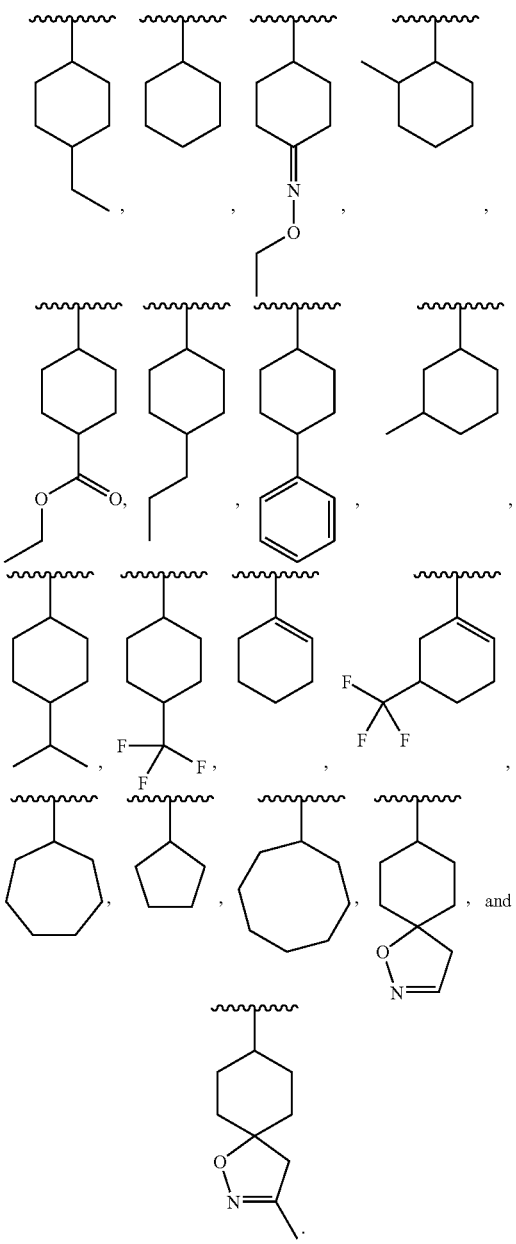

In several embodiments, G is an optionally substituted monoheterocycloaliphatic group. Examples of G include, but are not limited to, optionally substituted 5 to 7 membered monoheterocycloaliphatic groups.

In several embodiments, G includes at least 1 nitrogen atom. G can be substituted with 1 to 3 substituents independently selected from $Q_2$, and —C(O)—$X_2$-aliphatic, where $X_2$ is absent, —O—, —NH—, or —$NQ_2$-, and the aliphatic group is optionally substituted with 1-3 substituents independently selected from $Q_3$. In several embodiments, G is piperidinyl, piperazinyl, imidazolidinyl, or pyrrolidinyl, each of which is optionally substituted.

In several embodiments, G is optionally substituted with 1 to 2 substituents independently selected from alkoxycarbonyl, alkynyloxycarbonyl, alkoxyalkoxycarbonyl, haloalkoxycarbonyl, heterocycloalkoxycarbonyl, and cycloalkoxycarbonyl.

In other embodiments, G is one selected from
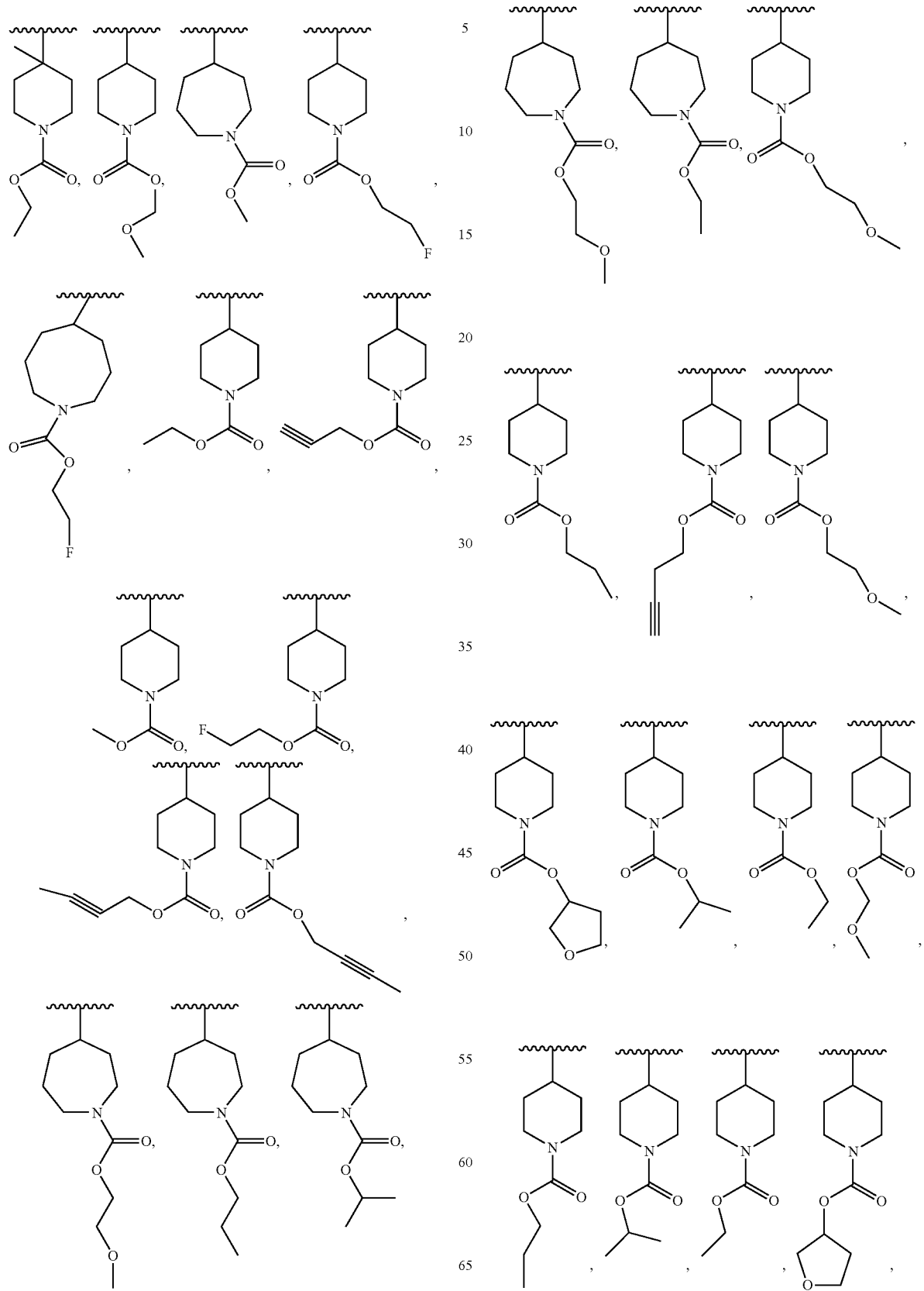

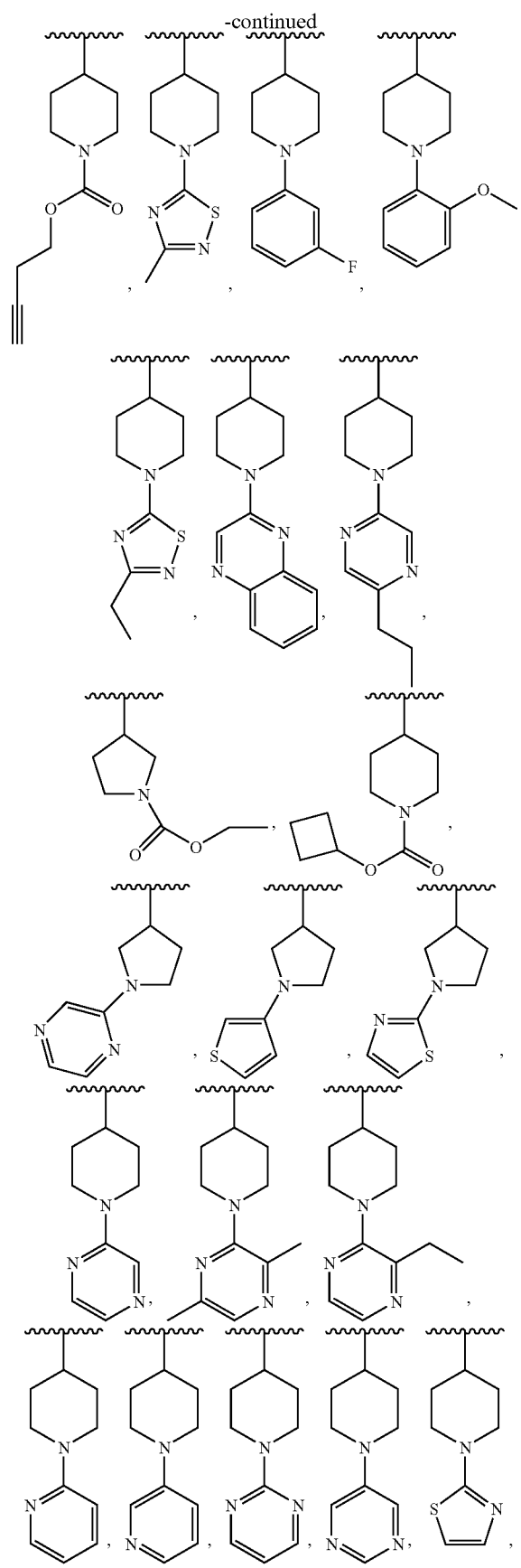

-continued

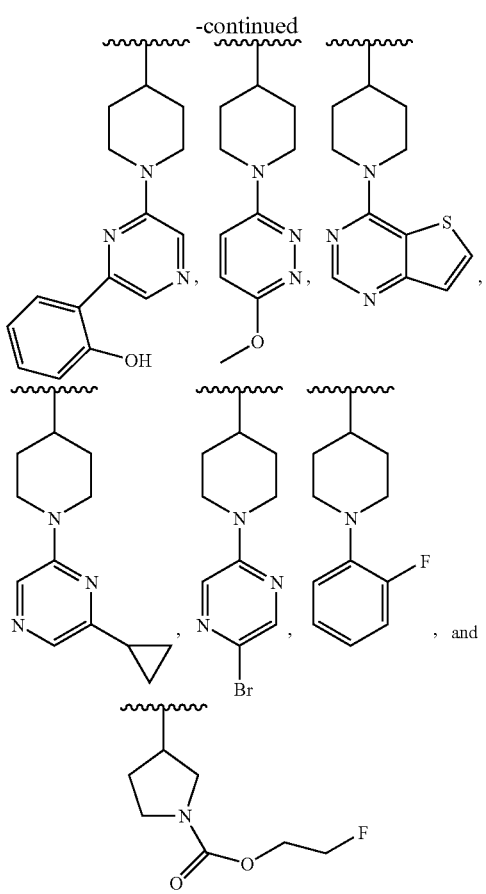

In several embodiments, G includes at least one O atom. In several examples, G is optionally substituted with 1 to 3 substituents independently selected from alkoxycarbonyl, alkynyloxycarbonyl, alkoxyalkoxycarbonyl, haloalkoxycarbonyl, heterocycloalkoxycarbonyl, and cycloalkoxycarbonyl. In other examples, G is unsubstituted.

In several embodiments, G is one selected from

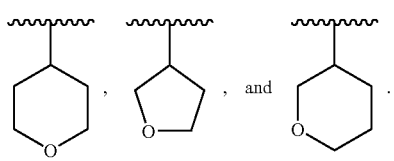

In other embodiments, G is an optionally substituted bicyclic group of formula (III). In one group of examples, ring B is absent from the bicyclic group of formula (III).

In several embodiments, $X_1$ is —$(CH)_{2i}$—, where i is defined above.

In several alternative embodiments, the bicyclic group of formula (III) includes 7 to 9 ring atoms. In specific examples, G is an optionally substituted bicyclo[2.2.1]heptyl, bicyclo[3.2.1]octyl, bicyclo[3.3.1]nonyl, bicyclo[2.2.2]octyl, or bicyclo[2.2.1]heptanyl. In yet another group of the examples, G can be substituted with 1 to 3 substituents independently selected from $Q_2$, and —C(O)—$X_2$-aliphatic, where $X_2$ is absent, —O—, —NH—, or —$NQ_2$-, and the aliphatic group is optionally substituted with 1-3 substituents independently selected from $Q_3$.

In several embodiments, G is one selected from

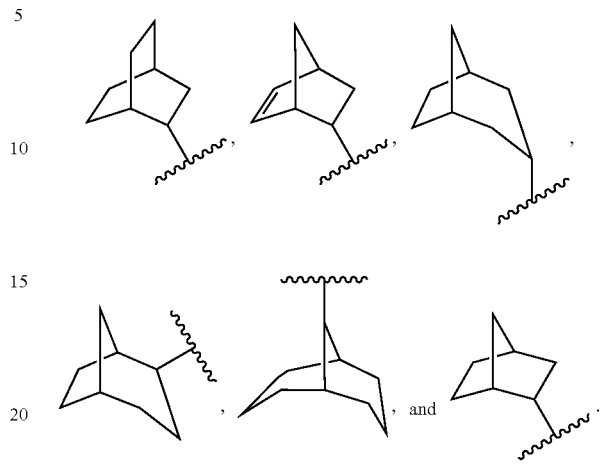

In other embodiments, G is optionally substituted adamantly.

In several embodiments, $X_1$ is —O—, —N($Q_2$)-, or —N(C(O)—$X_2$-aliphatic), where $X_2$ is absent, —O—, —NH—, or —$NQ_2$-, and the aliphatic group is optionally substituted with 1-3 substituents independently selected from $Q_3$. In one group of examples, G is an optionally substituted tropane.

In other examples, G is substituted with $Q_2$, and —C(O)—$X_2$-aliphatic, where $X_2$ is absent, —O—, —NH—, or —$NQ_2$-, and the aliphatic group is optionally substituted with 1-3 substituents independently selected from $Q_3$.

In several embodiments, G is substituted with alkoxycarbonyl, alkoxyalkoxycarbonyl, heterocycloalkoxycarbonyl, cycloalkoxycarbonyl, alkoxyaryloxycarbonyl, alkylaminocarbonyl, haloalkoxycarbonyl, alkynyloxycarbonyl, or heterocycloalkylalkoxycarbonyl.

In several embodiments, G is one selected from

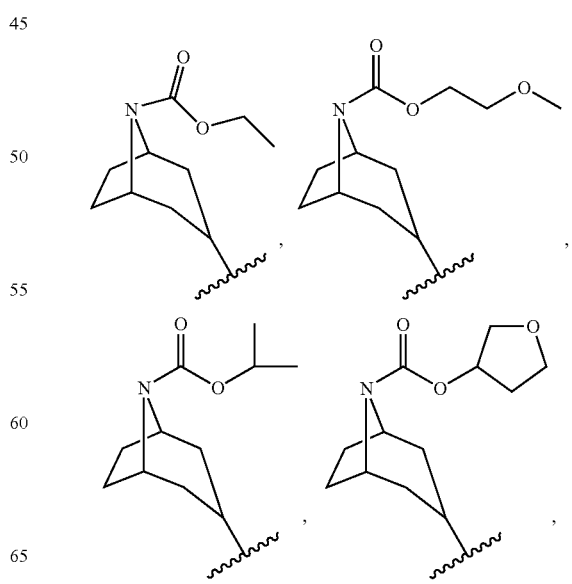

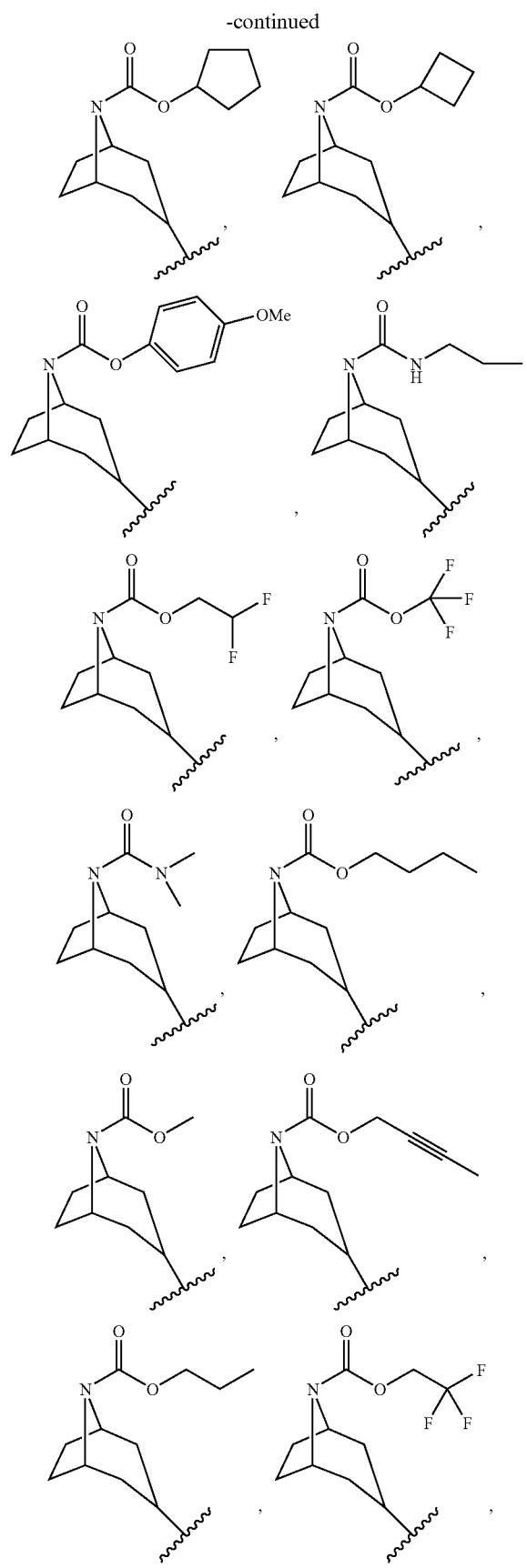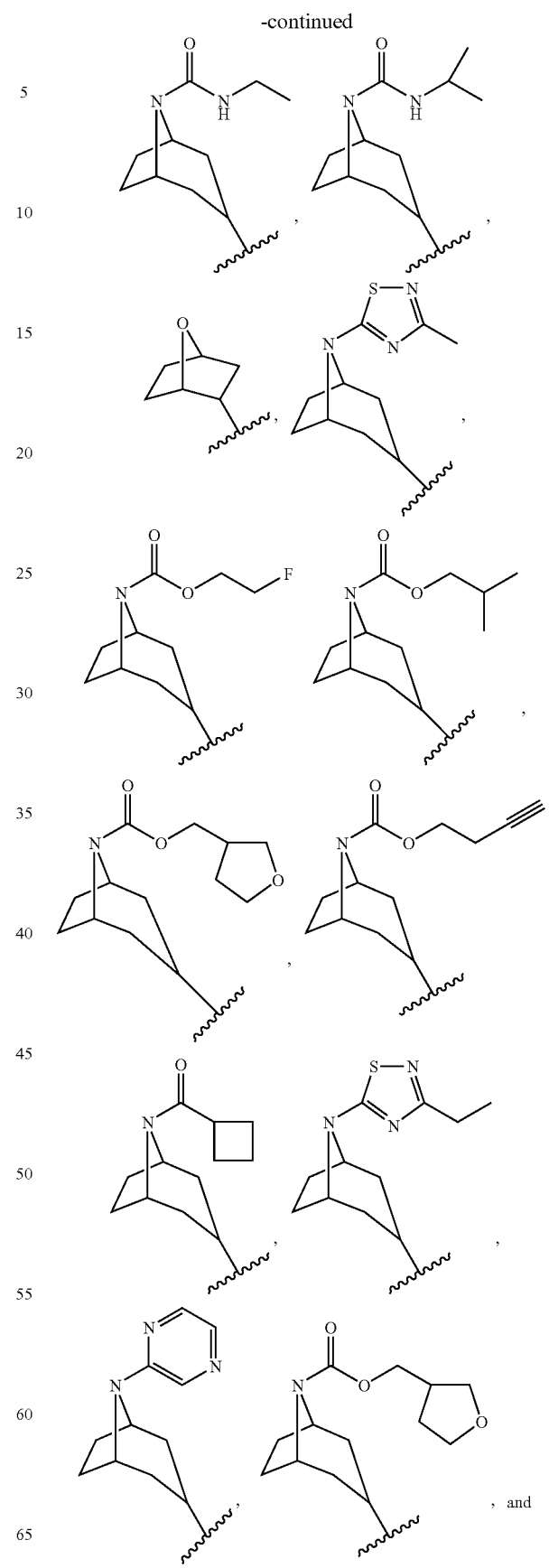

-continued

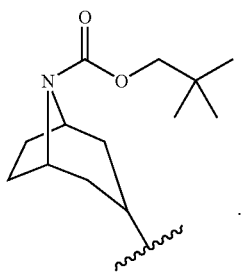

In still other embodiments, G is

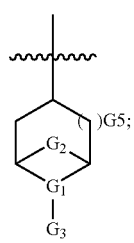

$G_1$ is —N— or —C(H)—;
$G_2$ is absent or a $C_{1-3}$ alkyl;
$G_3$ is an aryl or heteroaryl, each optionally substituted with 1-3 substituents independently selected from $Q_2$ and $Q_3$; and 1. G5 is 0 or 1 when $G_2$ is absent or 0 when $G_2$ is a $C_{1-3}$ alkyl. This embodiment may include one or more of the following features. $G_2$ is absent. $G_1$ is N. $G_3$ is an aryl optionally substituted with 1-3 of halo, cyano, $C_{1-4}$ alkoxy, $C_{1-4}$ alkyl, cyclopropyl or phenyl optionally substituted with 1-3 of halo, cyano, hydroxy, $C_{1-4}$ alkoxy, or $C_{1-4}$ alkyl. $G_3$ is a heteroaryl optionally substituted with 1-3 of halo, cyano, $C_{1-4}$ alkoxy, $C_{1-4}$ alkyl, cyclopropyl or phenyl optionally substituted with 1-3 of halo, cyano, hydroxy, $C_{1-4}$ alkoxy, or $C_{1-4}$ alkyl. G5 is 0. G5 is 1. $G_2$ is —(CH$_2$)— or —(CH$_2$)—(CH$_2$)—. G is one selected from

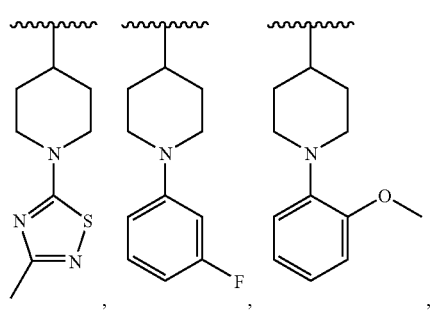

-continued

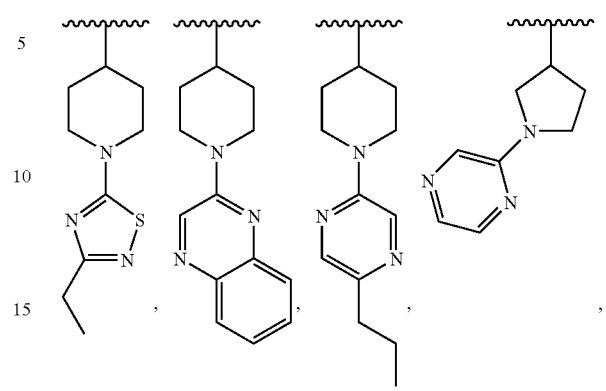

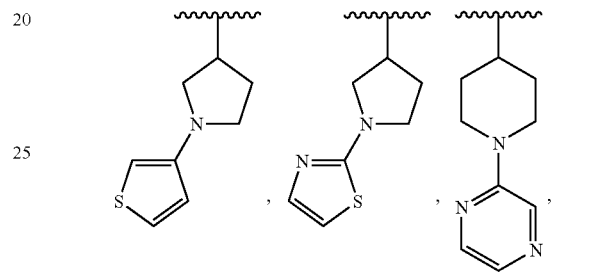

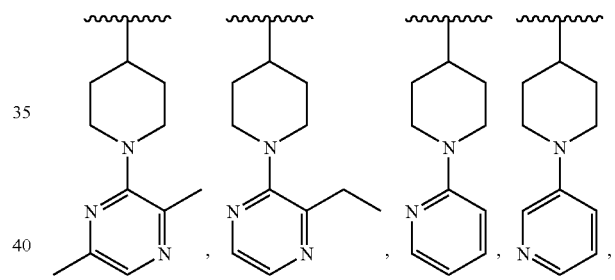

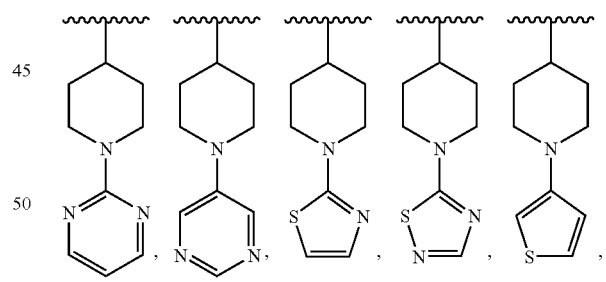

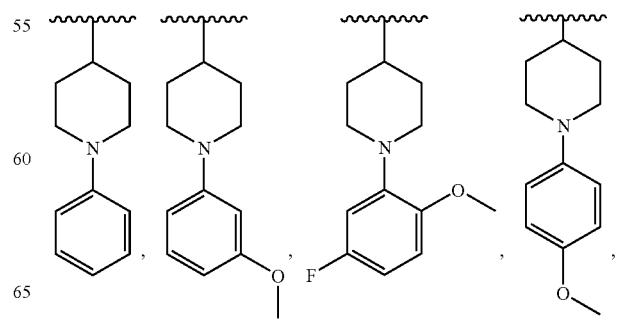

-continued

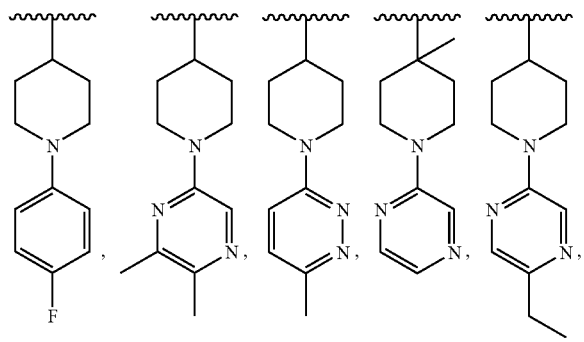

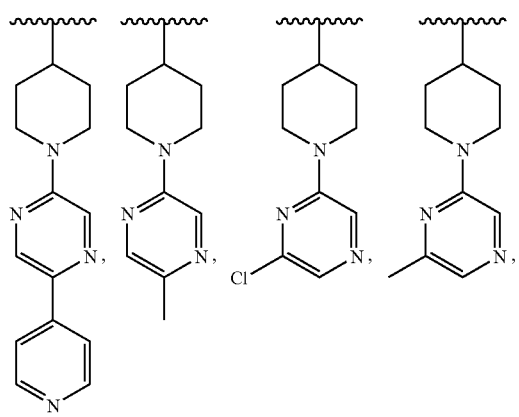

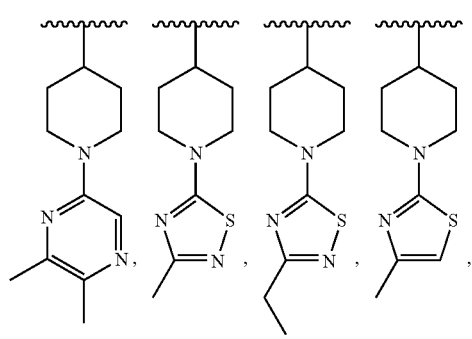

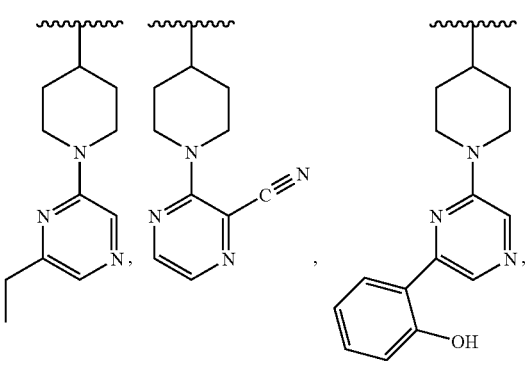

-continued

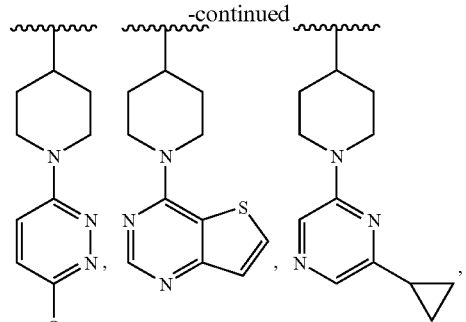

, and

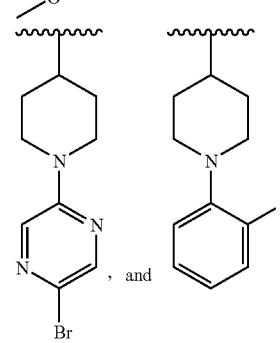

. G is selected from

G is selected from

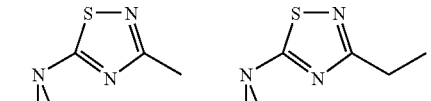

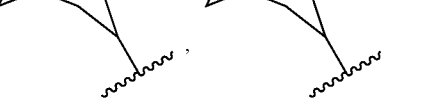

, and

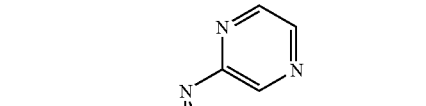

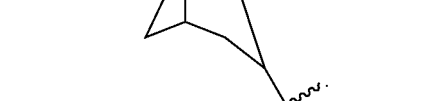

.

B. Substituent $Z_1$ $Z_1$ is —C($Q_1$)$_2$-, —C(H)($Q_1$)-, —C(H)($Q_5$)-, —C(O)—, —CH$_2$—, —N($Q_1$)-, —N($Q_2$)-, or O.

In several embodiments, $Z_1$ is an optionally substituted carbon or nitrogen atom. In one group of examples, $Z_1$ is substituted with amino, alkylcarbonylamino, alkylsulfonylamino, alkoxycarbonylamino, aminocarbonyl, alkylcarbonylalkyl, alkoxyalkoxycarbonyl, alkoxyalkyl, alkylaminocarbonyl, alkoxycarbonyl, haloarylcarbonyl, haloarylsulfonyl, alkylheteroarylcarbonyl, heteroarylcarbonyl, heterocycloalkylcarbonyl, haloarylaminocarbonyl, alkylheteroarylsulfonyl, cyanoalkylarylcarbonyl, heterocycloalkoxycarbonyl, alkynyloxycarbonyl, cycloalkoxycarbonyl, heterobicycloarylcarbonyl, alkylheteroarylaminocarbonyl, alkylsulfonyl, alkylcarbonylalkyl, alkoxyarylcarbonyl, haloalkoxycarbonyl, alkylarylcarbonyl, haloalkoxyarylcarbonyl, or arylaminocarbonyl.

In several embodiments, $Z_1$ is —$NQ_1$- or —$NQ_2$. In several examples, $Z_1$ is —$NQ_1$- where $Q_1$ is —$C(O)Q_2$, or —$C(O)N(Q_2)_2$. In other embodiments, $Z_1$ is —$NQ_1$- where $Q_1$ is —$C(O)Q_2$, or —$C(O)N(Q_2)_2$, and $Q_2$ is aliphatic.

In several embodiments, $Z_1$ is one selected from —$CH_2$—, —$C(O)$—, —$NH$—, —$O$—

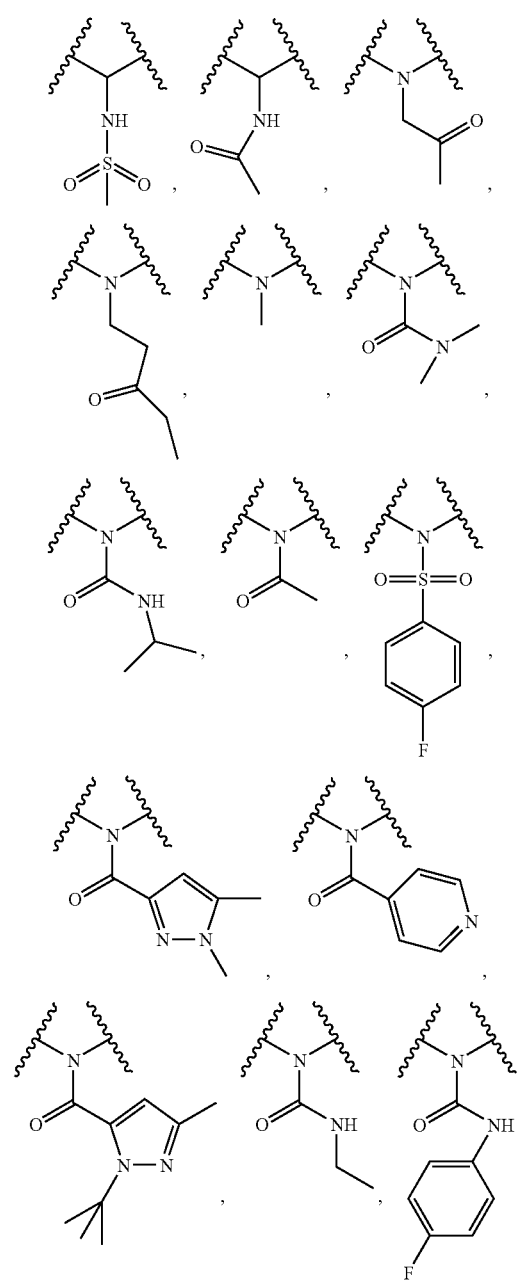
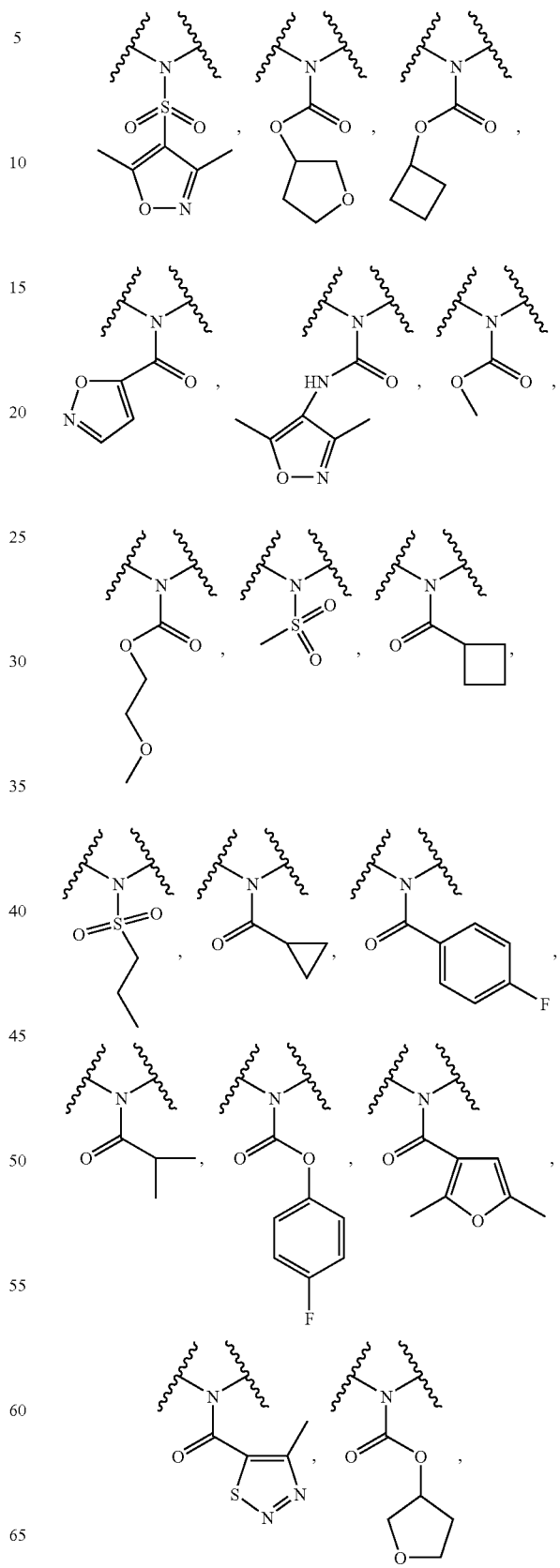

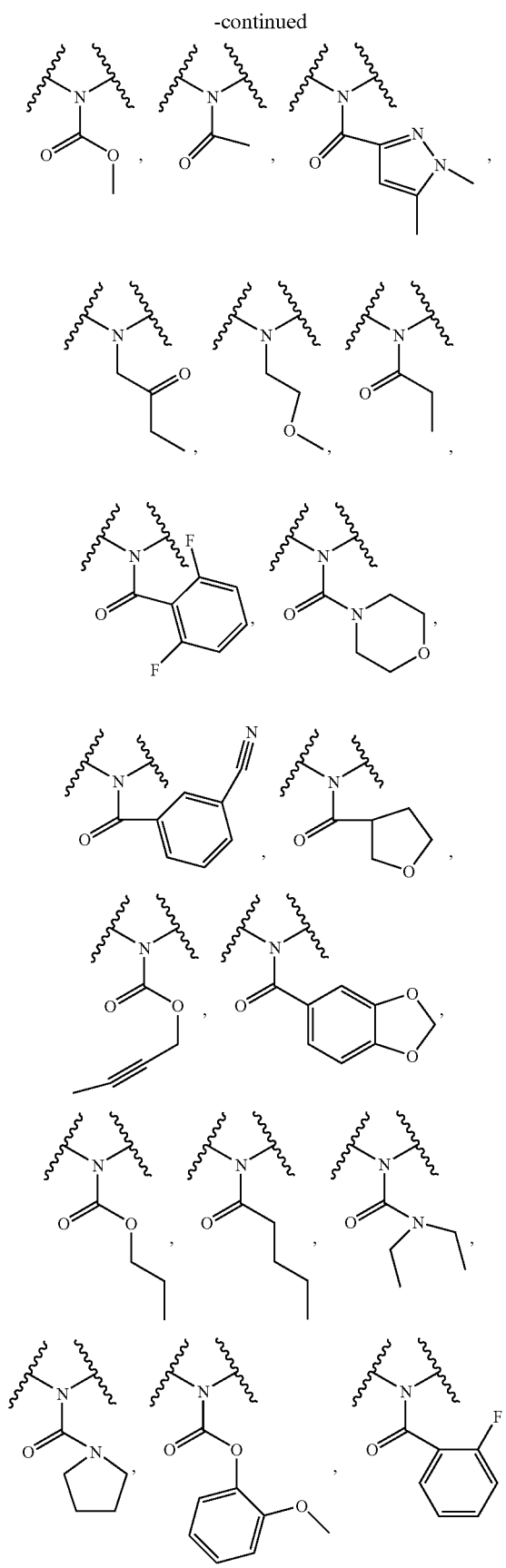
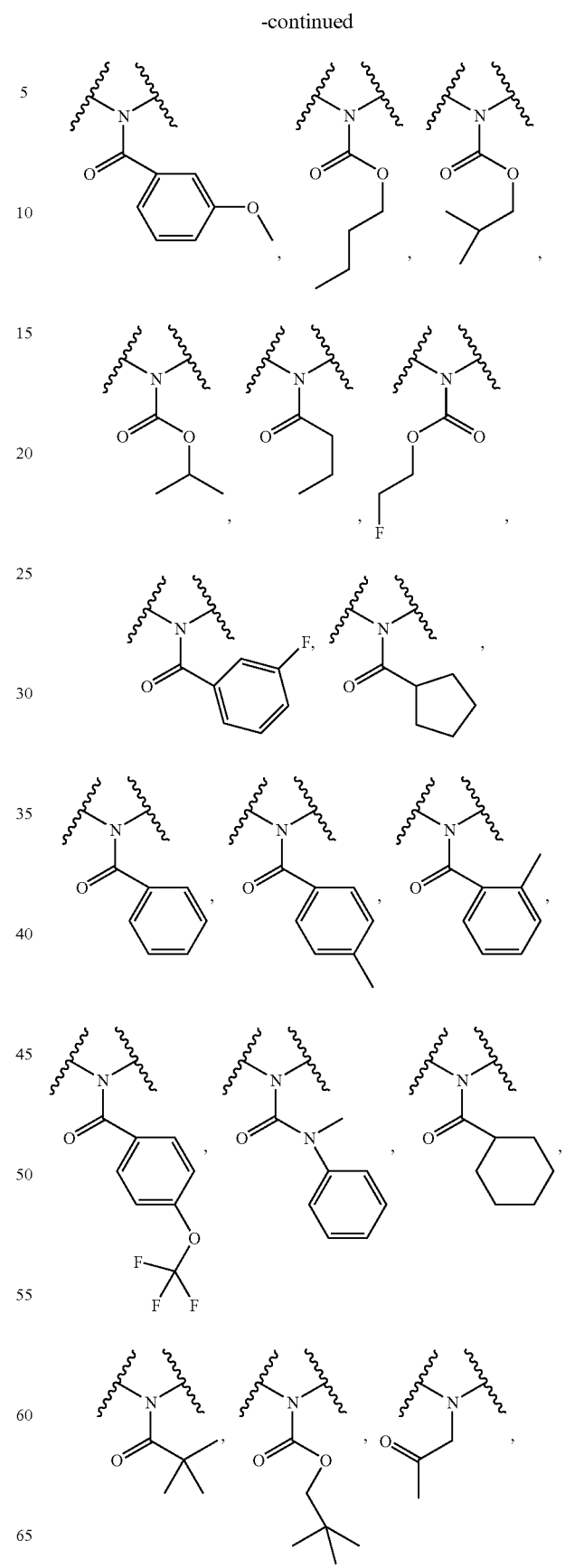

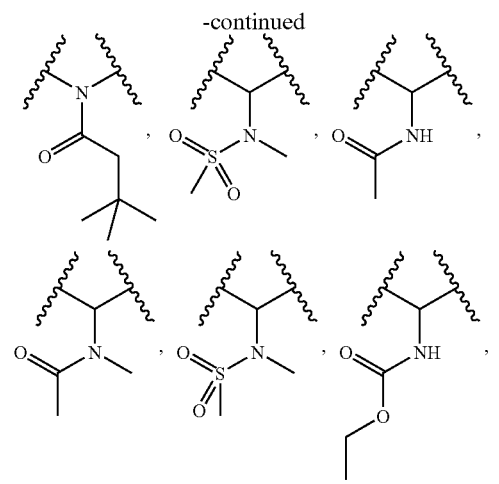

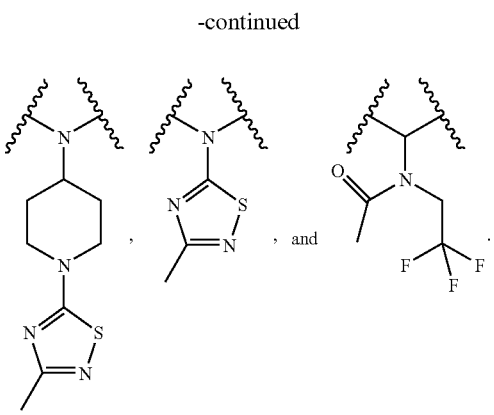

C. Substituents $R_1$, $R_2$, and $R_3$

Each of $R_1$, $R_2$, $R_3$ is independently $Q_1$ or $Q_2$, or $R_2$ and $R_3$ together form oxo.

In several embodiments, $R_1$ is hydrogen, halo, or optionally substituted alkyl, heteroaryl, alkoxy, alkenyl, cycloalkyl, cyanoalkylaryl, alkylaryl, alkylsulfonylaryl, alkylcarbonylaryl, aryl, aminocarbonylaryl, alkylcarbonylaminoaryl, cycloalkenyl, or alkoxyaryl. $R_1$ groups can be optionally substituted with 1 to 3 substituents selected from amino, carbonyl, alkoxycarbonyl, aminocarbonyl, aryl, aliphatic, alkoxy, and sulfonyl.

In other embodiments, $R_1$ is one selected from hydrogen, halo, methyl, —$OCH_3$,

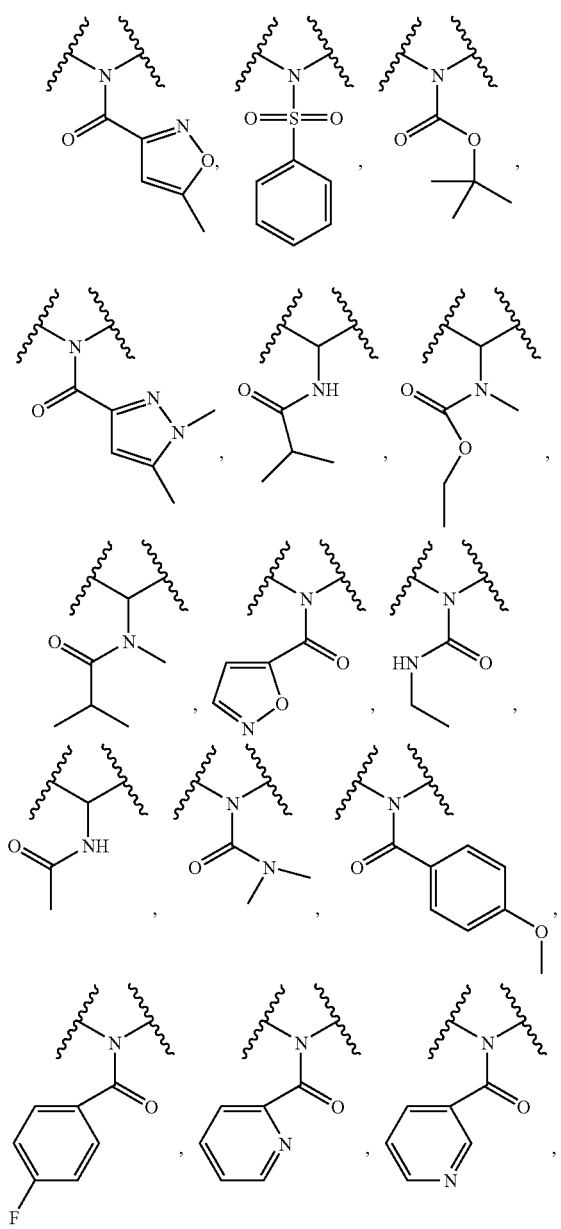

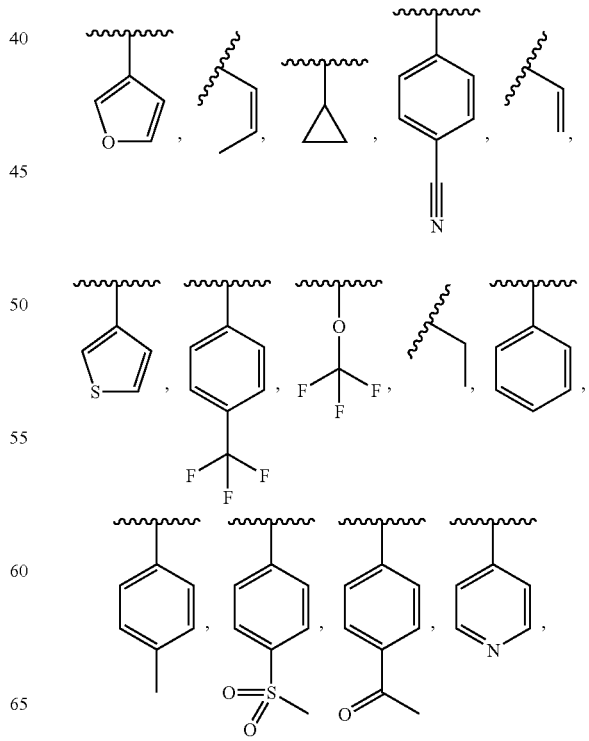

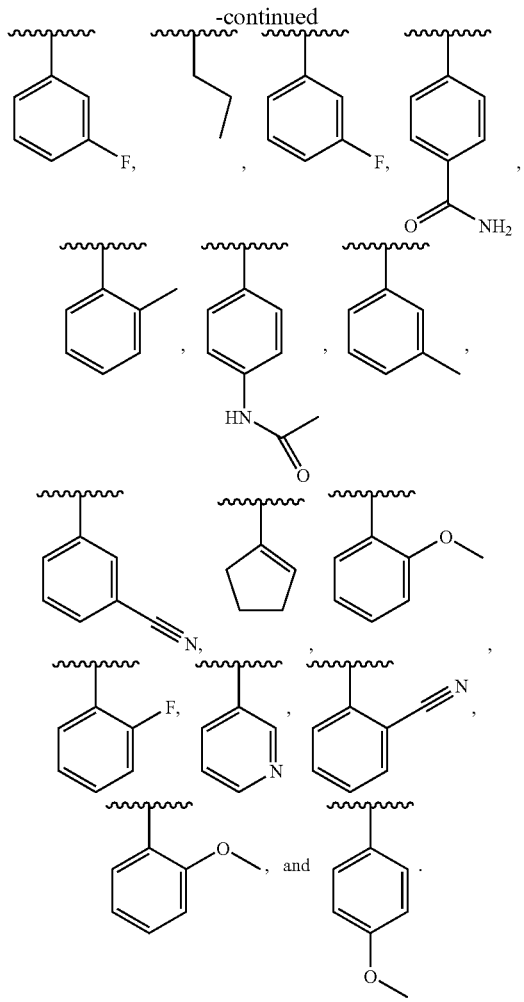

In several embodiments, $R_2$ and $R_3$ are independently hydrogen, alkyl, arylalkyl, or $R_2$ and $R_3$ together form an oxo or amino.

In still other embodiments, $R_2$ and $R_3$ are independently hydrogen, alkyl, or $R_2$ and $R_3$ together form an oxo.

D. L Groups

L is a bond, an aliphatic group, $C_{3-6}$ cycloaliphatic, —O—, —S(O)$_z$—, —S(O)$_z$—(C$_{1-4}$)alkyl-, —C(O)N(Q$_2$)-, or —S(O)$_z$N(Q$_2$)-, in which the aliphatic group is optionally substituted with 1-3 of oxo, Q$_1$, or Q$_2$. In some embodiments, L is a bond or an aliphatic group in which the aliphatic group is optionally substituted with 1-3 of oxo, Q$_1$, or Q$_2$. In other embodiments, L is a bond. In still further embodiments, L is an aliphatic group optionally substituted with 1-3 of oxo, Q$_1$, or Q$_2$. L is CH$_2$.

E. Combinations of Embodiments

Other embodiments include any combination of the aforementioned substituents G, $Z_1$, L, $R_1$, $R_2$, and $R_3$.

F. Excluded Compounds

In several embodiments, when $Z_1$ is —CH$_2$— or —N(CH$_3$)—, L is a bond, and G is an optionally substituted monocycloaliphatic, an optionally substituted monocycloheteroaliphatic group, or a norbornanyl group, then the $R_1$ substituent on the indane or indole is other than H.

In several embodiments, when L is —C(O)—CH$_2$— and $Z_1$ is —N(Q$_1$)-, and Q$_1$ on $Z_1$ is —S(O)$_2$-optionally substituted phenyl, then the $R_1$ substituent on the indole is other than H.

In several embodiments, when L is —S(O)$_2$—(C$_{1-4}$)alkyl-, $Z_1$ is —CH$_2$—, then the $R_1$ substituent on the indane or tetrahydronaphthyl is other than H.

In several embodiments, when L is —S(O)$_2$—(C$_{1-4}$)alkyl-, $R_2$ and $R_3$ form =O, $Z_1$ is —N(Q$_1$)-, and Q is aliphatic or —S(O)$_2$-aliphatic, then the $R_1$ substituent on the indole is other than H.

In several embodiments, when L is aliphatic, and $R_2$ and $R_3$ form =O, and $Z_1$ is —N(Q$_1$)-, Q$_1$ is aliphatic, G is a substituted monocycloheteroaliphatic group, then the $R_1$ substituent on the indole is other than H.

In certain embodiments, L is not —S(O)$_2$—(C$_{1-4}$)alkyl-.

G. Specific Embodiments

Specific compounds of formulae (I or II) are shown below. Compounds 1-120 and 122-430 share the core structure of formula II.

TABLE 1

Exemplary compounds of formulae I and II.

1

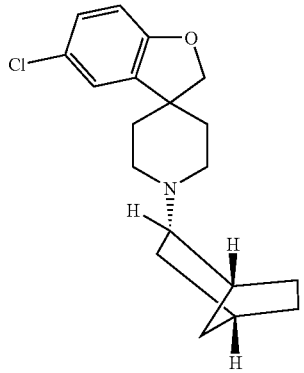

2

TABLE 1-continued
Exemplary compounds of formulae I and II.
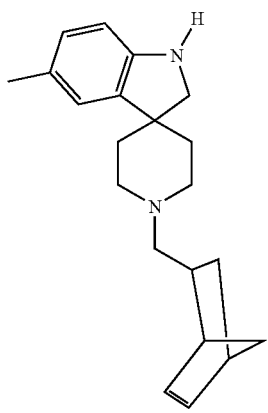
3
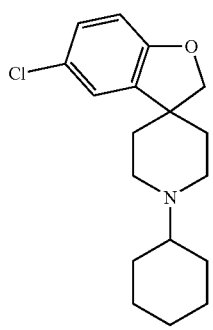
5
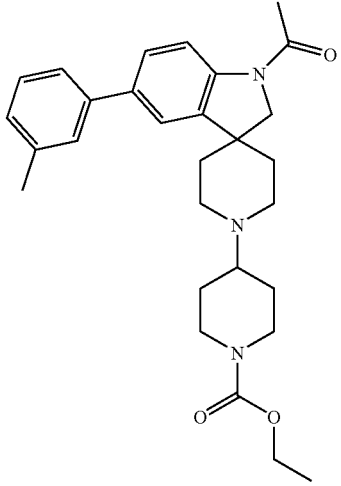
6
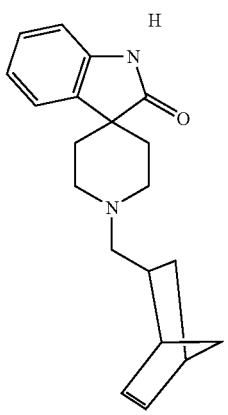
7
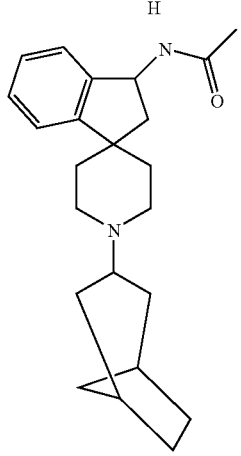
8

TABLE 1-continued
Exemplary compounds of formulae I and II.
9
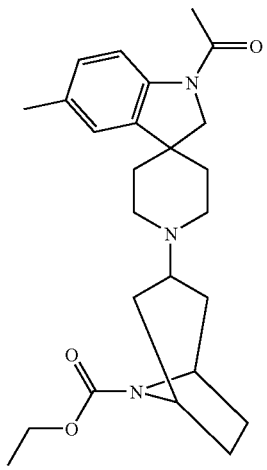
10
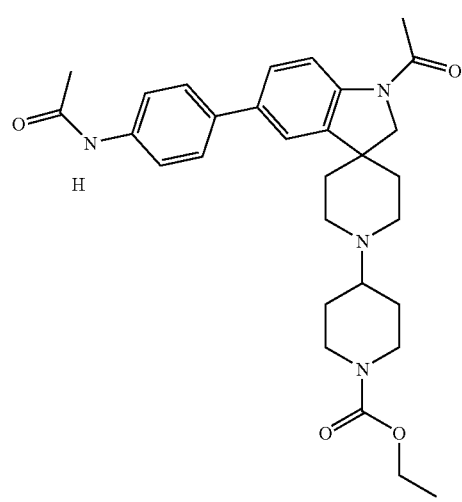
11
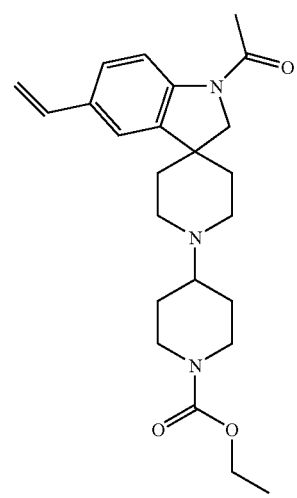
TABLE 1-continued
Exemplary compounds of formulae I and II.
12
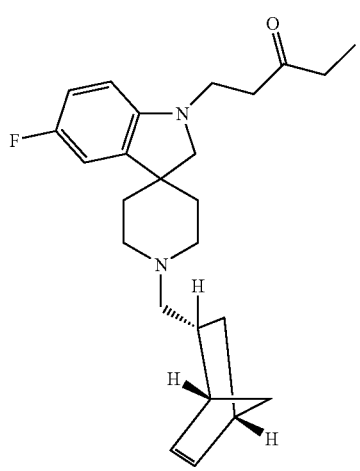
13
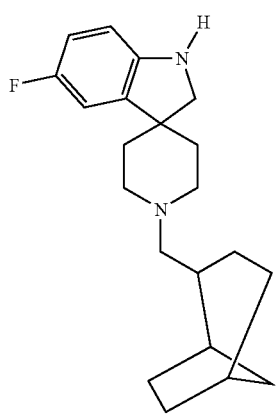
14
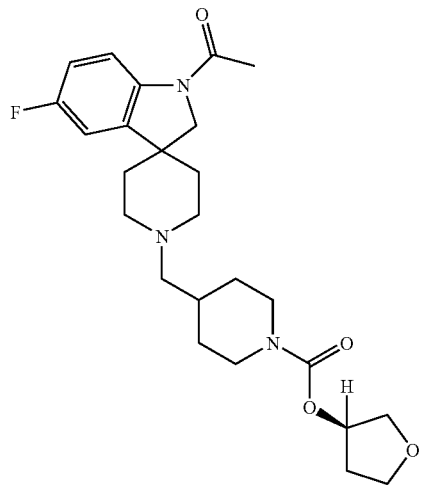

TABLE 1-continued
Exemplary compounds of formulae I and II.
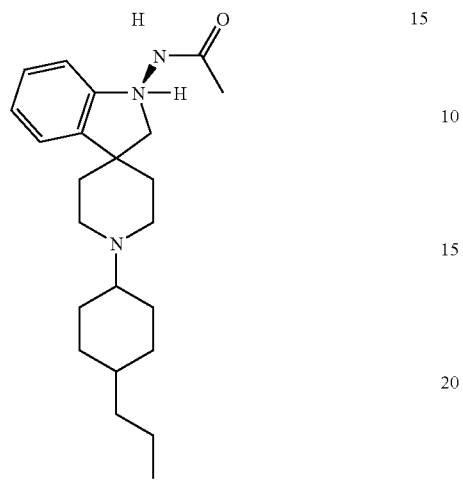
15
16
17
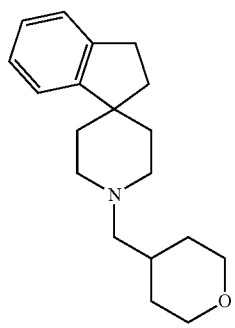
18
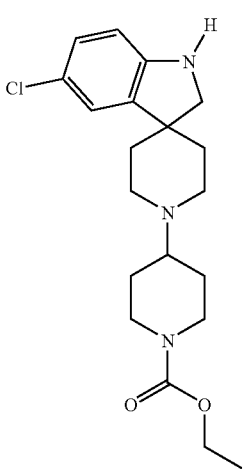
19
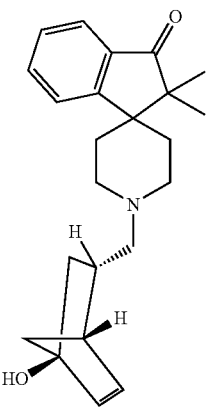
20

TABLE 1-continued
Exemplary compounds of formulae I and II.
21
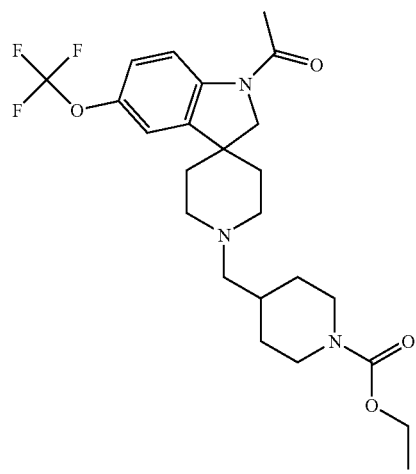
22
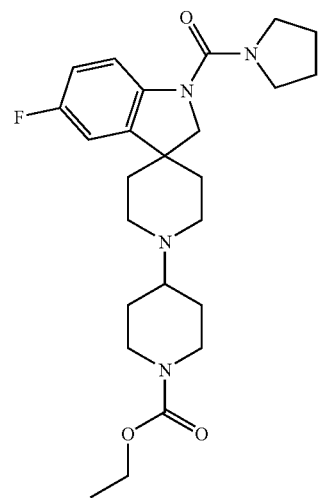
23
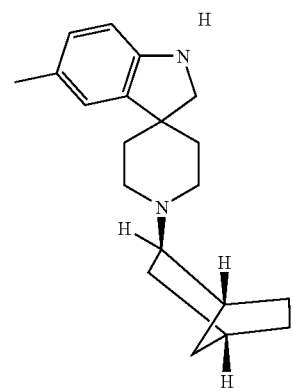
TABLE 1-continued
Exemplary compounds of formulae I and II.
24
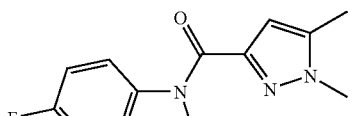
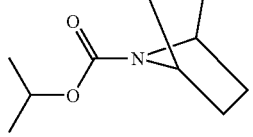
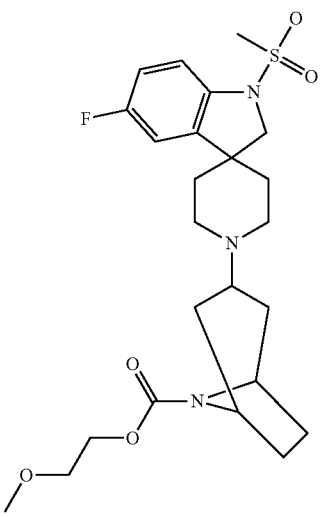
25
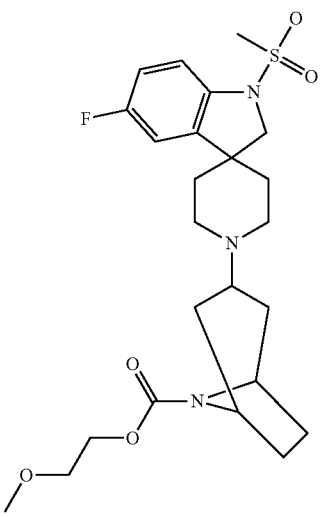
26
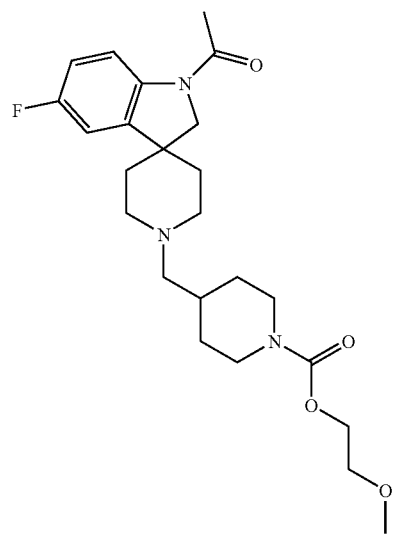

TABLE 1-continued
Exemplary compounds of formulae I and II.
| | |
|---|---|
| 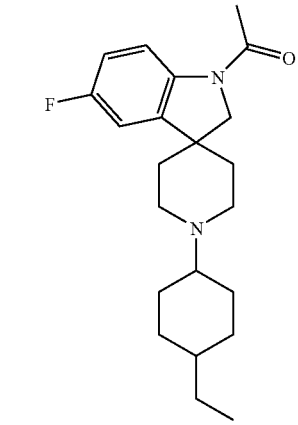 | 27 |
| 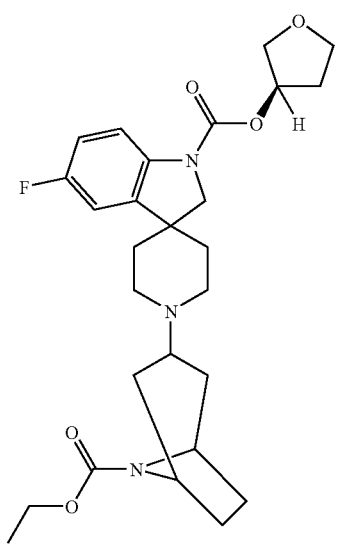 | 28 |
| 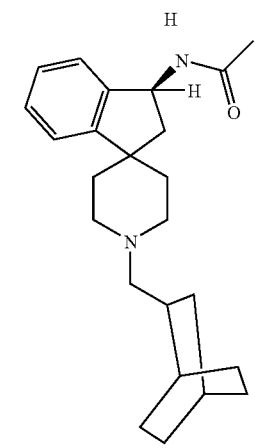 | 29 |
| 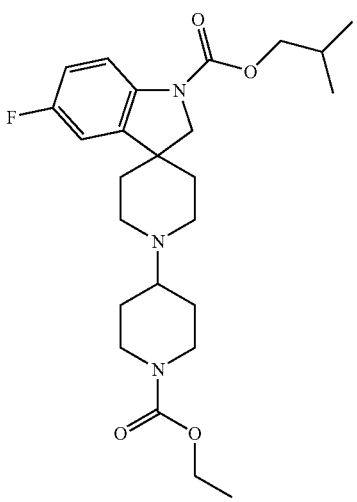 | 30 |
| 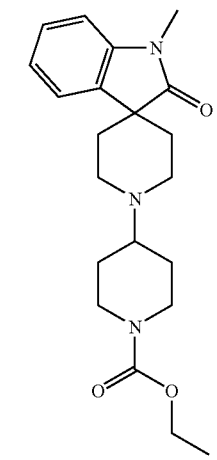 | 31 |
| 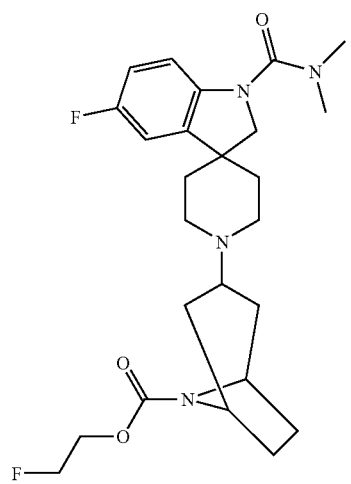 | 32 |

TABLE 1-continued
Exemplary compounds of formulae I and II.
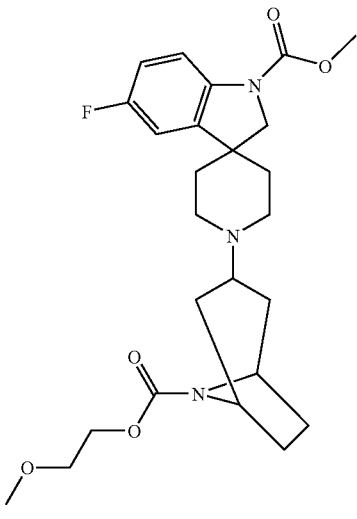 33
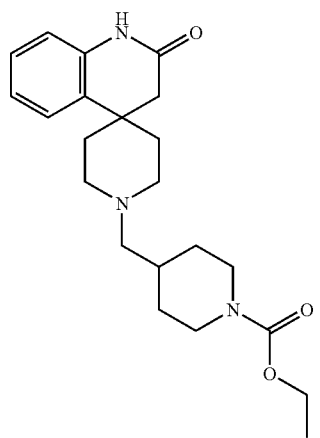 34
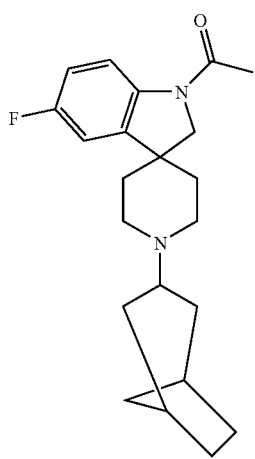 35
TABLE 1-continued
Exemplary compounds of formulae I and II.
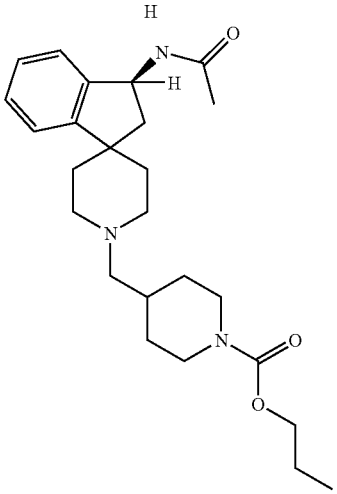 36
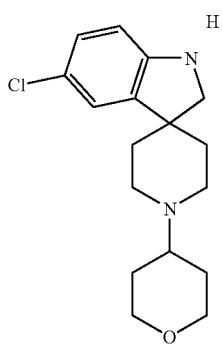 37
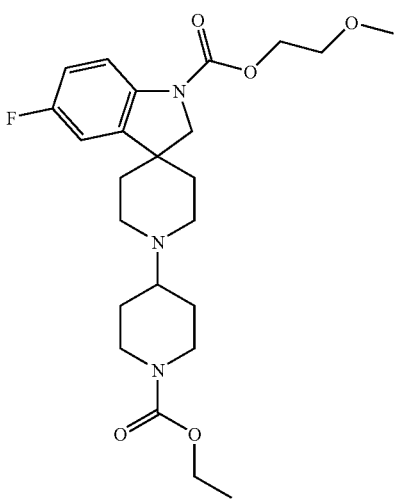 38

TABLE 1-continued
Exemplary compounds of formulae I and II.
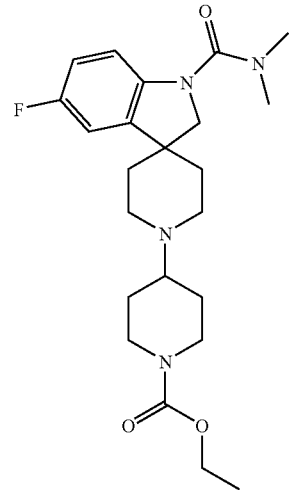
39
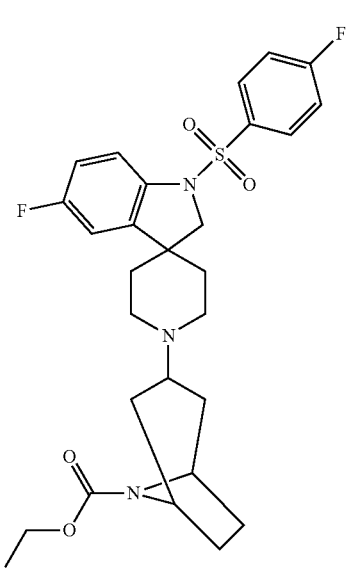
40
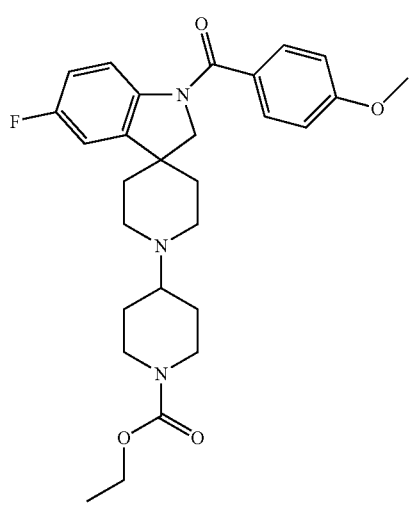
41
TABLE 1-continued
Exemplary compounds of formulae I and II.
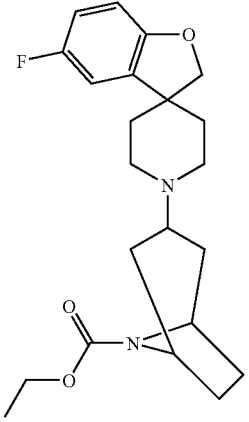
42
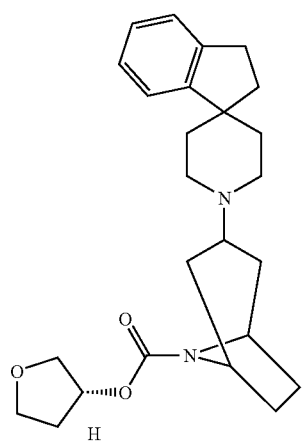
43
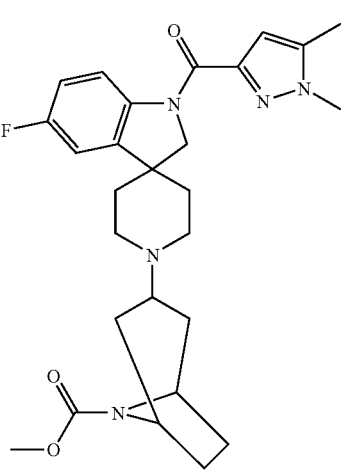
44

TABLE 1-continued
Exemplary compounds of formulae I and II.
| | |
|---|---|
| 45 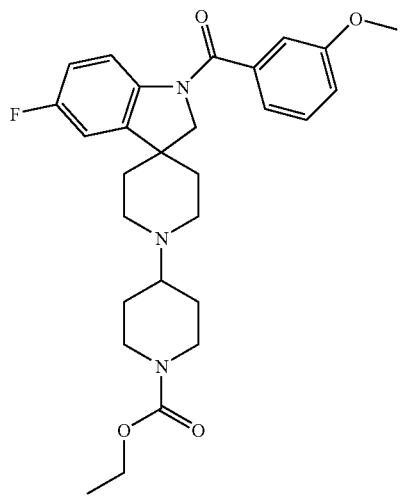 | 48 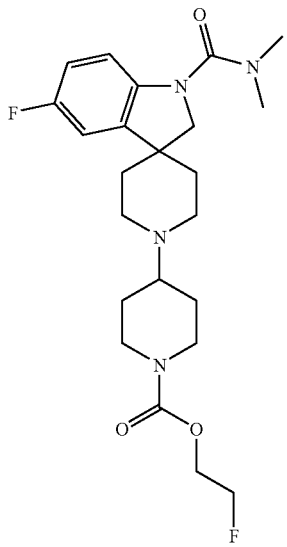 |
| 46 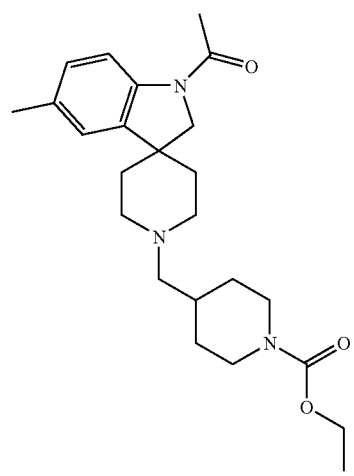 | 49 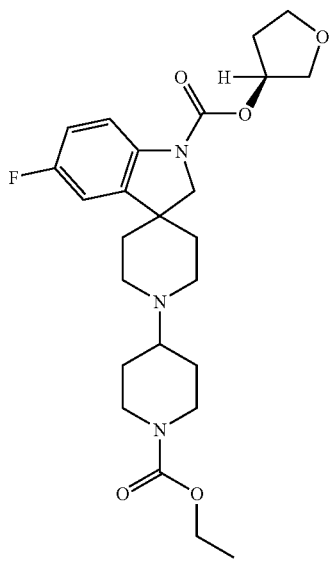 |
| 47 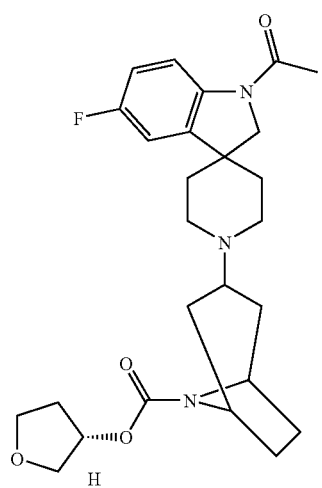 | 50 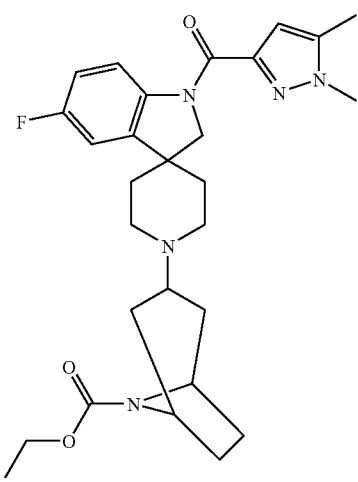 |

TABLE 1-continued
Exemplary compounds of formulae I and II.
51 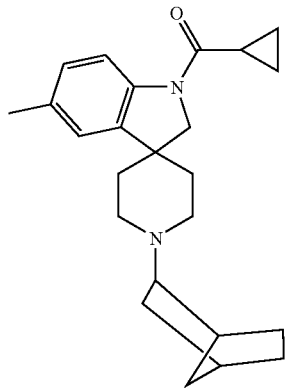
52 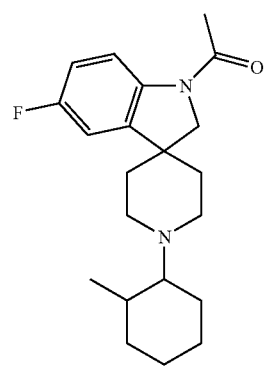
53 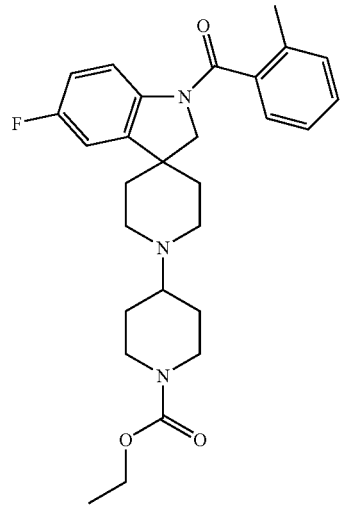
TABLE 1-continued
Exemplary compounds of formulae I and II.
54 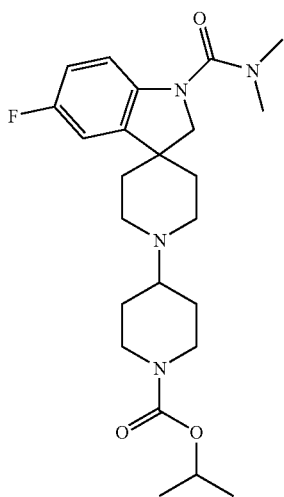
55 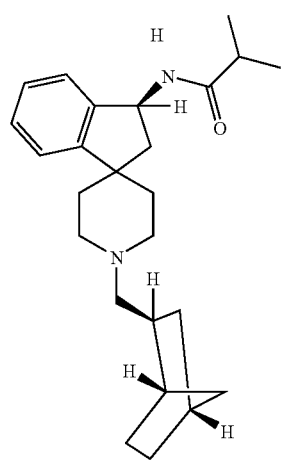
56 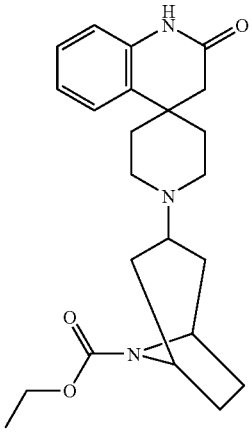

TABLE 1-continued
Exemplary compounds of formulae I and II.
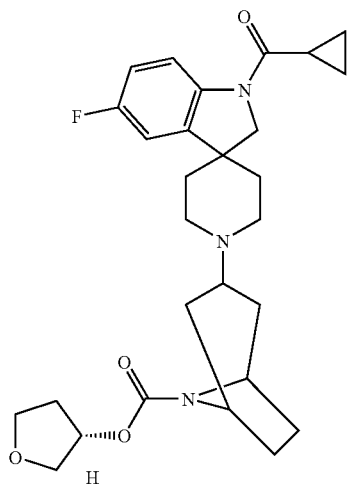
57
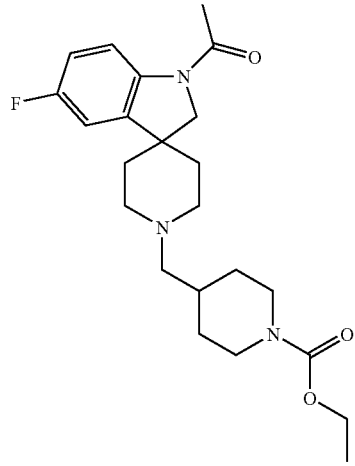
60
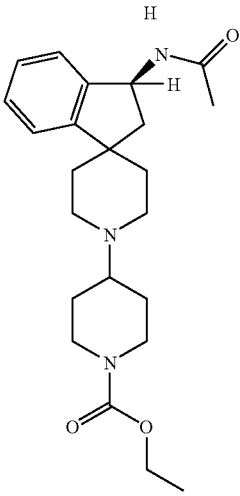
61
58
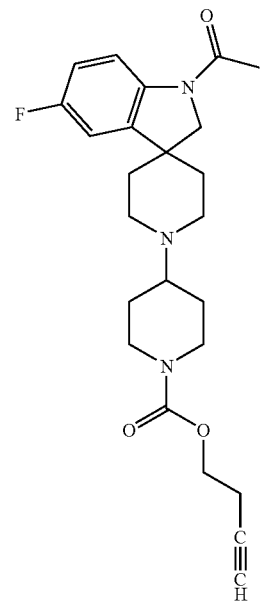
62
59

TABLE 1-continued
Exemplary compounds of formulae I and II.
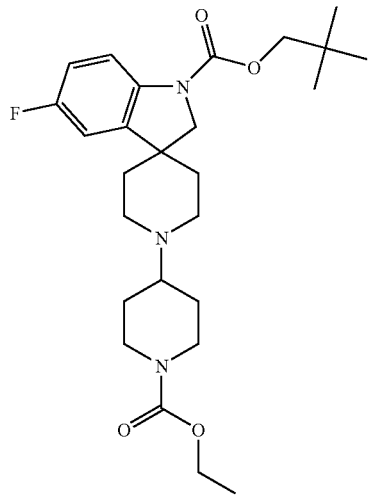
63
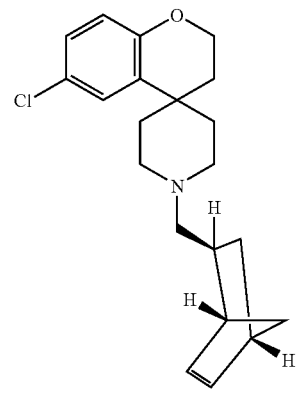
64
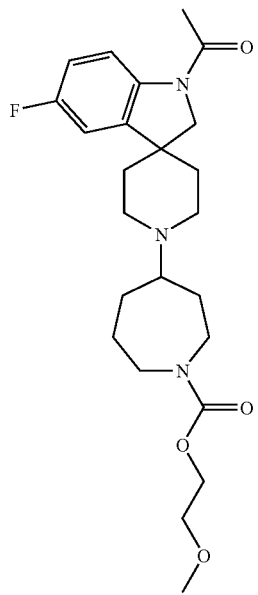
65
TABLE 1-continued
Exemplary compounds of formulae I and II.
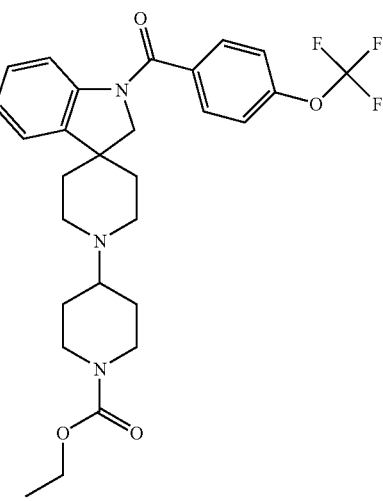
66
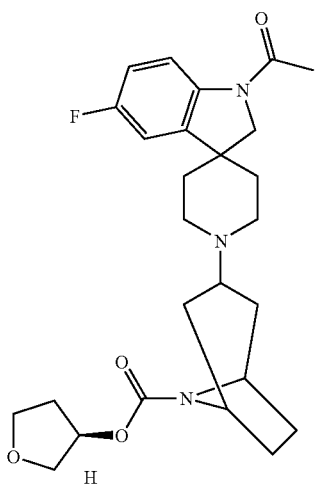
67
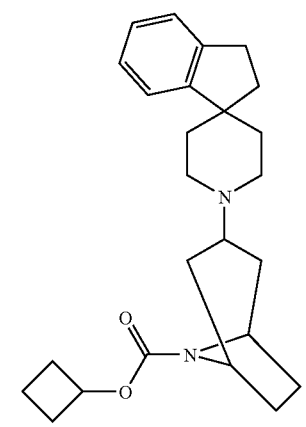
68

TABLE 1-continued
Exemplary compounds of formulae I and II.
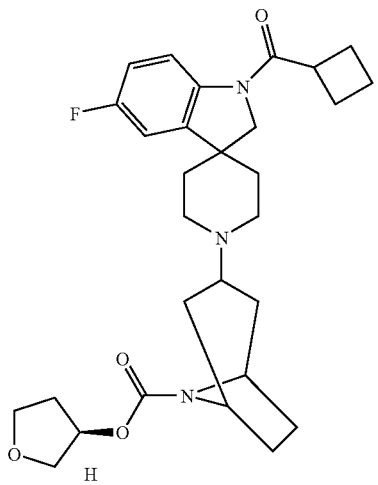
69
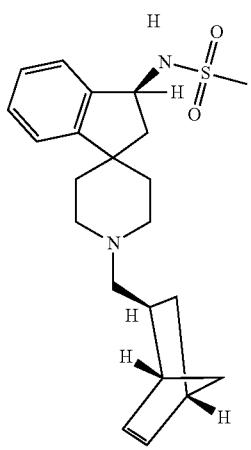
70
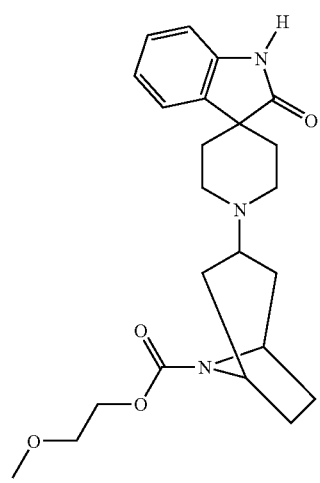
71
TABLE 1-continued
Exemplary compounds of formulae I and II.
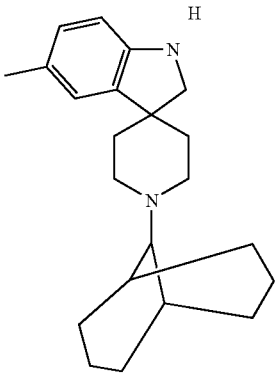
72
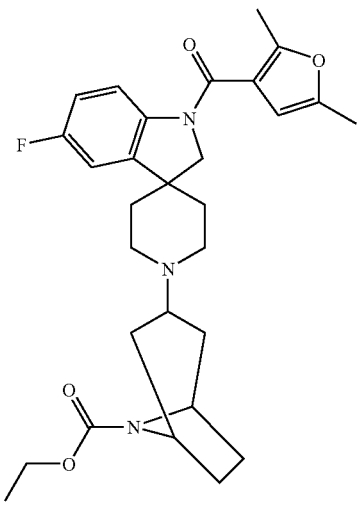
73
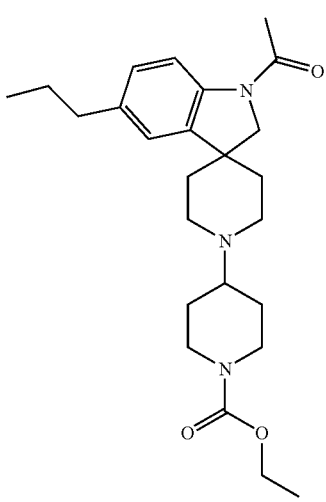
74

TABLE 1-continued
Exemplary compounds of formulae I and II.
75
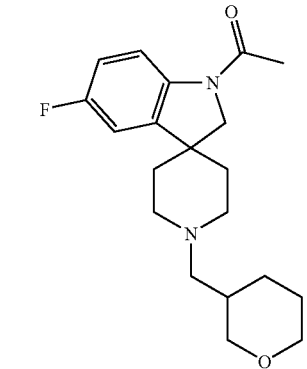
76
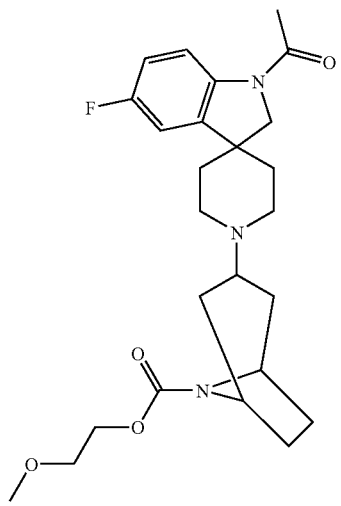
77
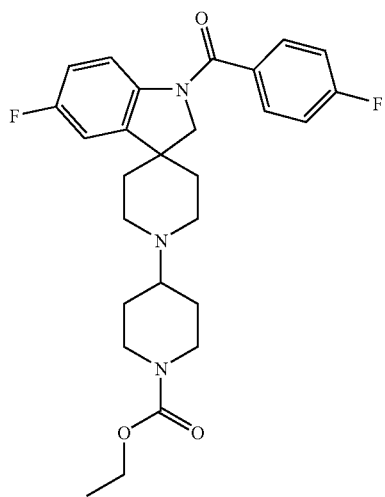
TABLE 1-continued
Exemplary compounds of formulae I and II.
78
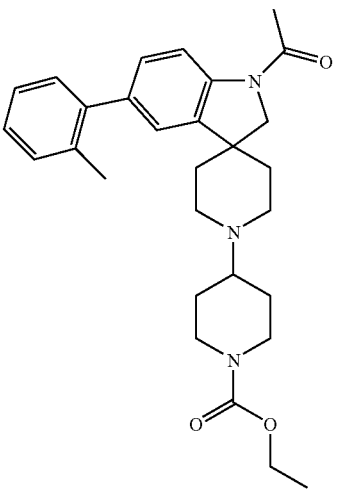
79
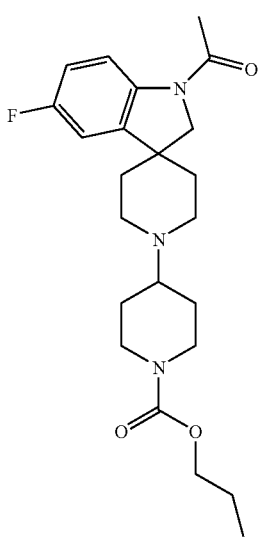
80
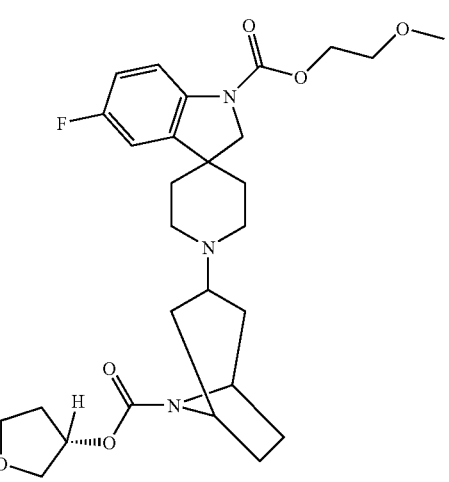

TABLE 1-continued
Exemplary compounds of formulae I and II.
| | |
|---|---|
| 81 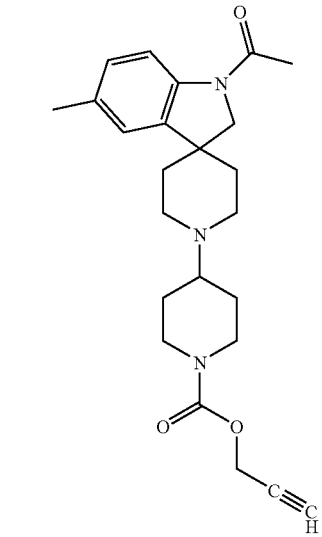 | 84 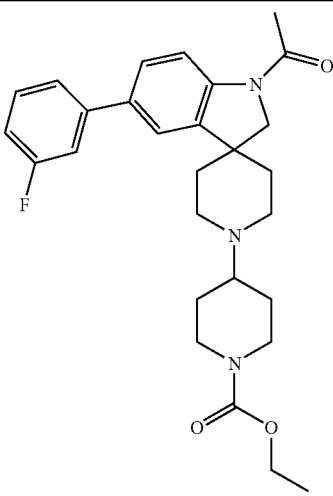 |
| 82 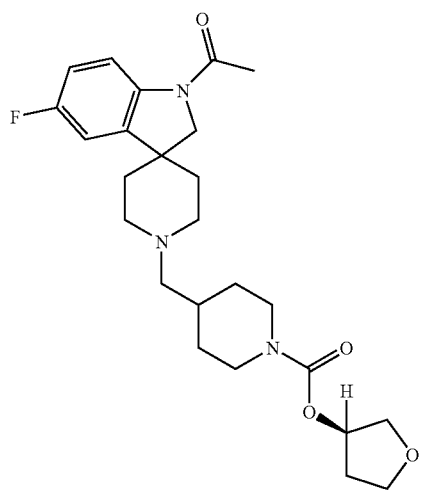 | 85 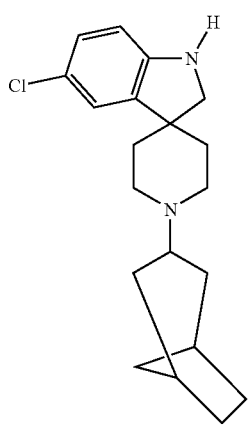 |
| 83 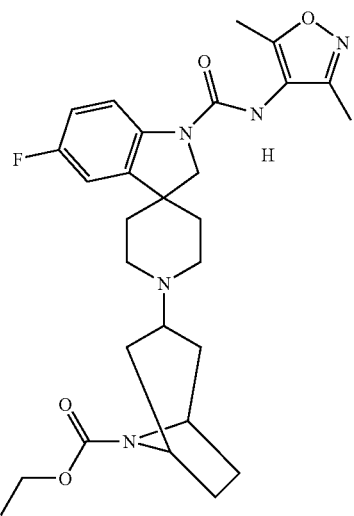 | 86 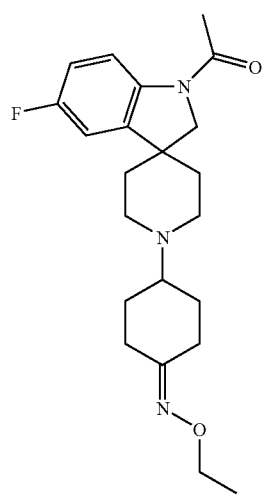 |

TABLE 1-continued
Exemplary compounds of formulae I and II.
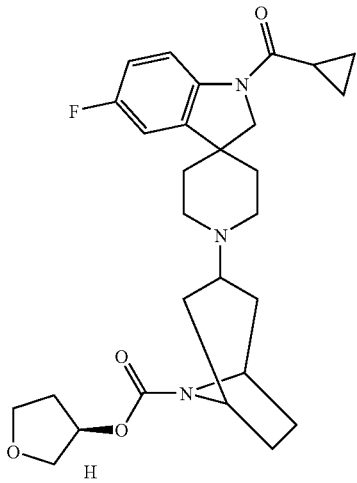 87
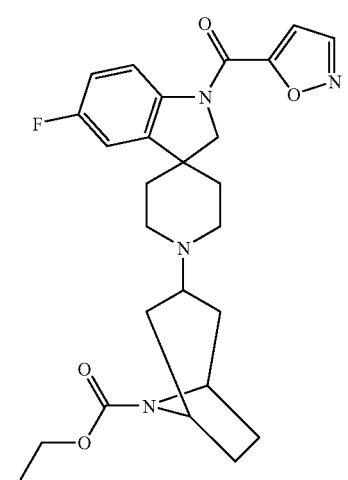 88
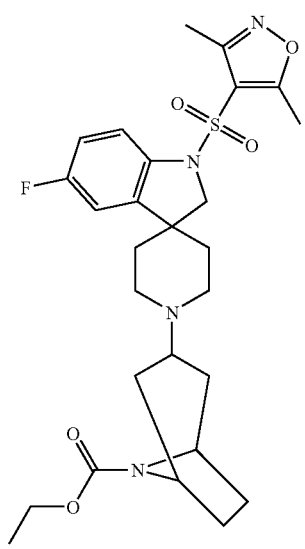 89
TABLE 1-continued
Exemplary compounds of formulae I and II.
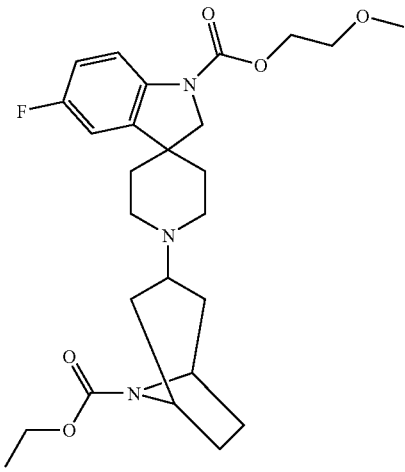 90
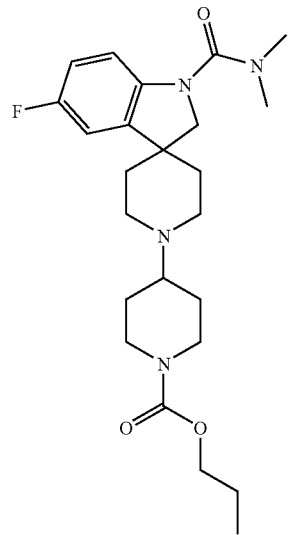 91
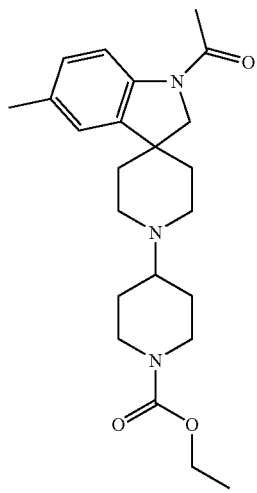 92

TABLE 1-continued
Exemplary compounds of formulae I and II.
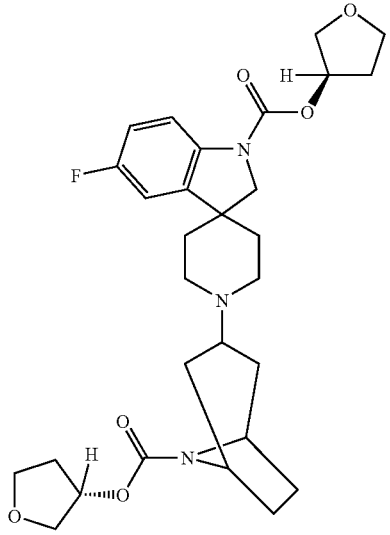 93
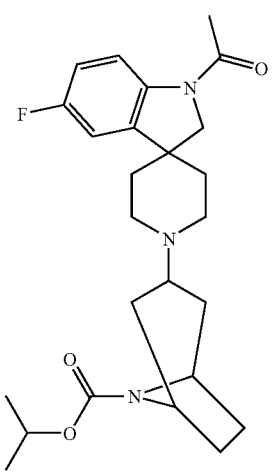 94
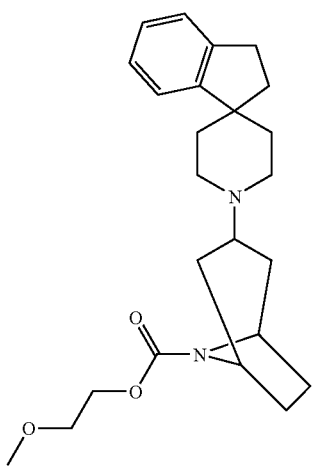 95
TABLE 1-continued
Exemplary compounds of formulae I and II.
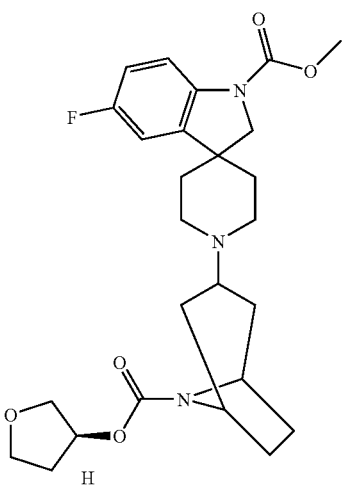 96
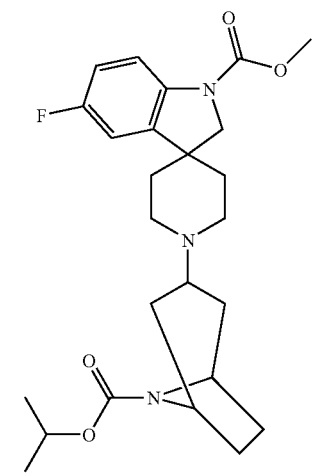 97
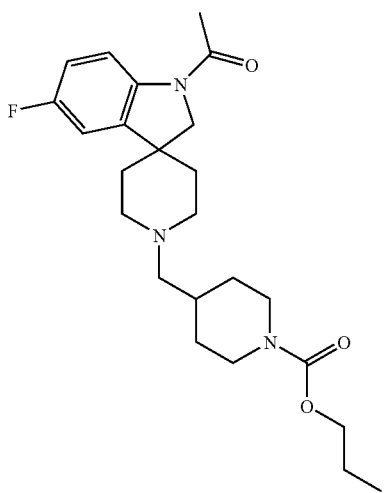 98

TABLE 1-continued
Exemplary compounds of formulae I and II.
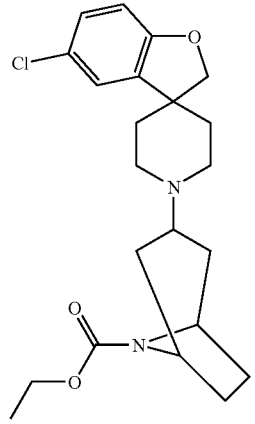
99
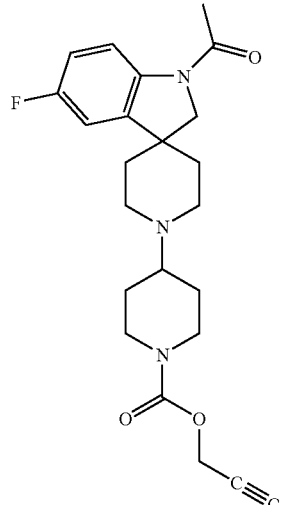
102
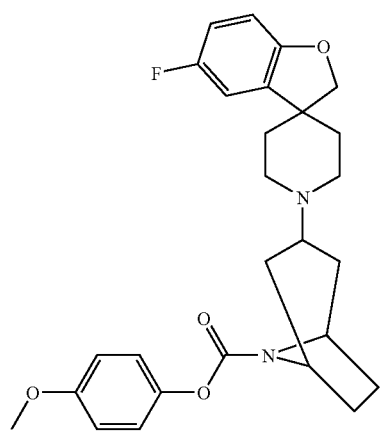
100
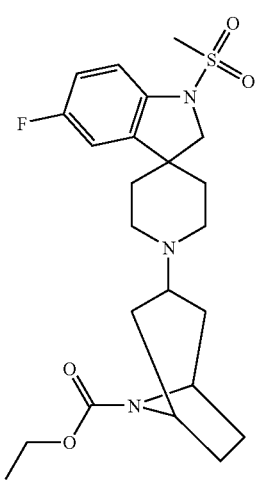
103
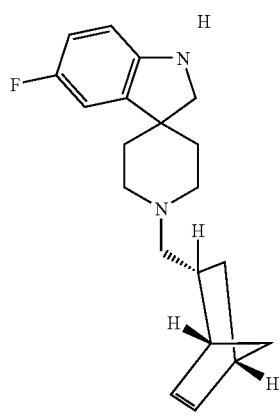
101
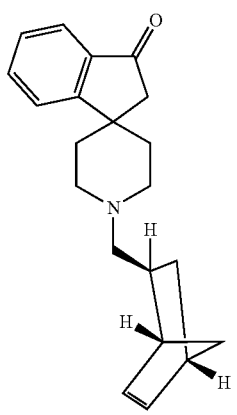
104

TABLE 1-continued
Exemplary compounds of formulae I and II.
105 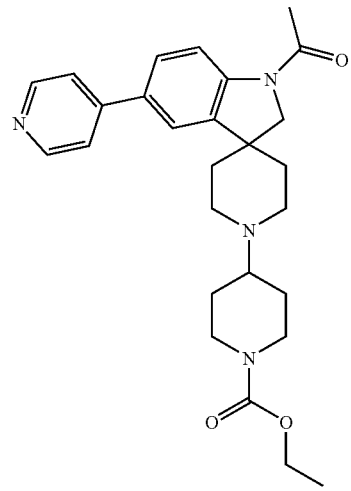
106 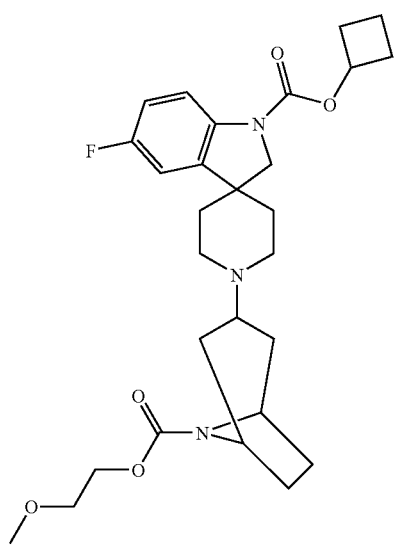
107 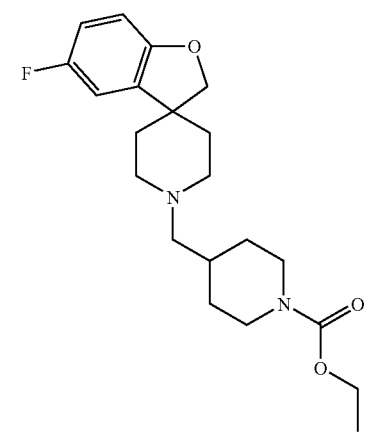
TABLE 1-continued
Exemplary compounds of formulae I and II.
108 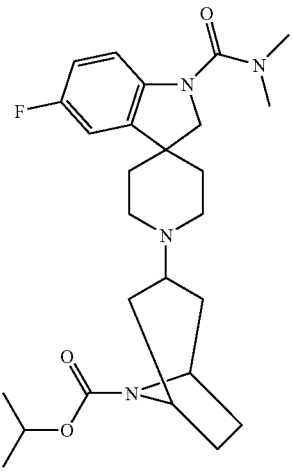
109 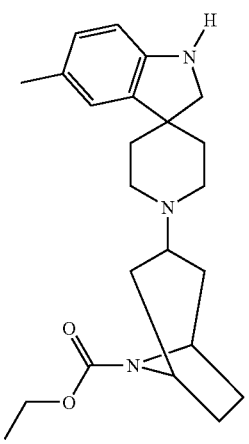
110 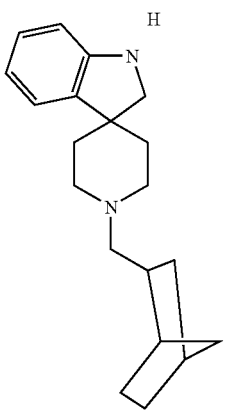

TABLE 1-continued
Exemplary compounds of formulae I and II.
111 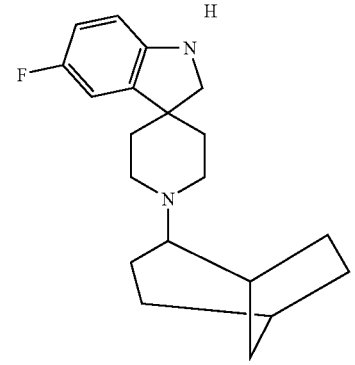
112 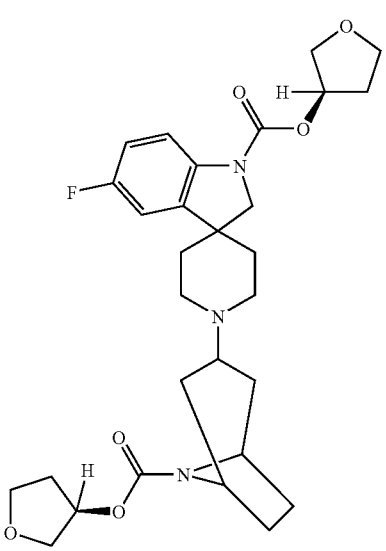
113 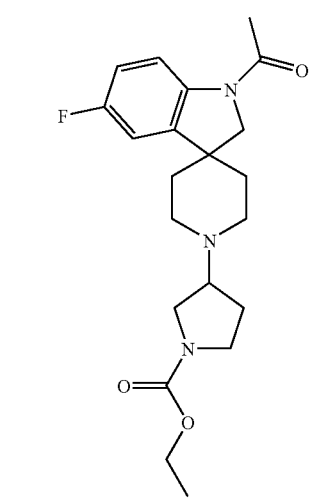
TABLE 1-continued
Exemplary compounds of formulae I and II.
114 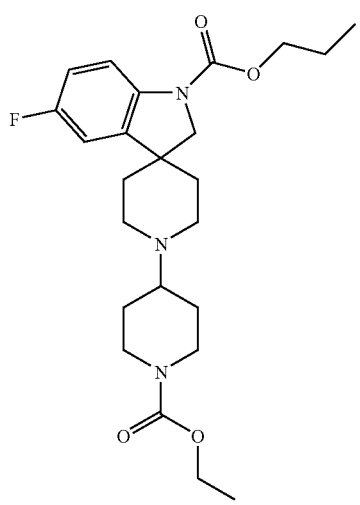
115 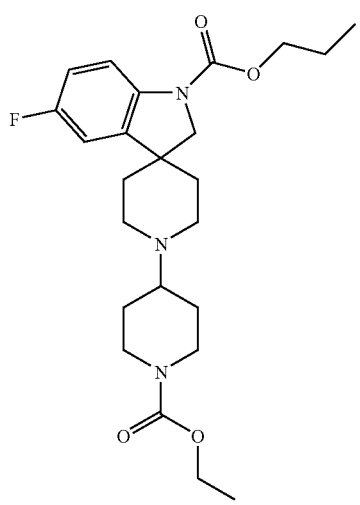
116 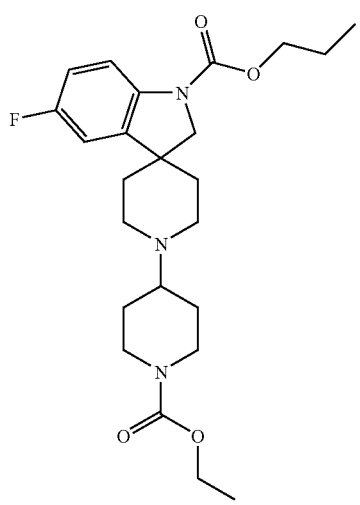

TABLE 1-continued
Exemplary compounds of formulae I and II.
117
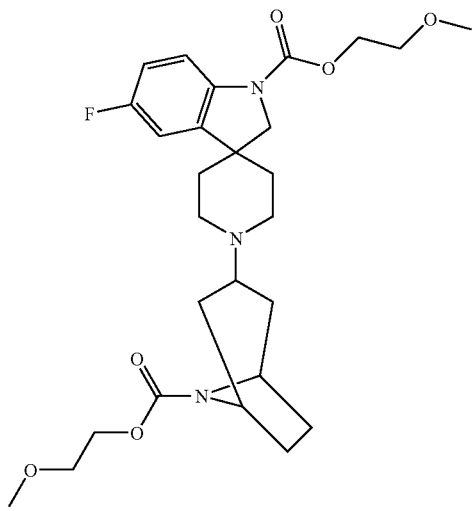
118
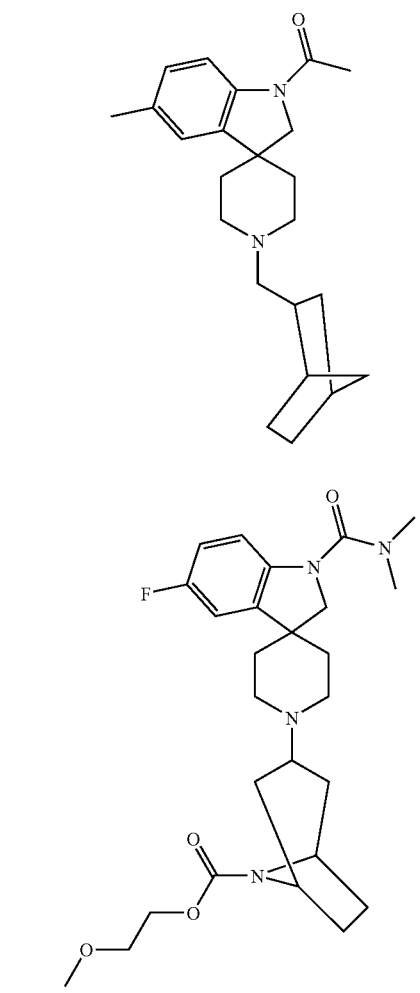
119
TABLE 1-continued
Exemplary compounds of formulae I and II.
120
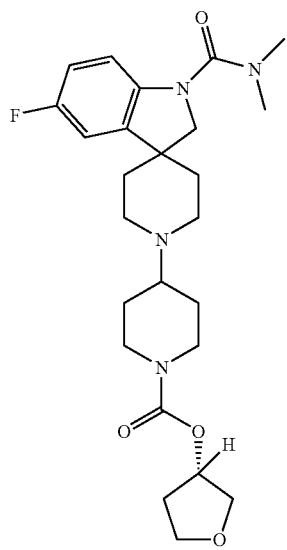
122
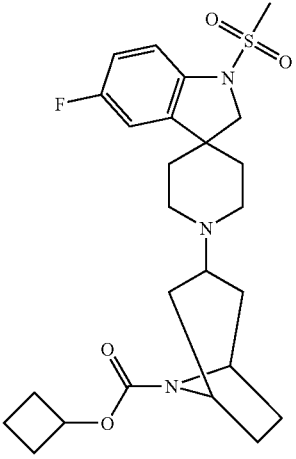
123
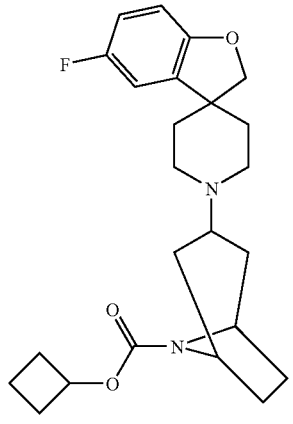

TABLE 1-continued
Exemplary compounds of formulae I and II.
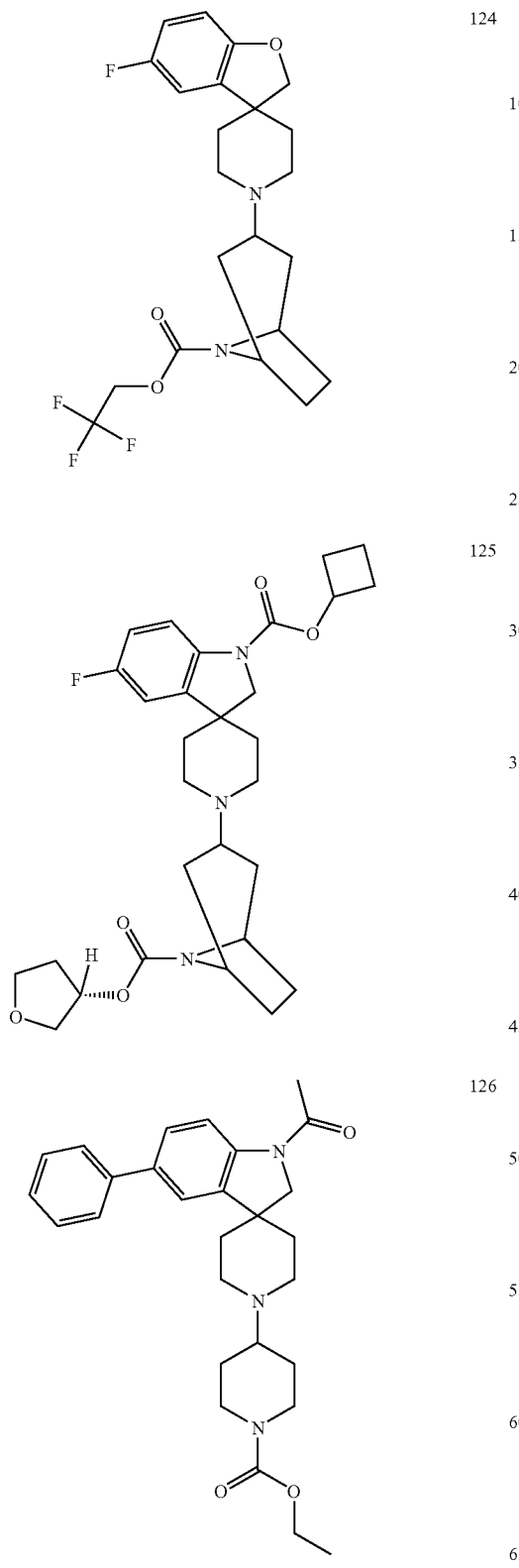
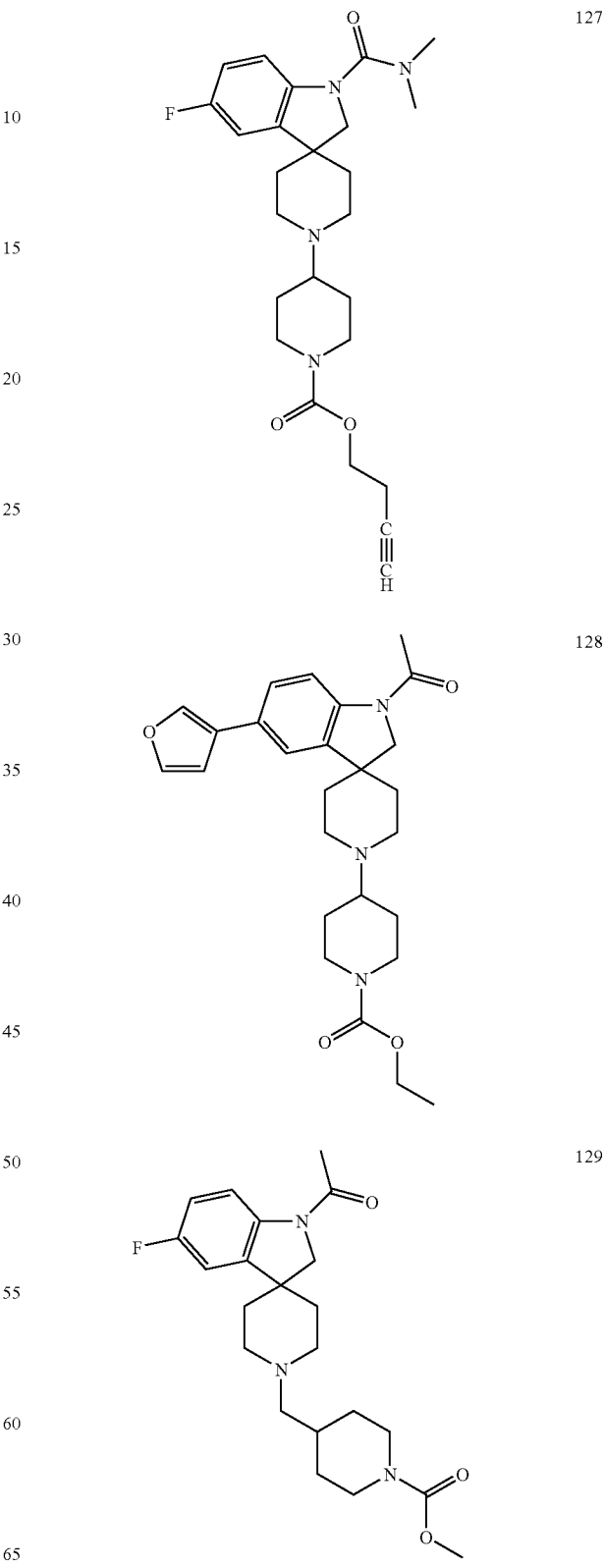

TABLE 1-continued
Exemplary compounds of formulae I and II.
130 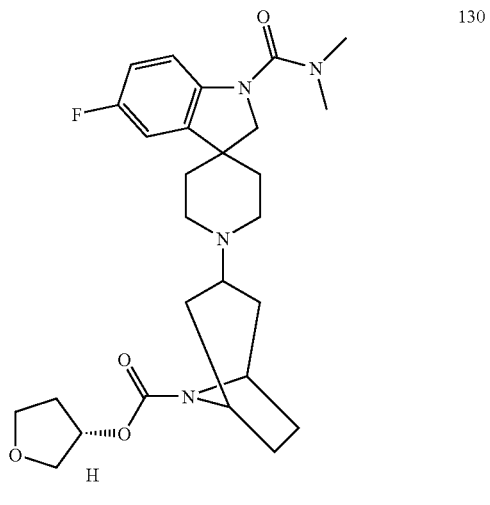
131 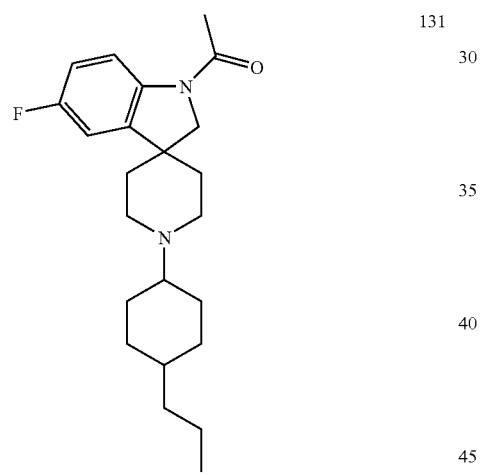
132 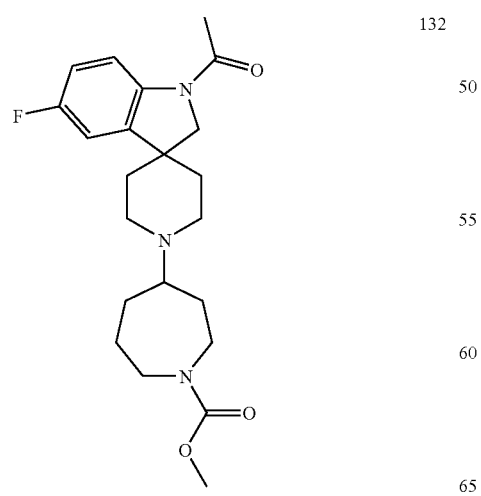
TABLE 1-continued
Exemplary compounds of formulae I and II.
133 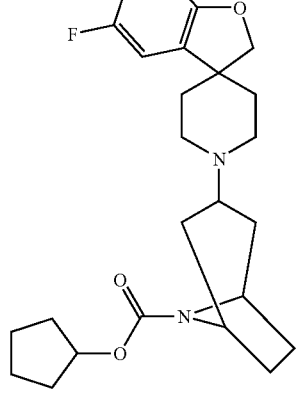
134 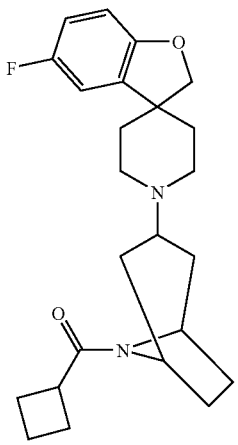
135 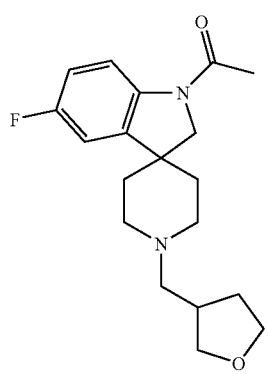

TABLE 1-continued
Exemplary compounds of formulae I and II.
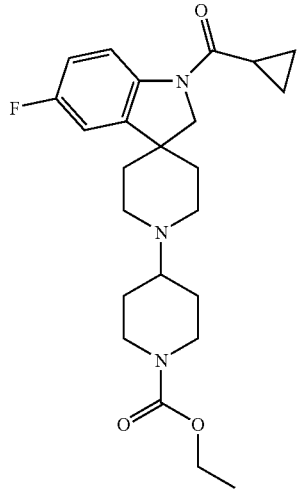 136
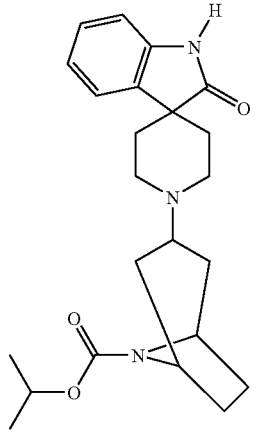 139
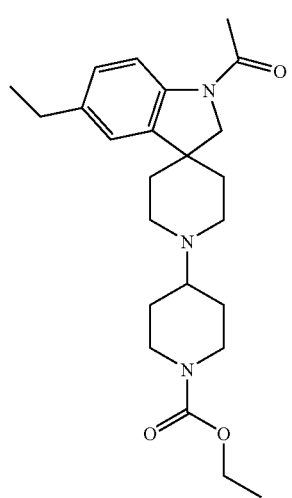 137
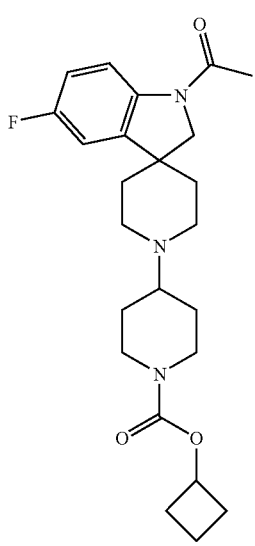 140
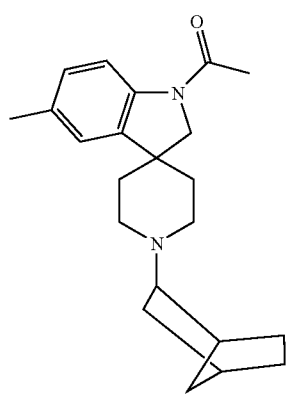 138
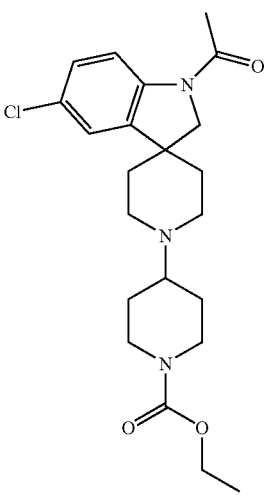 141

TABLE 1-continued
Exemplary compounds of formulae I and II.
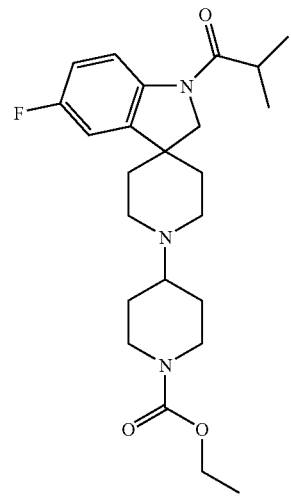
142
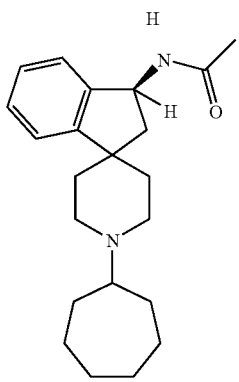
143
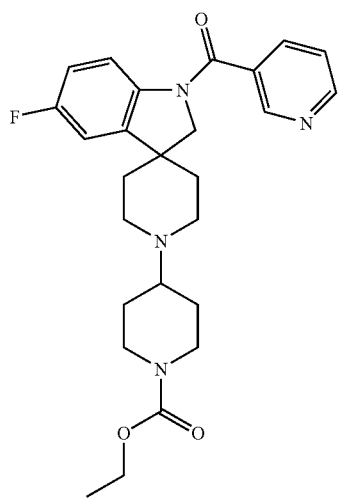
144
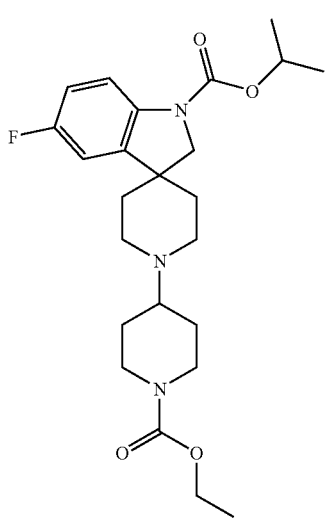
145
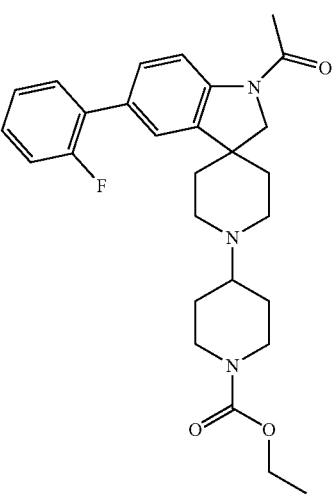
146
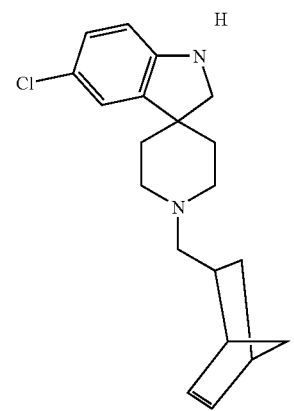
147

TABLE 1-continued
Exemplary compounds of formulae I and II.
148 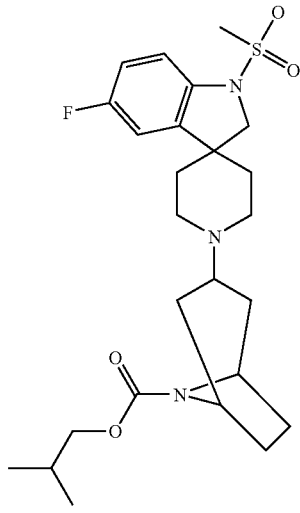
149 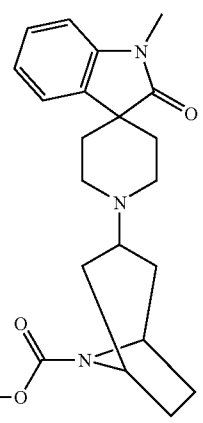
150 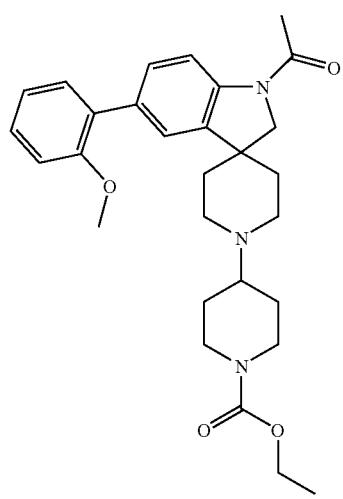
TABLE 1-continued
Exemplary compounds of formulae I and II.
151 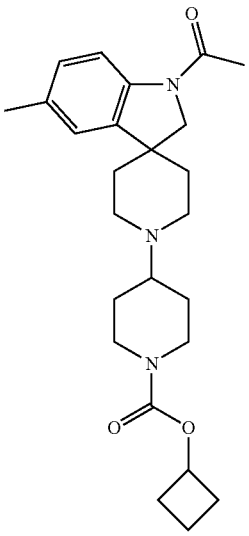
152 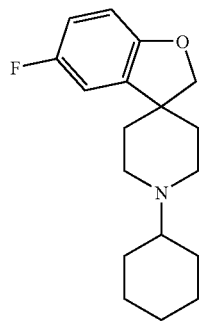
153 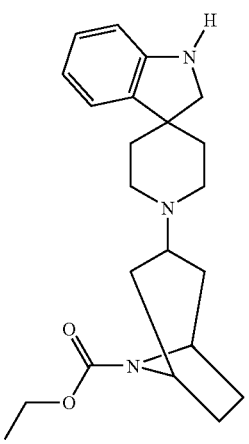

TABLE 1-continued
Exemplary compounds of formulae I and II.
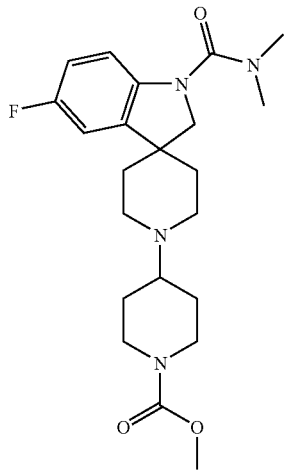
154
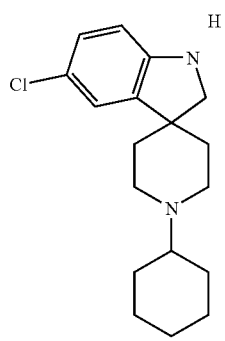
155
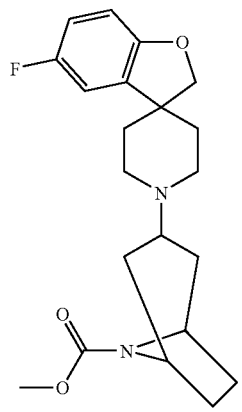
156
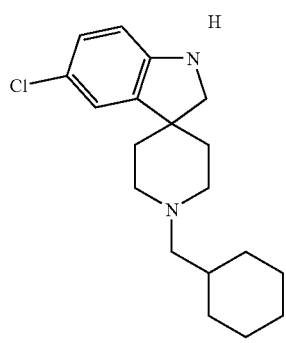
157
TABLE 1-continued
Exemplary compounds of formulae I and II.
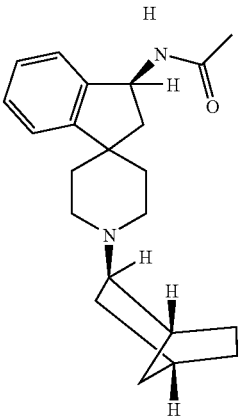
158
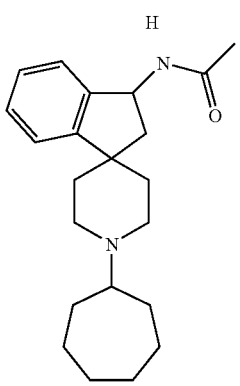
159
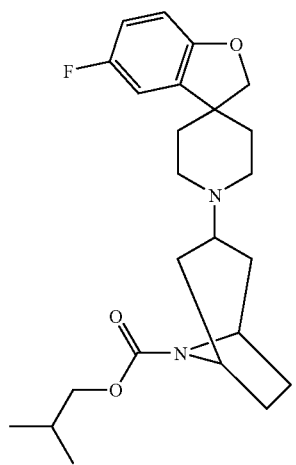
160

TABLE 1-continued
Exemplary compounds of formulae I and II.
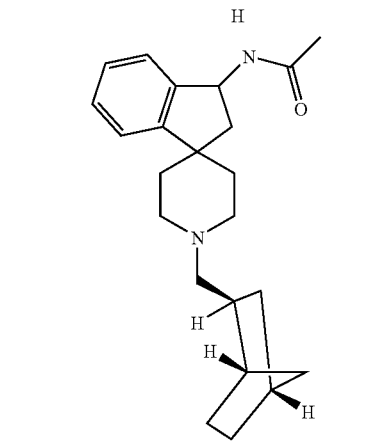
161
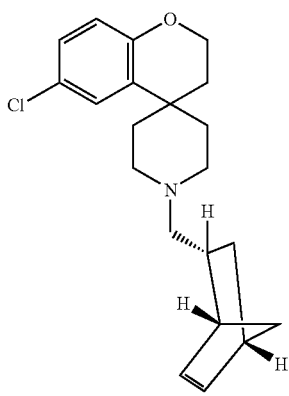
164
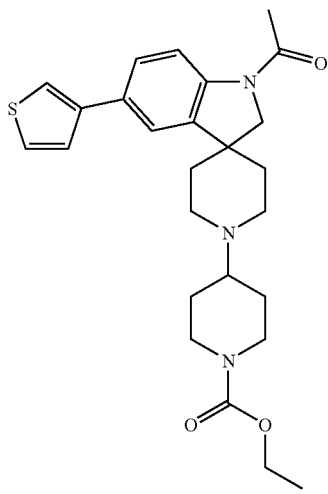
162
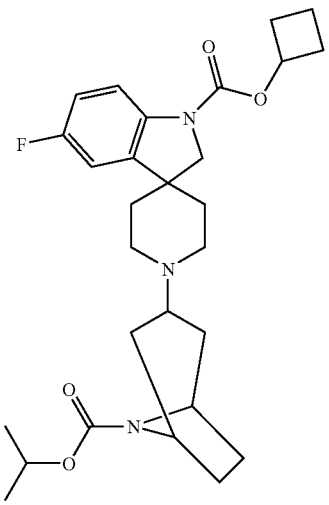
163
TABLE 1-continued
Exemplary compounds of formulae I and II.
165
166

TABLE 1-continued
Exemplary compounds of formulae I and II.
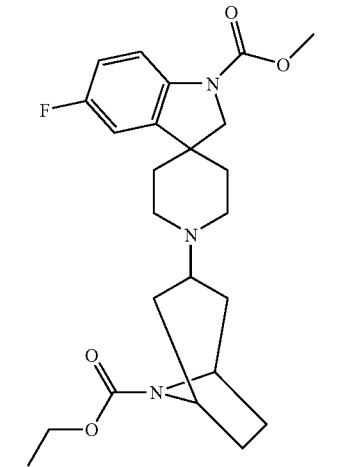
167
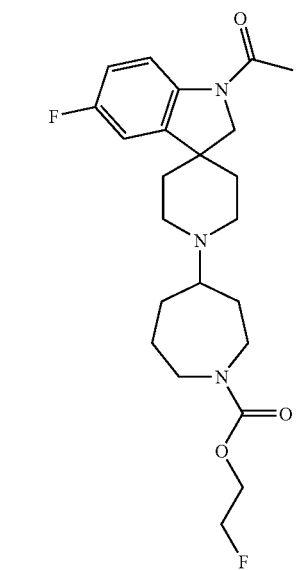
168
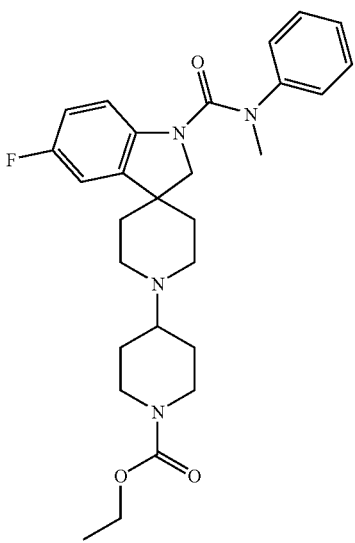
169
TABLE 1-continued
Exemplary compounds of formulae I and II.
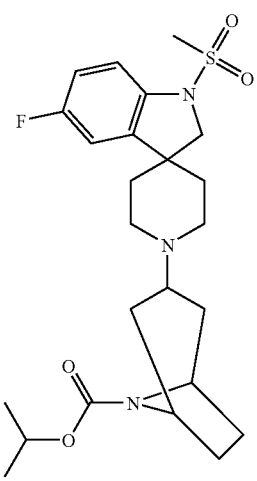
170
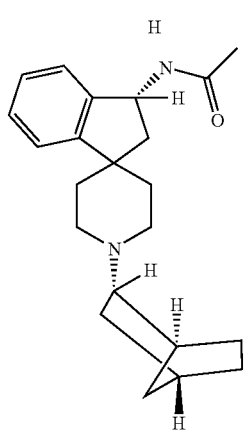
171
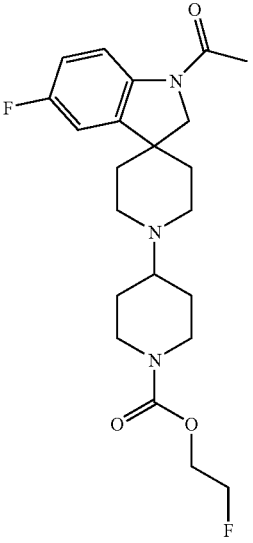
172

TABLE 1-continued
Exemplary compounds of formulae I and II.
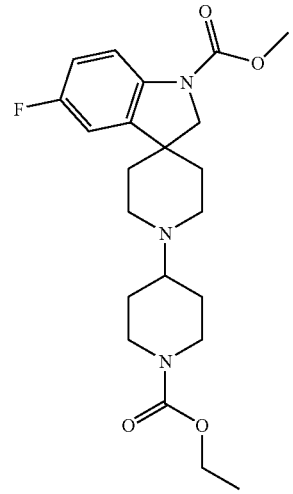
173
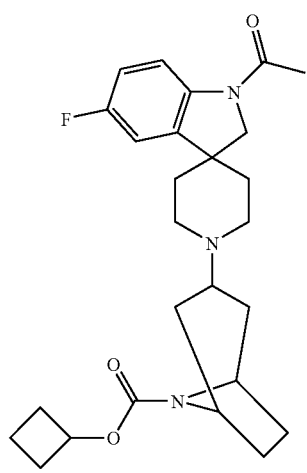
174
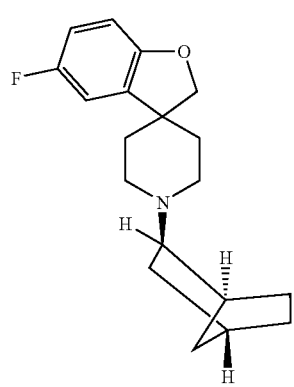
175
TABLE 1-continued
Exemplary compounds of formulae I and II.
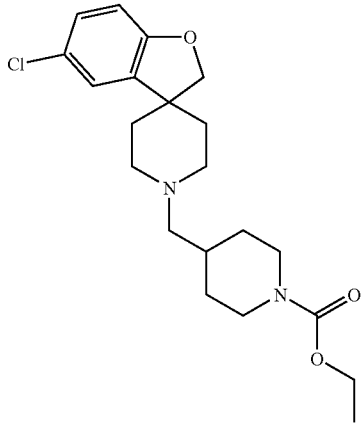
176
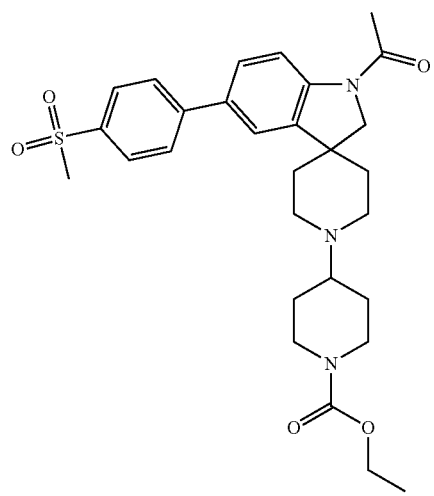
177
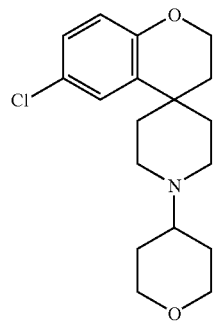
178

TABLE 1-continued
Exemplary compounds of formulae I and II.
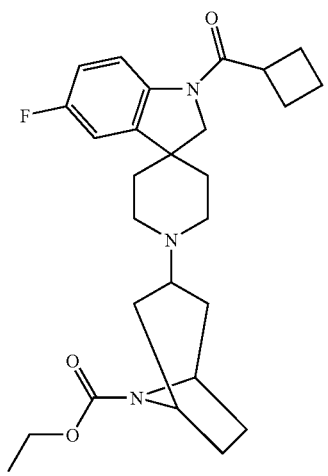
179
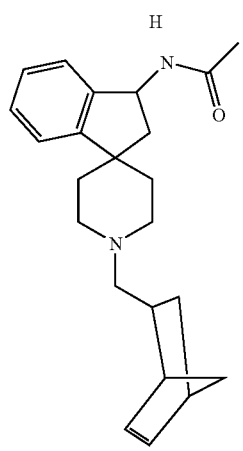
180
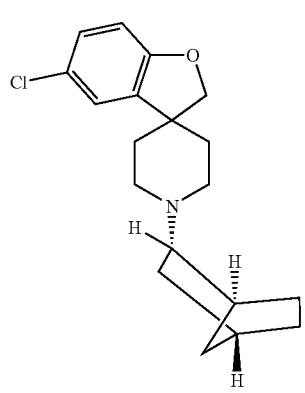
181
TABLE 1-continued
Exemplary compounds of formulae I and II.
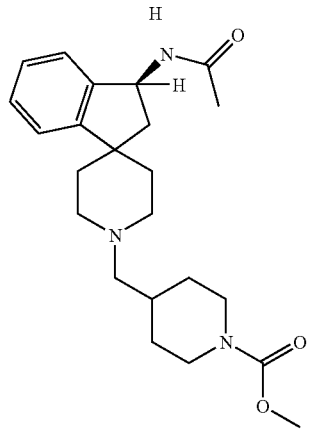
182
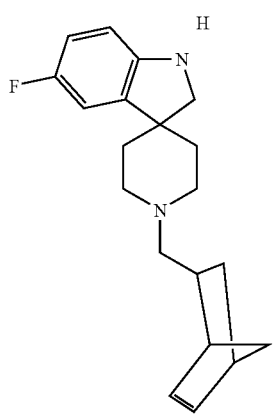
183
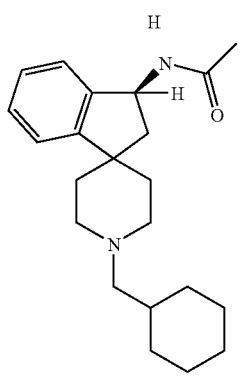
184

TABLE 1-continued
Exemplary compounds of formulae I and II.
185 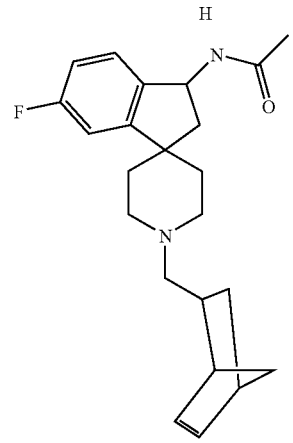
186 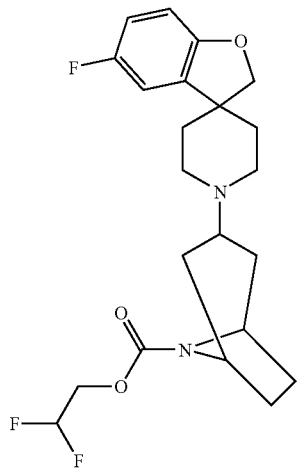
187 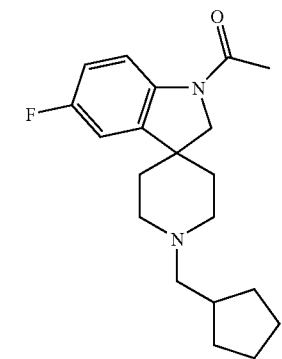
TABLE 1-continued
Exemplary compounds of formulae I and II.
188 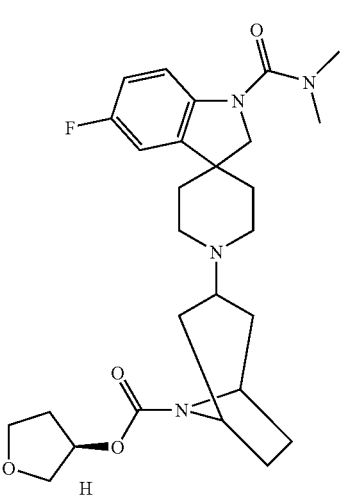
189 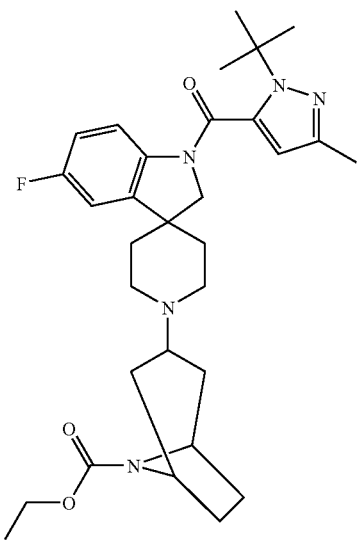
190 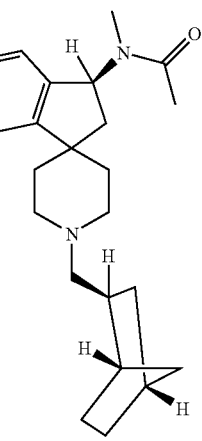

TABLE 1-continued
Exemplary compounds of formulae I and II.
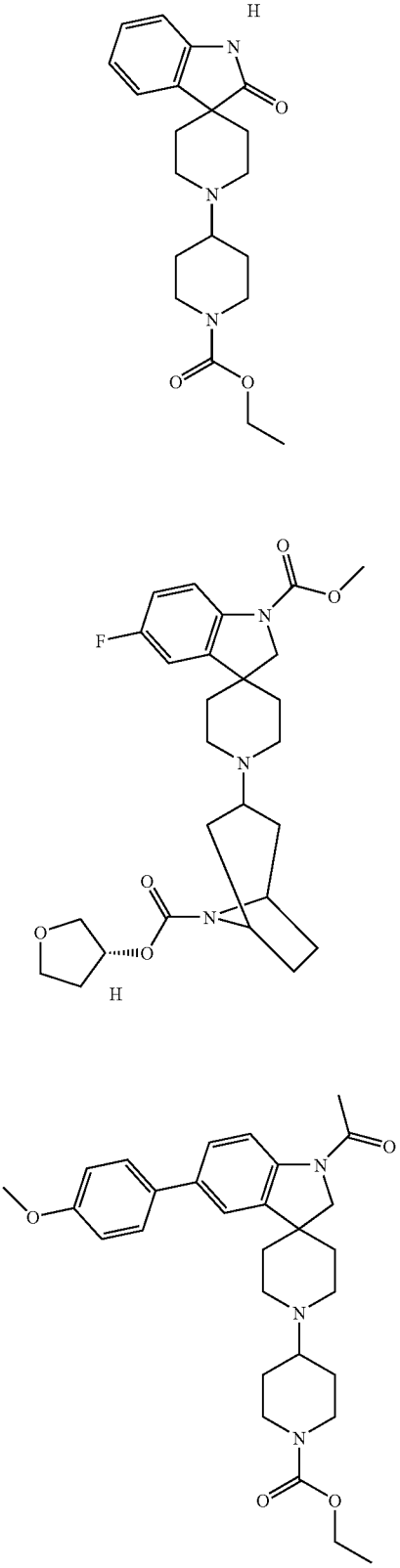
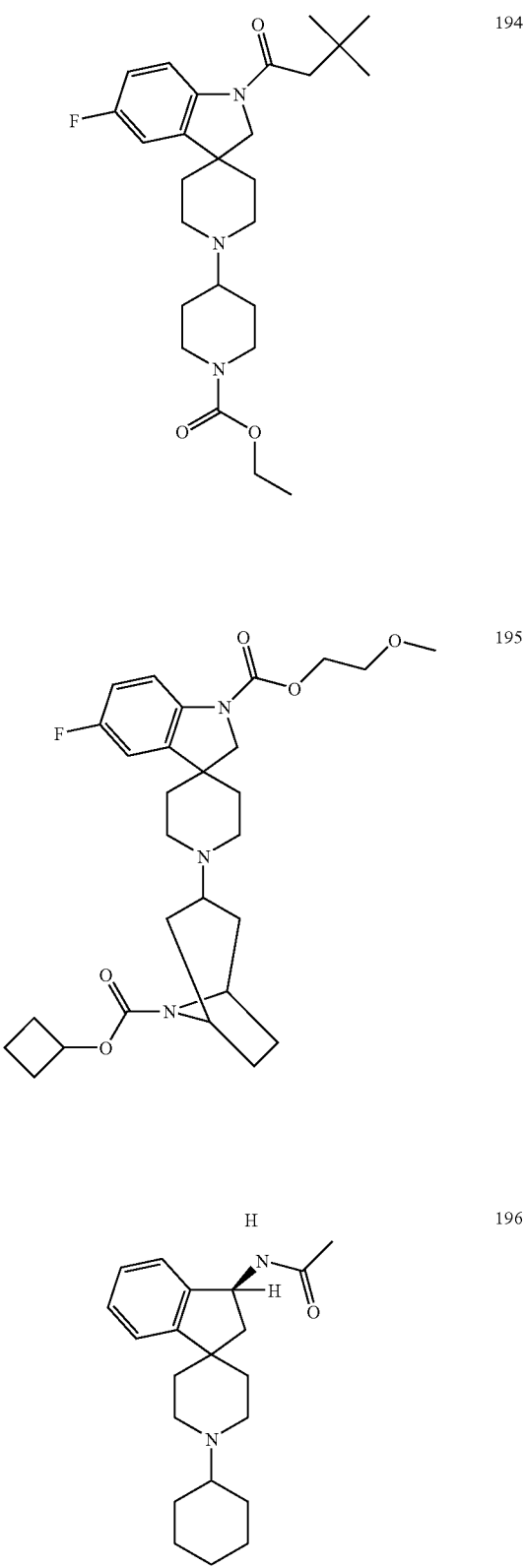

TABLE 1-continued
Exemplary compounds of formulae I and II.
197
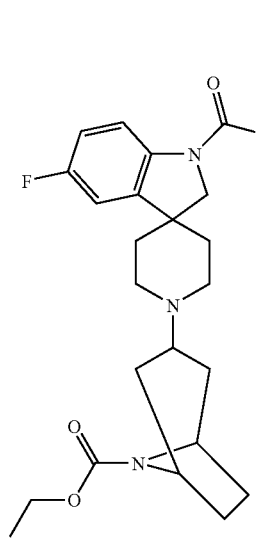
198
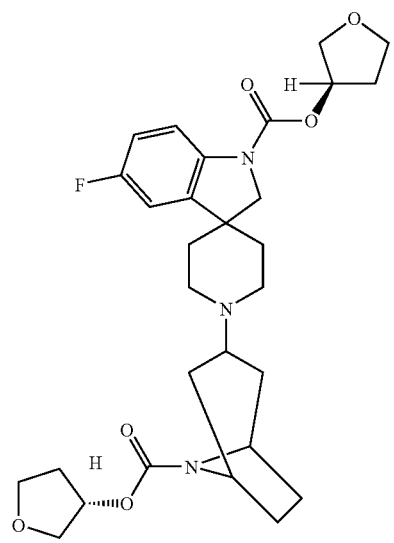
199
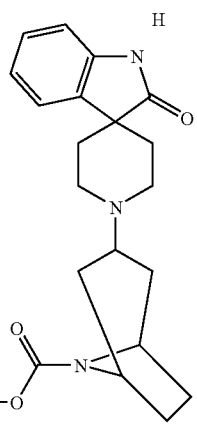
TABLE 1-continued
Exemplary compounds of formulae I and II.
200
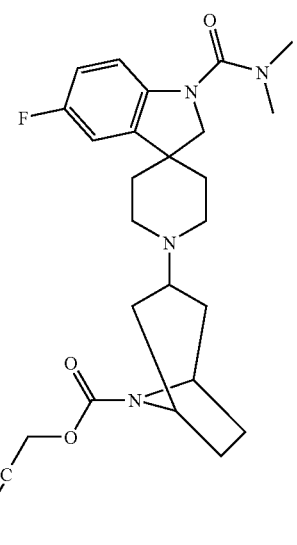
202
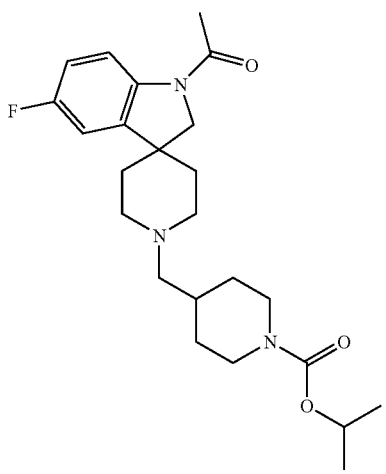
203
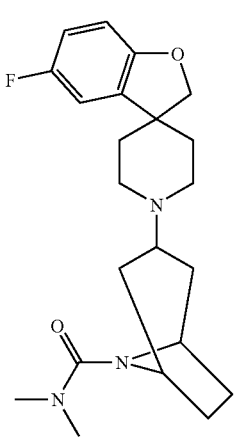

TABLE 1-continued
Exemplary compounds of formulae I and II.
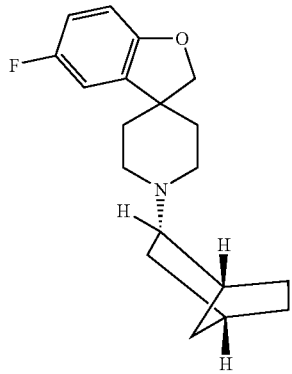
204
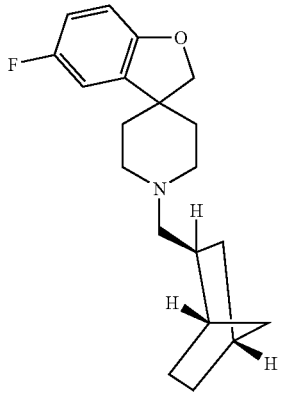
207
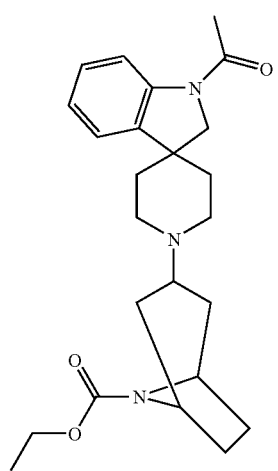
205
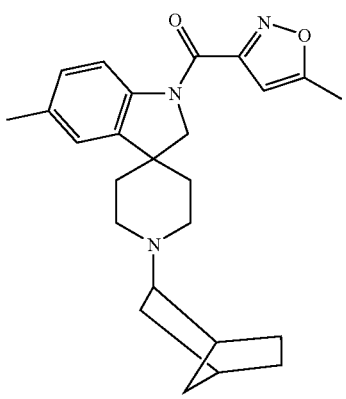
208
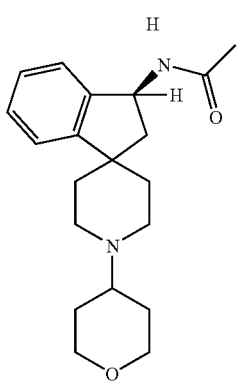
206
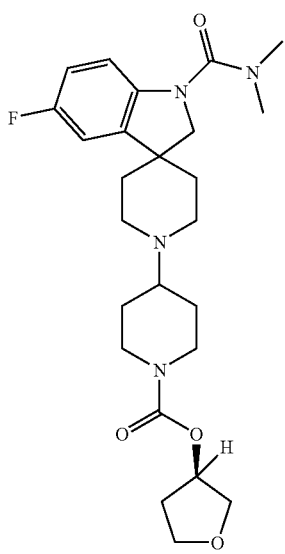
209

TABLE 1-continued
Exemplary compounds of formulae I and II.
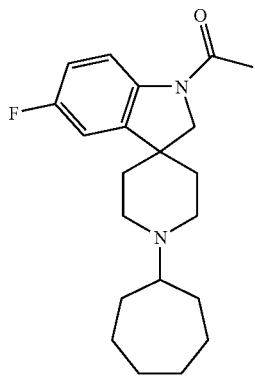 210
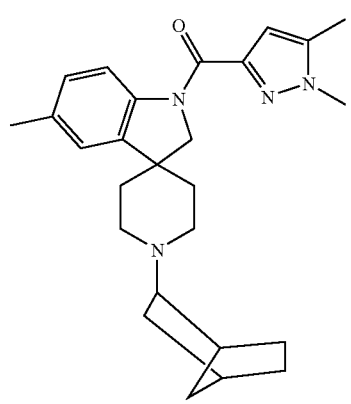 211
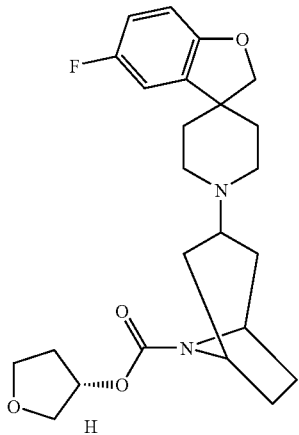 212
TABLE 1-continued
Exemplary compounds of formulae I and II.
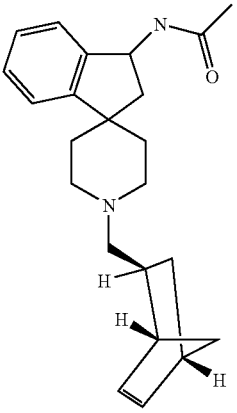 213
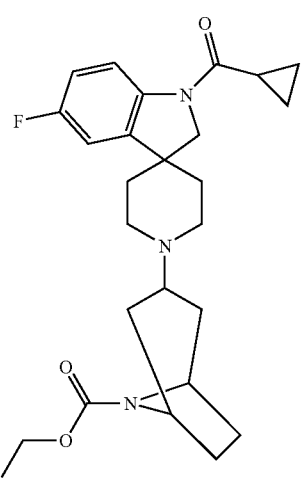 214
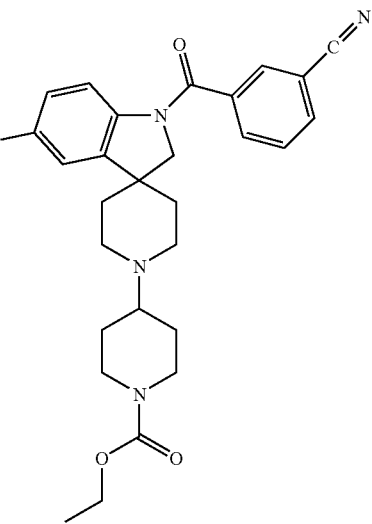 215

TABLE 1-continued
Exemplary compounds of formulae I and II.
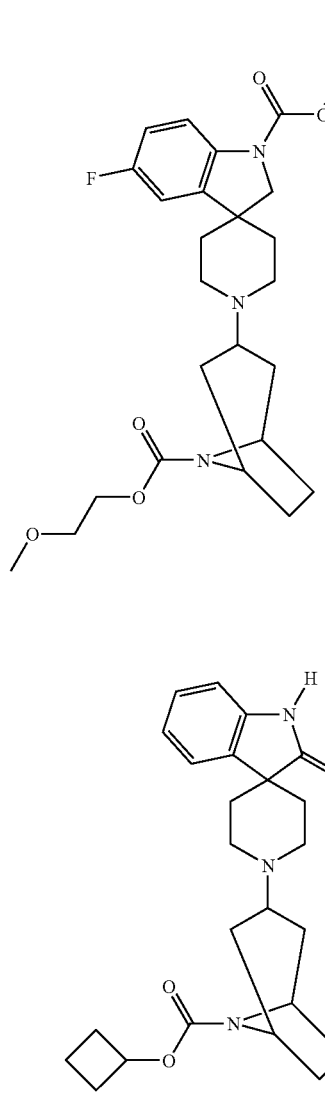
216
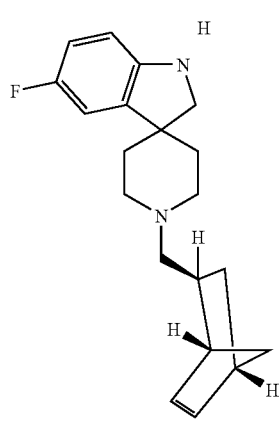
217
218
TABLE 1-continued
Exemplary compounds of formulae I and II.
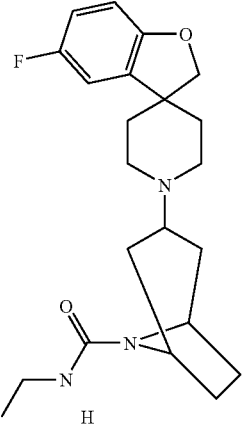
219
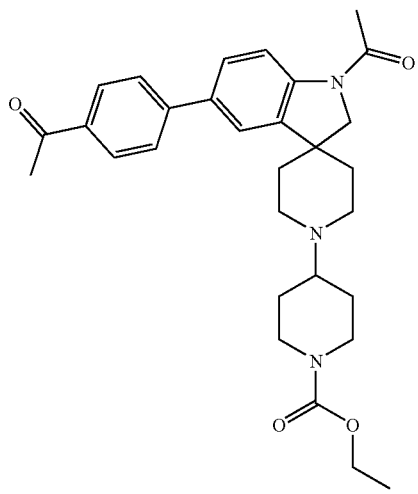
220
221

TABLE 1-continued
Exemplary compounds of formulae I and II.
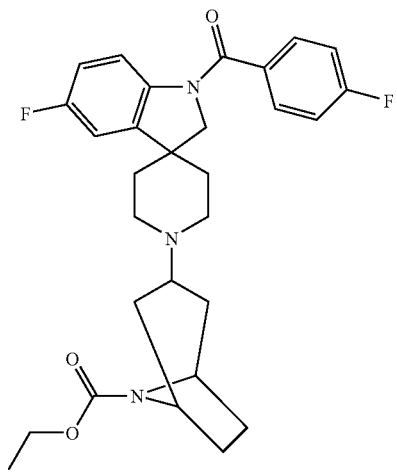
222
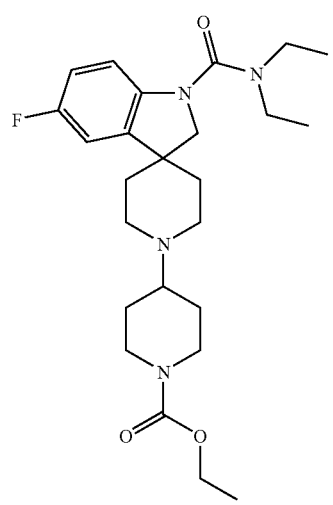
223
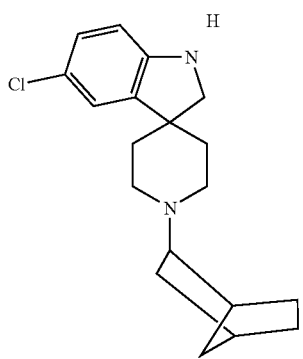
224
TABLE 1-continued
Exemplary compounds of formulae I and II.
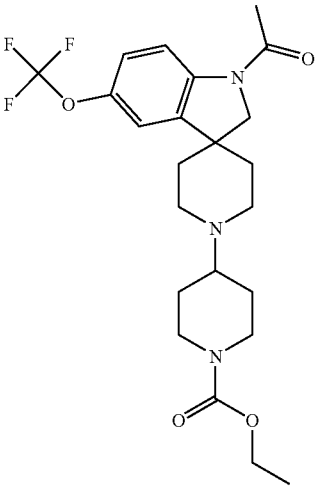
225
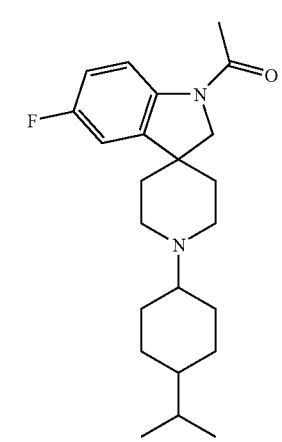
226
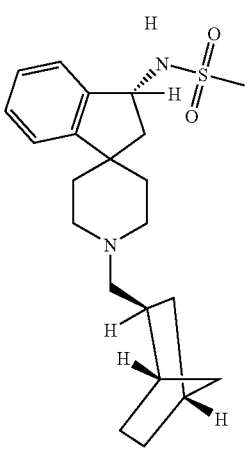
227

TABLE 1-continued
Exemplary compounds of formulae I and II.
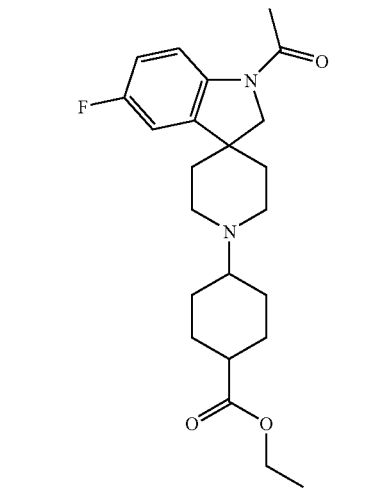
228
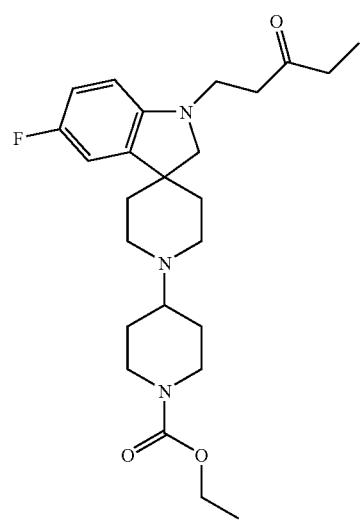
229
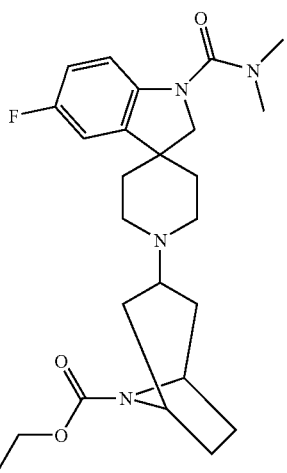
230
TABLE 1-continued
Exemplary compounds of formulae I and II.
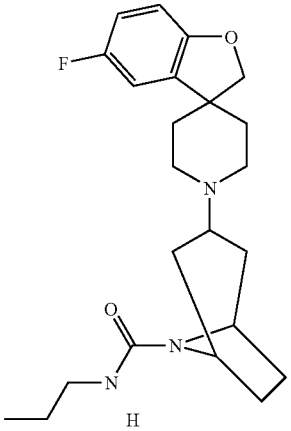
231
232
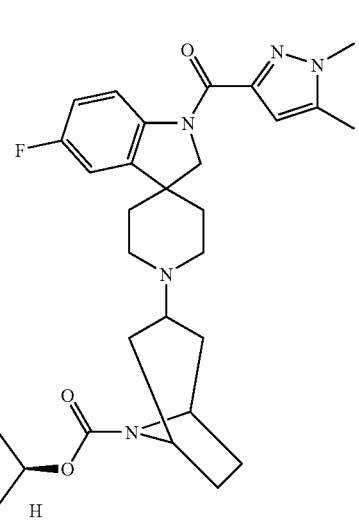
233

TABLE 1-continued
Exemplary compounds of formulae I and II.
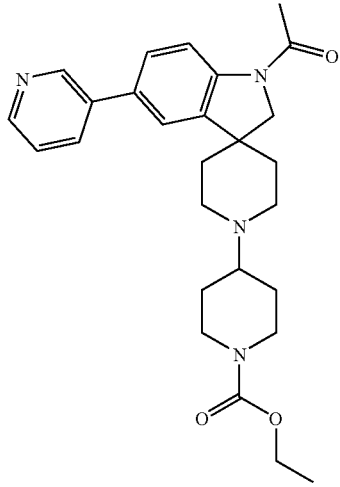
234
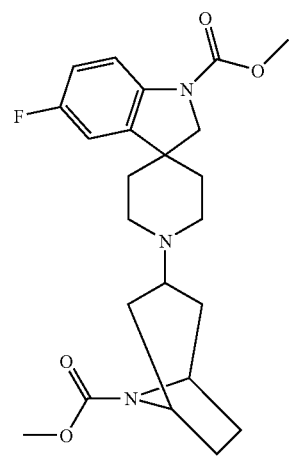
235
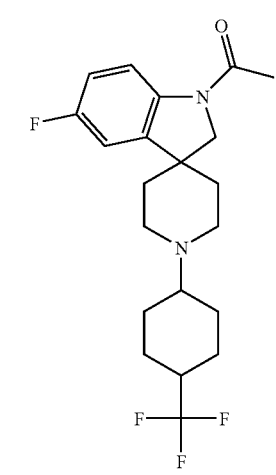
236
TABLE 1-continued
Exemplary compounds of formulae I and II.
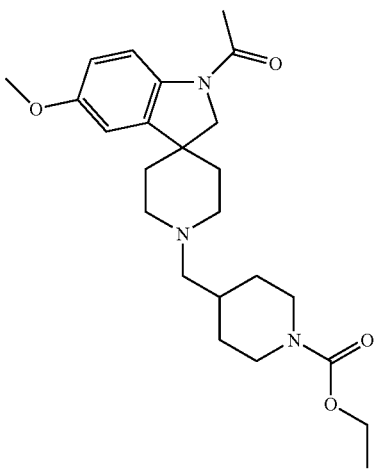
237
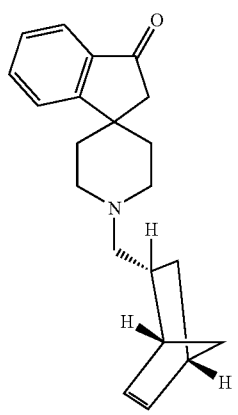
238
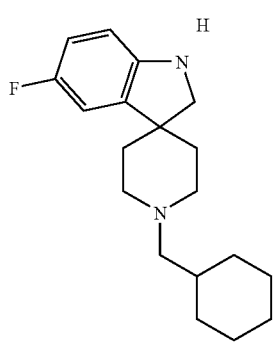
239
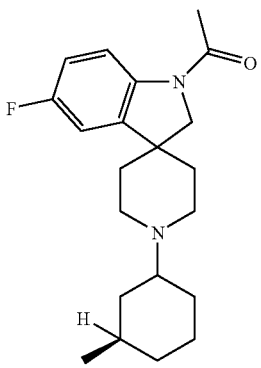
240

TABLE 1-continued
Exemplary compounds of formulae I and II.
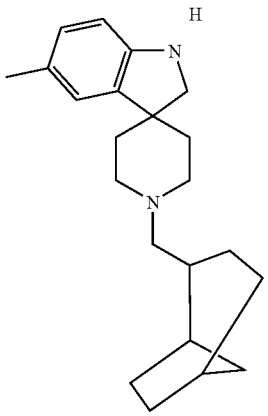 241
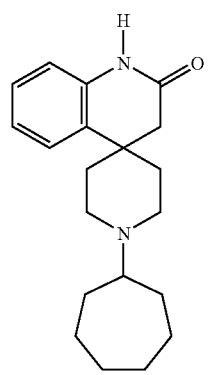 242
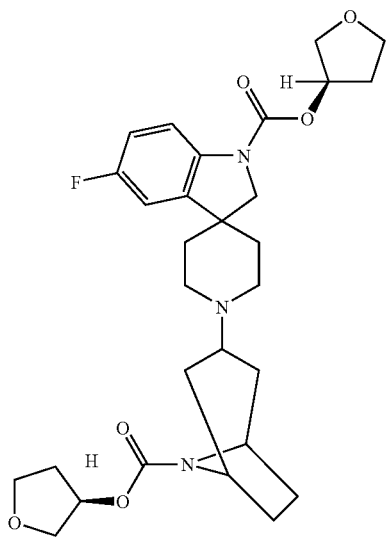 243
TABLE 1-continued
Exemplary compounds of formulae I and II.
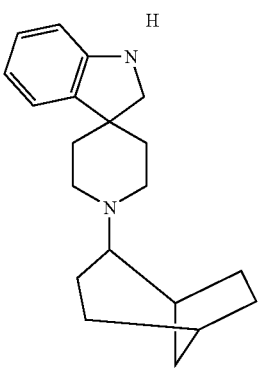 244
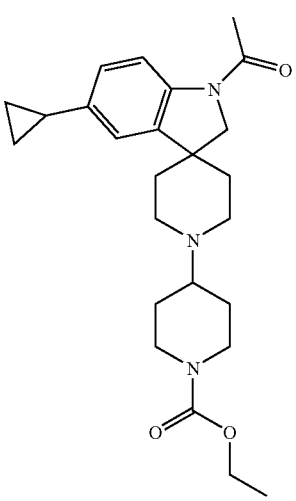 245
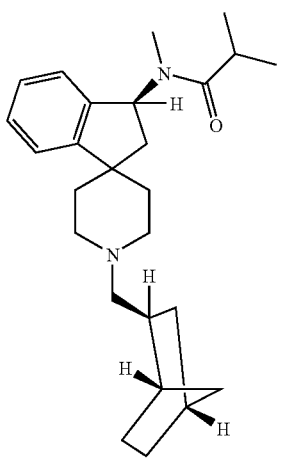 246

TABLE 1-continued
Exemplary compounds of formulae I and II.
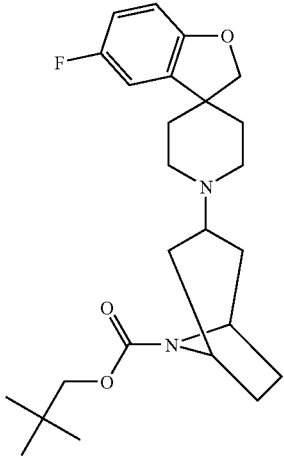 247
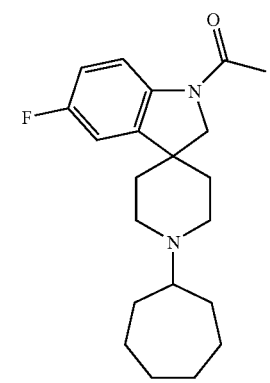 248
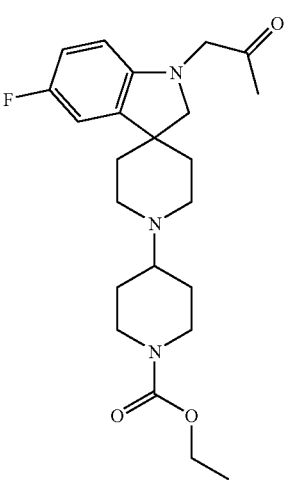 249
TABLE 1-continued
Exemplary compounds of formulae I and II.
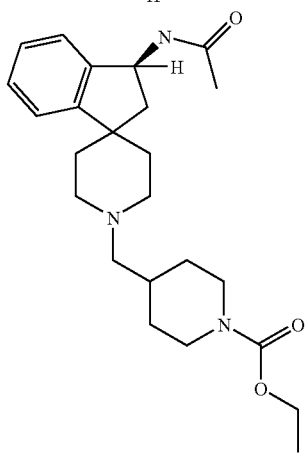 250
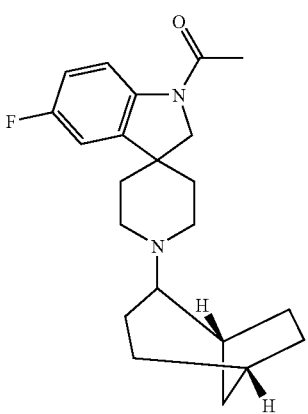 251
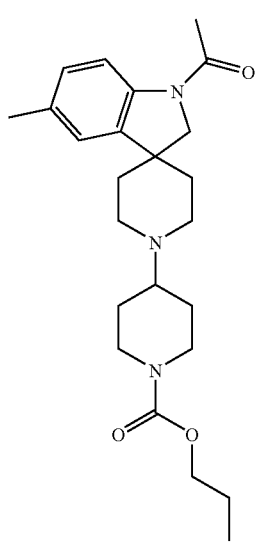 252

TABLE 1-continued
Exemplary compounds of formulae I and II.
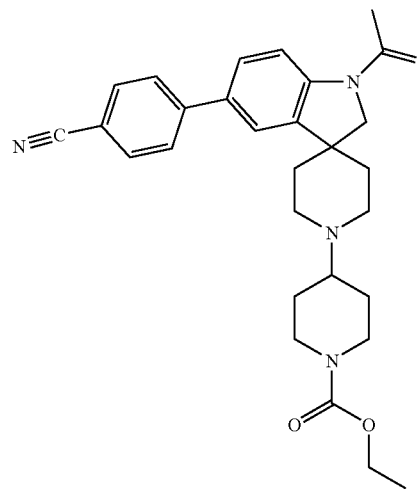 253
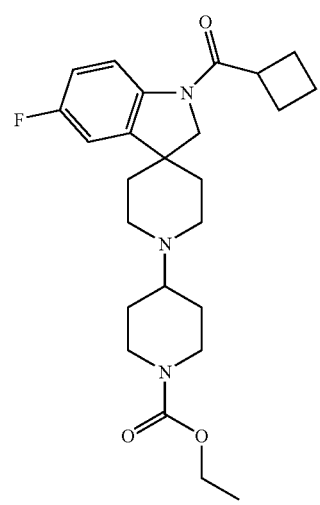 254
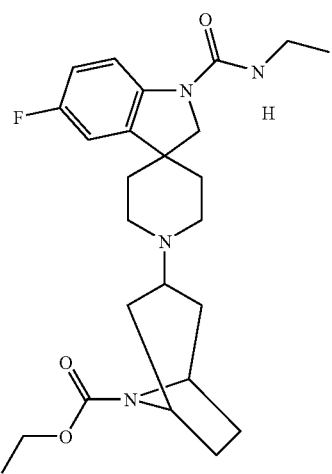 255
TABLE 1-continued
Exemplary compounds of formulae I and II.
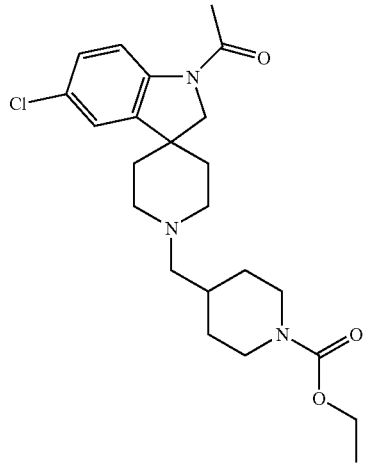 256
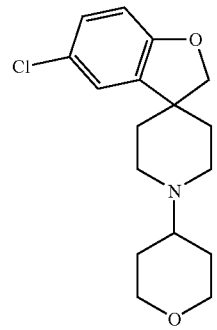 257
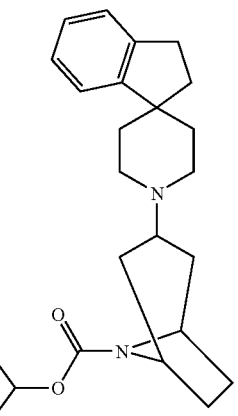 258
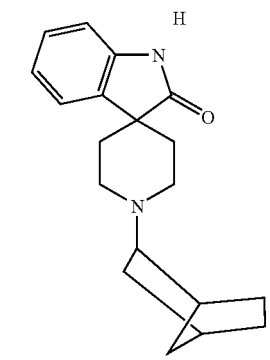 259

TABLE 1-continued
Exemplary compounds of formulae I and II.
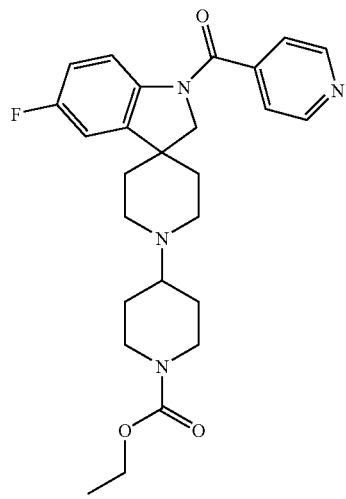 260
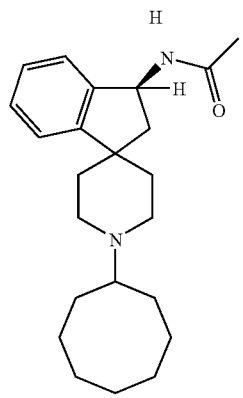 261
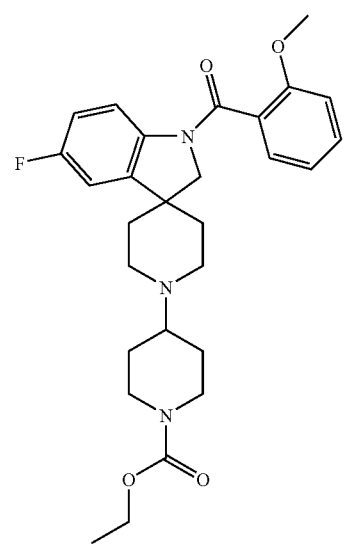 262
TABLE 1-continued
Exemplary compounds of formulae I and II.
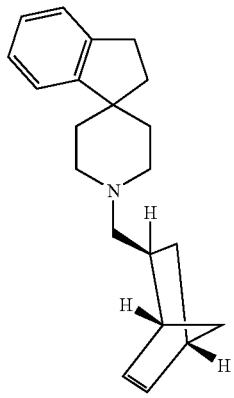 263
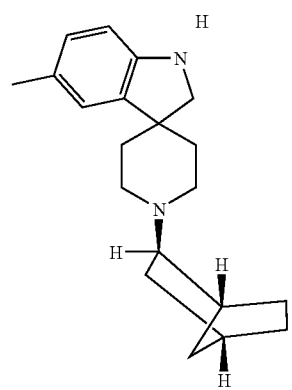 264
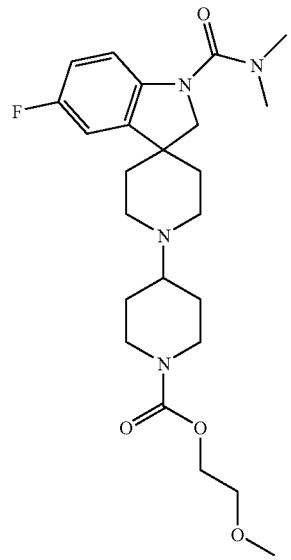 265

TABLE 1-continued
Exemplary compounds of formulae I and II.
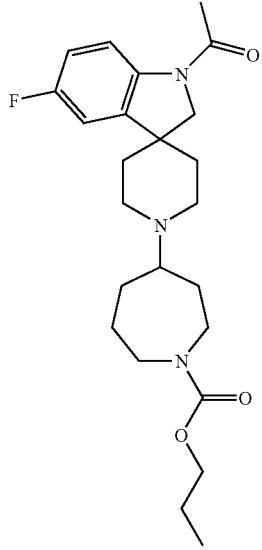
266
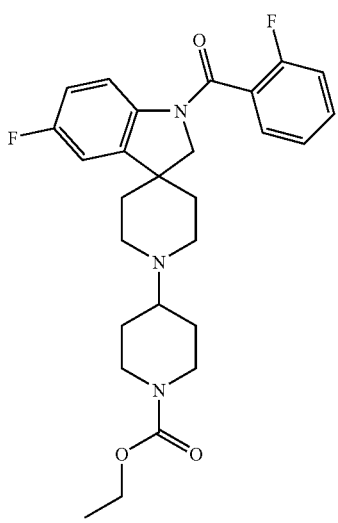
267
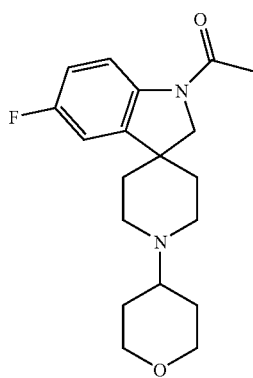
268
TABLE 1-continued
Exemplary compounds of formulae I and II.
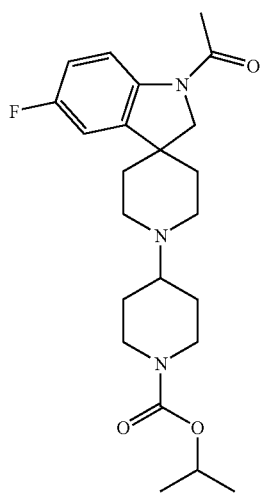
269
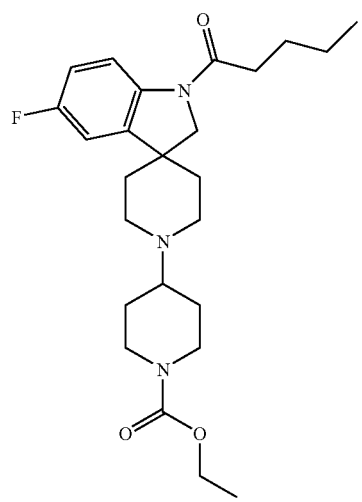
270
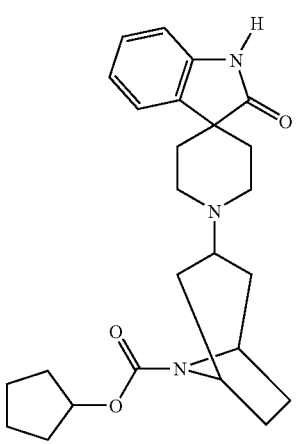
271

TABLE 1-continued
Exemplary compounds of formulae I and II.
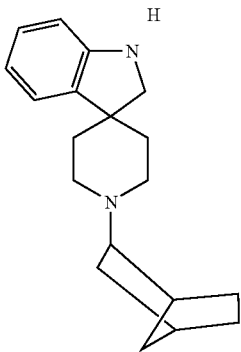 272
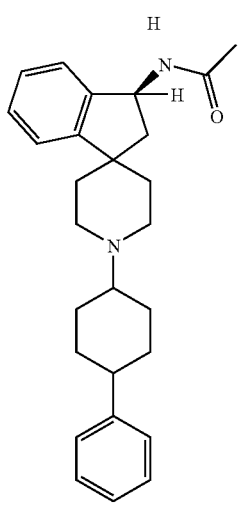 273
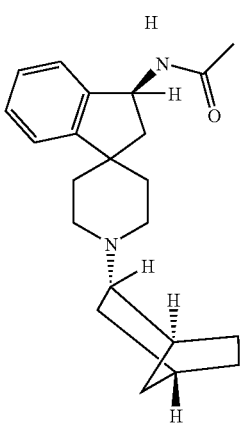 274
TABLE 1-continued
Exemplary compounds of formulae I and II.
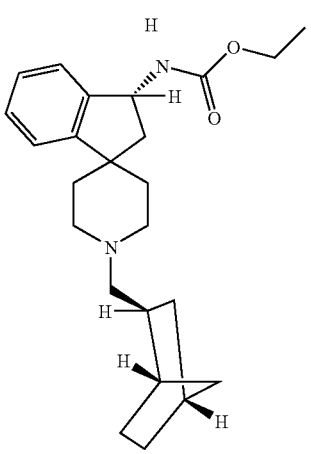 275
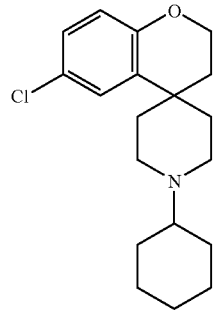 276
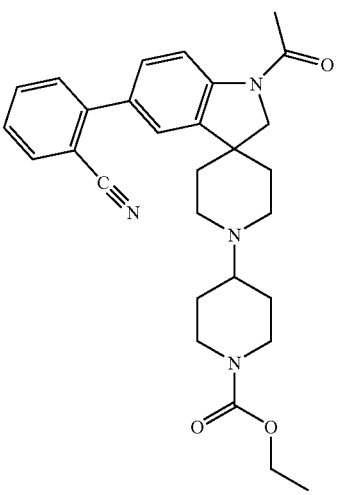 277

TABLE 1-continued
Exemplary compounds of formulae I and II.
278 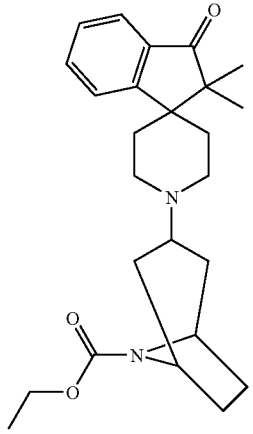
279 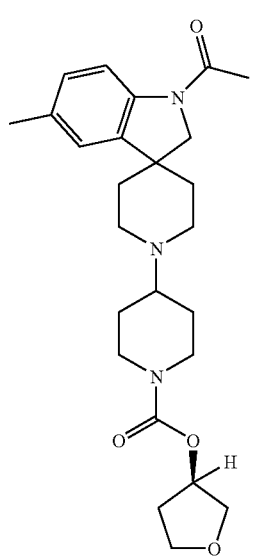
280 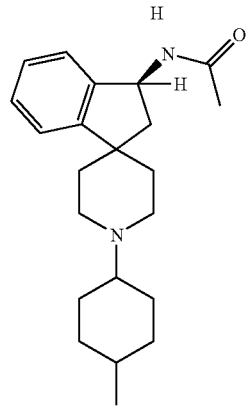
TABLE 1-continued
Exemplary compounds of formulae I and II.
281 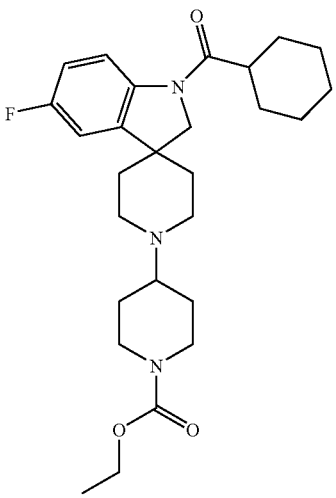
282 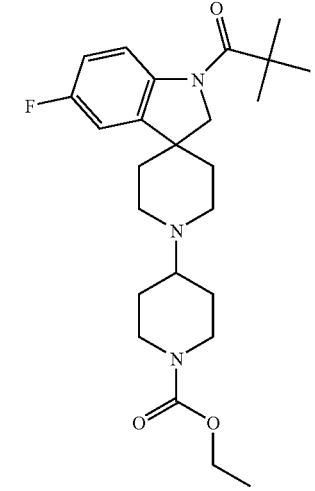
283 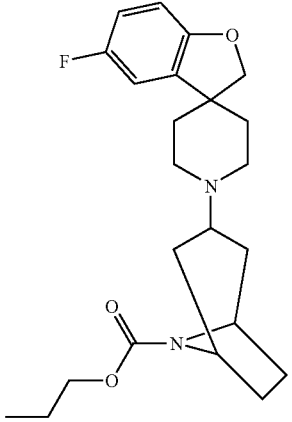

TABLE 1-continued
Exemplary compounds of formulae I and II.
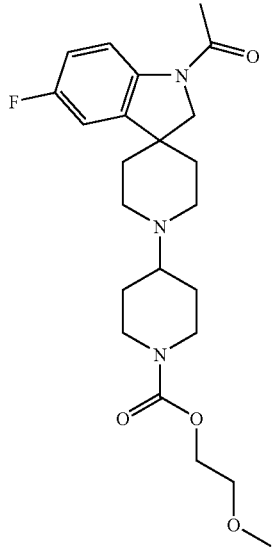 284
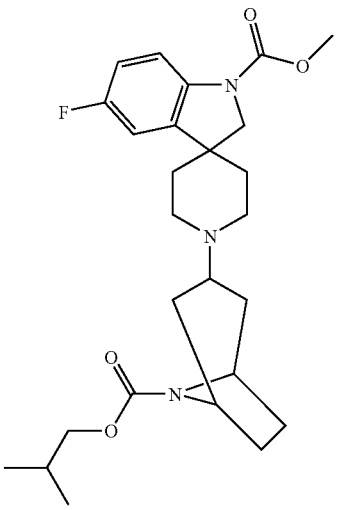 287
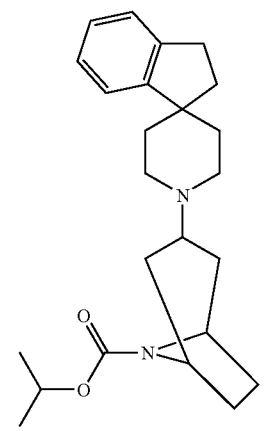 285
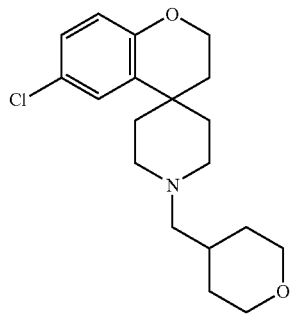 288
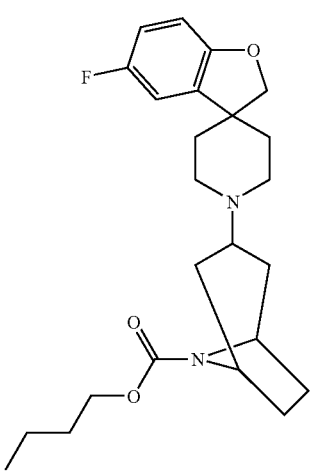 286
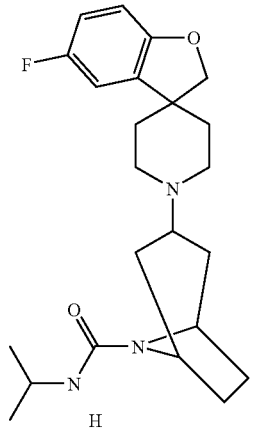 289

TABLE 1-continued
Exemplary compounds of formulae I and II.
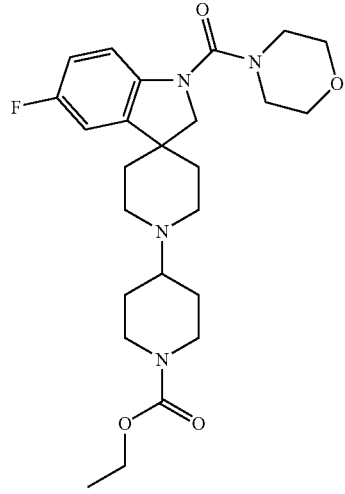
290
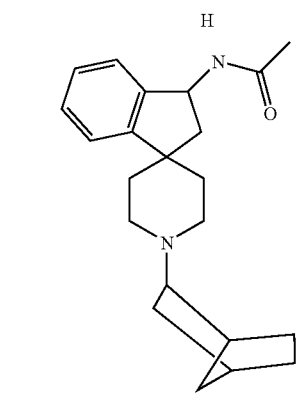
291
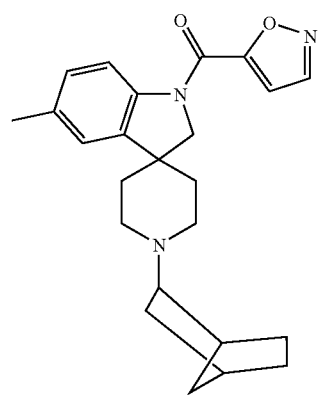
292
TABLE 1-continued
Exemplary compounds of formulae I and II.
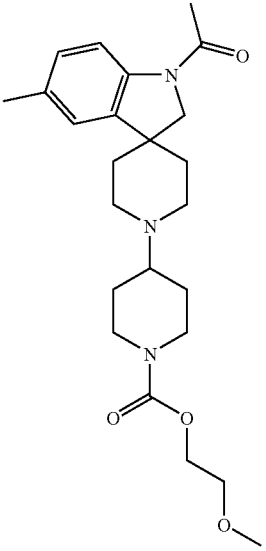
293
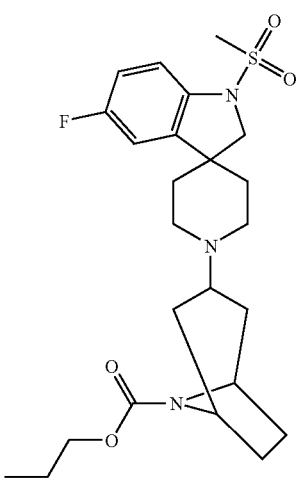
294
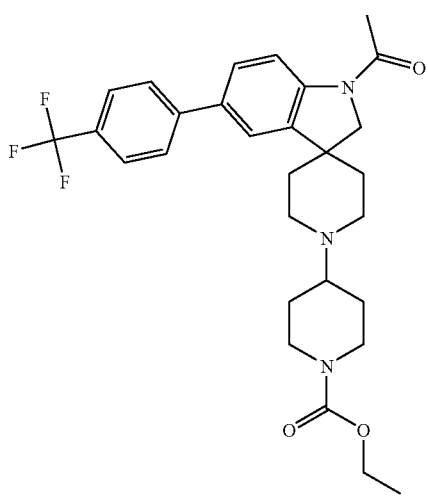
295

TABLE 1-continued
Exemplary compounds of formulae I and II.
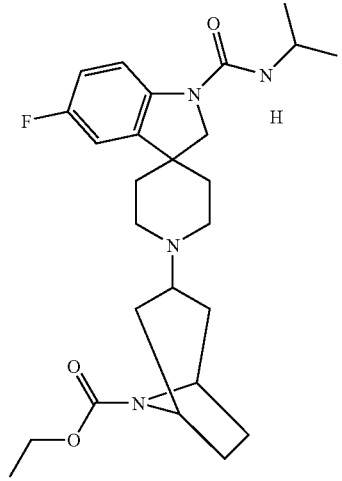 296
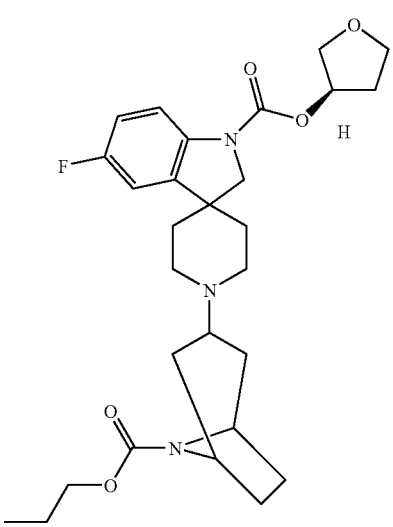 297
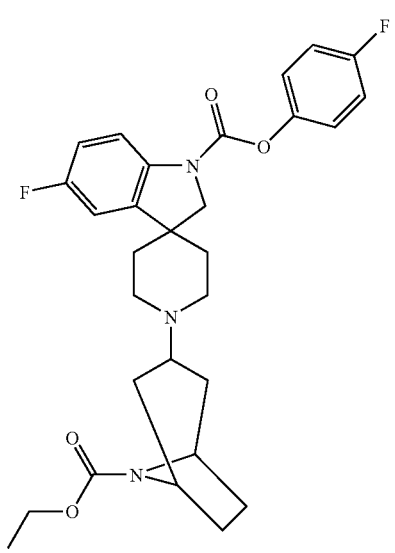 298
TABLE 1-continued
Exemplary compounds of formulae I and II.
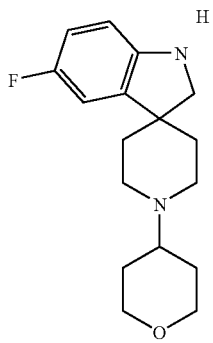 299
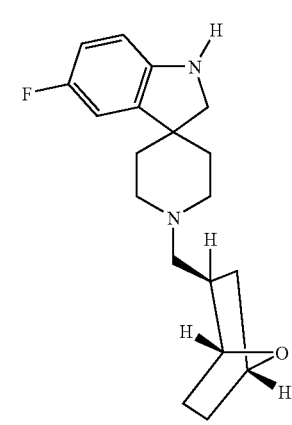 300
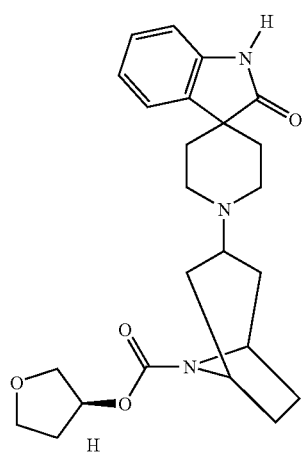 301

TABLE 1-continued
Exemplary compounds of formulae I and II.
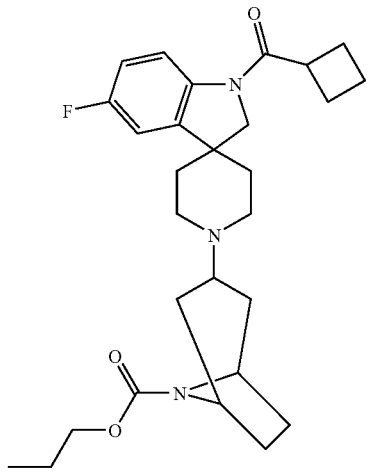 302
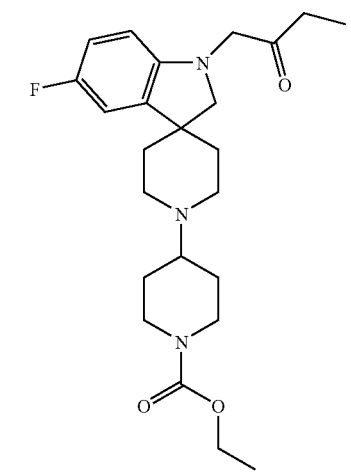 303
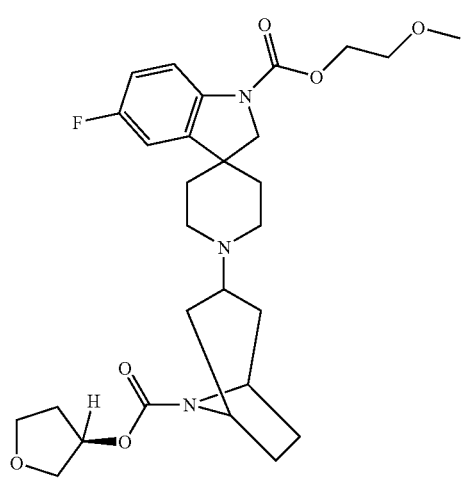 304
TABLE 1-continued
Exemplary compounds of formulae I and II.
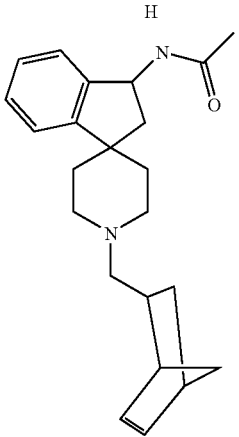 305
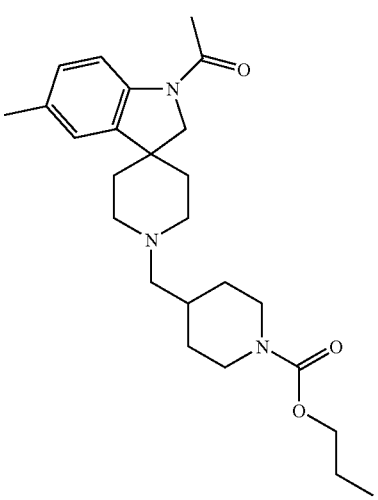 306
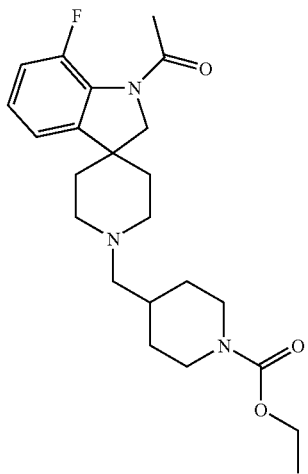 307

TABLE 1-continued
Exemplary compounds of formulae I and II.
308
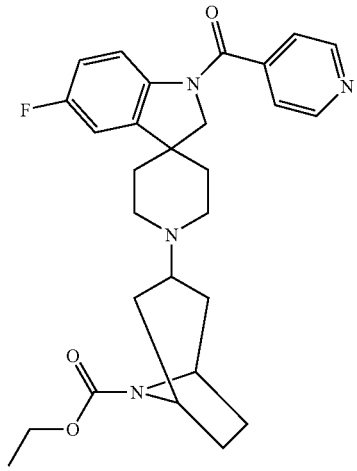
309
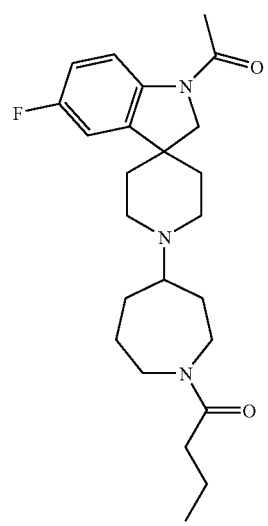
310
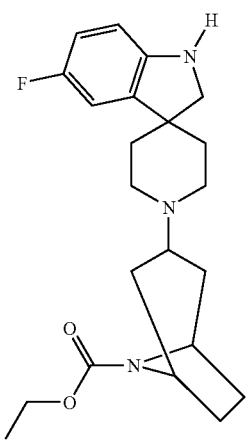
TABLE 1-continued
Exemplary compounds of formulae I and II.
311
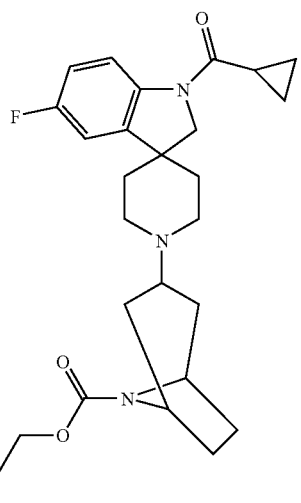
312
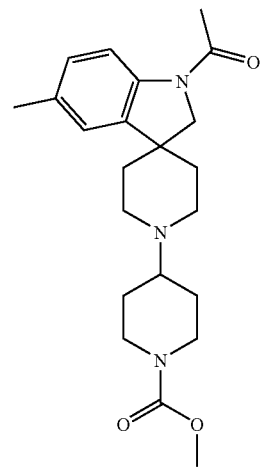
313
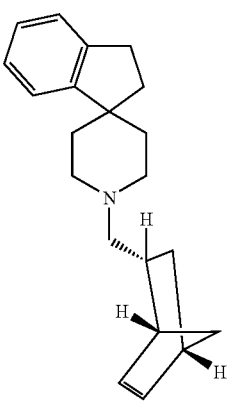

TABLE 1-continued
Exemplary compounds of formulae I and II.
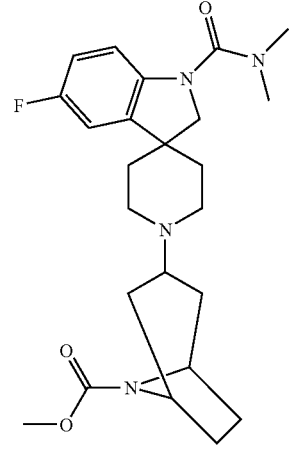 314
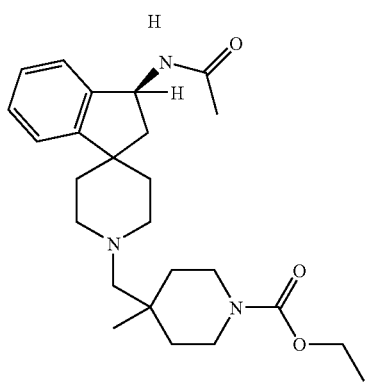 315
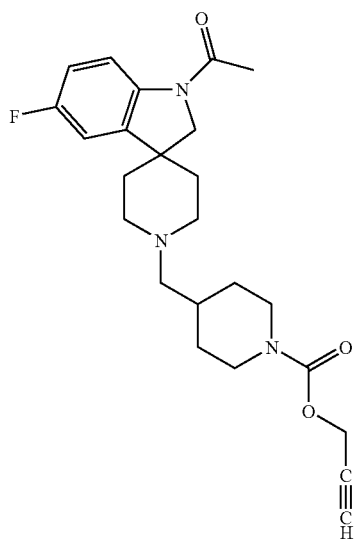 316
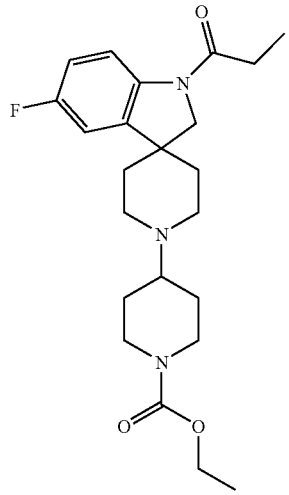 317
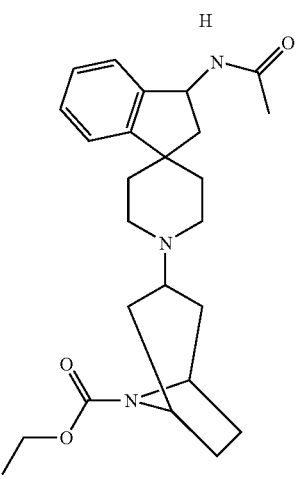 318
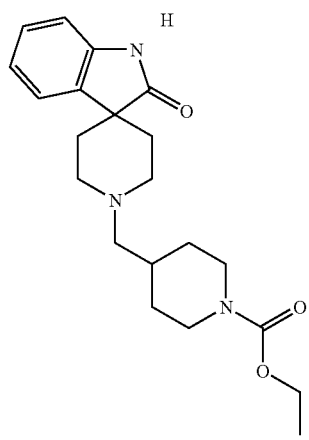 319

TABLE 1-continued
Exemplary compounds of formulae I and II.
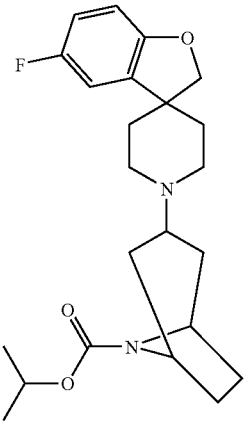 320
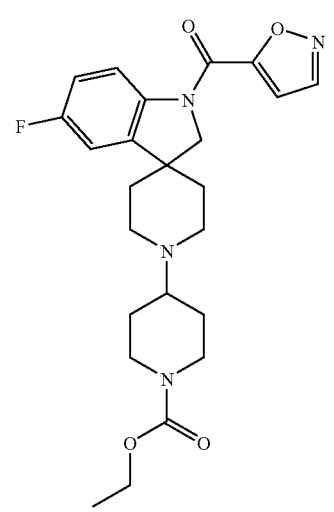 321
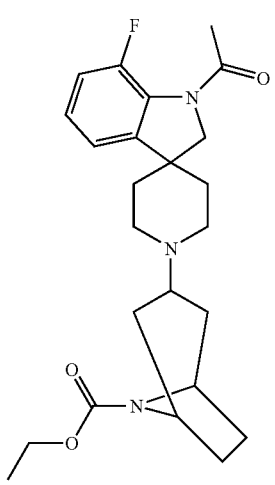 322
TABLE 1-continued
Exemplary compounds of formulae I and II.
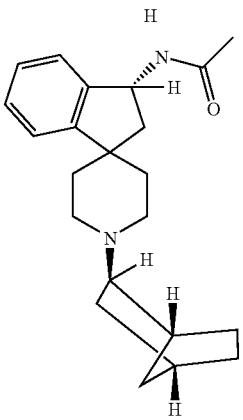 323
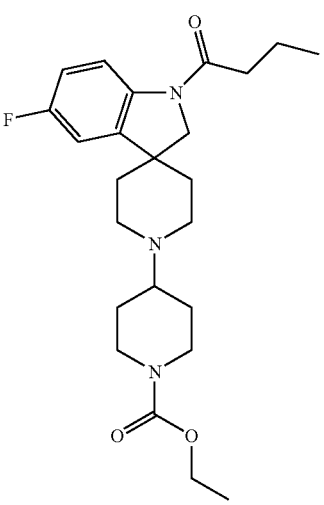 324
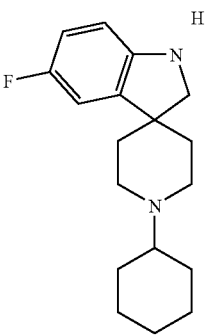 325

TABLE 1-continued
Exemplary compounds of formulae I and II.
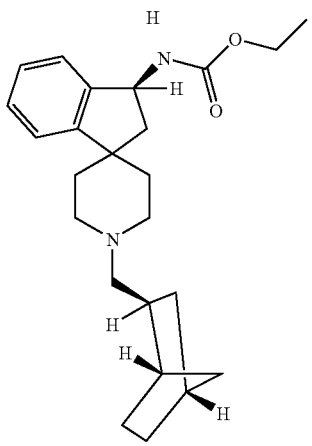
326
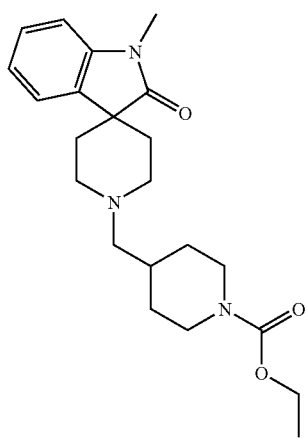
327
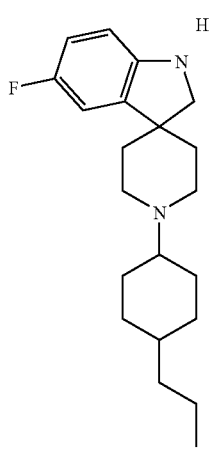
328
TABLE 1-continued
Exemplary compounds of formulae I and II.
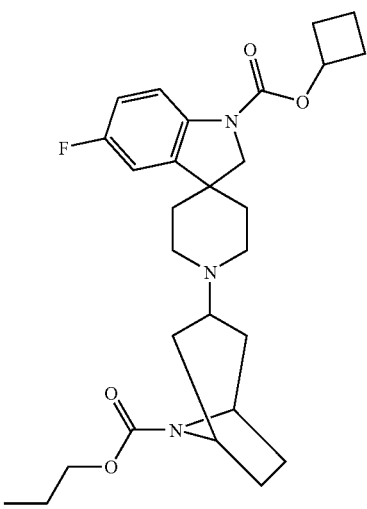
329
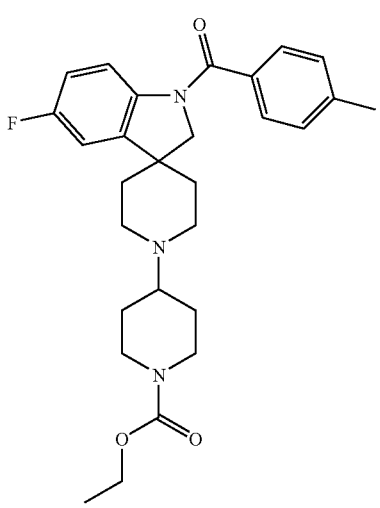
330
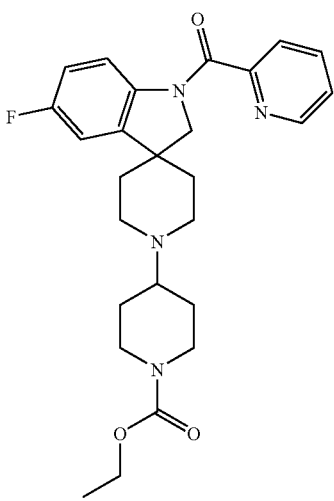
331

TABLE 1-continued
Exemplary compounds of formulae I and II.
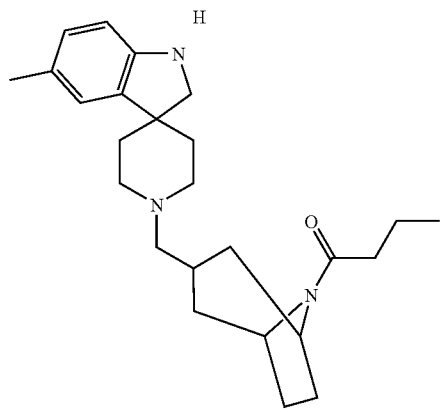 332
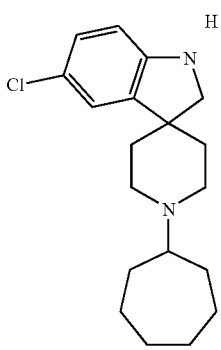 333
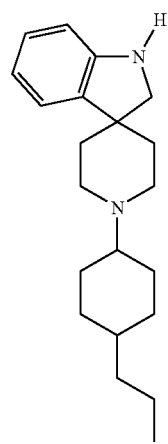 334
TABLE 1-continued
Exemplary compounds of formulae I and II.
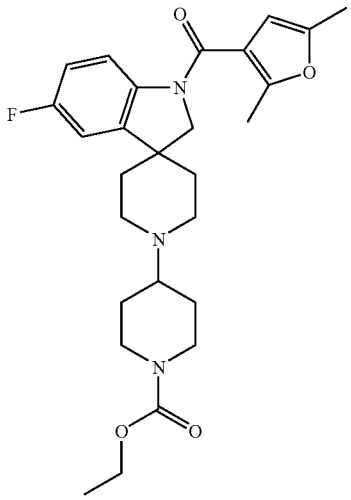 335
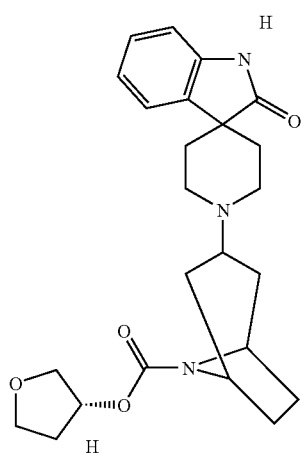 336
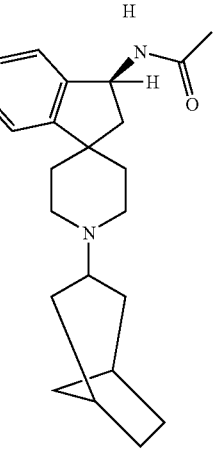 337

TABLE 1-continued
Exemplary compounds of formulae I and II.
| | |
|---|---|
| 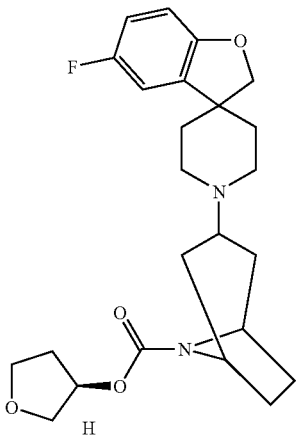 | 338 |
| 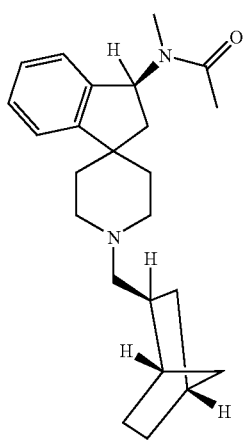 | 339 |
| 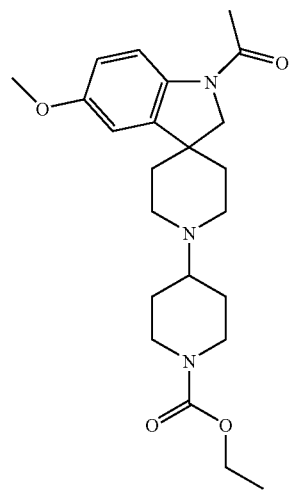 | 340 |
| 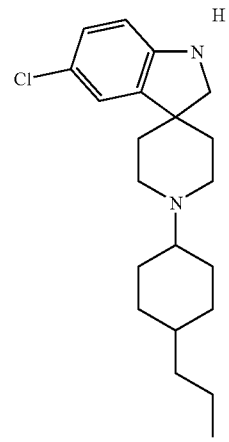 | 341 |
| 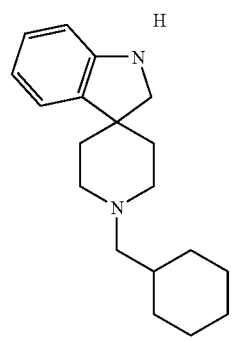 | 342 |
| 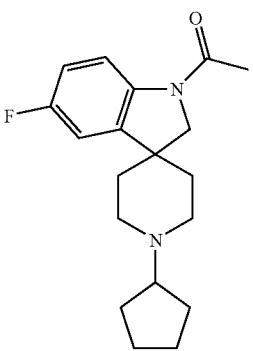 | 343 |

TABLE 1-continued
Exemplary compounds of formulae I and II.
| | |
|---|---|
| 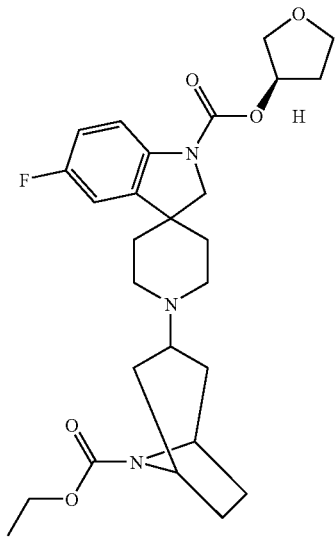 | 344 |
| 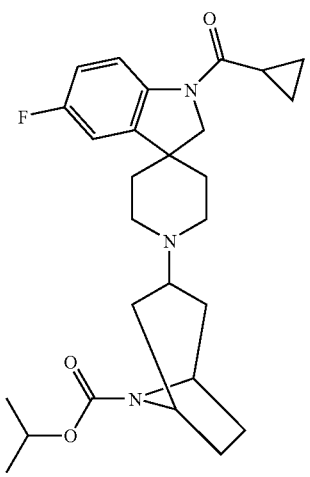 | 345 |
| 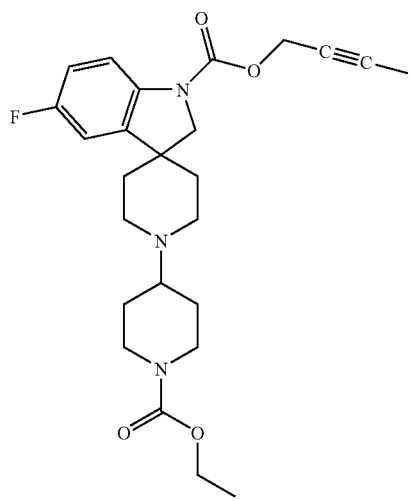 | 346 |
| 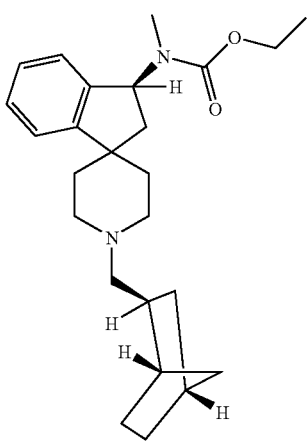 | 347 |
| 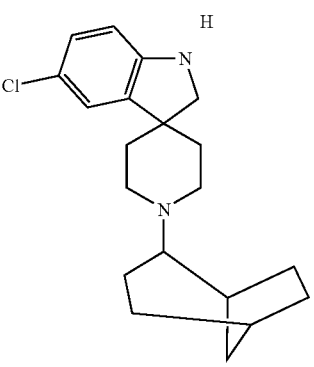 | 348 |
| 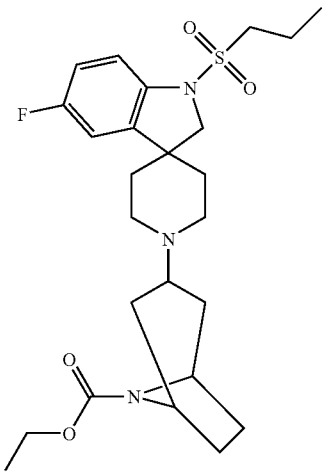 | 349 |

TABLE 1-continued
Exemplary compounds of formulae I and II.
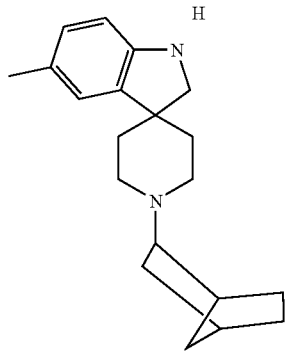 350
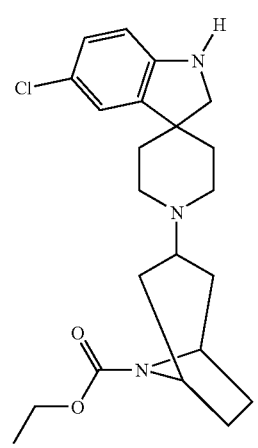 351
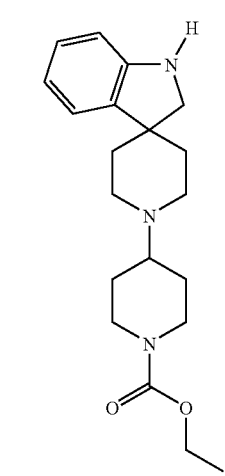 352
TABLE 1-continued
Exemplary compounds of formulae I and II.
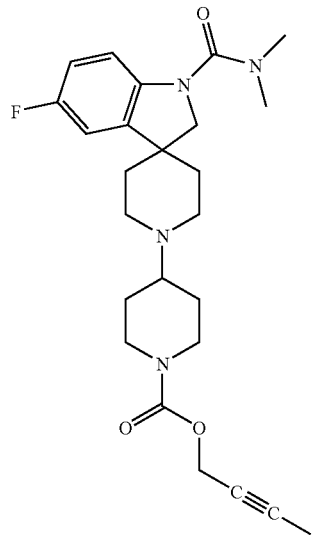 353
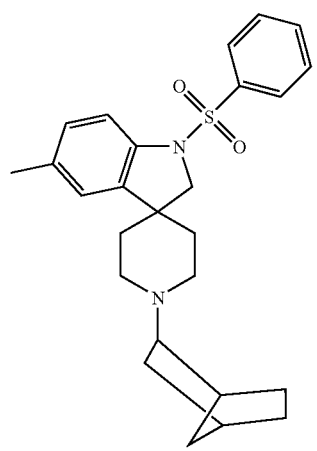 354
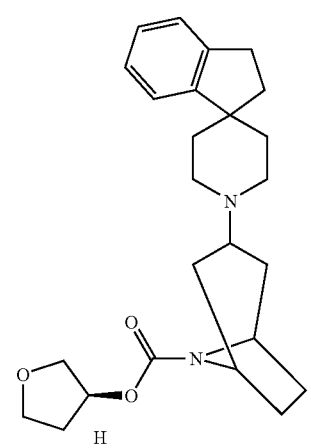 355

TABLE 1-continued
Exemplary compounds of formulae I and II.
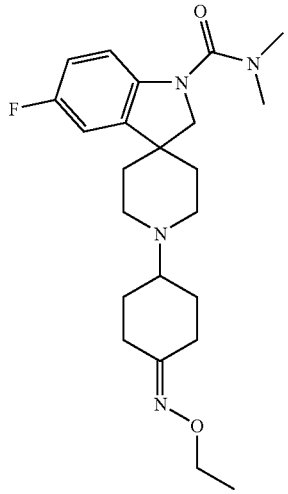
356
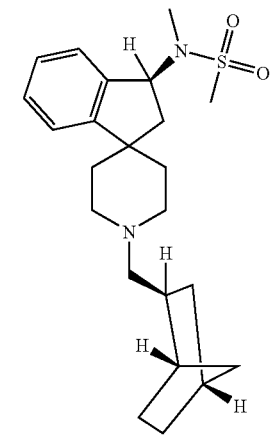
357
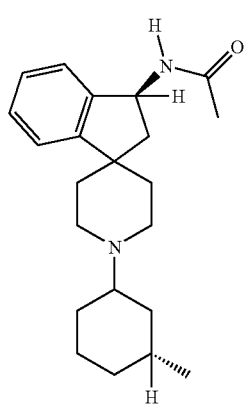
358
TABLE 1-continued
Exemplary compounds of formulae I and II.
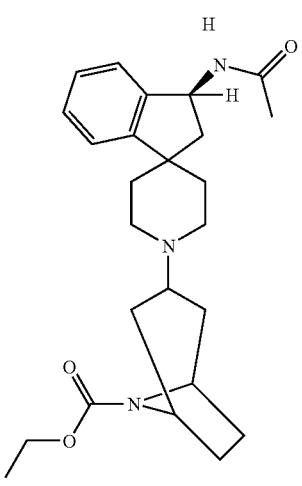
359
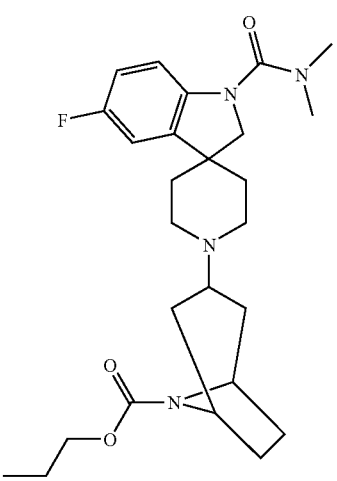
360
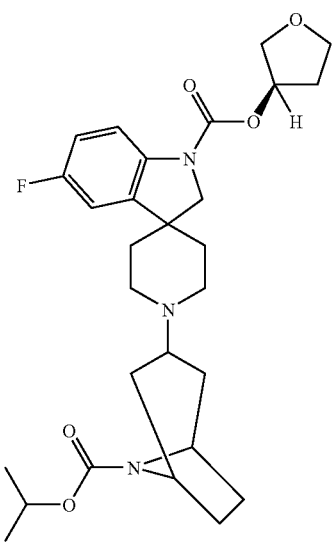
361

TABLE 1-continued
Exemplary compounds of formulae I and II.
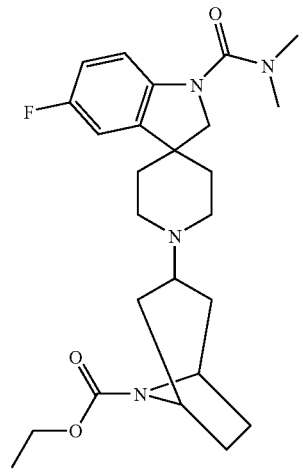 362
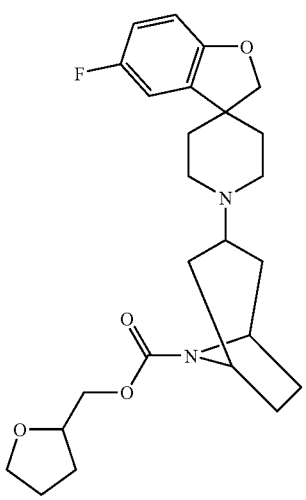 363
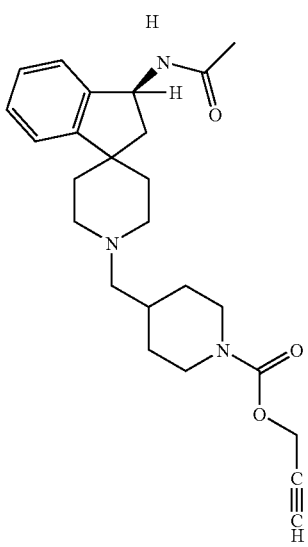 364
TABLE 1-continued
Exemplary compounds of formulae I and II.
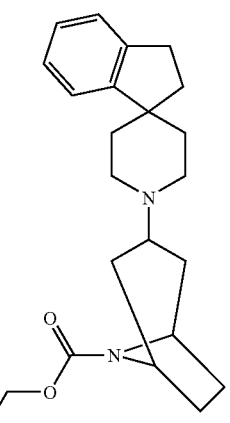 365
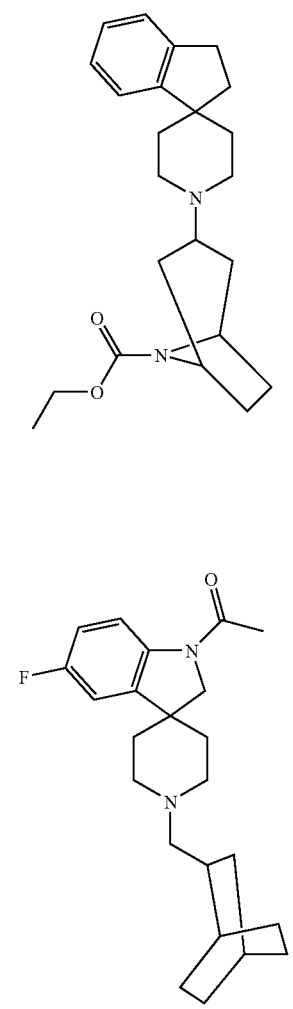 366
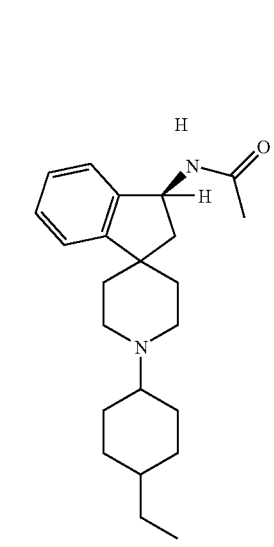 367

TABLE 1-continued
Exemplary compounds of formulae I and II.
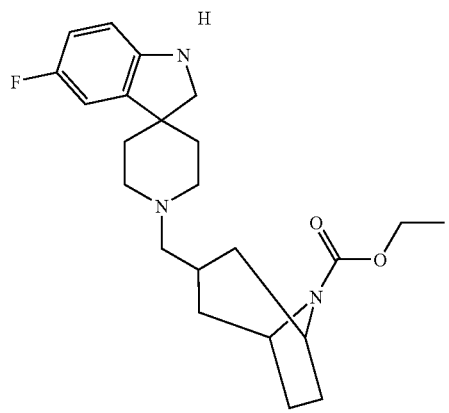
368
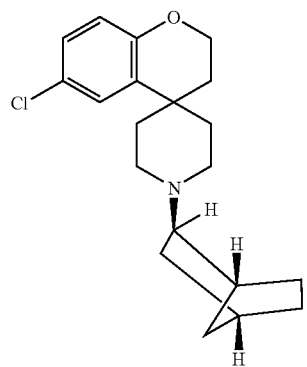
369
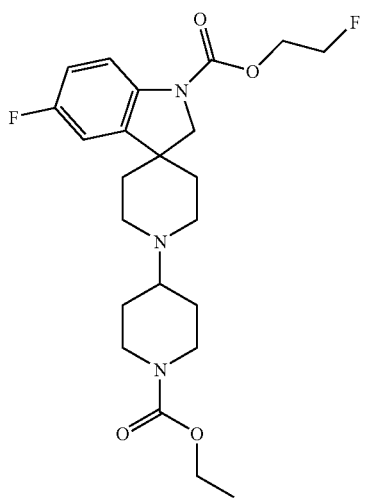
370
TABLE 1-continued
Exemplary compounds of formulae I and II.
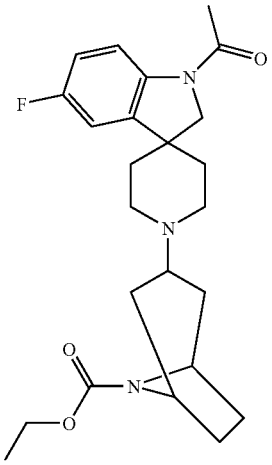
371
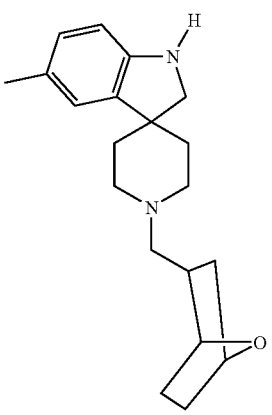
372
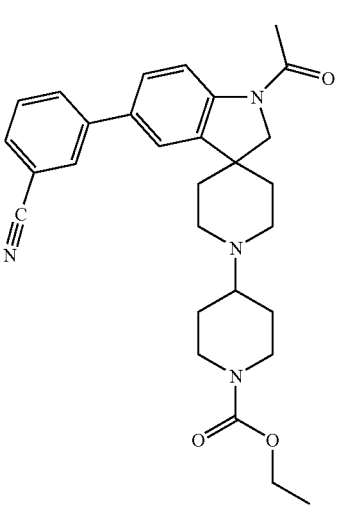
373

TABLE 1-continued
Exemplary compounds of formulae I and II.
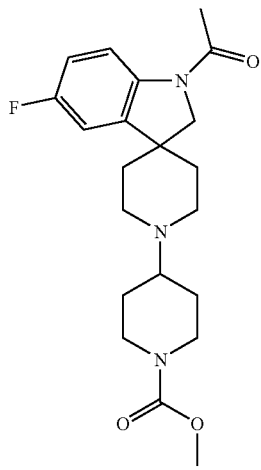 374
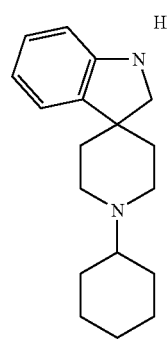 375
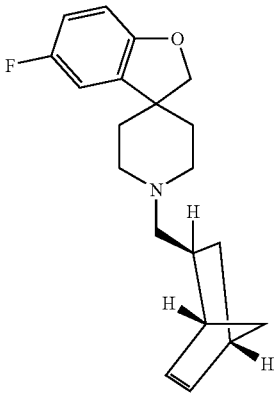 376
TABLE 1-continued
Exemplary compounds of formulae I and II.
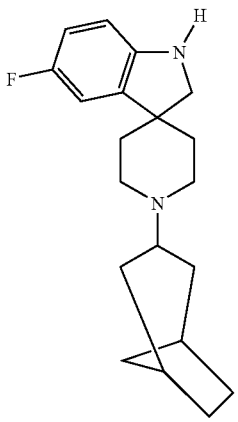 377
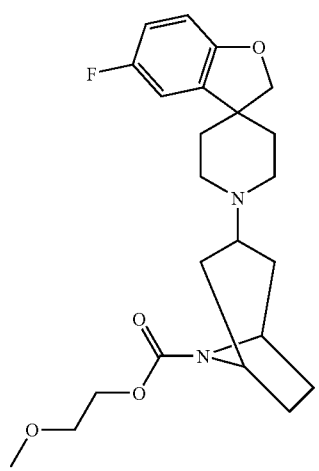 378
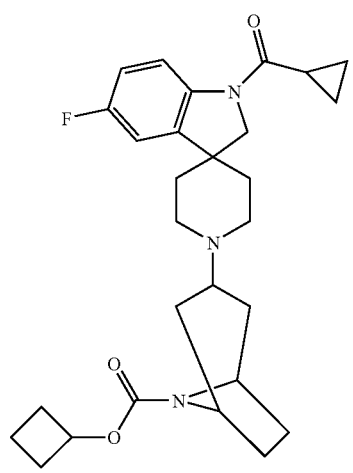 379

TABLE 1-continued
Exemplary compounds of formulae I and II.
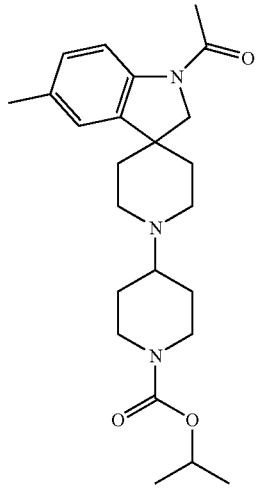 380
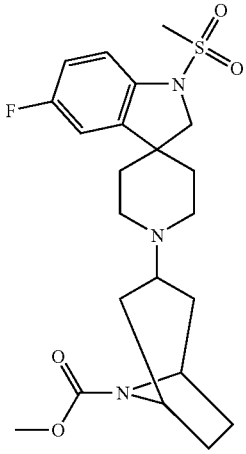 383
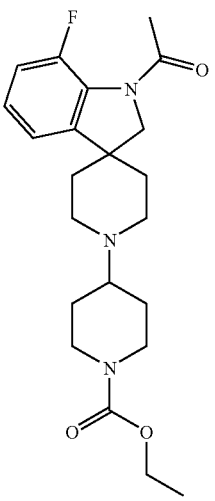 381
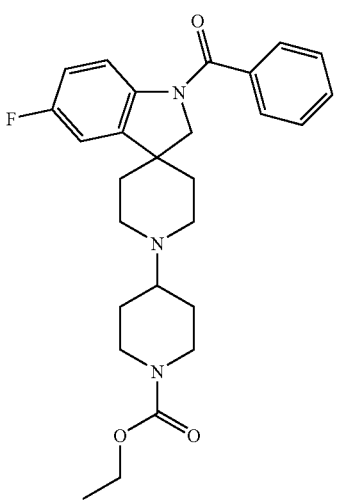 384
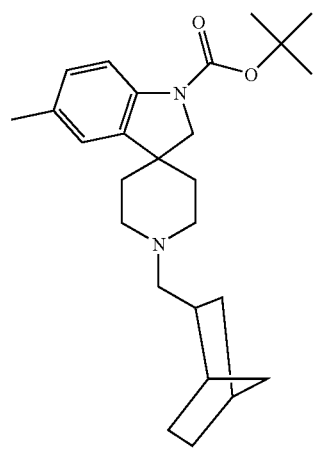 382
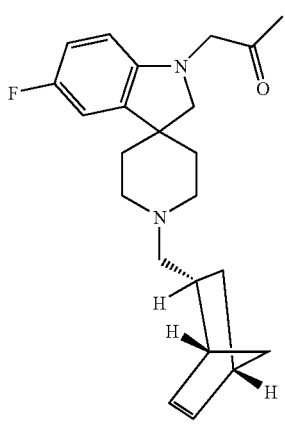 385

TABLE 1-continued
Exemplary compounds of formulae I and II.
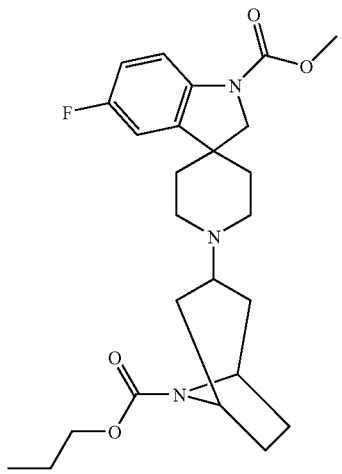 386
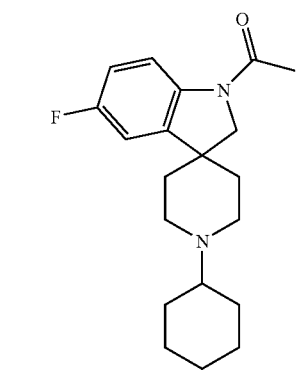 387
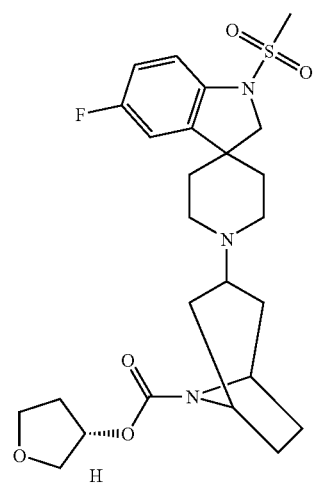 388
TABLE 1-continued
Exemplary compounds of formulae I and II.
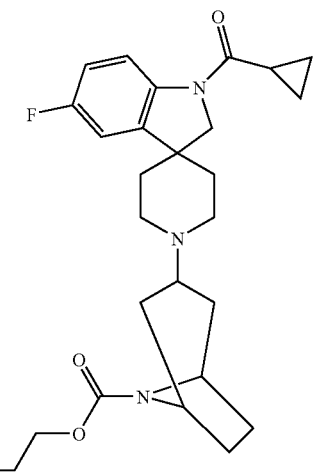 389
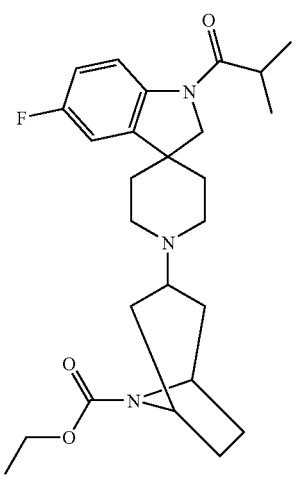 390
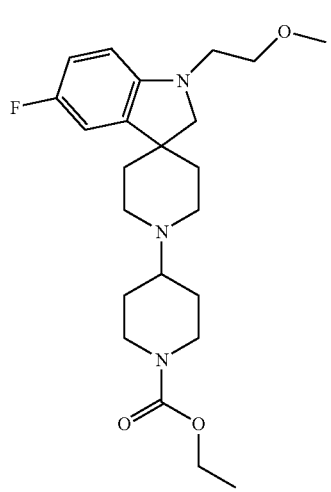 391

TABLE 1-continued
Exemplary compounds of formulae I and II.
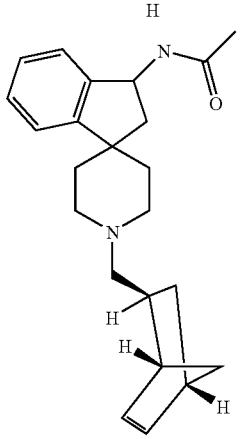
392
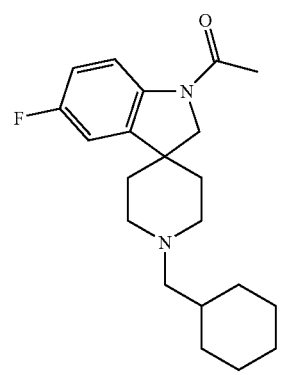
393
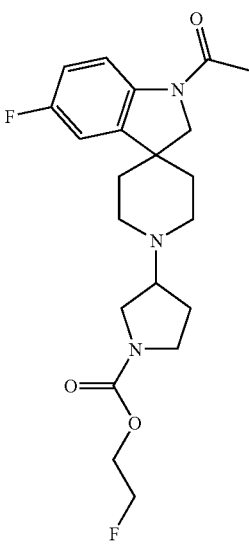
394
TABLE 1-continued
Exemplary compounds of formulae I and II.
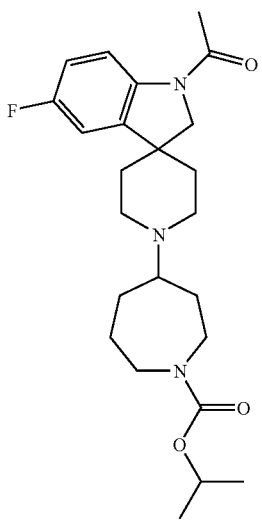
395
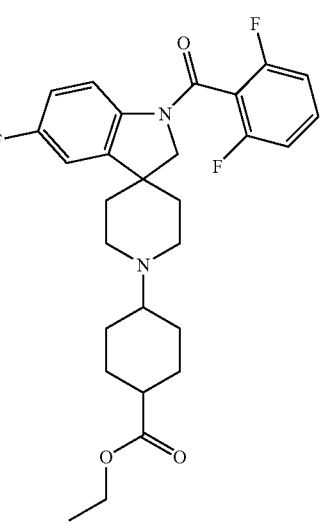
396
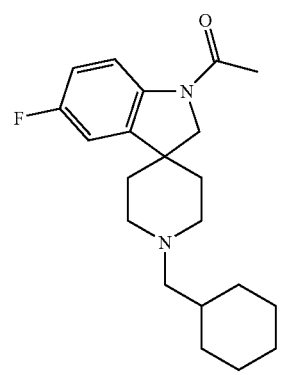
397

TABLE 1-continued
Exemplary compounds of formulae I and II.
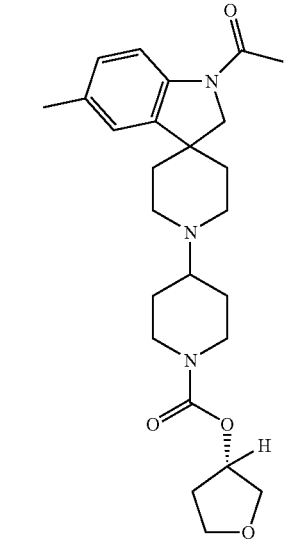
398
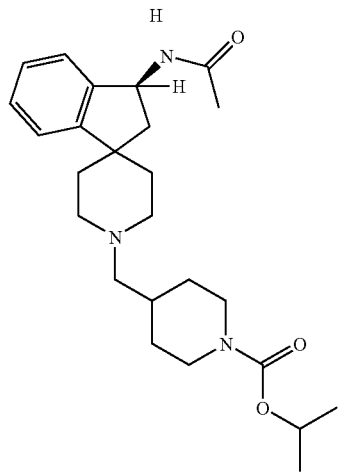
399
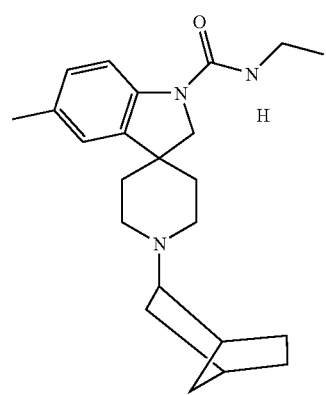
400
TABLE 1-continued
Exemplary compounds of formulae I and II.
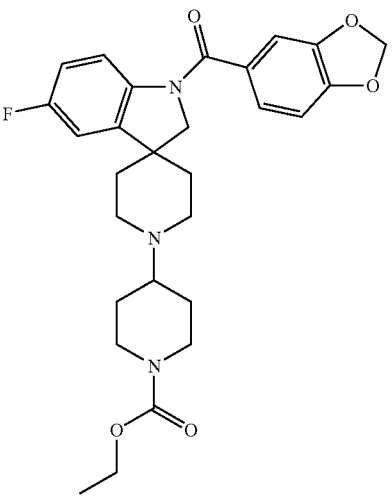
401
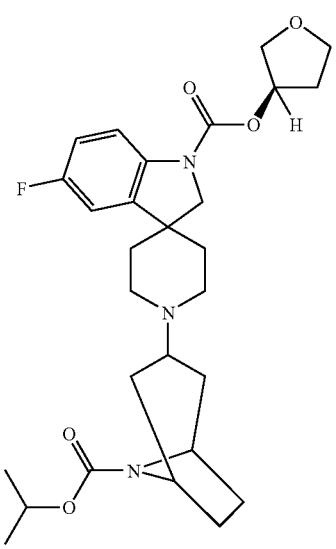
402
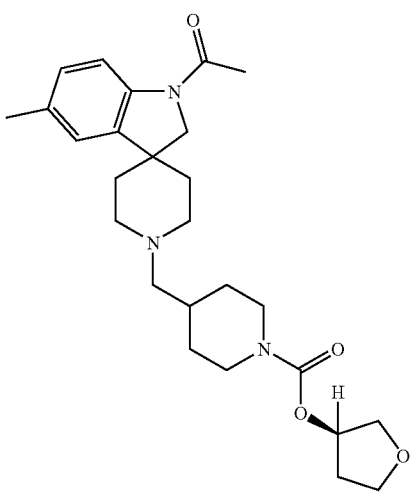
403

TABLE 1-continued
Exemplary compounds of formulae I and II.
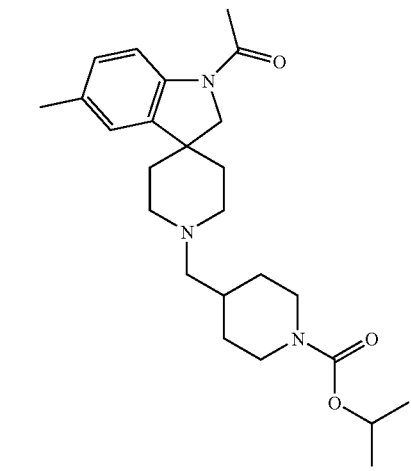
404
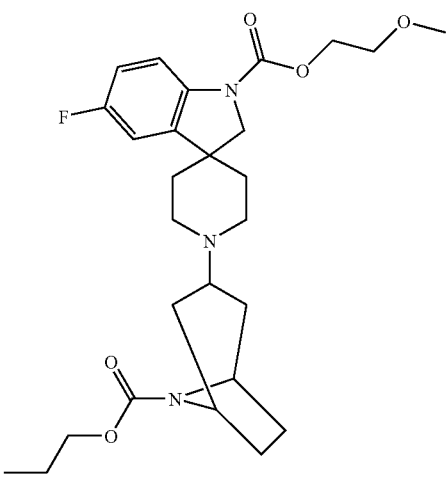
405
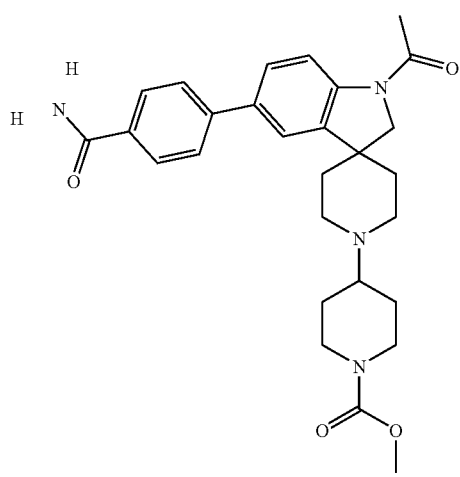
406
TABLE 1-continued
Exemplary compounds of formulae I and II.
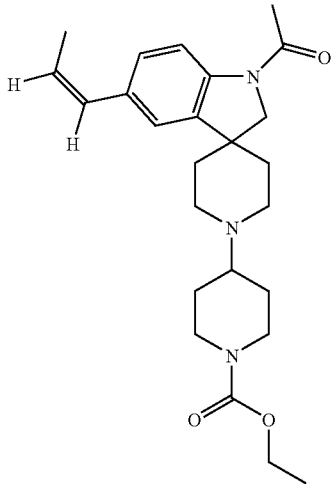
407
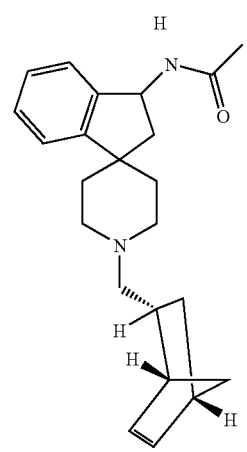
408
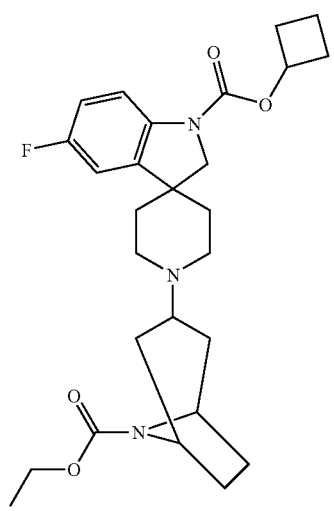
409

TABLE 1-continued
Exemplary compounds of formulae I and II.
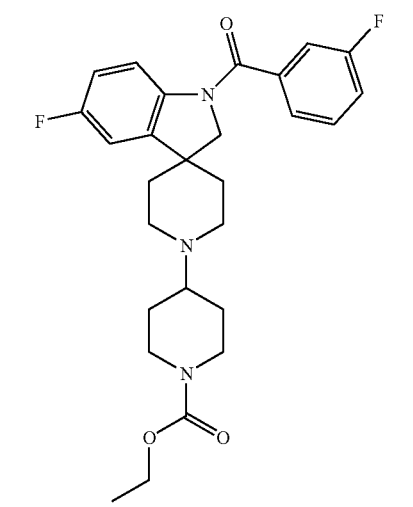
410
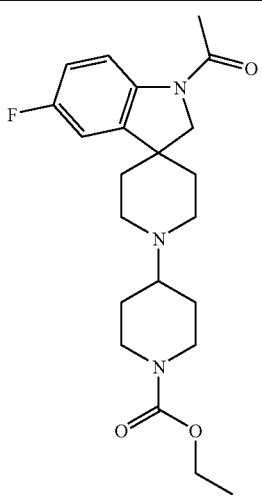
413
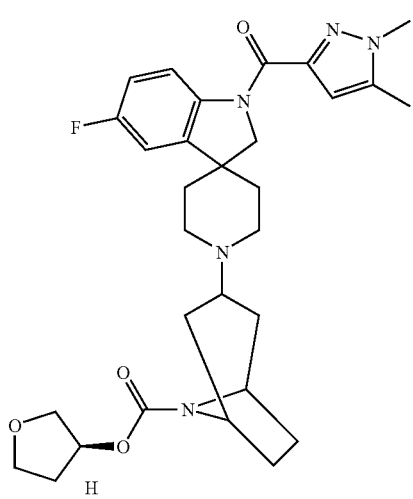
411
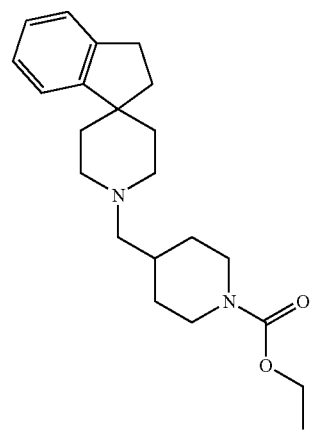
414
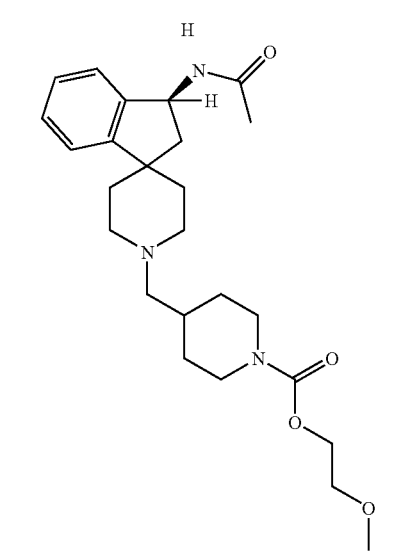
412
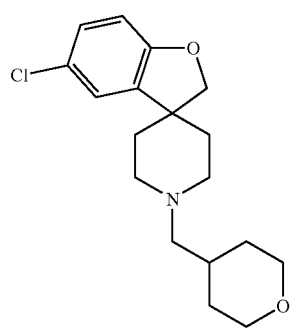
415

TABLE 1-continued
Exemplary compounds of formulae I and II.
| | |
|---|---|
| 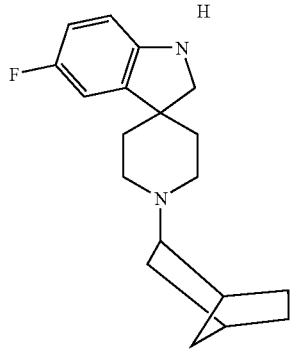 | 416 |
| 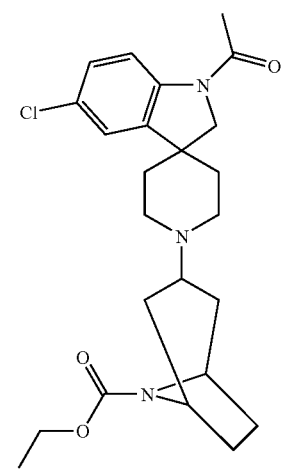 | 417 |
| 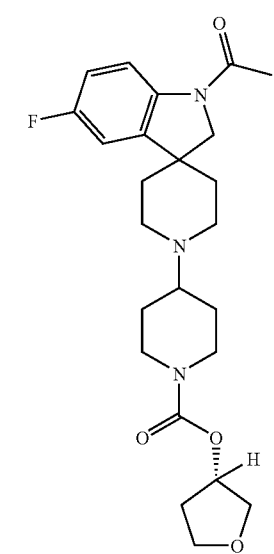 | 418 |
| 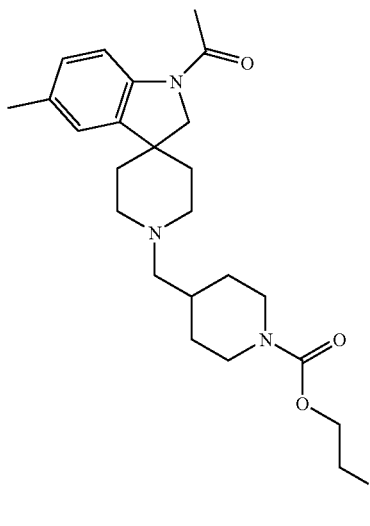 | 419 |
| 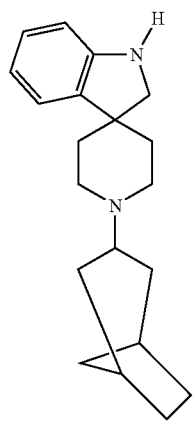 | 420 |
| 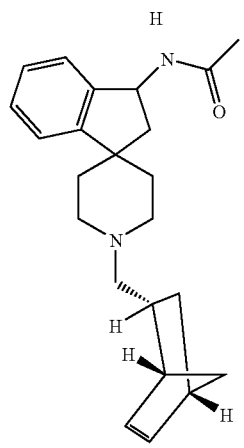 | 421 |

TABLE 1-continued
Exemplary compounds of formulae I and II.
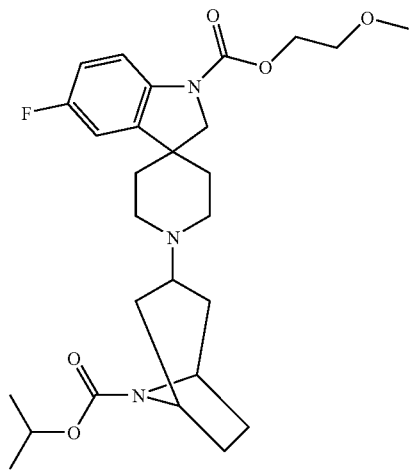 422
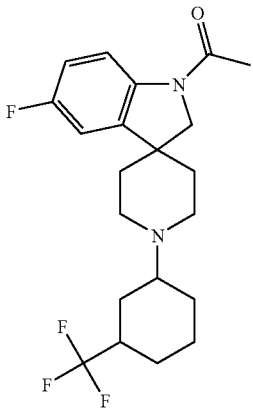 425
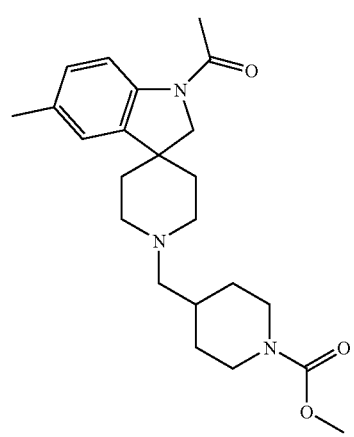 423
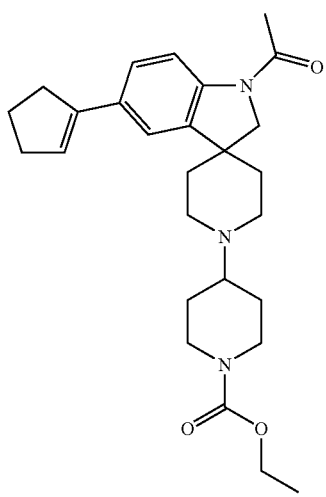 426
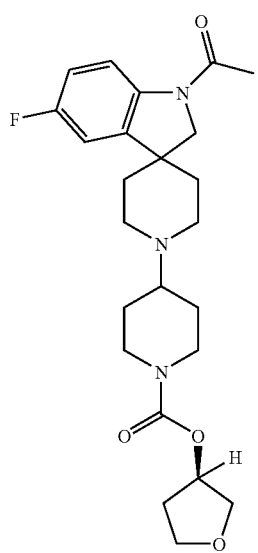 424
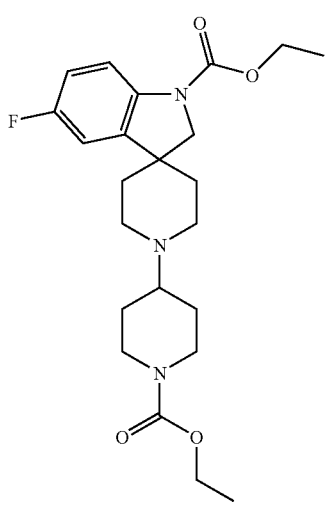 427

TABLE 1-continued
Exemplary compounds of formulae I and II.
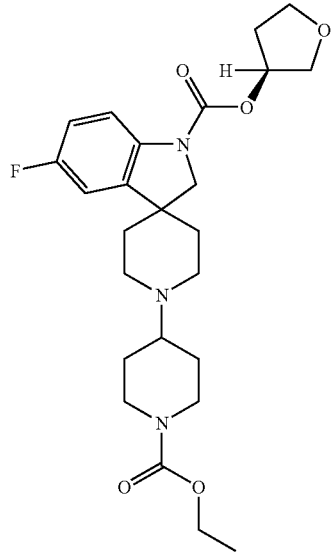 428
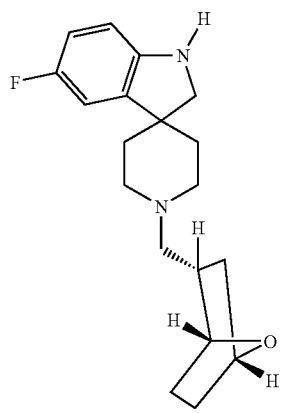 429
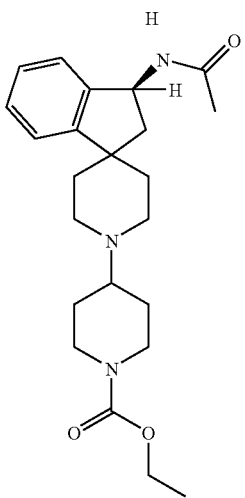 430
TABLE 1-continued
Exemplary compounds of formulae I and II.
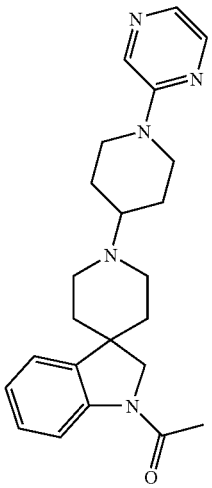 431
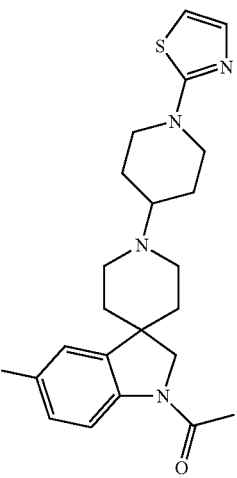 432
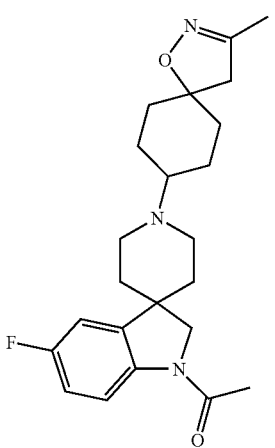 433

TABLE 1-continued
Exemplary compounds of formulae I and II.
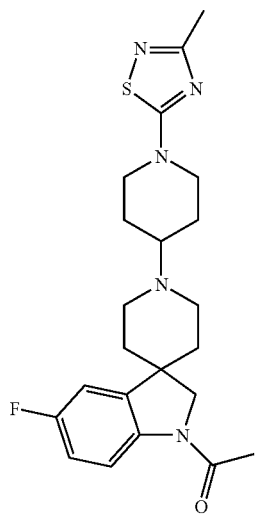 434
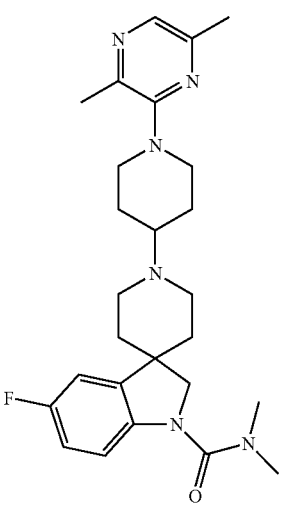 435
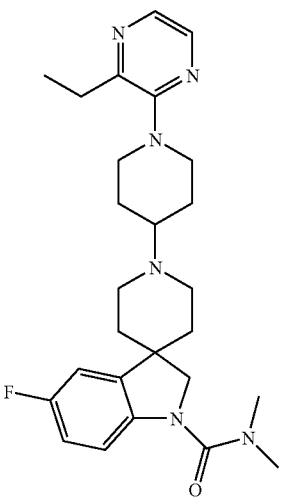 436
TABLE 1-continued
Exemplary compounds of formulae I and II.
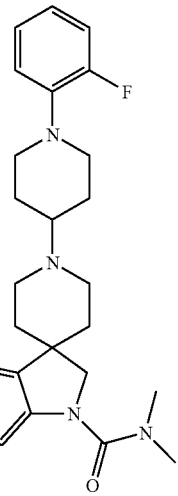 437
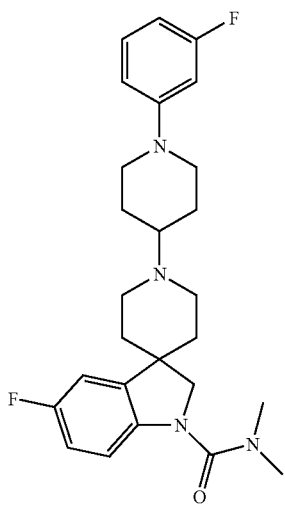 438
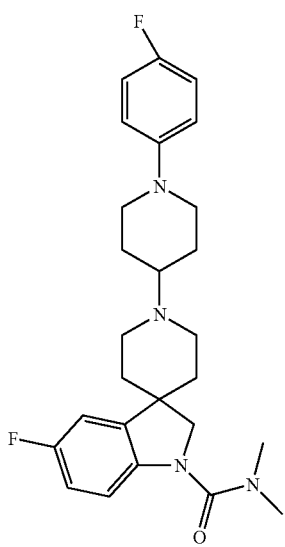 439

TABLE 1-continued
Exemplary compounds of formulae I and II.
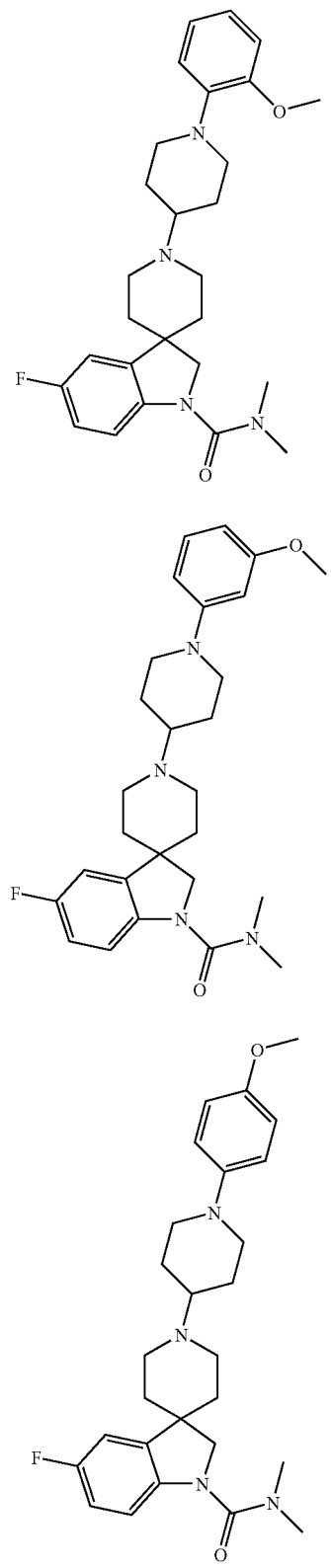
440
441
442
TABLE 1-continued
Exemplary compounds of formulae I and II.
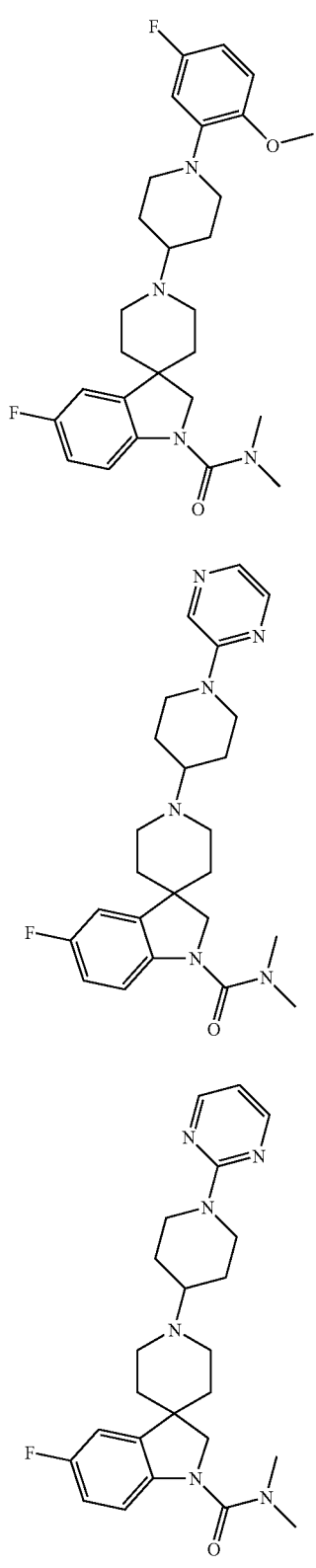
443
444
445

TABLE 1-continued
Exemplary compounds of formulae I and II.
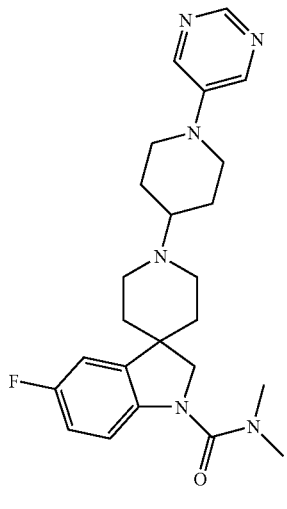
446
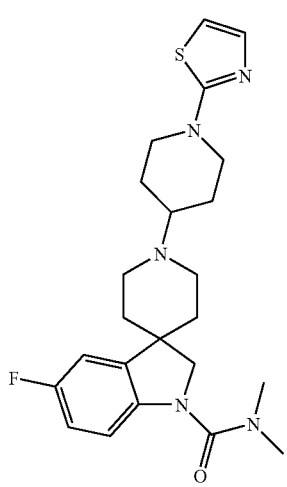
447
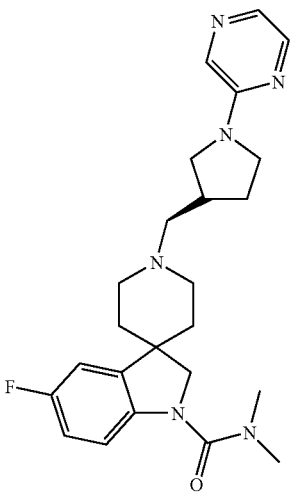
448
TABLE 1-continued
Exemplary compounds of formulae I and II.
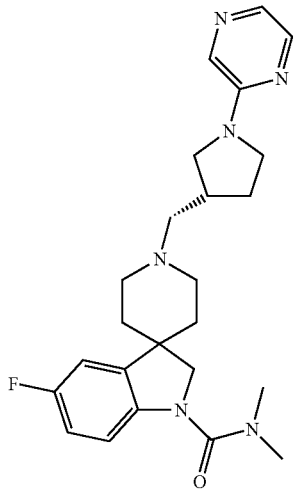
449
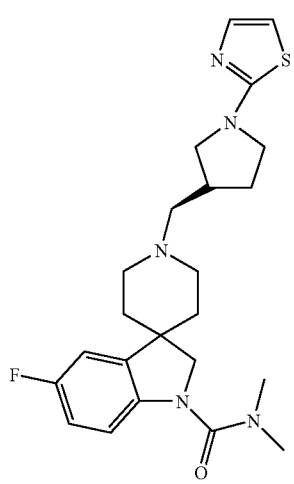
450
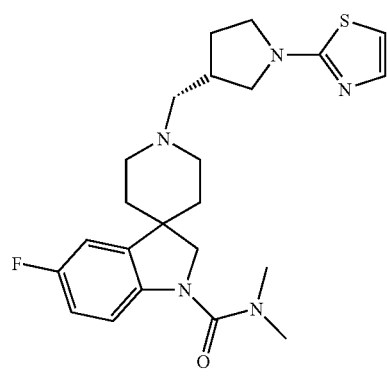
451

TABLE 1-continued
Exemplary compounds of formulae I and II.
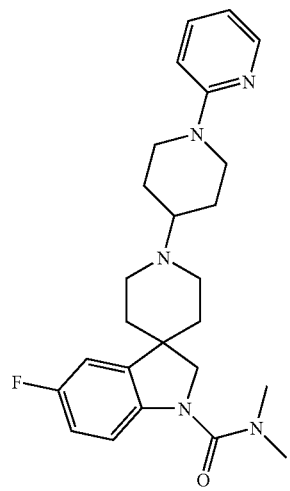
452
453
454
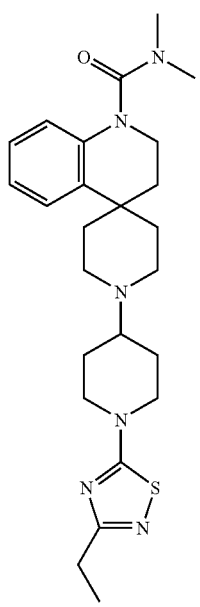
TABLE 1-continued
Exemplary compounds of formulae I and II.
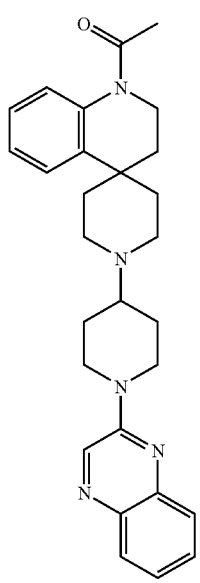
455
456

TABLE 1-continued
Exemplary compounds of formulae I and II.
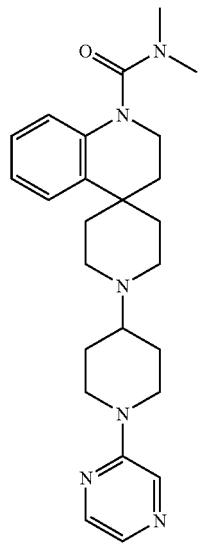 457
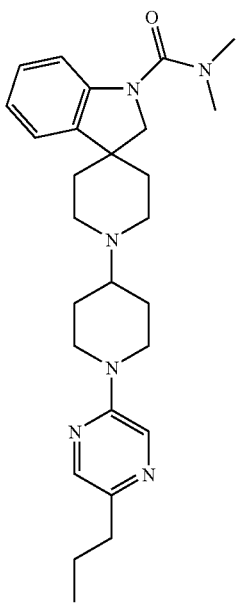 459
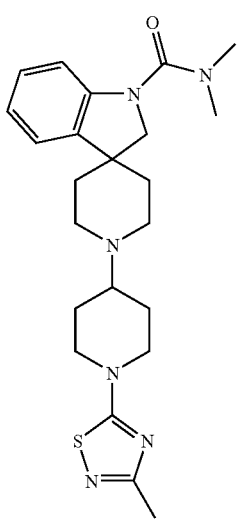 458
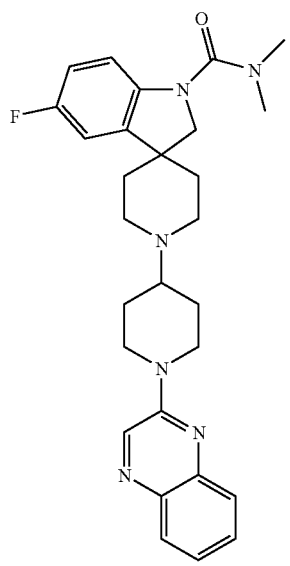 460

TABLE 1-continued
Exemplary compounds of formulae I and II.
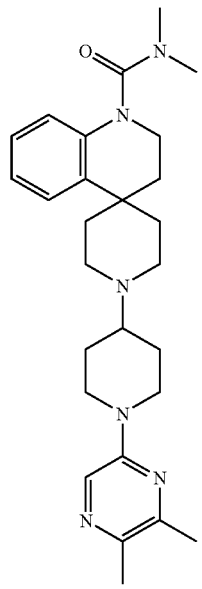
461
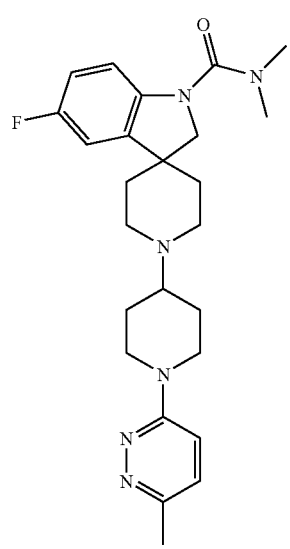
462
TABLE 1-continued
Exemplary compounds of formulae I and II.
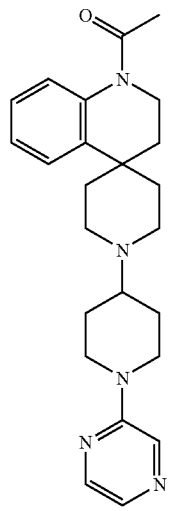
463
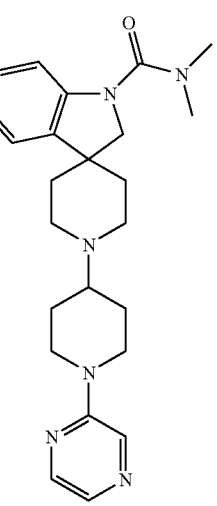
464
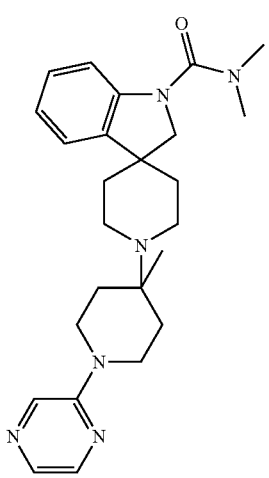
465

TABLE 1-continued
Exemplary compounds of formulae I and II.
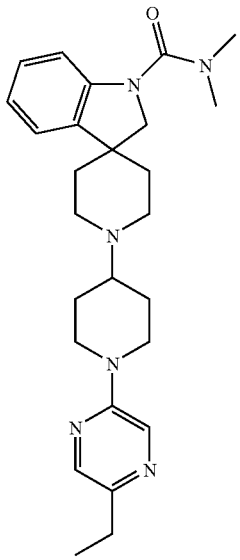
466
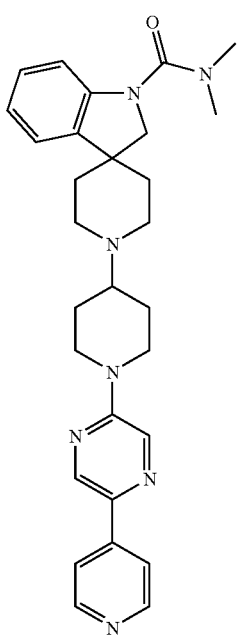
467
TABLE 1-continued
Exemplary compounds of formulae I and II.
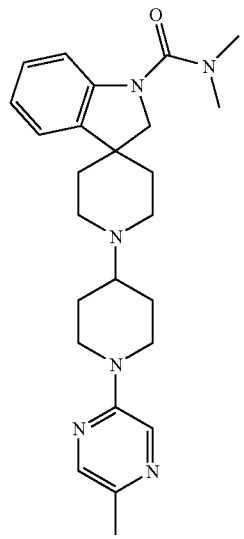
468
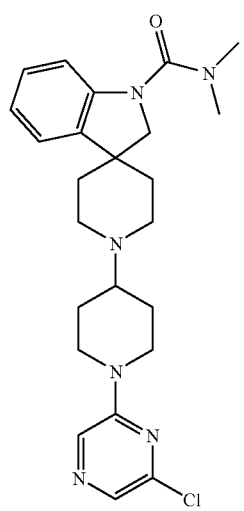
469
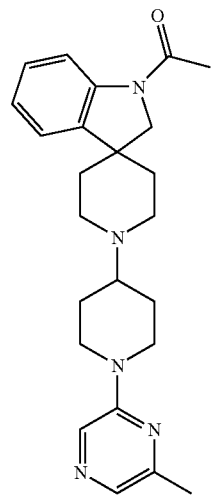
470

TABLE 1-continued
Exemplary compounds of formulae I and II.
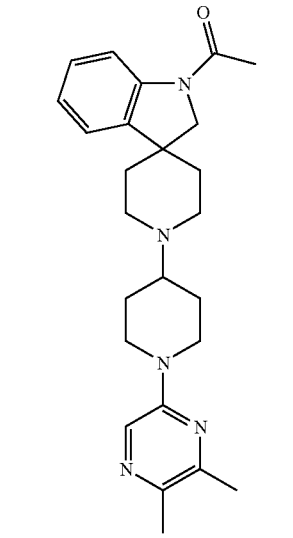
471
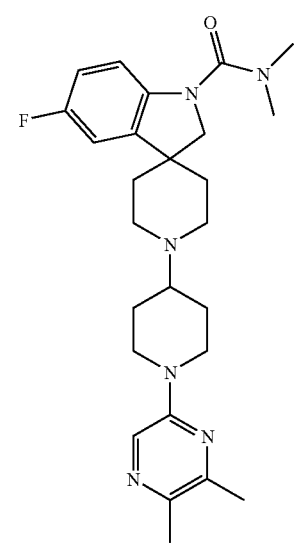
472
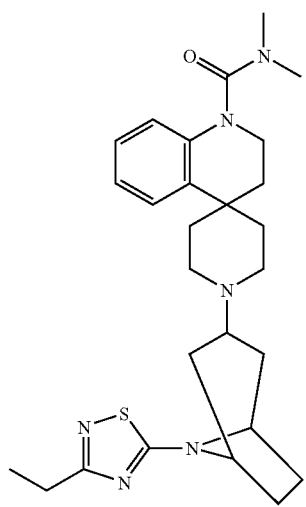
473
TABLE 1-continued
Exemplary compounds of formulae I and II.
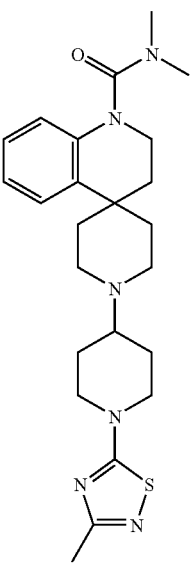
474
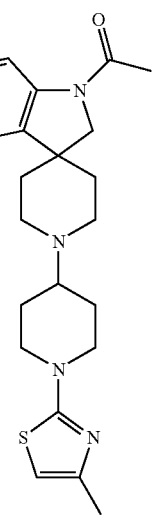
475

TABLE 1-continued

Exemplary compounds of formulae I and II.

TABLE 1-continued
Exemplary compounds of formulae I and II.
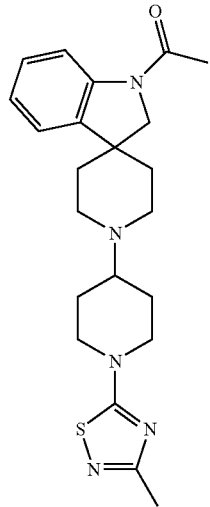
482
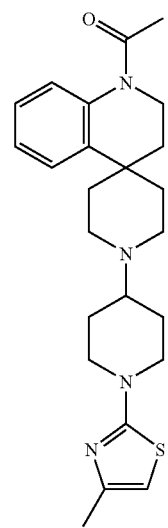
483
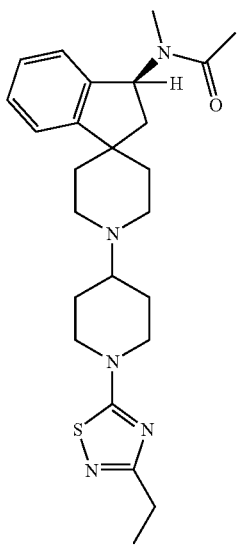
484
TABLE 1-continued
Exemplary compounds of formulae I and II.
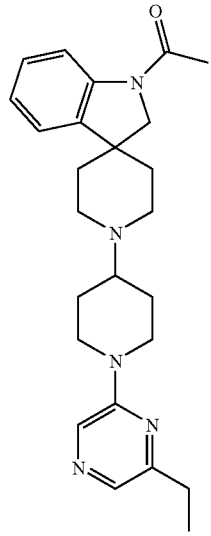
485
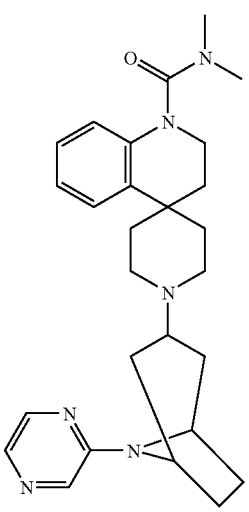
486
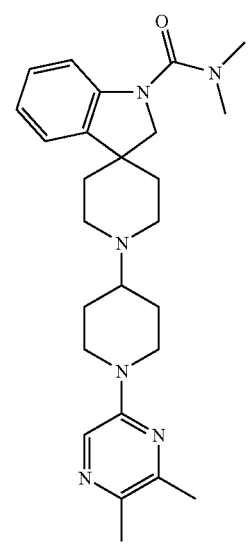
487

TABLE 1-continued
Exemplary compounds of formulae I and II.
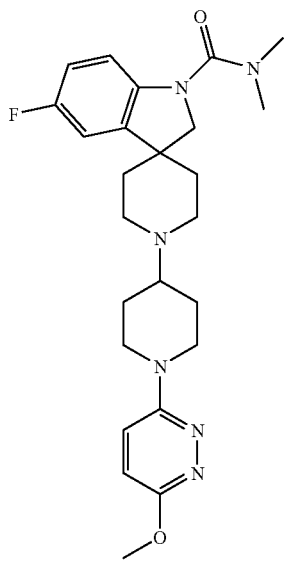
488
490
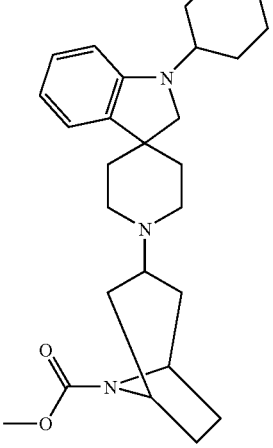
491
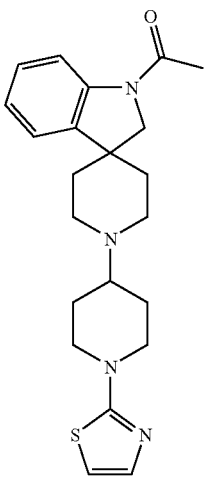
489
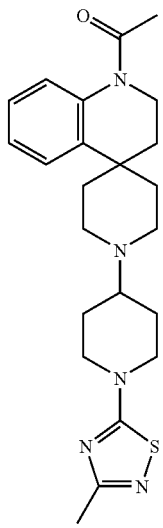
492

TABLE 1-continued
Exemplary compounds of formulae I and II.
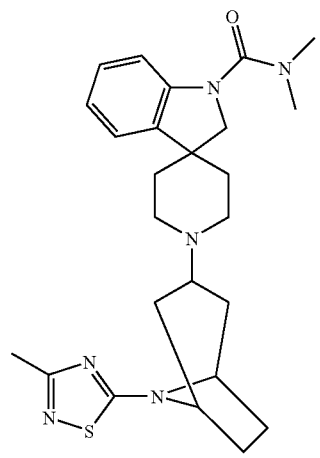
493
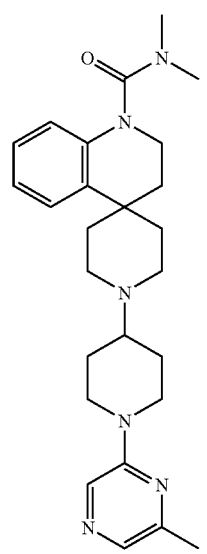
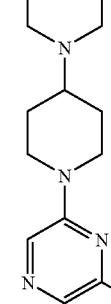
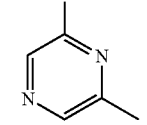
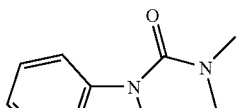
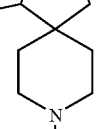
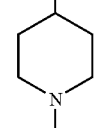
494
495
TABLE 1-continued
Exemplary compounds of formulae I and II.
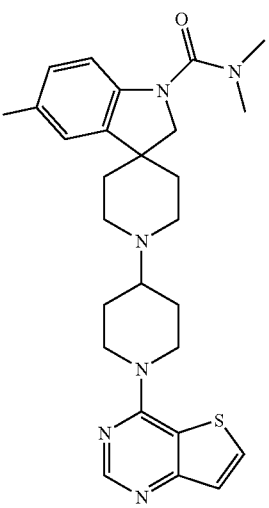
496
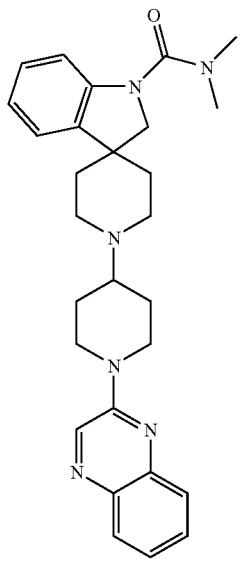
497

TABLE 1-continued
Exemplary compounds of formulae I and II.
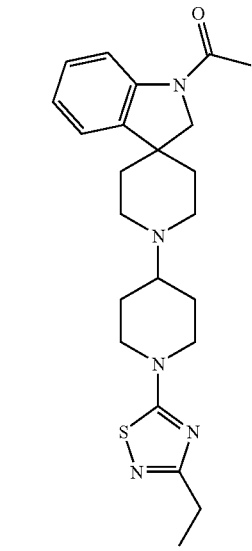 498
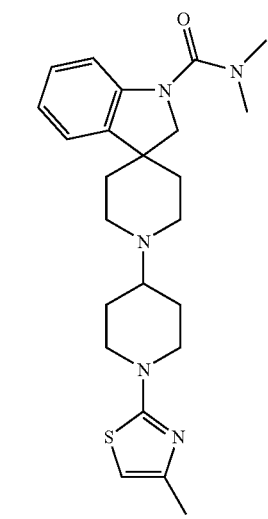 499
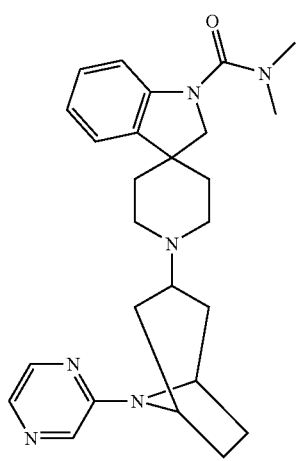 500
TABLE 1-continued
Exemplary compounds of formulae I and II.
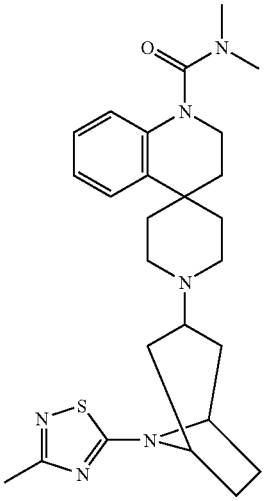 501
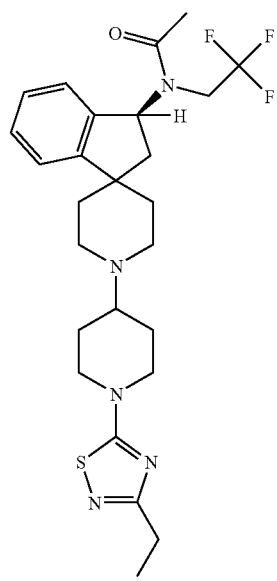 502
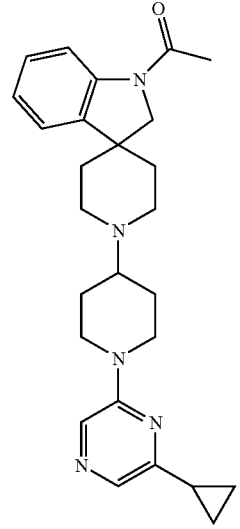 503

TABLE 1-continued
Exemplary compounds of formulae I and II.
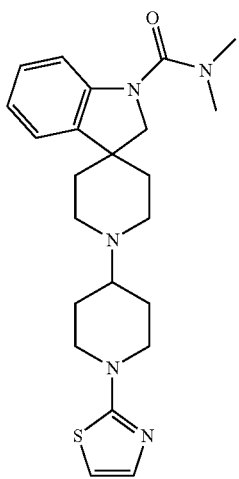 504
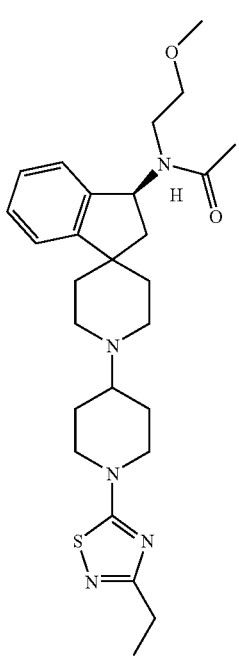 505
TABLE 1-continued
Exemplary compounds of formulae I and II.
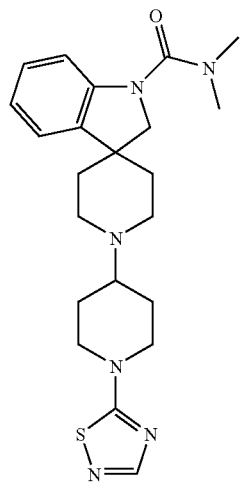 506
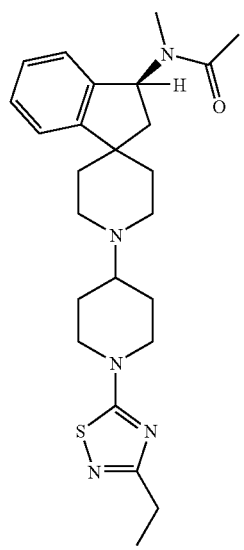 507
508

TABLE 1-continued

Exemplary compounds of formulae I and II.

509

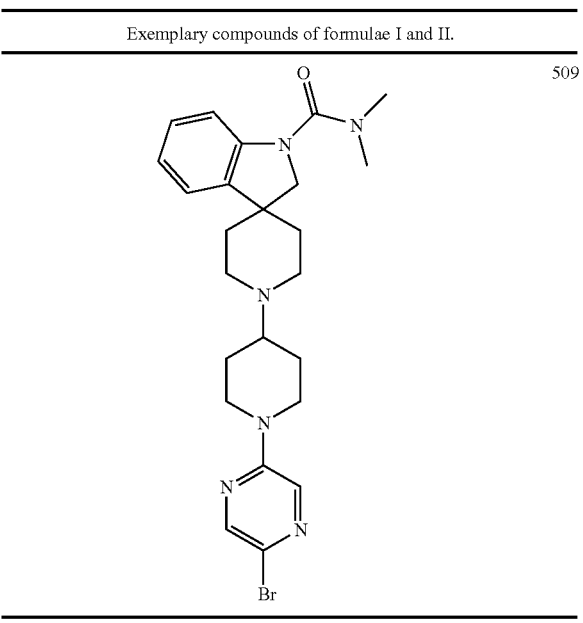

IV. Synthetic Schemes

The compounds of formulae (I and II) may be readily synthesized from commercially available starting materials using methods known in the art. Exemplary synthetic routes to produce compounds of formulae (I and II), are provided below in Preparations A-F and Schemes 1-10. For simplicity of illustration, schemes 1-10 depict only a single $R_1$ substituent on the fused phenyl ring of formulae I and II, the compounds of this invention may include 1 to 4 $R_1$ substituents on the fused phenyl ring.

Scheme 1 below depicts general conditions for the synthesis of compounds of formula (I).

Scheme 1:

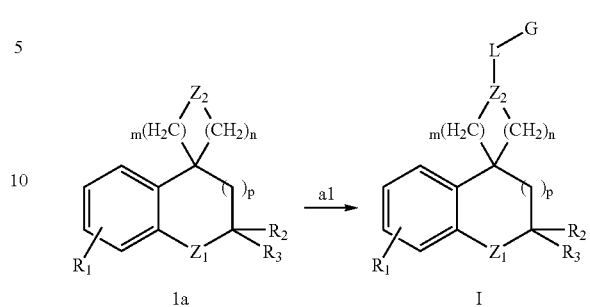

The reaction of amine (1a) with an appropriate aldehyde or ketone under reductive amination conditions (step a1), typically using $NaBH(OAc)_3$ in DCE/AcOH/TEA at room temperature, may be used to provide the desired compounds of formula I. For less reactive ketones, more forcing conditions may be used. For example, the treatment of the amine (1a) and the ketone in a neat solution of $Ti(OiPr)_4$, followed by treatment with $NaBH_4$ in MeOH, may be used to provide the desired compounds of formula I. See Abdel-Magid, A. F. et al., "Reductive Amination of Aldehydes and Ketones with Sodium Triacetoxyborohydride. Studies on Direct and Indirect Reductive Amination Procedures," J. Org. Chem., 61, pp. 3849-3862 (1996) and the references sited therein.

Alternatively, the spiroamine of type 1a may be alkylated with an alkyl halide in the presence of an appropriate base to provide the desired compounds of formula I. Typically, the amine (1a) is reacted with an alkyl iodide, bromide, or chloride in the presence of an appropriate base to yield compounds of formula I. Bases may be organic such as triethylamine, or inorganic such as $Na_2CO_3$ or $Cs_2CO_3$. Typical reaction solvents include but are not limited to DMF, acetone, and acetonitrile.

Scheme 2 illustrates alternative conditions for the synthesis of compounds of formula I in which $Z_1$ is —C(H)$_2$— and $R_2$ and $R_3$ are hydrogen (Synthetic route a2), or in which $Z_1$ is —C(O)— (Synthetic route b2).

Scheme 2:

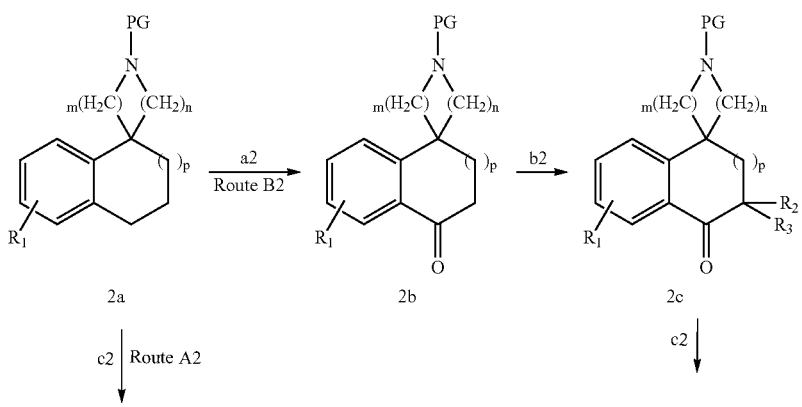

-continued

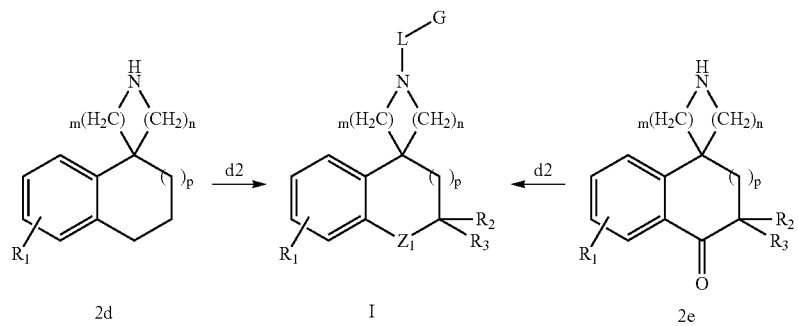

Compounds of type 2a in Scheme 2 may be prepared using procedures as described in Evans, B. E, et al., J. Med. Chem. 1992, 35, 3919 and M. S. Chambers J. Med. Chem. 1992, 35, 2033. Intermediate compounds may be produced from compound of type 2a using the following conditions: (a2) KMnO$_4$ oxidation, TBAB, aqueous KOH; (b2) NaH, X—R$_2$ and/or X—R$_3$, where X=halo, and THF; (c2) Ammonium formate, MeOH, Pd/C, room temperature or heat; or Pd/C, MeOH, H$_2$; or if PG=Boc, then TFA, CH$_2$Cl$_2$, −10° C.; (d2) NaBH(OAC)$_3$, DCE, AcOH, TEA, appropriate ketone or aldehyde; or i.) neat Ti(OiPr)$_4$, appropriate ketone followed by ii.) NaBH$_4$, MeOH; or the appropriate alkyl halide, Cs$_2$CO$_3$, acetonitrile, heat.

Scheme 3 illustrates alternative conditions for the synthesis of compounds of formula I in which Z$_1$ is —O— and R$_2$ and R$_3$ are hydrogen.

Scheme 3:

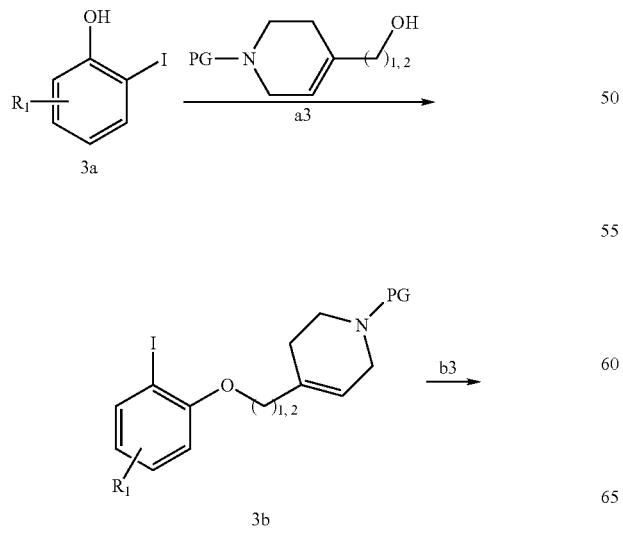

-continued

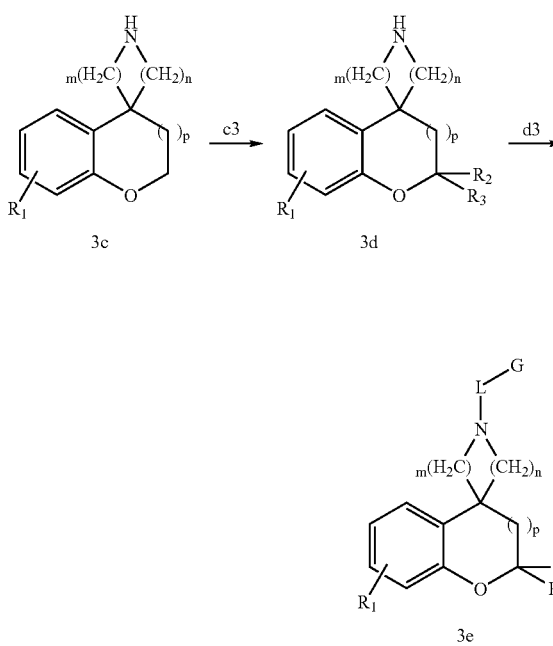

Amines of type 3d were prepared using procedures analogous to those found in the following references: WO 96/11934 "Tricyclic spiro compounds process for their preparation" and US006013652A "Spiro-substituted azacyclics as neurokinin antagonists". Conditions: (a3) Ph$_3$P/DEAD; (b3) Bu$_3$SnH, AIBN; (c3) Ammonium formate, MeOH, Pd/C, room temperature or heat; or Pd/C, MeOH, H$_2$; or if PG=Boc, then TFA, CH$_2$Cl$_2$, −10° C.; (d3) NaBH(OAc)$_3$, DCE, AcOH, TEA, appropriate ketone or aldehyde; or i.) neat Ti(OiPr)$_4$, appropriate ketone followed by ii.) NaBH$_4$, MeOH; or the appropriate alkyl halide, Cs$_2$CO$_3$, acetonitrile, and/or heat.

Scheme 4 illustrates alternative conditions for the synthesis of compounds of formula I in which Z$_1$ is —N(Q$_1$)- and R$_2$ and R$_3$ are hydrogen.

Scheme 4:

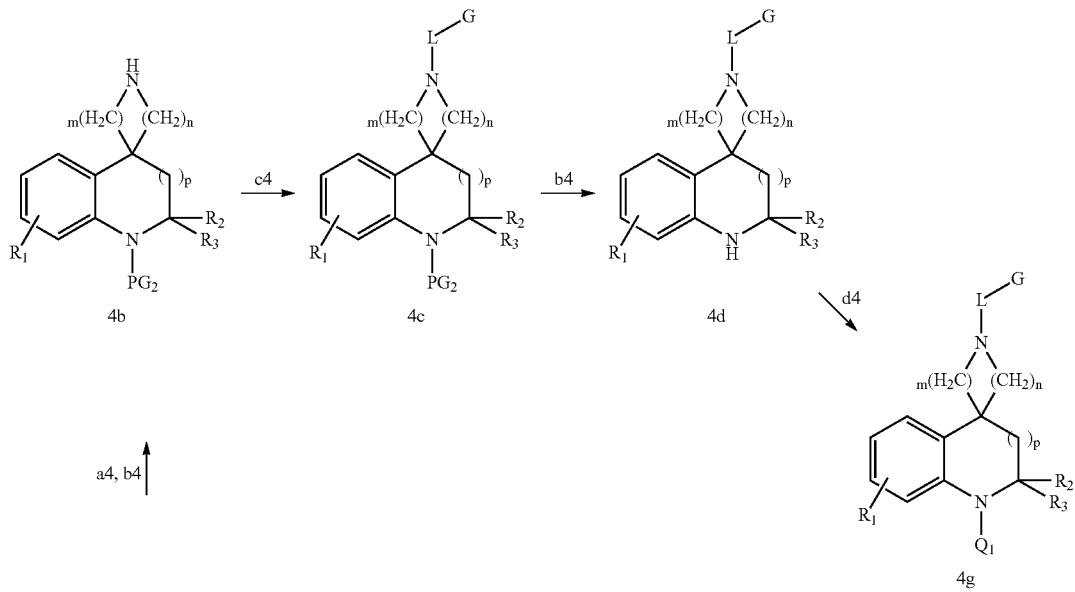

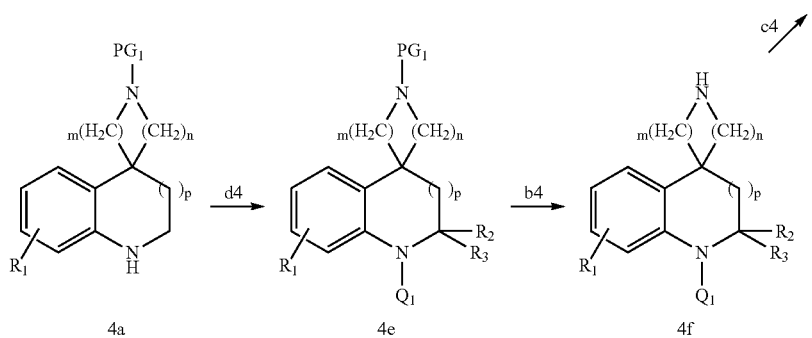

Amines of type 4a in Scheme 4 may be prepared from methods known in the art and by using procedures analogous to those found in the following references: WO 03/106457 "Spiroindolinepiperidine Derivatives"; Maligres, P. E., et al., Tetrahedron, 1997, 53, 10983-10992; Cheng, Y. and Chapman, K. T., Tet. Lett. 1997, 38, 1497-1500; US006013652A "Spiro-substituted azacyclics as neurokinin antagonists". Conditions: (a4) amine protection orthogonal to $PG_1$; (b4) amine deprotection of $PG_1$ (e.g. $PG_1$=Boc: TFA, $CH_2Cl_2$, −10° C.); (c4) $NaBH(OAc)_3$, DCE, AcOH, TEA, appropriate ketone or aldehyde; or i.) neat $Ti(OiPr)_4$, appropriate ketone followed by ii.) $NaBH_4$, MeOH; or the appropriate alkyl halide, $Cs_2CO_3$, acetonitrile, heat; (d4) $Q_2X$ ($Q_2$ may be, for example, H and aliphatic, X is halogen), $K_2CO_3$, DMF/THF, room temperature to 60° C.; or electrophile (e.g. $RSO_2Cl$, RCOCl, ROC(=O)Cl, where R is H or $Q_2$, TEA, $CH_3CN$.

Scheme 5:

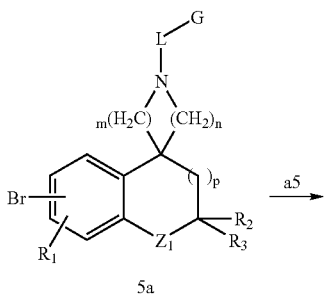

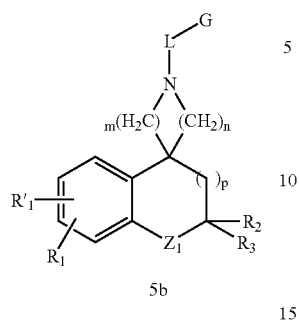

5b

Reaction of 5a with intermediate under palladium cross coupling conditions (step a5) Pd(dppf)Cl2 or (Ph₃P)₄Pd, 2M K₂CO₃, and acetonitrile under microwave irradiation at 150° C. for 10-20 minutes yields compound 5b. Unsaturated compounds of type 5b may be further elaborated (e.g. reduction; oxidation) to provide additional compounds of formula (I).

Scheme 6 illustrates alternative conditions for the synthesis of compounds of formula I in which $Z_1$ is —N(Q₁)- or —N(Q₂)-, $R_2$ and $R_3$ together form oxo, and p=1.

Scheme 6:

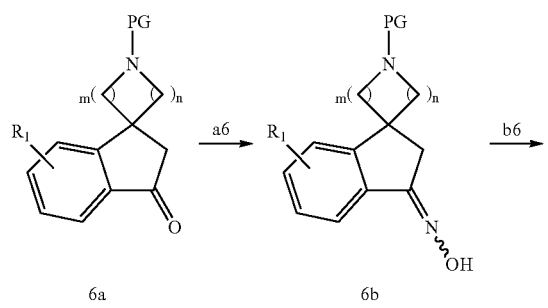

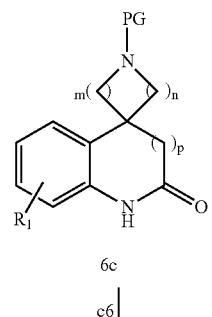

6c

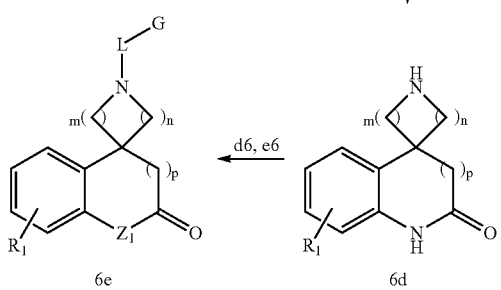

Compound 6a may be produced by methods disclosed above and by those known in the art. Intermediate compounds may be produced from compounds of type 6a using the following conditions: (a6) NH₂OH, HCl; (b6) 2,4,6-trichloro-1,3,5-triazine; (c6) PG=Bn or Cbz; ammonium formate, MeOH, Pd/C, room temperature; or Pd/C, MeOH, H₂; (d6) NaBH(OAc)₃, DCE, AcOH, TEA, appropriate ketone or aldehyde; or i.) neat Ti(OiPr)₄, appropriate ketone followed by ii.) NaBH₄, MeOH; or the appropriate alkyl halide, Cs₂CO₃, acetonitrile, heat; (e6) optional alkylation, NaH, THF, appropriate alkyl halide.

Scheme 7 illustrates alternative conditions for the synthesis of compounds of formula I in which $Z_1$ is —CH(Q₁)- and $R_2$ and $R_3$ are hydrogen.

Scheme 7:

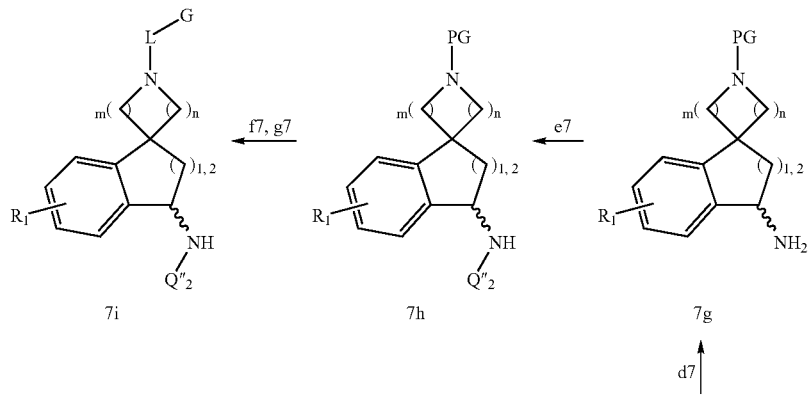

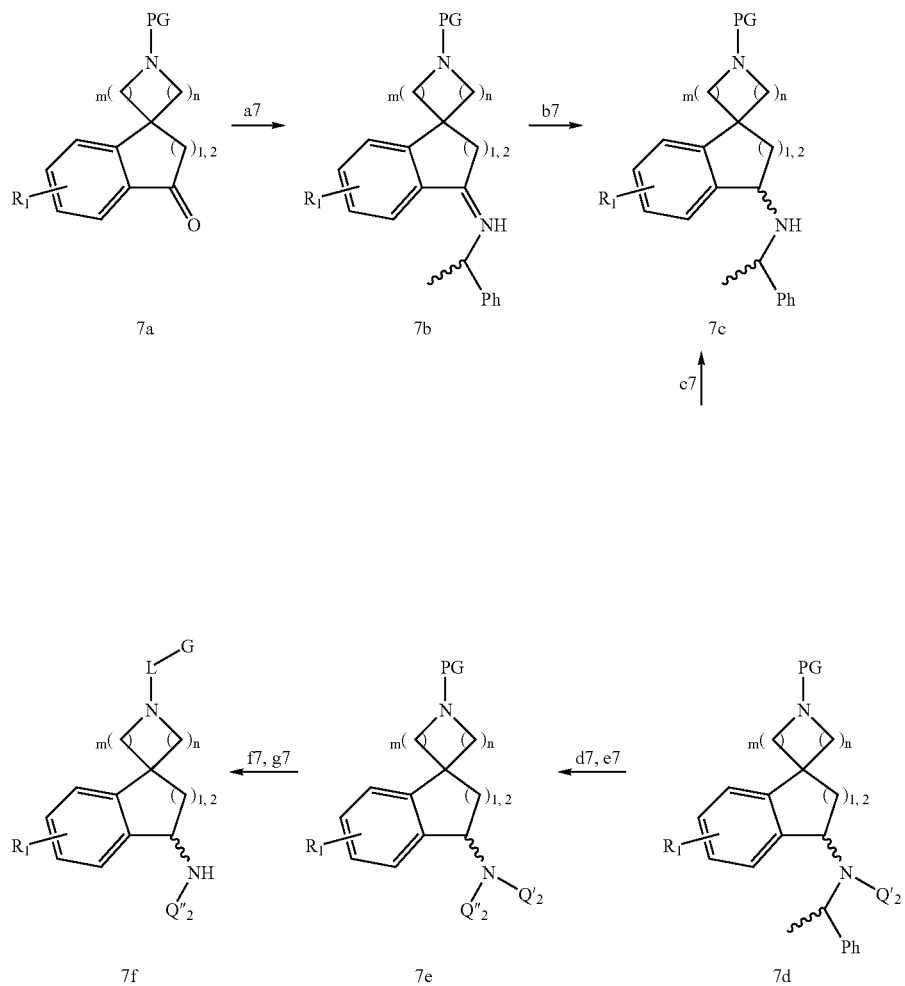

Compound 7a may be produced by methods disclosed above and by those known in the art. Compounds 7b through 7i may be produced from compound 7a using the following conditions: (a7) ZnCl$_2$ or other Lewis acid, (R)- or (S)-1-phenylethanamine, PhCH$_3$ reflux, Dean-Stark; (b7) NaBH$_4$, MeOH, −30° C.; (c7) Q$_2$'X, where Q$_2$' may be, for example, H or aliphatic, and X is halogen, K$_2$CO$_3$, DMF/THF, room temperature to 60° C. (d7) ammonium formate, MeOH, Pd/C, room temperature; or Pd/C, MeOH, H$_2$; (e) electrophile (e.g. RSO$_2$Cl, RCOCl, ROC(=O)Cl, where R is H or alkyl, and Q$_2$" is RSO$_2$—, RC(O)—, ROC(O)—, TEA, CH$_3$CN; (f7) PG=Boc: TFA, CH$_2$Cl$_2$, −10° C.; (g7) NaBH(OAc)$_3$, DCE, AcOH, TEA, appropriate ketone or aldehyde; or i.) neat Ti(O-iPr)$_4$, appropriate ketone followed by ii.) NaBH$_4$, MeOH; or the appropriate alkyl halide, Cs$_2$CO$_3$, acetonitrile, heat.

Scheme 8 illustrates alternative conditions as example for the synthesis of compounds of formula I in which ring G contains or is substituted with a protected functionality which may be either be retained, deprotected and retained, or deprotected and further elaborated to produce additional compounds of formula I.

Scheme 8:

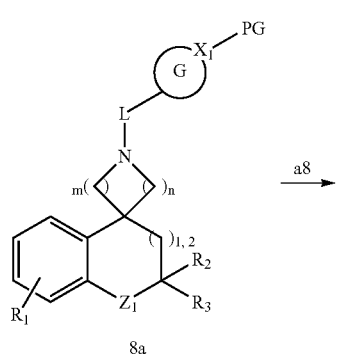

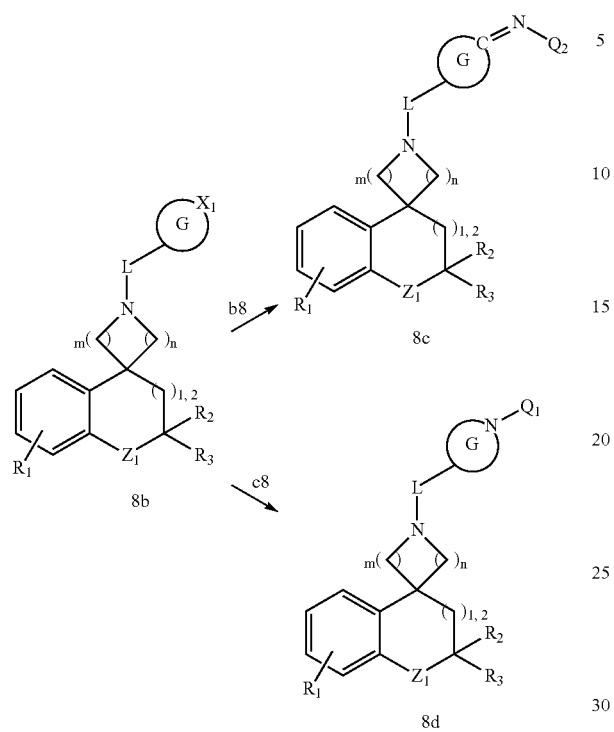

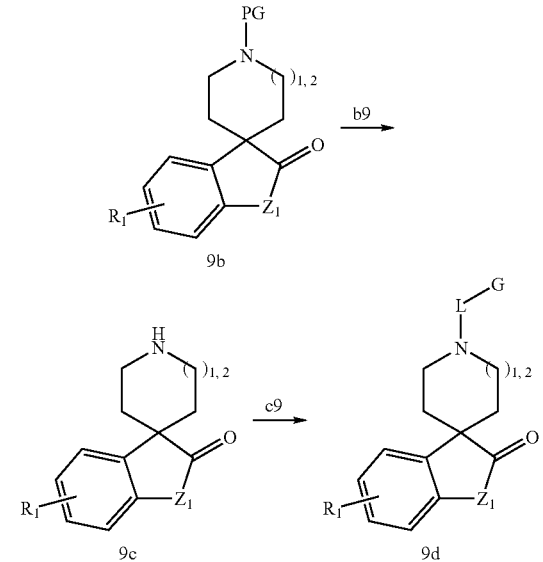

Compound 8a may be produced by methods disclosed above and by those known in the art. Compounds 8b through 8d may be produced from compound 8a using the following conditions: (a8) e.g. PG=ketal: AcOH/H$_2$O, heat; PG=Boc: TFA, CH$_2$Cl$_2$; (b8) e.g. if ring G is substituted by oxo, the compound of formula I may be further elaborated to the oxime: NH$_2$—O-Q$_2$, pyridine; (c8) e.g. if ring G contains or is substituted by —NH— or —N(Q$_2$)-, it may be elaborated with an appropriate electrophile to produce 8d.

Scheme 9 illustrates alternative conditions for the synthesis of compounds of formula I in which Z$_1$ is —N(Q$_1$)- or —N(Q$_2$)-, and R$_2$ and R$_3$ are oxo, and p=0.

Scheme 9:

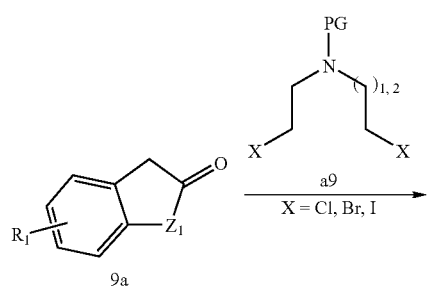

Compounds of type 9a may be purchased commercially or produced by methods known in the art. Conditions: (a9) NaH/HMDS/THF; (b9) e.g. PG=Bn: Pd(OH)$_2$; (c9) NaBH(OAc)$_3$, DCE, AcOH, TEA, appropriate ketone or aldehyde; or i.) neat Ti(OiPr)$_4$, appropriate ketone followed by ii.) NaBH$_4$, MeOH; or the appropriate alkyl halide, Cs$_2$CO$_3$, acetonitrile, heat.

Scheme 10 outlines the general preparation of the appropriate aldehydes from the corresponding ketone.

Scheme 10:

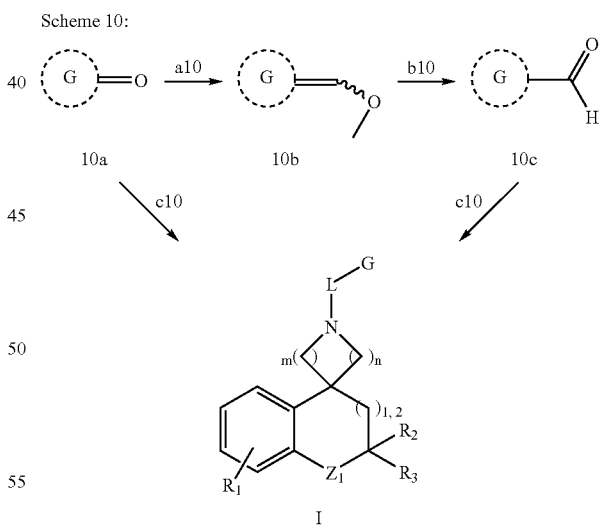

Ketone electrophiles of type 10a may be purchased commercially or produced by methods disclosed above and by those known in the art. Aldehydes of type 10c may be purchased commercially or produced from compounds of type 10a using the following conditions: (a10) Ph$_3$P$^+$CH$_2$OMeCl$^-$, NaN(SiMe$_3$)$_2$; (b10) aqueous HCl, CH$_3$CN. The following conditions may be used for the synthesis of compounds of formula I using ketones of type 10a and aldehydes of type 10c: (c10) spiro-amine of type 1a (see Scheme 1), NaBH(OAc)$_3$, DCE, AcOH, TEA, appropriate ketone or aldehyde; or i.) neat Ti(OiPr)$_4$, appropriate ketone followed by ii.) NaBH$_4$, MeOH.

V. Formulations, Administrations, and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N$^+$(C$_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I and II) are selective modulators of $M_1$, $M_2$ and $M_4$. More preferably, the compounds of formulae (I and II) are selective modulators of $M_1$ and/or $M_4$. Yet more preferably, certain compounds of formulae (I and II) are selective modulators of $M_1$. Or, preferably, certain compounds of formulae (I and II) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae I and II, or an embodiment thereof as set forth herein.

According to another embodiment, the present invention provides a method of treating a disease mediated by a muscarinic receptor including the step of administering to said mammal a composition comprising a compound of formulae (I and II), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, or GI disturbances.

According to a preferred embodiment, the present invention is useful for treating or reducing the severity of psychosis, Alzheimer's disease, pain, or Parkinson's disease.

All references cited within this document are incorporated herein by reference.

VII. Preparations and Examples

In order that the invention described herein may be more fully understood, the following examples are set forth. It should be understood that these examples are for illustrative purposes only and are not to be construed as limiting this invention in any manner.

Preparation A: Synthesis of N-(ethoxycarbonyl)-8-aza-bicyclo[3.2.1]octane-3-carbaldehyde (A3)

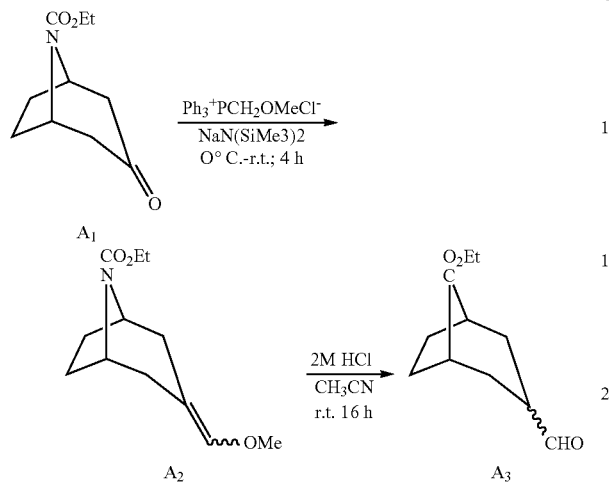

Sodium bis(trimethylsilyl)amide (6 mmol, 6 mL of 1 M solution in THF) was added to a suspension of 2.06 g (6.0 mmol) of methoxymethyltriphenylphosphonium chloride in 6 mL of THF at 0° C. under argon. After stirring at 0° C. for 15 min, the resulting dark red solution was added via syringe to a solution of 0.79 g (4.0 mmol) of N-(ethoxycarbonyl) tropinone (A1) in 8 mL of THF at 0° C. and then stirred at room temperature for 4 h (an orange color persisted). The reaction mixture was quenched by adding saturated aqueous NaCl (15 mL) and then extracted with ether (25 mL×3). The combined organic extracts were dried over $Na_2SO_4$. The solid residue obtained after solvent evaporation was loaded onto a short silica gel column (3.5 cm×4 cm) to remove the phosphorous impurities. The product was eluted with ether. After the solvent was evaporated, the product enol ether (A2) was obtained as a brown oil which was used in the next step without further purification.

The enol ether intermediate (A2) was dissolved in a solution of 12 mL of 2 N HCl and 20 mL of acetonitrile, and stirred at room temperature for 16 h. After removing the acetonitrile on a rotary evaporator, the aqueous solution was extracted with ether (25 mL×3). The combined organic extracts were washed with saturated aqueous $NaHCO_3$ (15 mL×2), saturated aqueous NaCl (15 mL) and then dried over $Na_2SO_4$. After the solution was evaporated to dryness, the residue was purified by chromatography ($SiO_2$, 10%-20% EtOAc in hexane as eluent). N-(ethoxycarbonyl)-8-aza-bicyclo[3.2.1]octane-3-carbaldehyde (A3) (0.65 g) was obtained as a colorless oil in an approximately 1:1 ratio of endo and exo isomers. ESI-MS m/z 212.1 (MH$^+$); $^1$H NMR (300 MHz, CDCl$_3$) δ 9.53 (s, 1H), 4.54 (br s, 1H), 4.38 (br s, 1H), 4.16 (m, 2H), 2.72 (m, 2H), 2.38 (s, 1H), 2.32 (s, 1H), 2.10 (m, 3H), 1.69 (m, 2H), 1.29 (m, 3H).

Preparation B: Synthesis of bicyclo[3.2.1]octane-2-carbaldehyde

Bicyclo[3.2.1]octane-2-carbaldehyde was prepared using an analogous procedure as for Intermediate 1 from commercially available bicyclo[3.2.1]octan-2-one. The crude products were used in the next step without further purification.

Preparation C: Synthesis of 7-oxa-bicyclo[2.2.1]hept-5-ene-2-carbaldehyde (C4)

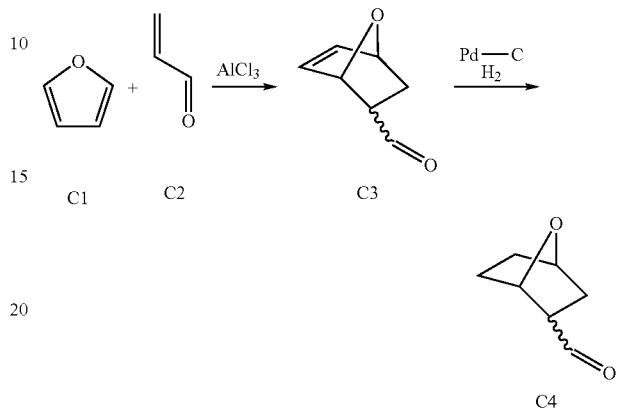

To a stirred solution of furan (C1) (15 mL, 200 mmol) and acrolein (C2) (6.7 mL, 100 mmol) in DCM (25 mL) was slowly added AlCl$_3$ (666 mg, 5 mmol) under argon at −43° C. (dry ice/isopropanol bath). The reaction mixture was stirred at −43° C. under argon for 30 min, and then quenched with saturated aqueous $K_2CO_3$ (50 mL). After the reaction mixture was gradually warmed to room temperature, it was extracted with ether (200 mL×5). The combined ether extracts were washed with saturated aqueous $K_2CO_3$ (200 mL×2) and saturated aqueous NaCl (200 mL×2), dried over MgSO$_4$, filtered, and concentrated to give 2.6 g of oily crude product 7-oxa-bicyclo[2.2.1]hept-5-ene-2-carbaldehyde (C3) which was used in the next step without further purification. See references Laszlo, P.; Lucchetti, J. Tetrahedron Lett. 1984, 25, 4387-4388. Moore, J. A., Partain, E. M. III. J. Org. Chem. 1983, 48, 1105-1106. Dauben, W. G.; Krabbenhoft, H. O. J. Am. Chem. Soc. 1976, 98, 1992-1993. Nelson, W. L.; Allen, D. R.; Vincenzi, F. F. J. Med. Chem. 1971, 14, 698-702.

To a stirred solution of crude product 7-oxa-bicyclo[2.2.1]hept-5-ene-2-carbaldehyde (C3) (2.6 g. 20 mmol) in 95% EtOH (200 mL) was added 10% Pd—C (0.25 g) at room temperature under argon. The mixture was shaken on a Parr hydrogenation apparatus for 4 h at room temperature under 30 psi of hydrogen. After the Pd catalyst was removed by filtration through a Celite pad, the Celite was washed with MeOH (15 mL×2), the combined extracts were concentrated under vacuum to yield 2.5 g of crude 7-oxa-bicyclo[2.2.1]hept-5-ene-2-carbaldehyde (C4) as a pale yellow oil, which was used in the next step without further purification.

Preparation D: Synthesis of ethyl 4-formylpiperidine-1-carboxylate (D3)

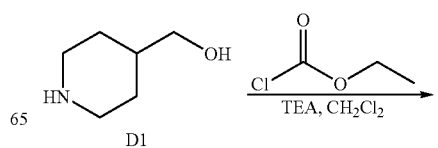

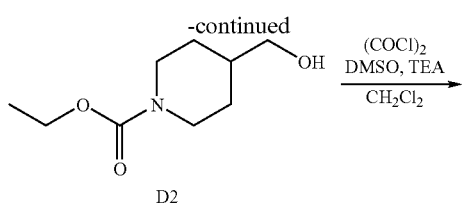

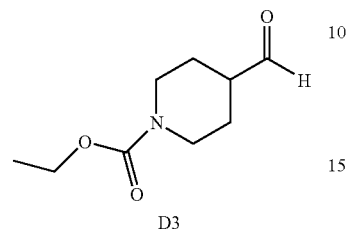

1.0 eq 4-piperidinemethanol (D1) (10.00 g, 86.8 mmol) was dissolved in dichloromethane (350 mL), cooled in an ice water bath and treated dropwise with a solution of 1.05 eq ethyl chloroformate (9.89 g, 91.1 mmol) in dichloromethane (50 mL), followed by the dropwise addition of a solution of 1.0 eq triethylamine (8.78 g) in dichloromethane (50 mL). The reaction was stirred at ~0° C. for 15 minutes, then at room temperature for 10 min. The reaction was diluted with dichloromethane (250 mL) and washed successively with (150 mL each) $H_2O$, 0.1 N HCl (aqueous) (×2), saturated brine, then dried ($Na_2SO_4$) and filtered. The filtrate was concentrated in vacuo to afford 15.60 g ethyl 4-(hydroxymethyl)-piperidine-1-carboxylate (D2) as a viscous, pale bluish-green oil. $^1$H-NMR (400 MHz, $CDCl_3$) δ4.15 (br m, 2H), 4.09 (q, J=7.1 Hz, 2H), 3.46 (d, J=6.4 Hz, 2H), 2.72 (br t, J=12.4 Hz, 2H), 2.07 (s, 1H), 1.70 (m, 2H), 1.63 (m, 1H), 1.23 (t, J=7.2 Hz, 3H), 1.12 (m, 2H); $t_R$=1.56 min [10-99% $CH_3CN$ gradient over 5 mins with 0.1% TFA (aq)]; Theoretical $(M+H)^+$ m/z for $C_9H_{17}NO_3$=188.1; Found 188.0.

A solution of 1.2 eq oxalyl chloride (12.69 g, 0.10 mol) in dichloromethane (150 mL) was cooled to approximately −78° C. and treated dropwise, under nitrogen, with a solution of 2.4 equivalents anhydrous dimethylsulfoxide (15.63 g, 0.20 mol) in dichloromethane (50 mL). 15 min. after the addition was complete, a solution of 1.0 equivalent ethyl 4-(hydroxymethyl)-piperidine-1-carboxylate (D2) (15.60 g, 83.3 mmol) in dichloromethane (50 mL) was added dropwise. 30 minutes after the addition was complete, a solution of 3.0 eq triethylamine (25.30 g, 0.25 mol) in dichloromethane (50 mL) was added dropwise and the reaction warmed to room temperature. The reaction was stirred at room temperature for 1 h, then quenched with saturated sodium bicarbonate (500 mL). The layers were separated and the aqueous layer extracted once with dichloromethane (200 mL). The pooled organic layers were washed with $H_2O$ (3×100 mL), saturated sodium bicarbonate (1×100 mL) and saturated brine, then dried ($Na_2SO_4$) and filtered. The filtrate was concentrated in vacuo to afford 13.84 g ethyl 4-formylpiperidine-1-carboxylate (D3) as a viscous amber oil. $^1$H-NMR (400 MHz, $CDCl_3$) δ 9.64 (s, 1H), 4.10 (q, J=7.2 Hz, 2H), 4.00 (br m, 2H), 2.97 (m, 2H), 2.40 (m, 1H), 1.87 (br m, 2H), 1.54 (m, 2H), 1.23 (t, J=7.0 Hz, 3H).

Preparation E: Synthesis of ethyl 4-formyl-4-methylpiperidine-1-carboxylate (E6)

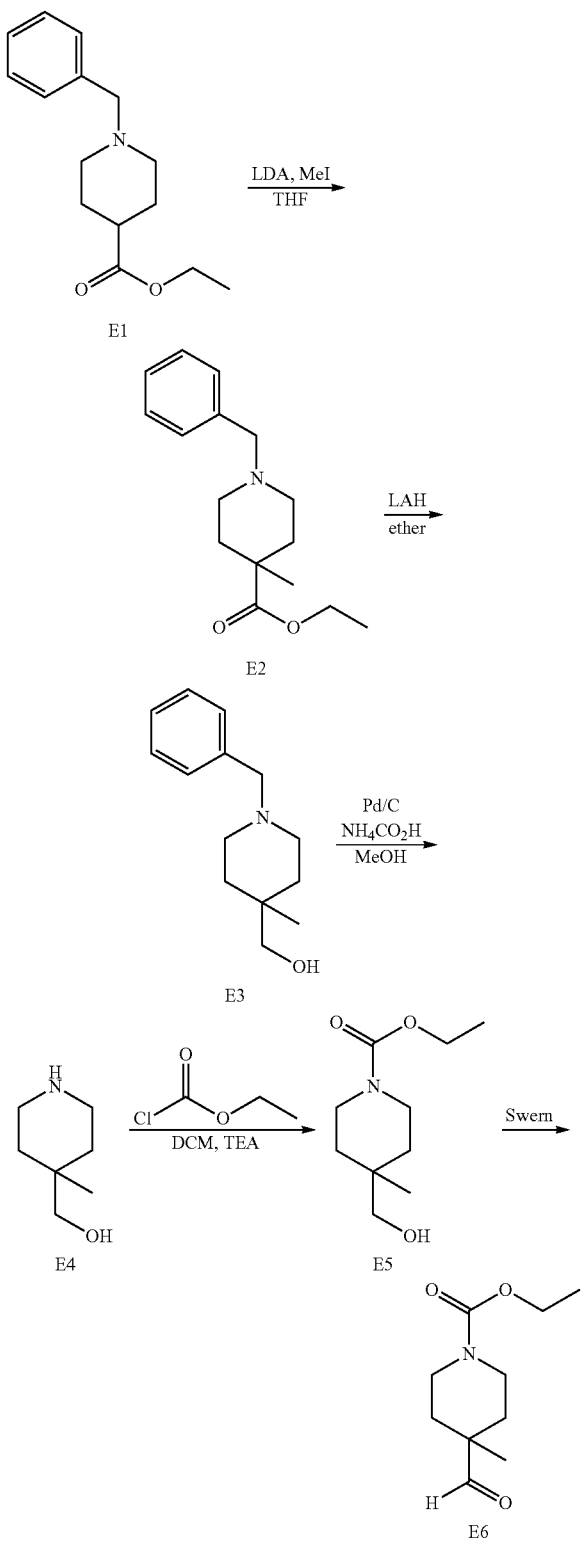

Diisopropylamine (3.14 mL; 22.23 mmol; 1.1 eq.) was dissolved in THF (60 mL) and cooled to −78° C. Butyl lithium (2.5 M in hexane; 8.89 mL; 22.23 mmol; 1.1 eq.) was then added and the solution was stirred for 30 minutes at −78° C. Ethyl 1-benzylpiperidine-4-carboxylate (E1) (5 g; 20.21 mmol; 1 eq.) was dissolved in THF (40 mL) and added to the LDA solution at −78° C. The solution was stirred at −78° C. for 30 min and iodomethane (1.32 mL; 21.22 mmol; 1.05 eq.) was added. The solution was slowly warmed to room temperature and stirred at room temperature for 1 h. Water (100 mL) was then added to the reaction followed by EtOAc (50 mL). The layers were separated and the aqueous layer was extracted with EtOAc (2×50 mL). The combined organic layers were dried over $Na_2SO_4$, filtered, and concentrated under reduced pressure to afford the product (E2) (5.0 g) as an oil. The product was analytically pure and used without further purification. LC/MS m/z (M+1) 262.0, Retention time 1.78 minutes; (10-99% $CH_3CN$—$H_2O$ gradient with 0.03% TFA, 5 min). $^1H$ NMR (400 MHz, $CDCl_3$) δ 7.24-7.14 (m, 5H), 4.08 (q, J=7.1 Hz, 2H), 3.40 (s, 2H), 2.60-2.57 (m, 2H), 2.08-2.02 (m, 4H), 1.47-1.40 (m, 2H), 1.17 (t, J=7.1 Hz, 3H), 1.10 (s, 3H).

1-Benzyl-4-methylpiperidine-4-carboxylate (E2) (5.0 g; 19.15 mmol) was dissolved in $Et_2O$ (50 mL) and cooled to 0° C. $LiAlH_4$ (1.0 g; 26.3 mmol) was slowly added portion-wise to the solution. After the addition was complete, the solution was slowly warmed to room temperature and stirred for 1 h. The solution was then cooled to 0° C. and slowly quenched with 1N NaOH (6 mL). The resultant white precipitate was filtered and washed with EtOAc (100 mL). The combined organic layers were concentrated under reduced pressure to provide the product (E3) (3.9 g) as an oil which was used without further purification. LC/MS m/z M+1 220.0, $t_R$ 0.64 minutes; (10-99% $CH_3CN$—$H_2O$ gradient with 0.03% TFA, 5 min). $^1H$ NMR (400 MHz, $CDCl_3$) δ 7.25-7.16 (m, 5H), 3.46 (s, 2H), 3.30 (d, J=3.9 Hz, 2H), 2.51-2.46 (m, 2H), 2.26-2.20 (m, 2H), 1.52-1.45 (m, 3H), 1.30-1.25 (m, 2H), 0.87 (s, 3H).

(1-benzyl-4-methylpiperidin-4-yl)methanol (E3) (3.9 g; 17.8 mmol) was dissolved in MeOH (50 mL) and $NH_4CO_2H$ (12.5 g; 178.0 mmol) was added. Pd/C (10% by weight, wet; 5.5 g) was then added and the system was flushed with nitrogen and then with hydrogen. The reaction was stirred at room temperature overnight (18 h) and then filtered through a pad of Celite. The solvent was removed under high vacuum to provide a solid that was a mixture of the amino alcohol and $NH_4CO_2H$. The crude product (E4) (2.4 g as a mixture with $NH_4COOH$) was used in the next step without further purification. LC/MS m/z (M+1) 130.0, retention time 0.35 min; (10-99% $CH_3CN$—$H_2O$ gradient with 0.03% TFA, 5 min). $^1H$ NMR (400 MHz, $CDCl_3$) δ 3.17 (s, 2H), 3.03-2.98 (m, 2H), 2.95-2.88 (m, 2H), 1.64-1.57 (m, 2H), 1.36-1.31 (m, 2H), 0.89 (s, 3H).

(4-methylpiperidin-4-yl)methanol (E4) (2.4 g, a mixture of the amino alcohol and $NH_4CO_2H$) was suspended in DCM (70 mL). $Et_3N$ (5 mL; 37.2 mmol) was then added followed by the drop-wise addition of ethyl chloroformate (1.05 mL, 13 mmol, 1.4 eq.). After 1 h at room temperature, 1N HCl (70 mL) was added and the layers were separated. The aqueous layer was extracted with DCM (70 mL) and the combined organic layers were dried over $Na_2SO_4$, filtered, and concentrated under high vacuum. The product (E5) (1.7 g) is obtained analytically pure as an oil and used without further purification. LC/MS m/z (M+1) 202.2, $t_R$ 1.89 minutes; (10-99% $CH_3CN$—$H_2O$ gradient with 0.03% TFA, 5 min). $^1H$ NMR (400 MHz, DMSO-$d_6$) δ 4.05 (q, J=7.1 Hz, 2H), 3.66 (dt, J=13.6, 4.7 Hz, 2H), 3.32 (s, 2H), 3.11 (t, J=5.2 Hz, 1H), 3.11 (dd, J=23.9, 3.5 Hz, 1H), 1.44-1.37 (m, 3H), 1.26-1.22 (m, 2H), 1.19 (t, J=7.1 Hz, 3H), 0.93 (s, 3H).

To a 100 mL round bottom flask was added DCM (30 mL) and oxalyl chloride (0.88 mL; 10.13 mmol). The solution was cooled to −78° C. and treated with DMSO (1.19 mL; 16.88 mmol). The solution was stirred at −78° C. for 20 minutes and then treated with ethyl 4-(hydroxymethyl)-4-methylpiperidine-1-carboxylate (E5) (1.7 g; 8.44 mmol, dissolved in 10 mL of DCM). The solution was stirred for 30 minutes at −78° C. and then treated with $Et_3N$ (3.53 mL; 25.32 mmol). The solution was stirred at −78° C. for 20 min and then slowly warmed to room temperature and stirred at room temperature for an additional 2 h. The solution was then treated with saturated aqueous $NaHCO_3$ (50 mL), diluted with DCM (50 mL), and the layers were separated. The organic layer was washed with brine (50 mL), dried over $Na_2SO_4$, filtered, and concentrated under reduced pressure to afford 1.6 g of the product (E6) as an oil which was used without further purification. LC/MS m/z (M+1) 200.0, $t_R$ 2.23 minutes; (10-99% $CH_3CN$—$H_2O$ gradient with 0.03% TFA, 5 min). $^1H$ NMR (400 MHz, $CDCl_3$) δ 9.40 (s, 1H), 4.06 (q, J=7.1 Hz, 2H), 3.66 (dt, J=13.6, 4.7 Hz, 2H), 3.09 (dd, J=10.1, 3.5 Hz, 1H), 3.06 (dd, J=10.2, 3.4 Hz, 1H), 1.86 (dt, J=13.6, 4.4 Hz, 2H), 1.42-1.30 (m, 2H), 1.19 (t, J=7.1 Hz, 3H), 1.02 (s, 3H).

Preparation F: Synthesis of benzyl 4-oxotropane-N-carboxylate (F3)

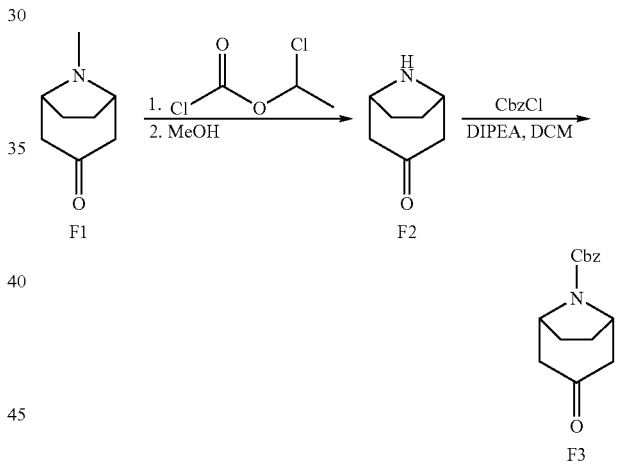

Tropinone (F1) (10.0 g; 71.84 mmol) was dissolved in DCE (60 mL) and treated drop-wise with 1-chloroethyl chloroformate ACE-Cl (14.5 mL; 19.11 g; 133.7 mmol). The reaction was allowed to stir at room temperature overnight and was then diluted with $Et_2O$ (400 mL) and filtered. The filtrate was concentrated under reduced pressure to provide the crude chloroethyl carbamate. This compound was taken in MeOH (200 mL) and stirred at room temperature for 1 h, then concentrated under reduced pressure (at 55° C.) to provide the crude des-methyltropinone (F3) as the HCl salt (tan solid, 11.4 g). The crude material was recrystallized from acetonitrile to furnish the pure product as a white crystalline solid (5 g). $^1H$ NMR (400 MHz, DMSO-d6) δ 1.79 (dd, J=15.0, 6.9 Hz, 2H), 2.09 (m, 2H), 2.40 (d, J=16.7 Hz, 2H), 3.02 (dd, J=17.1, 4.3 Hz, 2H), 4.23 (s, 2H), 10.00 (br s, 2H)

Des-methyl tropinone (5.10 g; 31.55 mmol) was dissolved in $CH_2Cl_2$ (50 mL) and treated with benzyl chloroformate (4.29 mL; 5.11 g; 29.98 mmol) DIPEA (16.48 mL; 12.23 g;

94.66 mmol) was added drop-wise (exothermic reaction). The resulting clear solution was allowed to stir at room temperature for 30 min and was subsequently diluted with 100 mL $CH_2Cl_2$. The organic phase was washed with 1 N HCl (2×100 mL), dried on $Na_2SO_4$ and concentrated to provide the crude product (7.2 g). $^1$H NMR (400 MHz, $CDCl_3$) δ 1.71 (dd, J=15.0, 7.2 Hz, 2H), 2.12 (m, 2H), 2.38 (d, J=15.9 Hz, 2H), 2.67 (m, 2H), 4.62 (s, 2H), 5.22 (s, 2H), 7.38 (m, 5H).

Example 1

1'-((1R,2R,4R)-bicyclo[2.2.1]hept-5-en-2-ylmethyl)spiro[indene-1,4'-piperidin]-3(2H)-one
(Cpd No. 237)

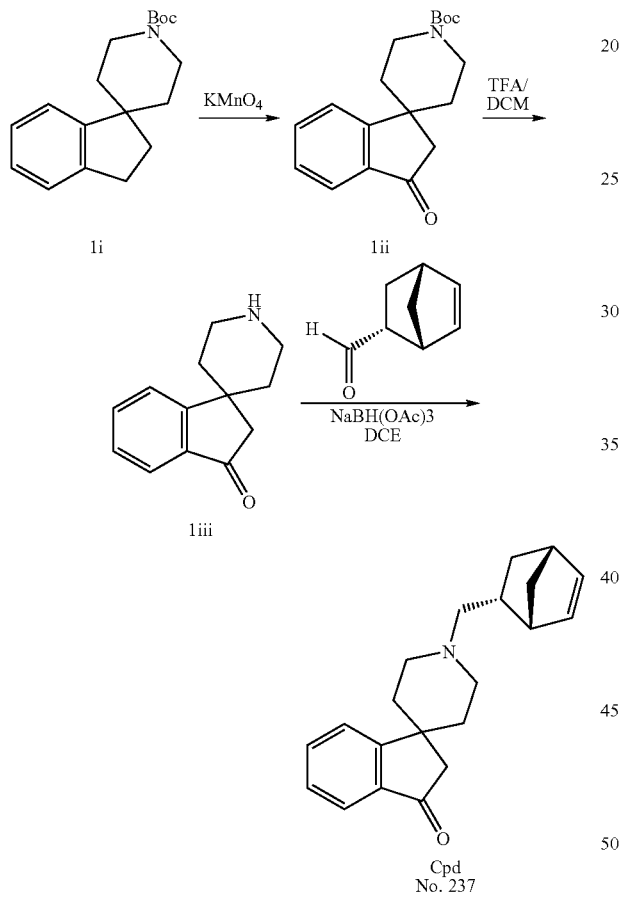

To a solution of compound N-Boc Spiroindane 1i (60.0 g, 0.21 mol) in $CH_2Cl_2$ (1000 mL) was added $H_2O$ (500 mL), TBAB (6.9 g, 0.02 mol) and KOH (3.5 g, 0.06 mol) and followed by addition of $KMnO_4$ (70.0 g, 0.45 mol) in several portions. After stirring for two days at 35° C., another quantity of $KMnO_4$ (70.0 g, 0.45 mol) was added and the mixture was continued to stir for 2 days. After $Na_2SO_3$ (103.0 g, 1.0 mol) was added in portions at 5° C., the mixture was extracted with EtOAc. The combined organic layers were dried over anhydrous $Na_2SO_4$ and evaporated under vacuum. The residue was purified by column chromatography (PE/EtOAc:5/1) to yield 1ii (30.0 g). $^1$H NMR ($CDCl_3$) δ: 7.74-7.72 (m, 1H), 7.66-7.64 (m, 1H), 7.62-7.61 (m, 1H), 7.49-7.38 (m, 1H), 4.22-4.20 (m, 2H), 2.89-2.82 (m, 2H), 2.63 (s, 2H), 2.02-1.94 (m, 2H), 1.56-1.52 (m, 2H), 1.49 (s, 9H). MS (ESI) m/z (M+H$^+$) 246.0/202.1.

Boc-protected starting material 1ii (400.0 mg; 1.33 mmol) was dissolved in $CH_2Cl_2$ (1.5 mL) and treated with TFA (1.5 mL). The reaction was allowed to stir at room temperature for 1 h and was then quenched by adding $H_2O$ (5 mL) and $Et_2O$ (7 mL). The layers were separated, and the aqueous layer was brought to a basic pH by addition of solid KOH. The resulting emulsion was extracted with $Et_2O$ (3×10 mL). The combined organic extracts were dried on $Na_2SO_4$ and concentrated to yield the desired product 1iii as a colorless oil that solidifies upon standing (220 mg). LC/MS m/z 202.2 [M+H]$^+$, $t_R$ 0.72 min (10-99% $CH_3CN$—$H_2O$ gradient with 0.03% TFA, 5 min).

Intermediate 1iii (40 mg; 0.2 mmol) was suspended in DCE (1 mL) and treated with (1R,2R,4R)-bicyclo[2.2.1]hept-5-ene-2-carbaldehyde (31 mg; 0.26 mmol; 1.300 eq.) in DCE (0.5 mL), followed by portion-wise addition of NaBH(OAc)$_3$ (127 mg; 0.6 mmol). The reaction was allowed to stir at room temperature for 1 h and was then quenched with MeOH (1 mL) and allowed to stir for another 30 min. The crude reaction mixture was purified by HPLC (10-99% $CH_3CN$ gradient with 0.03% TFA, 15 min) to provide purified 1'-((1R,2R,4R)-bicyclo[2.2.1]hept-5-en-2-ylmethyl)spiro[indene-1,4'-piperidin]-3(2H)-one (compound no. 237). LC/MS m/z 308.2 [M+H]$^+$, $t_R$ 2.08 (10-99% $CH_3CN$—$H_2O$ gradient with 0.03% TFA, 5 min). $^1$H NMR (400 MHz, DMSO-$d_6$) δ 9.47 (br s, 1H), 7.81-7.77 (m, 1H), 7.66 (d, J=7.4 Hz, 1H), 7.59 (d, J=7.8 Hz, 7.53-7.49 (m, 1H), 6.27 (dd, J=5.7, 3.0 Hz, 1H), 6.05 (dd, J=5.7, 2.8 Hz, 1H), 3.60 (t, J=12.7 Hz, 3H), 3.11-2.90 (m, 4H), 2.85-2.74 (m, 4H), 2.29 (t, J=13.0 Hz, 2H), 2.05-1.99 (m, 1H), 1.76 (d, J=14.2 Hz, 2H), 1.39-1.35 (m, 1H), 1.29 (d, J=8.2 Hz, 1H), 0.71-0.66 (m, 1H).

Example 2 ethyl 3-(2,2-dimethyl-3-oxo-2,3-dihydrospiro[indene-1,4'-piperidine]-1'-yl)-8-azabicyclo[3.2.1]octane-8-carboxylate (Cpd. No. 277)

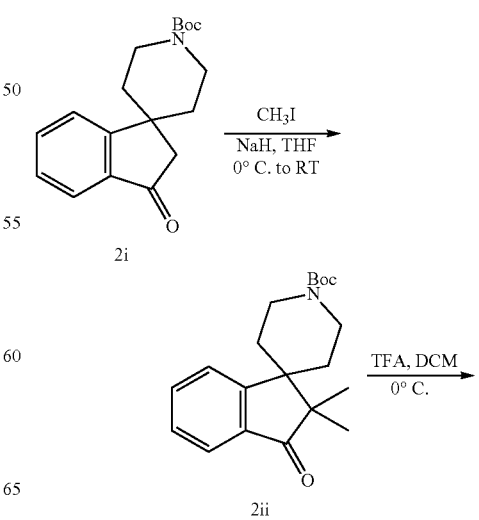

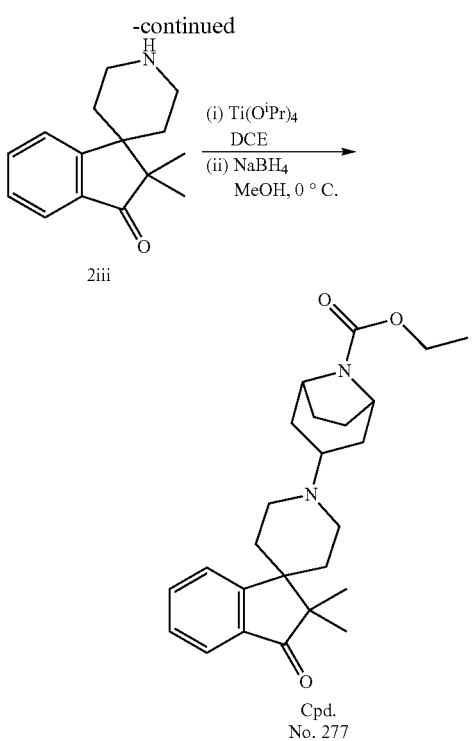

1.0 eq of the Boc-protected spiroindanone 2i (2.06 g, 6.84 mmol) was dissolved in anhydrous tetrahydrofuran (5 mL) and added drop-wise, under nitrogen, to an ice-cold (~0° C.) suspension of 2.2 eq sodium hydride (600 mg, 60% dispersion in mineral oil, 15.0 mmol) in anhydrous tetrahydrofuran (10 mL). A solution of 10.0 eq iodomethane (9.71 g, 68.4 mmol) in anhydrous tetrahydrofuran (5 mL) was then added drop-wise over 20 min. The reaction was warmed to room temperature and stirred for 2 h under nitrogen. The reaction mixture was concentrated under reduced pressure and slowly treated with $H_2O$ (25 mL). The product was extracted with ethyl acetate (2×50 mL) and the pooled extracts washed with saturated sodium bicarbonate and saturated brine, then dried ($Na_2SO_4$) and filtered. The filtrate was concentrated in vacuo to afford 2.41 g crude product 2ii as a viscous, pale yellow oil. $^1$H-NMR (400 MHz, acetone-$d_6$) δ 7.90 (d, J=6.8 Hz, 1H), 7.71 (m, 2H), 7.49 (t, J=7.4 Hz, 1H), 3.75 (m, 2H), 3.56 (br m, 2H), 1.89 (m, 2H), 1.64 (br m, 2H), 1.48 (s, 9H), 1.12 (s, 6H); $t_R$=3.50 min [10-99% $CH_3CN$ gradient over 5 min with 0.1% TFA (aq)]; Theoretical (M+H)$^+$ m/z for $C_{20}H_{27}NO_3$=330.2; Found 330.2.

The gem-dimethyl spiroindanone 2ii (379 mg, 1.15 mmol) was dissolved in dichloromethane (2.5 mL), cooled in an ice water bath and treated slowly with trifluoroacetic acid (2.5 mL). The reaction was stirred for 30 min at ~0° C., then concentrated under reduced pressure. The oil obtained was dissolved in acetonitrile and re-concentrated under reduced pressure. The crude TFA salt was treated with 1.0 N NaOH (5 mL) and extracted with ethyl acetate (2×30 mL). The pooled extracts were washed with $H_2O$ and saturated brine, then dried ($Na_2SO_4$) and filtered. The filtrate was concentrated in vacuo to afford 210 mg of the crude free base 2iii as a colorless semi-solid. $t_R$=1.52 min [10-99% $CH_3CN$ gradient over 5 min with 0.1% TFA (aq)]; Theoretical (M+H)+ m/z for $C_{15}H_{19}NO$=230.2; Found 230.2

The crude free base 2iii (53 mg, 0.23 mmol) was dissolved in anhydrous 1,2-dichloroethane (1.0 mL) and treated with N-(carbethoxy)-4-tropinone (55 mg, 0.28 mmol), followed by titanium tetraisopropoxide (202 μL, 196 mg, 0.69 mmol). The vial was flushed with nitrogen and stirred at room temperature for 2.5 days. The reaction was diluted with methanol (1.0 mL), cooled in an ice water bath and treated with sodium borohydride (17 mg, 0.46 mmol). The reaction was warmed to room temperature and stirred thereafter for 30 min. The reaction was then quenched with 1.0 N NaOH (750 μL), diluted with methanol (1.5 mL) and stirred at room temperature for 10 min. The suspension obtained was centrifuged (3K rpm, 10 min) and the supernatant concentrated under reduced pressure. The residue obtained was dissolved in DMSO: methanol (1.5 mL, 1:1 v/v), filtered, and purified by reverse-phase HPLC (2-40% $CH_3CN$ gradient over 10 min with 0.1% TFA (aq), 35 mL/min, 1.0 mL injected) to produce ethyl 3-(2,2-dimethyl-3-oxo-2,3-dihydrospiro[indene-1,4'-piperidine]-1'-yl)-8-azabicyclo[3.2.1]octane-8-carboxylate (compound. no. 277) as a TFA salt. $t_R$=2.12 min [10-99% $CH_3CN$ gradient over 5 min with 0.1% TFA (aq)]; Theoretical (M+H)$^+$ m/z for $C_{25}H_{34}N_2O_3$=411.3; Found 411.2.

Example 3

1'-((1S,2S,4S)-bicyclo[2.2.1]hept-5-en-2-ylmethyl)-2,3-dihydrospiro[indene-1,4'-piperidine]
(Cpd. No. 312)

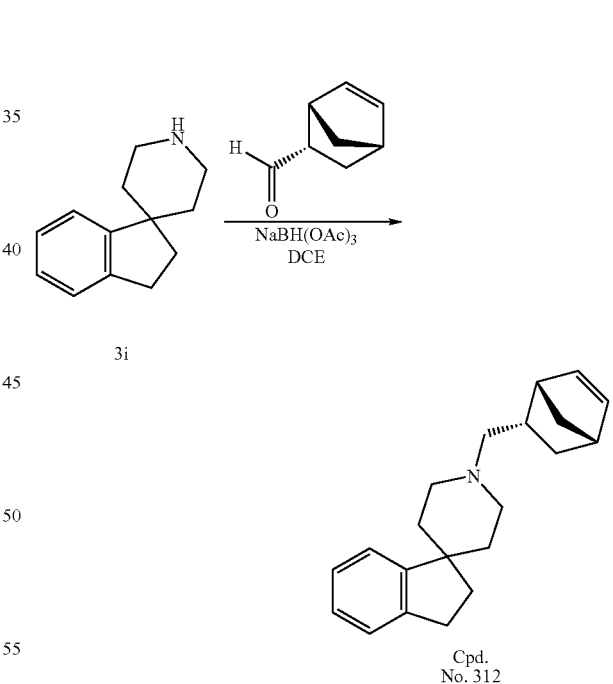

The starting Spiroindane 3i (45 mg, 0.2 mmol) was suspended in DCE (1 mL) and treated with (1S,2S,4S)-bicyclo [2.2.1]hept-5-ene-2-carbaldehyde (25 mg, 0.2 mmol) in DCE, followed by the addition of NaBH(OAc)$_3$ (63 mg, 0.3 mmol). The reaction was allowed to stir at room temperature for 1 h and was then quenched with MeOH (0.5 mL) and allowed to stir for another 30 min (until gas evolution stopped). The crude reaction mixture was filtered, then purified by HPLC (10-99% CH₃CN/0.05% TFA gradient) to yield 1'-((1S,2S,4S)-bicyclo[2.2.1]hept-5-en-2-ylmethyl)-2,3-dihydrospiro[indene-1,4'-piperidine] (compound no. 312). LC/MS m/z 294.4 [M+H]⁺, $t_R$ 2.33 min (RP—C$_{18}$, 10-99% CH₃CN/0.05% TFA); ¹H NMR (400 MHz, DMSO-d₆) δ 9.33 (br s, 1H), 7.25-7.17 (m, 3H), 7.13 (d, J=6.9 Hz, 1H), 6.27-6.26 (m, 1H), 6.06-6.04 (m, 1H), 3.56-3.40 (m, 3H), 3.11-3.03 (m, 2H), 2.98-2.78 (m, 6H), 2.09-1.98 (m, 5H), 1.67 (d, J=13.9 Hz, 2H), 1.36 (t, J=8.0 Hz, 1H), 1.29 (d, J=8.2 Hz, 1H), 0.70-0.66 (m, 1H).

Example 4

1'-((1S,2R,4R)-bicyclo[2.2.1]heptan-2-yl)-5-chloro-2H-spiro[benzofuran-3,4'-piperidine] (Cpd. No. 1)

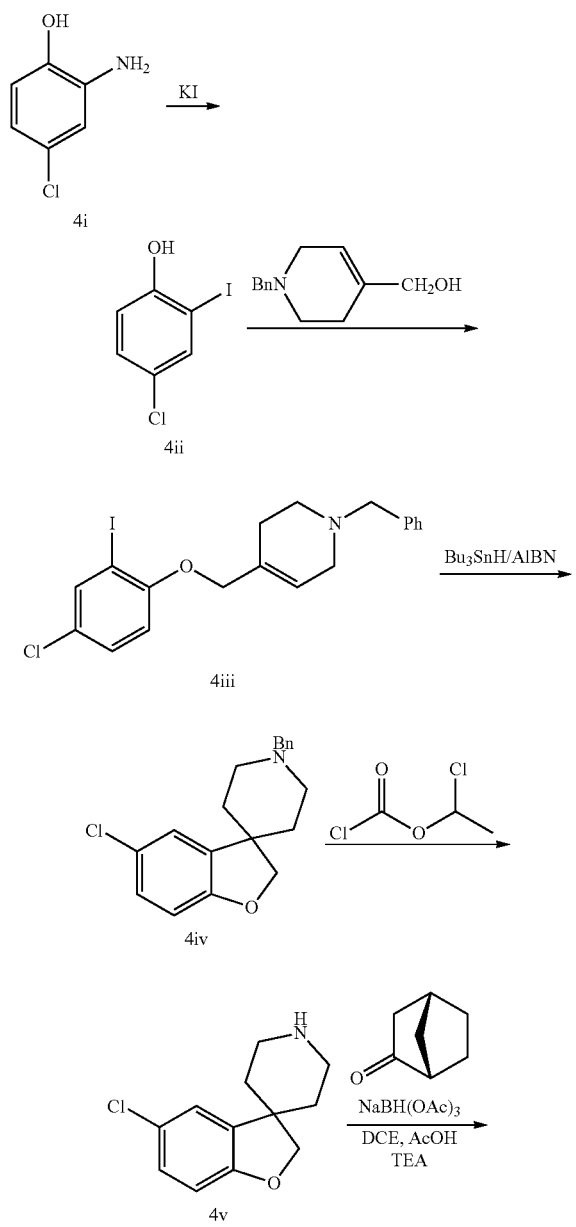

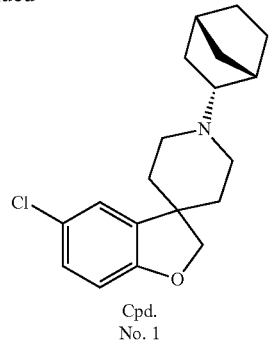

Cpd. No. 1

To a solution of 2-amino-4-chloro-phenol 4i (50 g, 0.35 mol) in HCl (2.5 mol, 500 mL) was added drop-wise a solution of sodium nitrite (25.25 g, 0.35 mol) in water (50 mL) at 0° C. The mixture was stirred at this temperature for 30 min. Then a cooled solution of KI (70 g, 0.42 mol) in H₂O (100 mL) was slowly added at 0° C. After addition, the mixture was allowed to warm to room temperature and stirred overnight. The reaction mixture was diluted with ethyl acetate (200 mL) and the separated aqueous phase was extracted with ethyl acetate (3×100 mL). The combined organic fraction was washed with Na₂S₂O₃ (10%, 100 mL), water (2×100 mL) and brine (200 mL), dried over Na₂SO₄ and concentrated to dryness. The residue was purified by column on silica gel to afford 4-chloro-2-iodo-phenol 4ii as a yellow solid (46 g). ¹H NMR (400 MHz, CDCl₃): δ 7.67 (d, J=2.4 Hz, 1H), 7.21 (dd, J=2.4, 8.4, Hz, 1H), 6.91 (d, J=8.4 Hz, 1H), 5.33 (s, 1H).

To a solution of 4-chloro-2-iodo-phenol 4ii (20.32 g, 0.08 mol), (1-benzyl-1,2,3,6-tetrahydro-pyridin-4-yl)-methanol (20.5 g, 0.08 mol) and triphenylphosphine (23.58 g, 0.09 mol) in dry THF (150 mL) was added DEAD (17.4 g, 0.09 mol) at 0° C. under nitrogen atmosphere. After addition, the mixture was stirred at room temperature overnight. The mixture was concentrated to dryness and the residue was basified by Na₂CO₃ solution (10% 100 mL) and extracted with ethyl acetate (3×100 mL). The combined organic layers were washed with water (2×100 mL) and brine (200 mL), dried over Na₂SO₄, concentrated to dryness. The residue was purified by column on silica gel to afford 1-benzyl-4-(4-chloro-2-iodo-phenoxymethyl)-1,2,3,6-tetrahydro-pyridine 4iii (30 g). ¹H NMR (400 MHz, CDCl₃): δ 7.73 (d, J=2.4 Hz, 1H), 7.22-7.38 (m, 6H), 6.70 (d, J=8.8 Hz, 1H), 5.82 (s, 1H), 4.43 (s, 2H), 3.63 (s, 2H), 3.05 (s, 2H), 2.67 (t, J=5.6 Hz, 2H), 2.28 (s, 2H).

To a refluxing solution of 1-benzyl-4-(4-chloro-2-iodo-phenoxymethyl)-1,2,3,6-tetrahydro-pyridine 4iii (26.7 g, 0.06 mol) and AIBN (0.05 g, 0.003 mol) in dry benzene was added a solution of Bu₃SnH (40 g, 0.137 mol) in benzene (100 mL) over 1 h under nitrogen atmosphere. After addition, the mixture was refluxed for 3 h and additional AIBN (0.5 g, 0.003 mol) and Bu₃SnH (20 g, 0.68 mol) were added. After refluxing for 4 h, the mixture was concentrated to dryness, and EtOAc (100 mL) and HCl (10%, 40 mL) were added. The precipitate was filtered and washed with petroleum ether to give 2,3-dihydro-1'-benzyl-5-chlorospiro (benzofuran-3,4'-piperidine) as its HCl salt, which was basified by NaHCO₃ solution to give 2,3-dihydro-1'-benzyl-5-chlorospiro(benzofuran-3,4'-piperidine) 4iv (13 g).

To a solution of 2,3-dihydro-1'-benzyl-5-chlorospiro(benzofuran-3,4'-piperidine) 4iv (13 g, 0.04 mol) in CH₂Cl₂ (130 mL) was added drop-wise 1-chloroethyl chloroformate (7.2 g, 0.05 mol). The mixture was stirred for 3 h at room temperature and then concentrated to dryness. The residue was dissolved in CH₃OH (30 mL) and the solution was heated to reflux for 30 min. After removing of the solvent, ether was added. The resulted solid was filtered and washed with ether to the debenzylated product 4v as the HCl salt (5.5 g). $^1$H NMR (400 MHz, DMSO-$d_6$): δ 9.08 (br s, 1H), 7.16-7.19 (m, 2H), 6.82 (d, J=8.4 Hz, 1H), 4.50 (s, 2H), 3.25-9.29 (m, 2H), 2.98-2.92 (m, 2H), 2.12-2.05 (m, 2H), 1.83-1.8 (m, 2H).

The chloro-dihydrobenzofuran spiro amine 4v (3.18 mmol) was dissolved in anhydrous DCE (15 mL) and treated with triethylamine (322 mg, 3.18 mmol), followed by (+)-2-norcamphor (421 mg, 3.82 mmol), acetic acid (382 mg, 6.36 mmol) and NaBH(OAc)₃ (1.35 g, 6.37 mmol). The reaction was stirred vigorously under nitrogen at room temperature for ~36 h. The reaction was quenched with methanol (15 mL) and stirred vigorously for 10 min at room temperature. The reaction mixture was then concentrated under reduced pressure and the residue obtained dissolved in a mixture of DMSO: CH₃OH (20 mL, 1:3 v/v). The solution was filtered and purified by reverse-phase HPLC (2-99% CH₃CN/0.05% TFA, 35 mL/min). The combined pure fractions were concentrated under reduced pressure until ~25 mL of solvent remained. The suspension was treated with 1 N NaOH (25 mL) and extracted with CH₂Cl₂ (3×50 mL). The combined organic extracts were washed with H₂O, saturated brine, dried over Na₂SO₄ and filtered. The filtrate was concentrated under reduced pressure to afford 522 mg pure free base (1.64 mmol) as a crystalline white solid. The free base was readily dissolved in anhydrous diethyl ether (10 mL) and treated with 1.0 eq 1 N ethereal HCl (1.7 mL). The thick, gelatinous suspension obtained was cooled in an ice water bath for 1 h, filtered, rinsed with Et₂O (3×10 mL), and dried overnight under reduced pressure to yield 1'-((1S,2R,4R)-bicyclo[2.2.1]heptan-2-yl)-5-chloro-2H-spiro[benzofuran-3,4'-piperidine] (compound no. 1) as a fine white powder. $^1$H-NMR (400 MHz, DMSO-$d_6$) δ 10.1 (br s, 1H), 7.77 (d, J=2.2 Hz, 0.2H), 7.21 (dd, J=2.3 Hz, 8.5 Hz, 1H), 7.08 (d, J=2.3 Hz, 0.8H), 6.85 (d, J=8.5 Hz, 0.8H), 6.84 (d, J=8.5 Hz, 0.2H), 4.52 (s, 1.6H), 4.45 (s, 0.4H), 3.41 (m, 1.8H), 3.24 (m, 0.8H), 3.01 (br m, 1.6H), 2.63 (br m, 2H), 2.44 (m, 0.9H), 2.27 (br s, 1.1H), 1.86 (br m, 4H), 1.51 (br m, 3.3H), 1.39 (br m, 2.7H), 1.24 (br m, 0.7H); LC/MS m/z 318.0 [M+H]⁺, $t_R$ 2.14 min (RP—$C_{18}$, 10-99% CH₃CN/0.05% TFA).

Example 5

1'-((1R,2R,4R)-bicyclo[2.2.1]hept-5-en-2-ylmethyl)-6-chlorospiro[chroman-4,4'-piperidine]
(Cpd. No. 64)

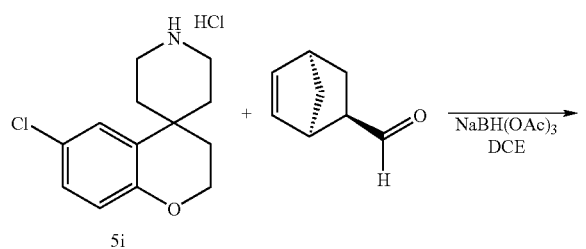

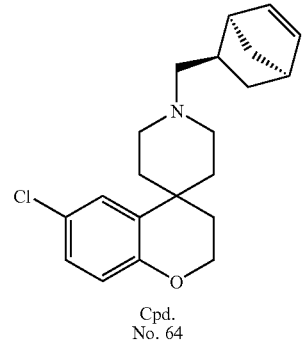

Cpd. No. 64

The starting material 5i (54 mg, 0.2 mmol, 1.0 eq) was suspended in DCE (1 mL) and treated with (1R,2R,4R)-bicyclo[2.2.1]hept-5-ene-2-carbaldehyde (31 mg, 0.26 mmol, 1.3 eq) in DCE (0.5 mL), followed by portion-wise addition of NaBH(OAc)₃ (127 mg, 0.6 mmol). The reaction was allowed to stir at room temperature for 3 h and was then quenched with MeOH (2 mL) and allowed to stir for 1 h (until gas evolution stopped). The reaction mixture was then diluted with H₂O (5 mL) and extracted with Et₂O (10 mL). The organic layer was treated with 1 N HCl (5 mL) and formation of an insoluble precipitate was observed. The biphasic emulsion was filtered, and the white precipitate was washed with Et₂O (3×5 mL) and hexane (2×10 mL) and dried under vacuum to provide the pure HCl salt of 1'-((1R,2R,4R)-bicyclo[2.2.1]hept-5-en-2-ylmethyl)-6-chlorospiro[chroman-4,4'-piperidine] (compound no. 64) as white shiny platelets. LC/MS m/z 344.0 [M+H]⁺, $t_R$ 2.56 min (RP—$C_{18}$, 10-99% CH₃CN/0.05% TFA). $^1$H NMR (400 MHz, DMSO-$d_6$) δ 10.11 (s, 1H), 7.37 (d, J=2.4 Hz, 1H), 7.10 (d, J=2.5 Hz, 1H), 6.74 (d, J=8.7 Hz, 1H), 6.18 (q, J=2.8 Hz, 1H), 6.02 (q, J=2.7 Hz, 1H), 4.05-4.03 (m, 2H), 3.37-3.32 (m, 2H), 3.08-2.97 (m, 3H), 2.85-2.77 (m, 2H), 2.72-2.65 (m, 1H), 2.49-2.45 (m, 3H), 1.98-1.90 (m, 3H), 1.72-1.70 (m, 2H), 1.26 (dd, J=33.4, 7.3 Hz, 2H), 0.63 (d, J=10.5 Hz, 1H).

Example 6

1'-((1R,2R,4R)-bicyclo[2.2.1]hept-5-en-2-ylmethyl)-5-fluorospiro[indoline-3,4'-piperidine]
(Cpd. No. 147)

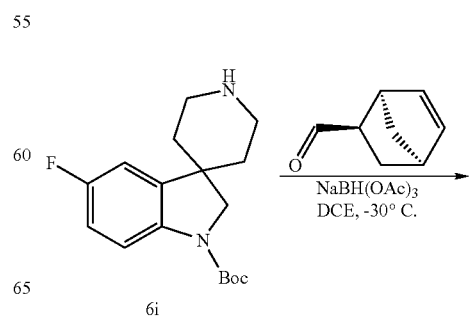

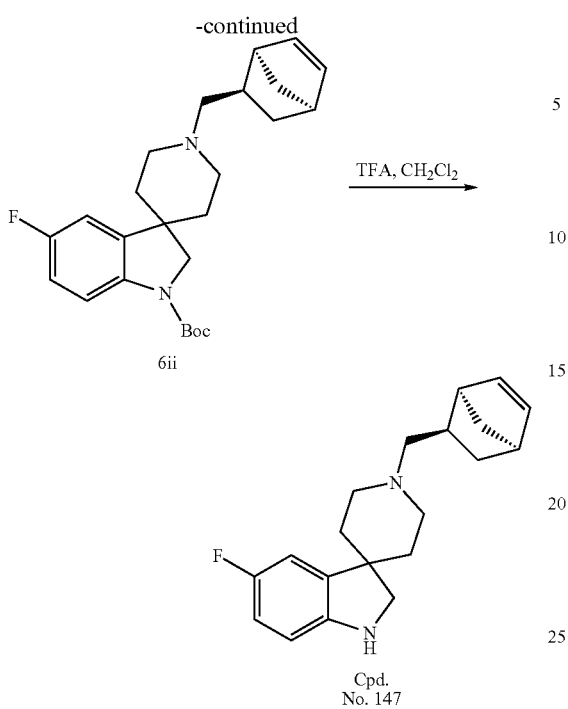

The fluoroindoline 6i (1.22 g; 4.0 mmol) was suspended in DCE (10 mL) and cooled to −30° C. A solution of (1R,2R,4R)-bicyclo[2.2.1]hept-5-ene-2-carbaldehyde (635 mg; 5.2 mmol) in dry DCE (2 mL) was added, followed by portionwise addition of NaBH(OAc)$_3$ (1.18 g; 5.6 mmol). The reaction was stirred at −30° C. under nitrogen for 90 min then at room temperature until complete consumption of starting material was observed by LC/MS (30 h). The reaction was quenched with MeOH (10 mL) and allowed to stir vigorously for 30 min (until gas evolution stopped). The reaction was diluted with 1N HCl (80 mL) and Et$_2$O (50 mL). Formation of a white precipitate can be observed as the HCl salt of the desired product is insoluble in both phases. The biphasic mixture was filtered, and the precipitate was washed with Et$_2$O (2×20 mL) and hexane (2×30 mL) and dried under high vacuum to provide the product 6ii as the corresponding HCl salt (white powder, 1.41 g).

The HCl salt 6ii (1.4 g; 3.1 mmol) was dissolved in CH$_2$Cl$_2$ (10 mL) and TFA (10 mL) was added. The reaction mixture was allowed to stir at room temperature for 1 h. The reaction was quenched with water (100 mL) and diluted with hexane (40 mL) and Et$_2$O (50 mL). The layers were separated, and the organic layer was extracted with H$_2$O (2×100 mL). The combined aqueous layers were washed with Et$_2$O (50 mL) then neutralized with solid KOH (under dry-ice bath cooling) until formation of an oily suspension was observed. The suspension was extracted with EtOAc (3×100 mL) and CH$_2$Cl$_2$ (100 mL), and the combined organic extracts were dried over Na$_2$SO$_4$ and concentrated to provide the crude product as a light brown oil. The amine was dissolved in 15 mL Et$_2$O and treated with 2 N HCl in ether (1.5 mL, 3.0 mmol, 0.96 eq). After 20 min of stirring the resulting precipitate was vacuum filtered under a nitrogen atmosphere, washed with 50 mL Et$_2$O, 30 mL Et$_2$O:CH$_3$CN (5:1) and 40 mL hexanes and dried under high vacuum to provide the HCl salt of 1'-((1R,2R,4R)-bicyclo[2.2.1]hept-5-en-2-ylmethyl)-5-fluorospiro[indoline-3,4'-piperidine] (compound no. 147) as an off-white powder. LC/MS m/z 313.30 [M+H]$^+$, $t_R$ 1.73 min (RP—C$_{18}$, 10-99% CH$_3$CN/0.05% TFA). $^1$H NMR (400 MHz, MeOD) δ 0.83 (ddd, J=5.8, 2.6 Hz, 1H), 1.41 (d, J=8.4 Hz, 1H), 1.54 (m, 1H), 2.01 (s, 1H), 2.05 (d, J=3.9 Hz, 1H), 2.15 (ddd, J=6.1, 3.1 Hz, 1H), 2.23 (m, 2H), 2.60 (m, 1H), 2.86 (dd, J=13.0, 7.4 Hz, 1H), 2.93 (s, 1H), 3.11 (m, 4H), 3.66 (m, 4H), 6.09 (d, J=2.8 Hz, 1H), 6.33 (d, J=3.0 Hz, 1H), 6.90 (m, 3H).

Example 7

1'-((1R,2S,4S)-bicyclo[2.2.1]heptan-2-yl)-5-methyl-1-(methylsulfonyl)spiro[indoline-3,4'-piperidine] (Cpd. No. 231)

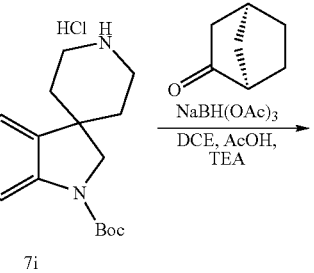

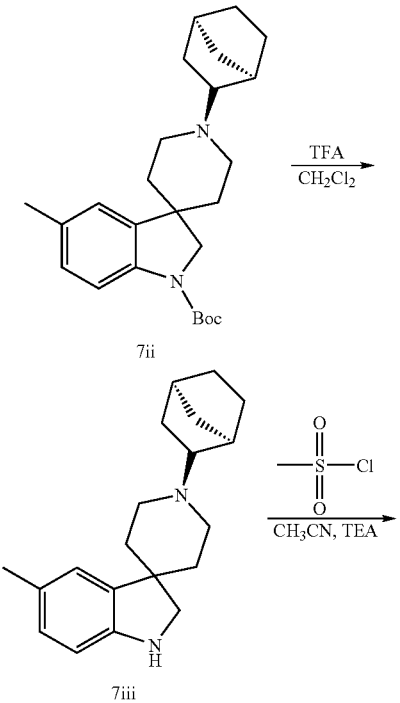

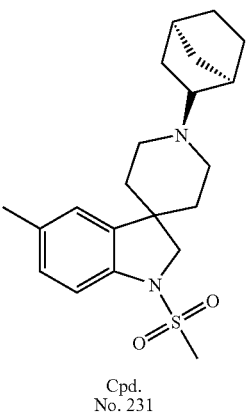

Starting material 7i hydrochloride (2.17 g, 6.40 mmol) was suspended in anhydrous DCE (30 mL) and treated with triethylamine (648 mg, 6.40 mmol), followed by (−)-2-norcamphor (706 mg, 6.40 mmol), acetic acid (770 mg, 12.8 mmol) and NaBH(OAc)$_3$ (2.72 g, 12.8 mmol). The reaction was stirred vigorously under nitrogen at room temperature for ~72 h (~77% conversion by LC/MS at 220 nm). The reaction was quenched with methanol (10 mL) and stirred vigorously for 10 min at room temperature. The reaction mixture was then concentrated under reduced pressure and the residue obtained dissolved in a 1:1 mixture of DMSO:CH$_3$OH (30 mL). The mixture was centrifuged (3,000 rpm, 10 min) and the supernatant filtered and purified by reverse-phase HPLC (10-99% CH$_3$CN/0.05% TFA, 50 mL/min). The combined pure fractions were concentrated under reduced pressure to afford 2.25 g of the N-Boc intermediate 7ii (isolated as the TFA salt) as an off-white solid. LC/MS (RP—C$_{18}$, 10-99% CH$_3$CN/0.05% TFA gradient over 5 min) m/z 397.4 [M+H]$^+$, $t_R$ 2.70 min.

The N-Boc intermediate 7ii (2.25 g, 4.41 mmol) was dissolved in dichloromethane (25 mL) and slowly treated with trifluoroacetic acid (15 mL). The reaction was stirred at room temperature for 30 min, and then concentrated under reduced pressure. The oil obtained was slowly treated with 1 N NaOH (100 mL) and extracted with CH$_2$Cl$_2$ (2×75 mL). The combined extracts were washed with H$_2$O, saturated brine, dried over Na$_2$SO$_4$ and filtered. The filtrate was concentrated under reduced pressure to afford 1.147 g (3.87 mmol) free base as a yellow oil. The free base was dissolved in a minimal volume of anhydrous diethyl ether and treated with 0.95 eq 1 N ethereal HCl. The suspension was cooled in an ice water bath for 1 h, filtered, rinsed with Et$_2$O, and dried overnight under reduced pressure to yield 1.213 g of the desired product 7ii as a fine, off-white to very pale yellow powder. LC/MS (RP—C$_{18}$, 10-99% CH$_3$CN/0.05% TFA gradient over 5 min) m/z 297.2 [M+H]$^+$, $t_R$ 1.72 min.

The deprotected amine HCl salt 7iii (33 mg, 0.10 mmol) was suspended in anhydrous CH$_3$CN (1.0 mL) and treated with triethylamine (20 mg, 0.20 mmol), followed by methanesulfonyl chloride (14 mg, 0.12 mmol). The reaction was stirred at room temperature for 10 min, then quenched with DMSO:CH$_3$OH (1.0 mL, 1:1 v/v) and centrifuged (4000 rpm, 7 min). The supernatant was filtered and purified by reverse-phase HPLC (2-99% CH$_3$CN, 50 mL/min, 2.0 mL injected) to yield 1'-((1R,2S,4S)-bicyclo[2.2.1]heptan-2-yl)-5-methyl-1-(methylsulfonyl)spiro[indoline-3,4'-piperidine] (compound no. 231) as the TFA salt. LC/MS (RP—C$_{18}$, 10-99% CH$_3$CN/0.05% TFA gradient over 5 min) m/z 375.0 [M+H]$^+$, $t_R$ 2.08 min.

Example 8

2-methoxyethyl 3-(1-(dimethylcarbamoyl)-5-fluorospiro[indoline-3,4'-piperidine]-1'-yl)-8-azabicyclo[3.2.1]octane-8-carboxylate (Cpd. No. 119)

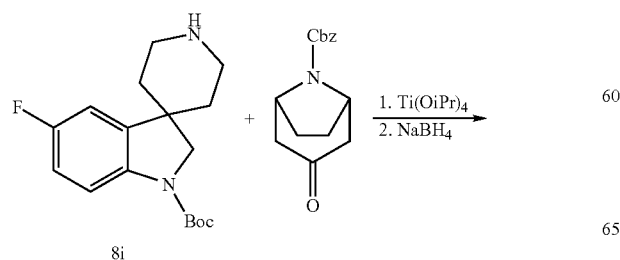

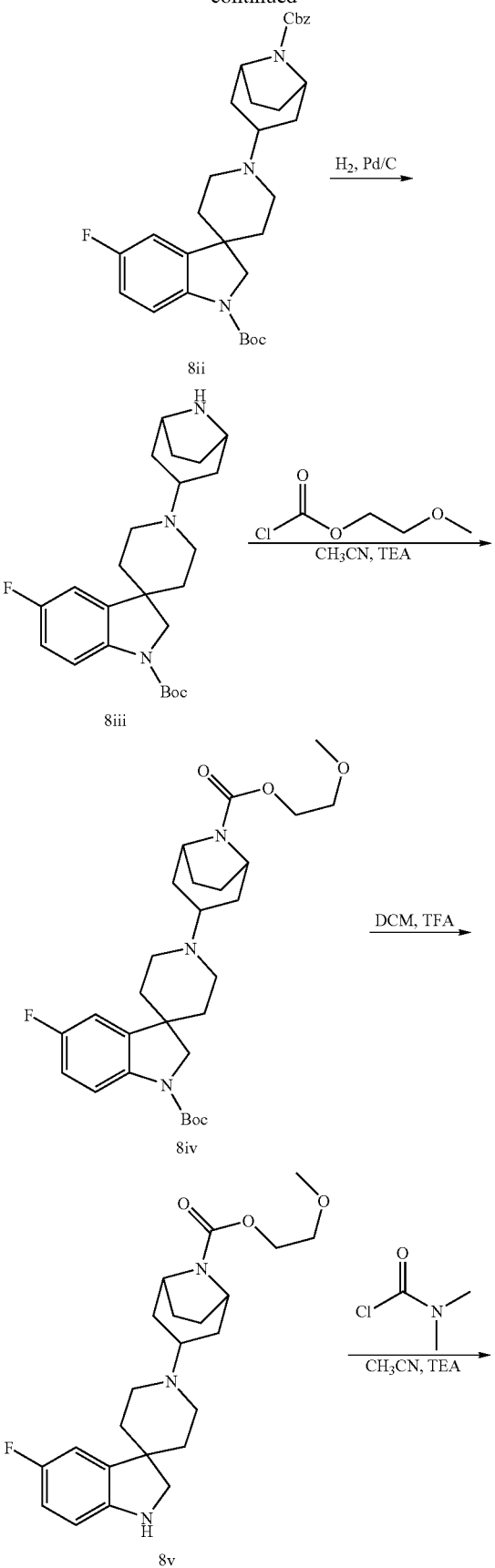

-continued

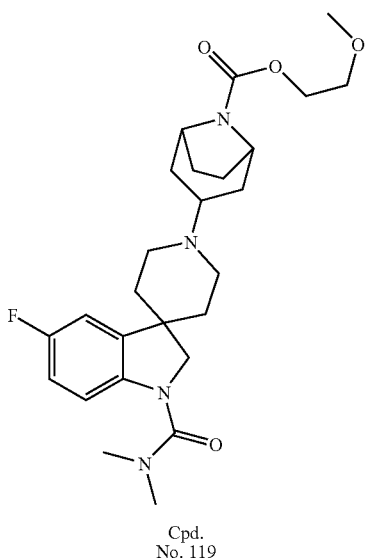

Cpd. No. 119

Boc-protected fluoroindoline 8i (1.41 g; 4.11 mmol) and benzyl 4-oxotropane-N-carboxylate (1.07 g; 4.11 mmol) were dissolved in a mixture of DCE (5 mL) and DME (5 mL) and placed under a nitrogen atmosphere. TEA (0.57 mL; 0.42 g; 4.11 mmol) was added, followed by Ti(OiPr)$_4$ (1.21 mL; 1.17 g; 4.11 mmol) and the reaction was allowed to stir at room temperature for 60 h. The reaction mixture was diluted with 30 mL MeOH and cooled to −40° C. to −50° C. NaBH$_4$ (0.6 g; 13.45 mmol) was added portion-wise over 30 min and the reaction was allowed to stir at −40° C. to −20° C. until bubbling subsided (3 h), then warmed slowly to room temperature and stirred for 2 h. The sticky suspension was filtered through a pad of Celite, and the filter cake was washed with MeOH (2×30 mL) and Et$_2$O (3×50 mL). The filtrate was separated into the corresponding layers, and the aqueous layer was extracted with Et$_2$O (2×50 mL). The combined organic extracts were dried over Na$_2$SO$_4$ and concentrated to provide the crude product as a white foam. This material was dissolved in Et$_2$O (400 mL) and treated with 1 N aq. HCl (500 mL) and the mixture was vigorously stirred for 20 min. The resulting biphasic suspension was filtered, the precipitate was washed with HCl 1N (2×30 mL), H$_2$O (2×30 mL) and Et$_2$O (3×30 mL) and dried. To remove the unreacted starting material by conversion to the corresponding ethyl carbamate, the crude HCl salt was suspended in acetonitrile (10 mL) and treated sequentially with ethyl chloroformate (1 mL) and triethylamine (2 mL). After 10 min, the mixture was diluted with Et$_2$O (300 mL) and poured onto 1 N aq HCl (300 mL). The biphasic suspension was filtered, and the precipitate was washed with HCl 1N (2×30 mL), H$_2$O (2×30 mL) and Et$_2$O (3×30 mL) and dried to provide the desired product 8ii hydrochloride salt. LC/MS m/z [M+H]$^+$ 550.4 t$_R$ 2.93 min (10-99% CH$_3$CN—H$_2$O gradient with 0.03% TFA, 5 min).

Cbz-protected starting material 8ii (1.140 g; 1.945 mmol) was dissolved in methanol (20 mL) and treated with 10% wet Pd/C (1.14 g) and NH$_4$COOH (2.45 g; 38.9 mmol) The mixture was allowed to stir vigorously overnight under an empty balloon (for venting). LC/MS analysis shows complete conversion to the desired product. The reaction mixture was filtered through a pad of Celite under a nitrogen atmosphere, and the filter cake was rinsed with methanol (4×30 mL). The filtrate was concentrated to provide the crude product, which was taken up in a mixture of EtOAc (100 mL) and NaHCO$_3$ sat. (100 mL). The layers were separated, the aqueous layer was extracted with EtOAc (2×100 mL), Et$_2$O (100 mL), and CH$_2$Cl$_2$ (2×100 mL). The combined organic layers were dried over Na$_2$SO$_4$ and concentrated to provide the crude product 8iii as white foam (707 mg). LC/MS m/z 416.4 [M+H]$^+$, t$_R$ 2.26 (10-99% CH$_3$CN—H$_2$O gradient with 0.03% TFA, 5 min)

Compound 8iii (250.0 mg; 0.60 mmol) was dissolved in DCM (15 mL) and treated sequentially with methoxyethyl chloroformate (138.4 uL; 166.1 mg; 1.203 mmol) and TEA (401.7 uL; 291.7 mg; 2.89 mmol). After 10 min, the reaction mixture was diluted with DCM (30 mL) and washed with saturated NaHCO$_3$ solution (30 mL). The aqueous layer was extracted with DCM (30 mL) and the combined organic extracts were dried on Na$_2$SO$_4$ and concentrated to provide the desired product 8iv which was taken to the next step without further purification. LC/MS m/z 518.0 [M+H]$^+$, t$_R$ 2.43 min (10-99% CH$_3$CN—H$_2$O gradient with 0.03% TFA, 5 min).

Intermediate 8iv was dissolved in a mixture of DCM (15 mL) and TFA (20 mL) and allowed to stir at room temperature for 2 h. The reaction mixture was concentrated, dissolved in water (20 mL) and the pH was adjusted to basic by portion-wise addition of solid KOH. The resulting suspension was extracted with DCM (3×30 mL) and Et$_2$O (30 mL) and the organic extracts were dried over Na$_2$SO$_4$, and then concentrated to provide the free base of the desired product. The material was dissolved in Et$_2$O (20 mL) and treated with excess 1N HCl in ether (2 mL). The resulting suspension was filtered under nitrogen and the filtrate was washed with Et$_2$O (3×10 mL) and dried under vacuum to provide the desired product 8v as an off white solid (232 mg). LC/MS m/z 418.2 [M+H]$^+$, t$_R$ 1.16 min (10-99% CH$_3$CN—H$_2$O gradient with 0.03% TFA, 5 min).

Intermediate 8v (230.0 mg; 0.51 mmol) was suspended in DCM (15 mL) and treated sequentially with dimethyl carbamoyl chloride (931.3 uL; 1089.7 mg; 10.13 mmol) and TEA (704.8 uL; 511.70 mg; 5.07 mmol). The reaction was allowed to stir overnight at room temperature, and then the mixture was diluted with DCM (30 mL) and washed with saturated NaHCO$_3$ solution (30 mL). The aqueous layer was extracted with DCM (30 mL) and the combined organic extracts were dried over Na$_2$SO$_4$ and concentrated to provide the free base of the desired product. This material was dissolved in Et$_2$O (20 mL) and treated with excess 1N HCl in ether (3 mL). The resulting suspension was filtered under nitrogen and the filtrate was washed with Et$_2$O (3×10 mL) and dried under vacuum to provide 2-methoxyethyl 3-(1-(dimethylcarbamoyl)-5-fluorospiro[indoline-3,4'-piperidine]-1'-yl)-8-azabicyclo[3.2.1]octane-8-carboxylate (compound no. 119) as an off-white solid. LC/MS m/z 489.4 [M+H]$^+$, t$_R$ 2.20 min (10-99% CH$_3$CN—H$_2$O gradient with 0.03% TFA, 5 min). $^1$H NMR (400 MHz, DMSO-d$_6$) δ 1.66 (d, J=7.0 Hz, 2H), 1.82 (s, 4H), 1.86 (s, 2H), 1.92 (s, 2H), 2.07 (s, 2H), 2.22 (t, J=12.1 Hz, 2H), 2.87 (s, 6H), 3.05 (q, J=11.1 Hz, 2H), 3.28 (s, 3H), 3.53 (m, 4H), 3.73 (m, 1H), 4.15 (d, J=4.4 Hz, 2H), 4.27 (s, 2H), 6.90 (dd, J=8.3, 2.4 Hz, 1H), 7.00 (m, 2H), 10.41 (s, 1H).

Example 9 ethyl 4-(1-acetyl-5-p-tolylspiro[indoline-3,4'-piperidine]-1'-yl)piperidine-1-carboxylate (Cpd. No. 58)

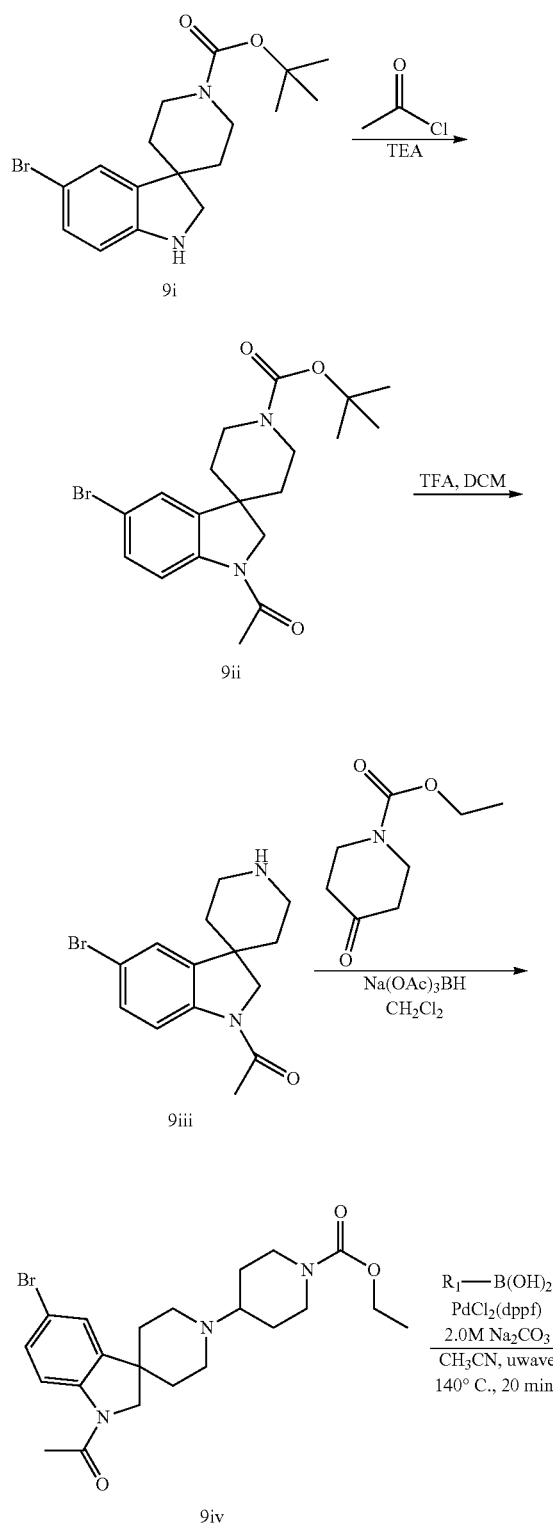

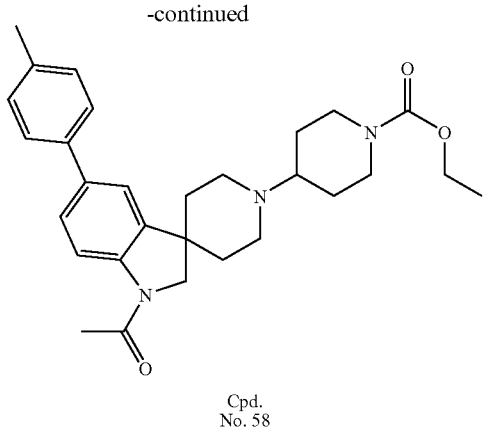

Cpd. No. 58

Bromo-spiroindoline 9i (1.5 g, 4.08 mmol) was dissolved in anhydrous dichloromethane (20 mL) and cooled to 0° C. To the rapidly stirring solution was added acetyl chloride (0.481 g, 6.13 mmol) followed by triethylamine (0.853 mL, 6.13 mmol). The reaction mixture was stirred at room temperature for 1 h. Then mixture was concentrated under reduced pressure to afford desired product 9ii as viscous pale yellow oil and carried to the next step without further purification. LC/MS (RP—$C_{18}$, 10-99% $CH_3CN$/0.05% TFA gradient over 5 min) m/z 411.0 $[M+H]^+$, $t_R$ 3.39 min.

The intermediate 9ii was dissolved in 10 mL of dichloromethane and treated with trifluoroacetic acid (10 mL). The reaction was stirred at room temperature for 30 min, and then concentrated under reduced pressure. The oil obtained was re-dissolved in acetonitrile, re-concentrated under reduced pressure, treated with 2 N NaOH (25 mL) and extracted with dichloromethane (2×50 mL). The combined extracts were washed with saturated $NaHCO_3$, saturated brine, dried over $Na_2SO_4$ and filtered. The filtrate was concentrated under reduced pressure to afford crude free base 9iii as a pale yellow oil. LC/MS (RP—$C_{18}$, 10-99% $CH_3CN$/0.05% TFA gradient over 5 min) m/z 309.7 $[M+H]^+$, $t_R$ 2.07 min.

Intermediate 9iii (1.260 g, 4.08 mmol) was dissolved in anhydrous 1,2-dichloroethane (10 mL) and treated with 2 eq of 1-carbethoxy-4-piperidone (1.393 g, 8.16 mmol), followed by glacial acetic acid (0.490 g, 8.16 mmol) and sodium triacetoxyborohydride (1.721 g, 8.16 mmol). The reaction was stirred at room temperature under nitrogen for 48 h. The reaction was diluted with dichloromethane (50 mL), quenched with 1.0 N NaOH (20 mL) and stirred vigorously at room temperature for 30 min. The layers were separated and the aqueous layer extracted with DCM (2×20 mL). The pooled organic layers were washed with $H_2O$ (20 mL), brine (20 mL), then dried over $Na_2SO_4$ and filtered. The filtrate was concentrated under reduced pressure to afford 1.8 g crude product 9iv as pale yellow oil. An analytical sample was subjected to reverse-phase HPLC purification (2-50% $CH_3CN$ gradient over 13 min with 0.1% TFA (aq), 35 mL/min, 1.0 mL injected). The remainder of the material was taken to the next step without purification. $^1H$ NMR (400 MHz, DMSO-$d_6$) δ 9.94 (s, 1H), 8.00 (d, J=8.6 Hz, 1H), 7.41 (d, J=8.6 Hz, 1H), 7.27 (d, J=2.0 Hz, 1H), 4.13 (m, 4H), 4.06 (q, J=7.1 Hz, 2H), 3.54-3.46 (m, 3H), 3.16 (q, J=1.0 Hz, 2H), 2.83 (bs, 2H), 2.21 (s, 3H), 2.17-2.07 (m, 4H), 1.93 (d, J=15.6 Hz, 2H), 1.66-1.55 (m, 2H), 1.20 (t, J=7.0 Hz, 3H). LC/MS (RP—$C_{18}$, 10-99% $CH_3CN$/0.05% TFA gradient over 5 min) m/z 467.2 $[M+H]^+$, $t_R$ 1.97 min.

Product 9iv (46.4 mg, 0.1 mmol) was mixed with 4-methylphenyl boronic acid (14 mg, 0.1 mmol) in 1 mL of $CH_3CN$ and 1 mL of 2 M aq. $Na_2CO_3$. The microwave tube was purged with $N_2$ and 7 mg (10 mol %) of $PdCl_2(dppf)$ was added and tube was again purged with $N_2$, then sealed and microwaved for 20 min at 150° C. After reaction was complete, organic layer was separated, filtered trough silica gel plug, concentrated and was subjected to reverse-phase HPLC purification (RP—$C_{18}$, 2-50% $CH_3CN$/0.1% aq. TFA gradient over 13 min, 35 mL/min) to yield ethyl 4-(1-acetyl-5-p-tolylspiro[indoline-3,4'-piperidine]-1'-yl)piperidine-1-carboxylate (compound no. 58). $^1$H NMR (400 MHz, DMSO-d6) δ 9.79 (s, 1H), 8.11 (d, J=8.4 Hz, 1H), 7.53 (d, J=1.9 Hz, 1H), 7.52 (d, J=8.1 Hz, 2H), 7.39 (d, J=1.5 Hz, 1H), 7.26 (d, J=8.0 Hz, 2H), 4.14 (s, 4H), 4.06 (q, J=7.1 Hz, 2H), 3.58 (m, 3H), 3.19 (q, J=11.1 Hz, 2H), 2.85 (bs, 2H), 2.34 (s, 3H), 2.29-2.23 (m, 5H), 2.09 (d, J=12.9 Hz, 2H), 1.96 (d, J=13.9 Hz, 2H), 1.67-1.57 (m, 2H), 1.20 (t, J=7.1 Hz, 3H). LC/MS (RP—$C_{18}$, 10-99% $CH_3CN$/0.05% TFA gradient over 5 min): m/z 476.2 [M+H]$^+$, $t_R$ 2.36 min.

Example 10 ethyl 4-(1-acetyl-5-fluorospiro[indoline-3,4'-piperidine]-1'-yl)azepane-1-carboxylate (Cpd. No. 308)

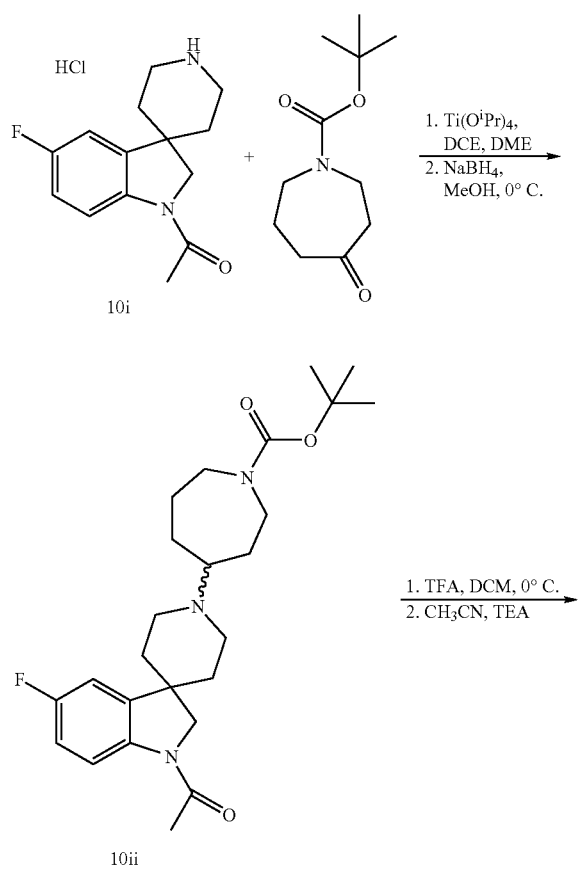

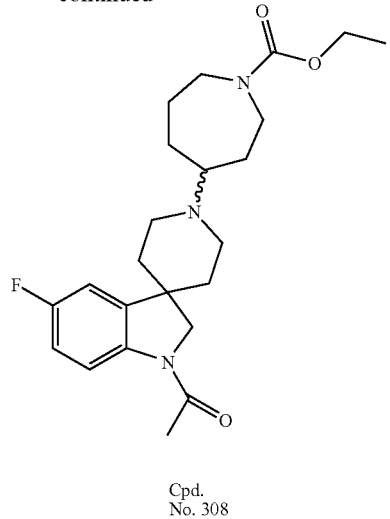

Cpd. No. 308

1.0 eq of the amine hydrochloride 10i (416 mg, 1.46 mmol) was suspended in anhydrous 1,2-dichloroethane: 1,2-dimethoxyethane (6.0 mL, 1:1 v/v) and treated with 1.0 eq triethylamine (148 mg), followed by 1.5 eq tert-butyl 4-oxoazepane-1-carboxylate (467 mg, 2.19 mmol) and 3.0 eq titanium tetraisopropoxide (1.3 mL, 1.26 g, 4.4 mmol). The reaction vial was flushed with nitrogen and stirred at room temperature for 3 days. The reaction was diluted with methanol (6.0 mL), cooled in an ice water bath and treated with sodium borohydride (110 mg, 2.92 mmol). The reaction was slowly warmed to room temperature and stirred thereafter for 90 min. The reaction was then further diluted with methanol (10 mL), quenched with 1.0 N NaOH (5.0 mL) and stirred vigorously at room temperature for 10 min. The suspension obtained was centrifuged (3K rpm, 10 min) and the supernatant concentrated under reduced pressure. The residue obtained was dissolved in dichloromethane (75 mL) and washed successively with $H_2O$, saturated sodium bicarbonate, and saturated brine, then dried over $Na_2SO_4$ and filtered. The filtrate was concentrated in vacuo to afford 704 mg crude product 10ii as a viscous, pale yellow oil. The crude product was used in the next step without further purification. $t_R$=2.14 min [10-99% $CH_3CN$ gradient over 5 mins with 0.1% TFA (aq)]; Theoretical (M+H)$^+$ m/z for $C_{25}H_{36}FN_3O_3$=446.3; Found 446.4.

The Boc-protected amine 10ii (573 mg) was dissolved in dichloromethane (5 mL), cooled in an ice water bath and treated slowly with ice-cold trifluoroacetic acid (5 mL). The reaction was stirred at ~0° C. for 1 h, then concentrated under reduced pressure. The oil obtained was dissolved in acetonitrile and re-concentrated under reduced pressure. The crude TFA salt was dissolved in methanol (6.0 mL) and purified by reverse-phase HPLC (2-25% $CH_3CN$/0.1% TFA gradient over 10 min, 6×1.0 mL injected, 35 mL/min). The combined pure fractions were concentrated in vacuo to afford 291 mg amine 10iii as the di-TFA salt, as a viscous, colorless oil. $^1$H-NMR (400 MHz, DMSO-d$_6$) δ 9.83 (br s, 1H), 8.74 (br s, 2H), 8.06 (dd, J=8.8 Hz, 5.0 Hz, 1H), 7.06 (br m, 1H), 6.97 (br m, 1H), 4.12 (s, 2H), 3.59 (br s, 1H), 3.13 (br m, 6H), 2.36 (m, 1H), 2.20 (s, 3H), 2.13 (m, 5H), 1.89 (m, 5H), 1.71 (m, 1H); $t_R$=1.06 min [10-99% $CH_3CN$ gradient over 5 min with 0.1% TFA (aq)]; Theoretical (M+H)$^+$ m/z for $C_{20}H_{28}FN_3O$=346.2; Found 346.0.

Deprotected amine 10iii (46 mg, 0.080 mmol, di-TFA salt) was dissolved in anhydrous acetonitrile (750 µL) and treated with 3.0 eq triethylamine (24 mg, 0.24 mmol). The mixture was then treated with ethyl chloroformate (9 µL, 10 mg, 0.096 mmol) and stirred at room temperature for 30 min. The reaction was quenched with methanol (500 µL) and purified by reverse-phase HPLC to provide ethyl 4-(1-acetyl-5-fluorospiro[indoline-3,4'-piperidine]-1'-yl)azepane-1-carboxylate (compound no. 308). (2-40% $CH_3CN/0.1\%$ TFA gradient over 10 min, 1.0 mL injected, 35 mL/min). $t_R$=1.90 min [10-99% $CH_3CN$ gradient over 5 min with 0.1% TFA (aq)]; Theoretical $(M+H)^+$ m/z for $C_{23}H_{32}FN_3O_3$=418.2; Found 418.4.

Example 11

1-(1'-(4-(ethoxyimino)cyclohexyl)-5-fluorospiro[indoline-3,4'-piperidine]-1'-yl)ethanone (Cpd. No. 86)

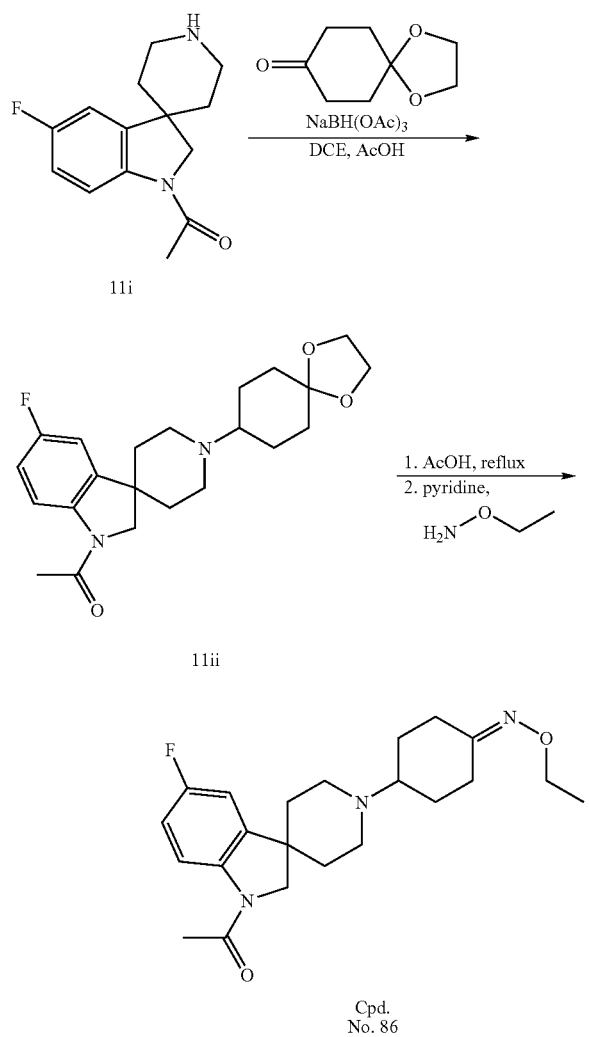

Spiroindoline 11i (300.0 mg; 1.21 mmol) and 4-oxocyclohexane spirodioxolane (283.1 mg; 1.81 mmol) were dissolved in DCE (5 mL). After 10 min, $NaBH(OAc)_3$ (512.1 mg; 2.42 mmol) was added, followed by AcOH (69.7 uL; 72.5 mg; 1.208 mmol) and the mixture was stirred at room temperature for 75 h. The reaction was quenched by adding MeOH (10 mL) and was stirred for 24 h. The resulting suspension was diluted with DCM (30 mL) and NaOH 1 N (5 mL) was added. The layers were separated, and the aqueous layer was extracted with DCM (3×30 mL). The combined organic extracts were dried on $Na_2SO_4$ and concentrated. The white solid residue was suspended in ether, the ethereal suspension was filtered and the precipitate was washed with ether (3×20 mL) and dried to provide the acetate salt of the desired product 11ii (400 mg). The material was used for the next step without further purification. LC/MS m/z 389.2 $[M+H]^+$, $t_R$ 1.73 min (10-99% $CH_3CN$—$H_2O$ gradient with 0.03% TFA, 5 min). $^1$H NMR (400 MHz, DMSO-$d_6$) δ 1.49 (m, 4H), 1.60 (d, J=13.0 Hz, 2H), 1.72 (d, J=9.4 Hz, 4H), 1.81 (td, J=13.4, 2.5 Hz, 2H), 2.19 (s, 3H), 2.28 (t, J=11.5 Hz, 2H), 2.37 (m, 1H), 2.80 (d, J=11.5 Hz, 2H), 3.85 (t, J=2.3 Hz, 4H), 3.95 (s, 2H), 6.97 (td, J=8.3, 1.8 Hz, 1H), 7.18 (dd, J=8.8, 2.7 Hz, 1H), 8.02 (dd, J=8.8, 5.0 Hz, 1H)

The ketal 11ii (350.0 mg; 0.82 mmol) was dissolved in 80% aq. acetic acid (20 mL) and the solution was refluxed overnight. LC/MS analysis shows complete deprotection of the ketal, along with some deacetylation of the indoline nitrogen. The reaction mixture was diluted with water (20 mL), cooled on an ice bath and neutralized by addition of solid KOH. The resulting suspension was filtered and the precipitate was washed with water (3×10 mL) and dried to provide the crude product as a tan powder. This material was dissolved in DCM (10 mL) and treated with excess AcCl (1 mL) and triethylamine (1 mL). After stirring at room temperature for 3 h, the mixture was diluted with DCM (30 mL) and washed with saturated $NaHCO_3$. The organic layer was dried on $Na_2SO_4$ and concentrated to provide the product 11iii as a yellow oil (253 mg), which was used for the next step without further purification. LC/MS m/z 345.0 $[M+H]^+$, $t_R$ 1.43 min (10-99% $CH_3CN$—$H_2O$ gradient with 0.03% TFA, 5 min); $^1$H NMR (400 MHz, $CDCl_3$) δ 1.68 (d, J=13.3 Hz, 2H), 1.82 (m, 2H), 1.91 (m, 2H), 2.07 (m, 2H), 2.18 (s, 3H), 2.29 (m, 6H), 2.45 (m, 2H), 2.78 (t, J=9.5 Hz, 1H), 2.97 (d, J=11.6 Hz, 2H), 3.81 (s, 2H) 6.88 (m, 2H), 8.16 (dd, J=8.5, 4.8 Hz, 1H).

The crude ketone (100.0 mg; 0.29 mmol) was dissolved in pyridine (1 mL) and treated with O-ethyl hydroxylamine hydrochloride (21.3 mg; 0.35 mmol). The vial was sealed and heated to 60° C. for 1 h. The solvent was evaporated under reduced pressure and the residue was dissolved in DMSO (2 mL) and the 1-(1'-(4-(ethoxyimino)cyclohexyl)-5-fluorospiro[indoline-3,4'-piperidine]-1'-yl)ethanone (compound no. 86) purified by reverse phase HPLC (2-99% $CH_3CN$—$H_2O$ gradient with 0.03% TFA, 15 min. run). LC/MS m/z 388.4 $[M+H]^+$, $t_R$ 1.87 min (10-99% $CH_3CN$—$H_2O$ gradient with 0.03% TFA, 5 min); $^1$H NMR (free base, 400 MHz, $CDCl_3$) δ 1.25 (t, J=7.0 Hz, 3H), 1.55 (m, 2H), 1.71 (d, J=13.1 Hz, 2H), 1.94 (m, 5H), 2.14 (m, 1H), 2.25 (s, 3H), 2.30 (td, J=11.9, 5.6 Hz, 2H), 2.50 (d, J=14.3 Hz, 1H), 2.62 (t, J=9.6 Hz, 1H), 2.94 (d, J=11.8 Hz, 2H), 3.25 (d, J=14.7 Hz, 1H), 3.86 (s, 2H), 4.07 (q, J=7.0 Hz, 2H), 6.88 (m, 2H), 8.16 (dd, J=8.5, 4.8 Hz, 1H).

Example 12 ethyl (S)-1'-((1R,2S,4S)-bicyclo[2.2.1]heptan-2-ylmethyl)-2,3-dihydrospiro[indene-1,4'-piperidine]-3-ylcarbamate (Cpd. No. 274)

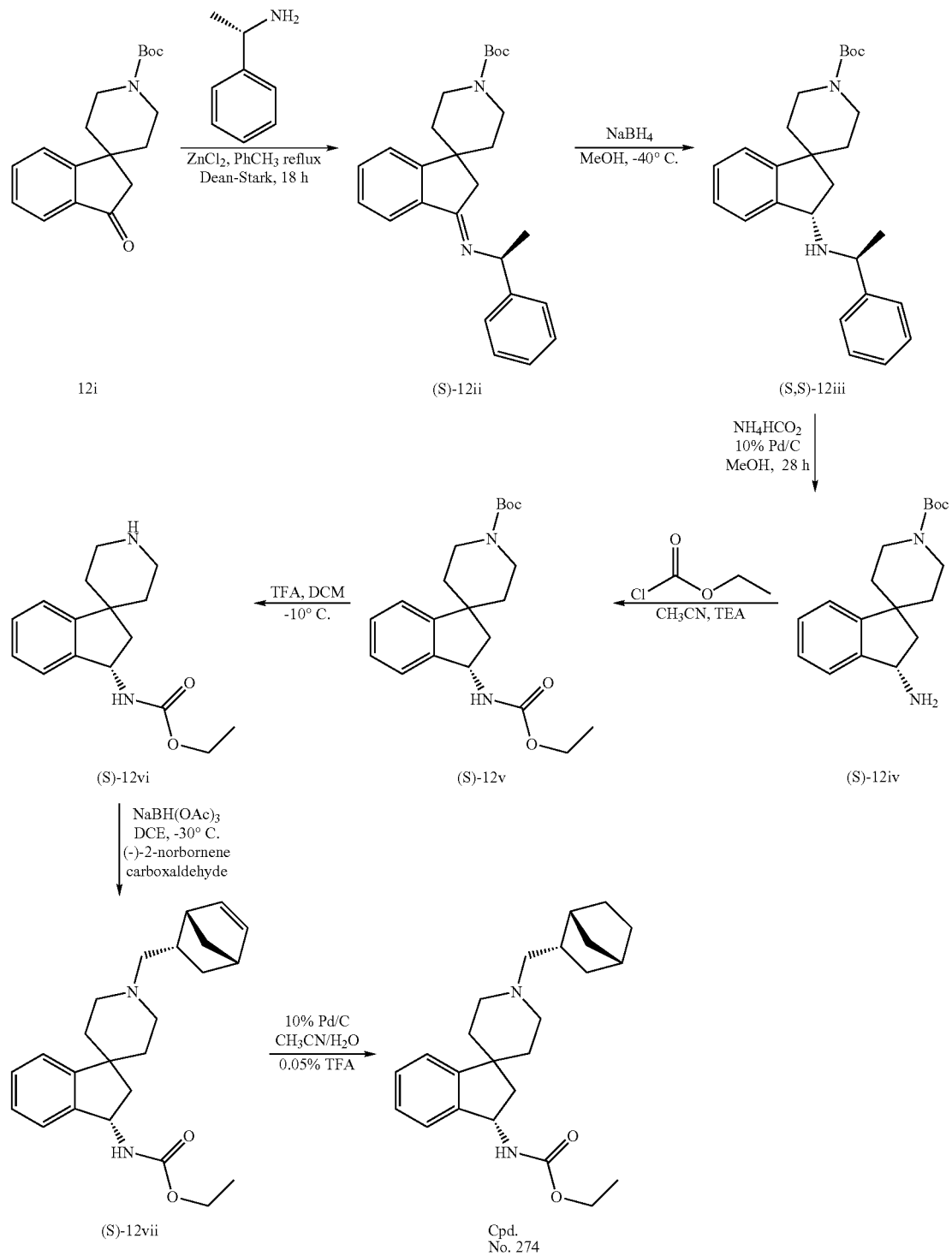

condenser for the removal of water. The reaction mixture was heated at reflux for 18 h. The reaction mixture was cooled, diluted with EtOAc (200 mL), and washed with 0.1 N NaOH (2×30 mL), 20% saturated $NH_4Cl$ (1×100 mL), and brine (1×100 mL). The organic layer was then dried over $Na_2SO_4$, The N-Boc protected indanone 12i (6.5 g, 21.6 mmol), (S)-1-phenylethanamine (2.875 g, 23.72 mmol, 1.1 eq), and anhydrous $ZnCl_2$ (88 mg, 0.647 mmol, 0.03 eq) were brought up in 35 mL dry toluene in a 100-mL flask under $N_2$ atmosphere. The flask was fitted with a Dean-Stark trap and reflux filtered, and dried down to afford imine (S)-12ii as a light orange solid. LC/MS analysis of the crude product indicated complete conversion to the desired product. LC/MS (10-99%) m/z 405.2 [M+H]$^+$, $t_R$ 2.76 min.

The crude imine (S)-12ii (21.6 mmol) was dissolved in anhydrous MeOH (30 mL) and cooled to −40° C. under $N_2$ atmosphere. $NaBH_4$ (816 mg, 21.6 mmol, 1.0 eq) was added in one portion. The reaction mixture was allowed to warm to −20° C. over 2 h, then warmed to −5° C. for 3 h. The reaction mixture was then diluted with EtOAc (200 mL), then washed with 50% saturated $NaHCO_3$ (100 mL), water (2×100 mL), and brine (100 mL). The organic layer was dried over $Na_2SO_4$, filtered, and dried down to yield (S, S)-12iii as a colorless oil. The oil was brought up in anhydrous diethyl ether, and 1 eq of ethereal HCl was added to precipitate the product as a fine white solid. The solid was filtered, washed with ether (100 mL), and dried under vacuum to obtain 7.2 g of (S, S)-12iii HCl salt as a white powder. $^1$H NMR (400 MHz, DMSO-$d_6$) δ 10.08 (m, 1H), 9.49 (m, 1H), 8.01 (d, J=7.5 Hz, 1H), 7.77 (d, J=7.1 Hz, 2H), 7.29-7.47 (m, 6H), 4.91 (m, 1H), 4.62 (m, 1H), 3.94 (m, 2H), 2.87 (bs, 2H), 2.62 (dd, J=13.5, 8.0 Hz, 1H), 1.99 (dd, J=13.5, 7.5 Hz, 1H), 1.92 (dt, J=12.9, 4.4 Hz, 1H), 1.76 (d, J=6.7 Hz, 3H), 1.58 (d, J=12.9 Hz, 1H), 1.42 (s+obscured m, 11H); LC/MS (10-99%) m/z 407.4 [M+H]$^+$, $t_R$ 2.70 min.

(S, S)-12iii (3.0 g, 6.8 mmol), ammonium formate (8.5 g, 135.4 mmol, 20 eq), and 800 mg 10% Pd/C (wet, 50% by weight) were brought up in MeOH (30 mL) in a 100-mL flask fixed with a $N_2$ balloon. The mixture was stirred at room temperature for 28 h. The reaction mixture filtered through packed Celite and concentrated in vacuo to ~10 mL. The concentrate was diluted with 50% saturated $NaHCO_3$ (200 mL), and the product extracted into EtOAc (3×100 mL). The combined extracts were washed with brine (50 mL), dried over $Na_2SO_4$, and concentrated in vacuo to obtain (S)-12iv as a colorless oil (2.0 g). $^1$H NMR (400 MHz, DMSO-$d_6$) δ 7.34 (m, 1H), 7.02-7.21 (m, 3H), 4.23 (t, J=7.7 Hz, 1H), 3.99 (m, 2H), 2.90 (br s, 2H), 2.57 (dd, J=12.7, 7.3 Hz, 1H), 2.00 (bs, 2H), 1.92 (dt, J=12.9, 4.5 Hz 1H), 1.42 (s+obscured m, 13H); LC/MS (10-99%) m/z 303.2 [M+H]$^+$, 286.2 [m/z-NH$_3$]$^+$, $t_R$ 2.31 min.

(S)-12iv (300 mg, 0.99 mmol) was dissolved in 1.5 mL anhydrous $CH_3CN$ and cooled to 0° C., followed by ethyl chloroformate (118 mg, 1.09 mmol, 1.1 eq) and triethylamine (200 μL). White precipitate formed upon addition of the triethylamine. The reaction was allowed to warm to room temperature and then stirred for 1 h. The reaction mixture was diluted with EtOAc (30 mL) and washed with 50% saturated $NaHCO_3$ (20 mL), water (20 mL), and brine (20 mL). The solution was dried over $Na_2SO_4$, filtered, and dried in vacuo to obtain product (S)-12v as a light yellow oil. LC/MS (10-99%) m/z 375.2 [M+H]$^+$, $t_R$ 3.43 min.

The crude (S)-12v was dissolved 5 mL $CH_2Cl_2$ and cooled to 0° C., followed by the addition of 5 mL TFA. The reaction mixture was stirred at 0° C. for 1 h, diluted with $CH_3CN$ (20 mL), and dried in vacuo to obtain the (S)-12vi TFA salt. The oil was dissolved in $CH_2Cl_2$ (30 mL), washed with 0.1 N NaOH (2×10 mL), brine (10 mL), dried over $Na_2SO_4$, filtered, and dried in vacuo to obtain the product (S)-12vi as a light yellow oil (269 mg). LC/MS (10-99%) m/z 275.2 [M+H]$^+$, $t_R$ 1.42 min.

(S)-12vi (269 mg, 0.98 mmol) was dissolved in cold DCE (1.5 mL) and treated with (1S,2S,4S)-bicyclo[2.2.1]hept-5-ene-2-carbaldehyde (119 mg, 0.98 mmol, 1.0 eq), followed by portion-wise addition of NaBH(OAc)$_3$ (300 mg, 1.4 mmol, 1.4 eq). The reaction was allowed to stir at room temperature for 1 h and was then quenched with MeOH (1 mL) and allowed to stir for another 30 min (until gas evolution stopped). The crude reaction mixture was purified by HPLC (10-99 $CH_3CN$ gradient, 0.05% TFA) to provide the desired product (S)-12vii as the TFA salt. LC/MS (10-99%) m/z 381.2 [M+H]$^+$, $t_R$ 2.28 min.

The combined HPLC fractions (~10 mL) were treated with 10% Pd/C (50 mg, wet, 50% by weight) under $H_2$ atmosphere with to cleanly provide (S)-12 g after 2 h of rapid stirring at room temperature. The solution was filtered through a 0.2 micron nylon filter and concentrated to provide 114 mg of ethyl (S)-1'-((1R,2S,4S)-bicyclo[2.2.1]heptan-2-ylmethyl)-2,3-dihydrospiro[indene-1,4'-piperidine]-3-ylcarbamate (compound no. 274) TFA salt. LC/MS (10-99%) m/z 383.2 [M+H]$^+$, $t_R$ 2.28 min; $^1$H-NMR(HCl salt, 400 MHz, DMSO-$d_6$) δ 10.39 (br s, 1H), 7.55 (d, J=8.4 Hz, 1H), 7.25 (m, 4H), 5.11 (m, 1H), 4.06 (q, J=7.0 Hz, 2H), 3.45 (m, 2H), 3.09 (m, 4H), 2.64 (m, 2H), 2.33 (br s, 2H), 2.15 (m, 2H), 1.84 (m, 1H), 1.67 (m, 3H), 1.48 (m, 2H), 1.34 (m, 3H), 1.20 (t, J=7.1 Hz, 3H), 1.14 (m, 1H), 0.88 (m, 1H).

Spiroindane (R)— compound no. 274 was produced utilizing an analogous synthetic route with the substitution of (R)-1-phenylethanamine for (S)-1-phenylethanamine in the synthesis of intermediate imine 12ii (step 1).

Example 13

N—((S)-1'-((1R,2S,4S)-bicyclo[2.2.1]heptan-2-ylmethyl)-2,3-dihydrospiro[indene-1,4'-piperidine]-3-yl)-N-methylacetamide (Cpd. No. 190)

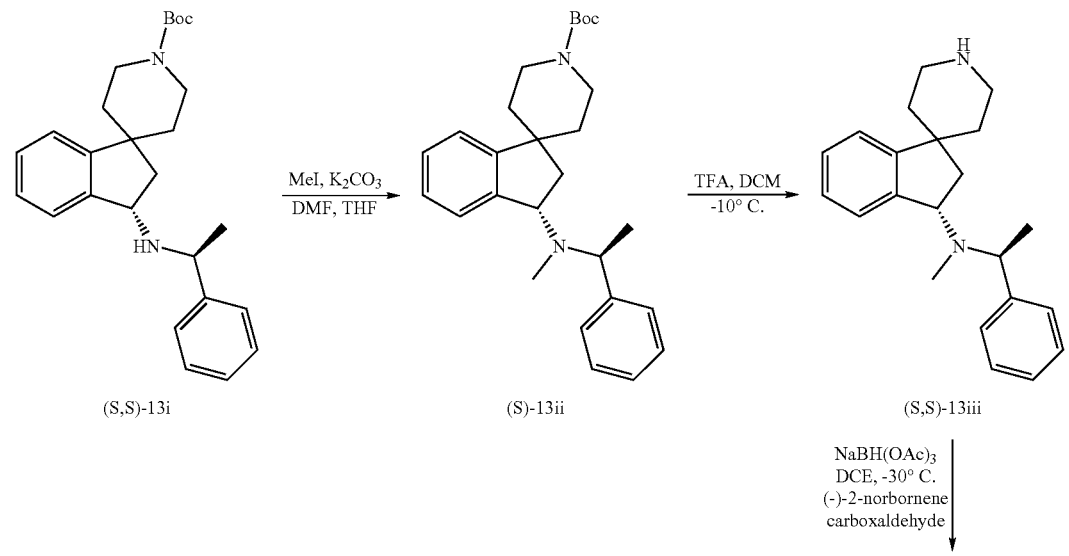

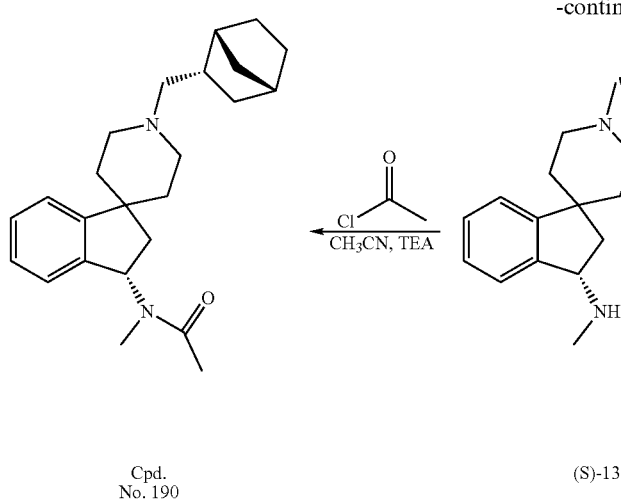
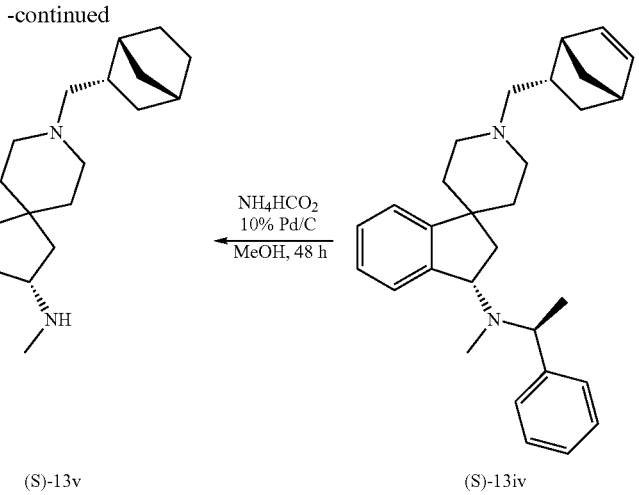

Cpd. No. 190    (S)-13v    (S)-13iv

To a flask containing (S, S)-13i (See Example 12, 1.5 g, 3.39 mmol) and K$_2$CO$_3$ (1.87 g, 13.54 mmol, 4 eq) was added 2 mL anhydrous DMF followed by 8 mL anhydrous THF. The mixture was treated with MeI (2.40 g, 16.93 mmol, 5 eq) and heated to 45° C. for 6 h, followed by stirring at room temperature for 16 h. The reaction mixture was diluted with EtOAc (200 mL) and washed with 20% saturated NH$_4$Cl (50 mL), 50% saturated NaHCO$_3$ (50 mL), brine (50 mL). The solution was dried over Na$_2$SO$_4$, filtered, and dried in vacuo to yield a reddish oil. The oil was dissolved in diethyl ether and filtered to remove insoluble material, followed by treatment with 1 eq of ethereal HCl. The resulting solution was dried down in vacuo to yield crude (S)-13ii as a light orange solid. LC/MS (10-99%) m/z 421.0 [M+H]$^+$, $t_R$ 2.77 min.

Crude (S)-13ii was dissolved in CH$_2$Cl$_2$ (50 mL) and cooled to −10° C., followed by the addition of 10 mL TFA. The reaction mixture was stirred at −10° C. for 1 h, diluted with CH$_3$CN (20 mL), and dried in vacuo to obtain the (S)-13iii TFA salt. The oil was dissolved in CH$_2$Cl$_2$ (30 mL), washed with 50% saturated NaHCO$_3$ (2×10 mL), brine (10 mL), dried over Na$_2$SO$_4$, filtered, and dried in vacuo to obtain the product (S)-13iii as a colorless oil (673 mg). $^1$H NMR (400 MHz, DMSO-d$_6$) δ 7.46 (d, J=7.2 Hz, 2H), 7.34 (t, J=7.4 Hz, 2H), 7.16-7.25 (m, 5H), 4.66 (t, J=8.0 Hz, 1H), 3.79 (q, J=6.7 Hz, 1H), 2.99 (app t, J=12.0 Hz, 2H), 2.79 (dt, J=12.4, 2.5 Hz, 1H), 2.69 (dt, J=12.7, 2.3 Hz, 1H), 2.07 (q, J=8.0 Hz, 1H), 1.97 (dt, J=13.3, 4.2 Hz, 1H), 1.85 (s, 3H), 1.73 (m, 1H), 1.52 (dt, J=12.7, 4.2 Hz, 1H), 1.42 (d, J=6.6 Hz, 3H), 1.36 (app t, J=12.9 Hz, 3H); LC/MS (10-99%) m/z 321.2 [M+H]$^+$, $t_R$ 1.60 min.

(S)-13iii (650 mg, 2.03 mmol) and (1S,2S,4S)-bicyclo[2.2.1]hept-5-ene-2-carbaldehyde (262 mg, 2.15 mmol) were dissolved in DCE (13 mL) and the mixture cooled to −30° C., followed by portion-wise addition of NaBH(OAc)$_3$ (646 mg, 3.05 mmol). The reaction was stirred at −30° C. for 2 h and was the allowed to warm to room temperature and stirred for 16 h. The reaction was quenched with MeOH (5 mL) and diluted with EtOAc (200 mL). The crude reaction was washed with 50% saturated NaHCO$_3$ (50 mL), water (50 mL), and brine (50 mL). The organic layer was dried over Na$_2$SO$_4$, filtered and dried in vacuo to yield the product (S)-13iv as a colorless oil (802 mg).

(S)-13iv (800 mg, 6.8 mmol), ammonium formate (2.36 g, 37.5 mmol), and 800 mg 10% Pd/C (wet, 50% by weight) were brought up in MeOH (8 mL) in a 25-mL flask fixed with a N$_2$ balloon. The mixture was stirred at room temperature for 24 h. 1.18 g of ammonium formate was added and the mixture stirred for an additional 24 h. The reaction mixture was filtered through packed Celite, diluted with 50% saturated NaHCO$_3$ (200 mL), and the product (S)-13v extracted into EtOAc (5×75 mL). The combined extracts were washed with brine (50 mL), dried over Na$_2$SO$_4$, and concentrated in vacuo to obtain (S)-13v as a colorless oil (493 mg). LC/MS (10-99%) m/z 325.4 [M+H]$^+$, $t_R$ 1.52 min.

(S)-13v (123 mg, 0.38 mmol) was dissolved in 1.5 mL anhydrous CH$_3$CN and cooled to 0° C., followed by the additional of acetyl chloride (33 mg, 0.42 mmol) and triethylamine (200 µL). White precipitate formed upon addition of the triethylamine. The reaction was allowed to warm to room temperature and then stirred for 1 h. The crude reaction mixture was purified by HPLC (10-99 CH$_3$CN gradient, 0.05% TFA) to provide N—((S)-1'-((1R,2S,4S)-bicyclo[2.2.1]heptan-2-ylmethyl)-2,3-dihydrospiro[indene-1,4'-piperidine]-3-yl)-N-methylacetamide (compound no. 190) as the TFA salt (65 mg). LC/MS (10-99%) m/z 367.2 [M+H]$^+$, retention time 1.99 min.

Spiroindane (R) form of compound no. 190 was produced utilizing an analogous synthetic route with the substitution of (R)-1-phenylethanamine for (S)-1-phenylethanamine in the synthesis of intermediate 13a (See Example 12).

Example 14

(S)-ethyl 4-((3-acetamido-2,3-dihydrospiro[indene-1,4'-piperidine]-1'-yl)methyl)-4-methylpiperidine-1-carboxylate

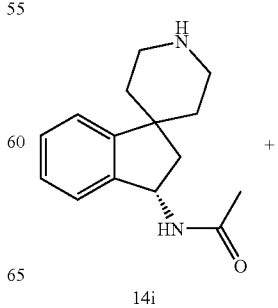

14i

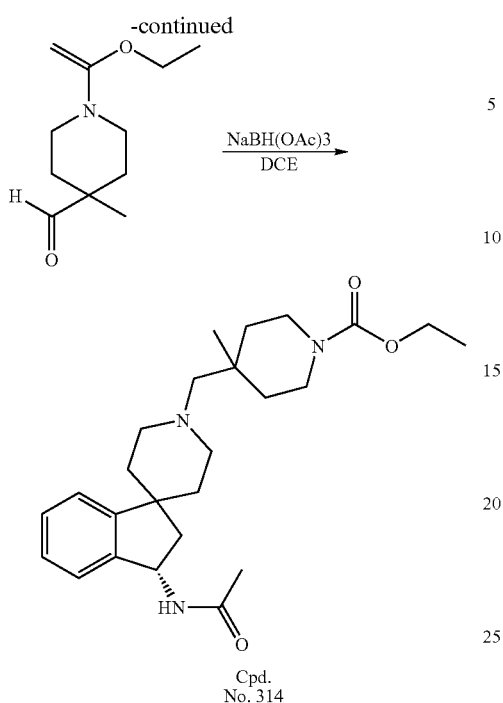

Intermediate 14i (49 mg; 0.2 mmol) and 4-formyl-4-methylpiperidine-1-carboxylate (40 mg; 0.2 mmol) were dissolved in DCE (2 mL) and NaBH(OAc)₃ (85 mg; 0.4 mmol) was added. The reaction was stirred at room temperature for 20 h. The reaction was diluted with DCM (10 mL) and 1N HCl (20 mL), the layers were separated, and the organic layer was discarded. The aqueous layer was washed with DCM (10 mL) and then was basified with NaOH. The aqueous layer was then washed with EtOAc (3×20 mL) and the combined organic layers were dried over Na₂SO₄, filtered, and concentrated under high vacuum. The crude product (S)-ethyl 4-((3-acetamido-2,3-dihydrospiro[indene-1,4'-piperidine]-1'-yl)methyl)-4-methylpiperidine-1-carboxylate (compound no. 314) was purified using reversed-phase chromatography (2-99% CH₃CN/H₂O gradient with 0.05% TFA). LC/MS m/z [M+H]⁺ 428.2, retention time 1.85 min (10-99% CH₃CN—H₂O gradient with 0.03% TFA, 5 min); ¹H-NMR (400 MHz, DMSO-d₆) δ 8.50 (br s, 1H), 8.26 (d, J=8.2 Hz, 1H), 7.27 (m, 4H), 5.35 (m, 1H), 4.04 (q, J=7.1 Hz, 2H), 3.69 (m, 2H), 3.53 (m, 2H), 3.31 (m, 2H), 3.18 (m, 5H), 2.69 (m, 1H), 2.07 (m, 1H), 1.89 (s, 3H), 1.66 (m, 3H), 1.50 (m, 4H), 1.19 (overlapping q and s, 6H).

Example 15 ethyl 4-((2',3'-dihydro-1'H-spiro[piperidine-4,4'-quinoline]-1-yl)methyl)cyclohexanecarboxylate (Cpd. No. 34)

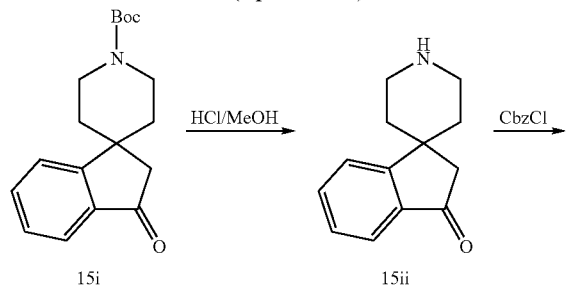

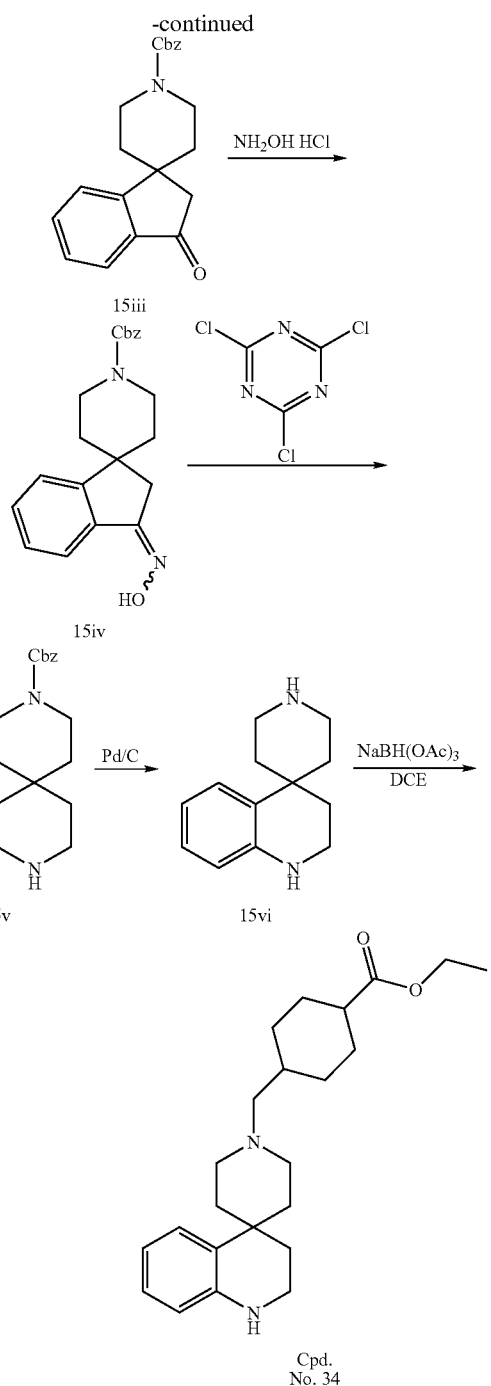

The mixture of N-Boc protected spiroindanone 15i (20 g, 66.4 mmol) and MeOH/HCl (2.5 mol/L, 100 mL) were stirred overnight. After evaporation the residue was washed by petroleum ether to give the corresponding amine hydrochloride 15ii (15.4 g).

To a solution of compound 15ii (5.0 g, 24.84 mmol) and Et₃N (7.54 g, 74.53 mol) in CH₂Cl₂ (50 mL) was added drop-wise Cbz-Cl (4.66 g, 27.33 mmol) at 0° C. The reaction was allowed to warm to room temperature and stirred overnight. The precipitate was filtered, washed with Et₂O and dried to furnish compound 15iii (6.1 g).

A solution of compound 15iii (3 g, 10.3 mmol) in EtOH (30 mL) containing NH₂OH.HCl (1.43 g, 20.6 mmol) and NaOAc (1.52 g, 18.53 mmol) was heated under reflux for 1.5 h. The solvent was removed by evaporation and the residue was partitioned between CH$_2$Cl$_2$ and water. The organic phase was washed with brine, dried over Na$_2$SO$_4$, and concentrated to give compound 15iv (3.14 g), which could be used directly in the next step.

2,4,6-trichloro-[1,3,5]-triazine (1.32 g, 7.16 mmol) was added to DMF (9.6 mL) maintained at 25° C. The reaction was monitored by TLC until TCT was consumed. Then compound 15iv (1.6 g, 4.77 mmol) in DMF (17 mL) was added. After the addition, the mixture was stirred at room temperature overnight. Water was added. The mixture was extracted with EtOAc. The combined organic layers were washed with saturated Na$_2$CO$_3$, followed by 1N HCl and brine, dried over Na$_2$SO$_4$ and concentrated. The residue was purified by prep HPLC to obtain compound 15v (260 mg).

The mixture of compound 15v (1.2 g, 3.4 mmol) and Pd/C (200 mg) in MeOH (20 mL) was hydrogenated under atmosphere pressure at room temperature for 3 h. The catalyst was filtered and the filtrate was concentrated under reduced pressure. The residue was purified by preparative HPLC twice to give 15vi (110 mg) as a TFA salt. $^1$H NMR (CDCl$_3$) δ 7.65 (d, J=7.5 Hz, 1H), 7.29-7.45 (m, 3H), 3.45 (d, J=12.3 Hz, 2H), 3.20 (t, J=12.3 Hz, 2H), 2.96 (s, 2H), 2.10-2.21 (m, 2H), 1.70 (d, J=14.1 Hz, 2H). MS (ESI) m/z 217.06 [M+H]$^+$.

Amine 15vi (22 mg, 0.1 mmol) and ethyl 4-formylpiperidine-1-carboxylate (28 mg, 0.15 mmol) were dissolved in DCE (1 mL) and NaBH(OAc)$_3$ (42 mg; 0.2 mmol) was added. The reaction was stirred at room temperature for 16 h. The reaction was diluted methanol (0.5 mL), filtered, and ethyl 4-((2',3'-dihydro-1'H-spiro[piperidine-4,4'-quinoline]-1-yl)methyl)cyclohexanecarboxylate (compound no. 34) was purified using reversed-phase chromatography (10-99% CH$_3$CN/H$_2$O gradient with 0.05% TFA). LC/MS m/z 386.2 [M+H]$^+$, retention time 2.05 min (10-99% CH$_3$CN—H$_2$O gradient with 0.03% TFA, 5 min); $^1$H NMR (free base, 400 MHz, DMSO-d$_6$) δ 7.71 (d, J=3.9 Hz, 2H), 7.61 (d, J=7.6 Hz, 1H), 7.47-7.41 (m, 1H), 4.05-3.96 (m, 4H), 2.86-2.67 (m, 4H), 2.56 (d, J=9.7 Hz, 2H), 2.18 (s, 2H), 2.01 (d, J=7.7 Hz, 4H), 1.73 (d, J=11.1 Hz, 4H), 1.45 (d, J=8.7 Hz, 2H), 1.18 (t, J=7.1 Hz, 3H), 1.03-0.96 (m, 2H).

Example 16 ethyl 3-(1'-methyl-2'-oxospiro[cyclohexane-1,3'-indoline]-4-yl)-8-azabicyclo[3.2.1]octane-8-carboxylate (Cpd. No. 149)

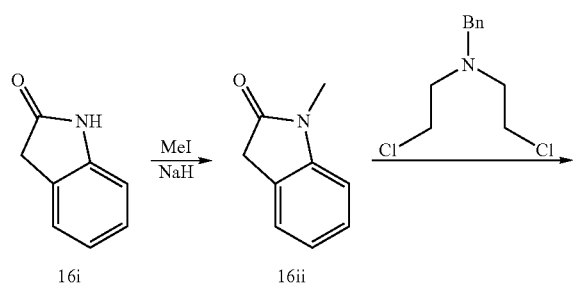

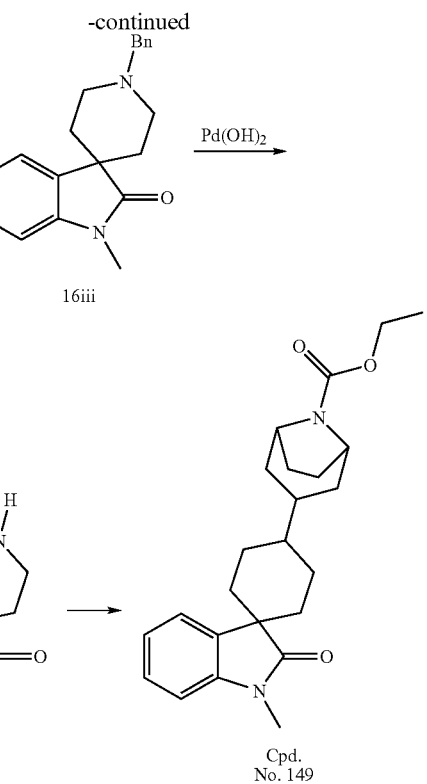

A stirred mixture of sodium hydride (60%, 31 g, 0.79 mol) in dry xylene (500 mL), under a nitrogen atmosphere, was heated to reflux for 30 min. 1,3-Dihydro-indol-2-one 16i (100 g, 0.75 mol) was then slowly added via an addition funnel and stirred at reflux for 1.5 h. Dimethyl sulfate (104 g, 0.83 mol) was added drop-wise, whereupon the resulting homogeneous solution was refluxed for an additional 2 h. After cooling to room temperature, the reaction mixture was washed with water, dried over Na$_2$SO$_4$, and concentrated under reduced pressure to afford 1-methyl-1,3-dihydro-indol-2-one 16ii (74 g). $^1$H NMR (300 MHz, CDCl$_3$) δ 7.23-7.31 (m, 2H), 7.04 (t, J=7.5 Hz, 1H), 6.82 (d, J=7.8 Hz, 1H), 3.52 (s, 2H), 3.21 (s, 3H).

A suspension of NaH (60%, 70 g, 0.48 mol) in THF (300 mL) was stirred for 10 min at 0° C. Then a solution of 1-methyl-1,3-dihydro-indol-2-one 16ii (70 g, 2.88 mol) in THF (200 mL) was added at 0° C., and the mixture was stirred for 1 h at room temperature. Benzyl-bis-(2-chloro-ethyl)-amine (129 g, 0.48 mol) was added in portions at 0° C. The mixture was stirred overnight at room temperature, and then was poured into ice water, extracted with EtOAc. The combined organic layers were dried over Na$_2$SO$_4$, and concentrated under reduced pressure. The residue was purified by column on silica gel (P.E./E.A. 2:1) to give compound 16iii (24 g). $^1$H NMR (300 MHz, CDCl$_3$) δ 7.25-7.42 (m, 7H), 7.02-7.07 (m, 1H), 6.83 (d, J=7.5, 1H), 3.68 (s, 2H), 3.19 (s, 3H), 2.74-2.99 (m, 2H), 2.66-2.72 (m, 2H), 1.93-2.01 (m, 2H), 1.79-1.85 (m, 2H).

To a solution of compound 16iii (12 g, 39.2 mmol) in MeOH (100 mL) was added Pd(OH)$_2$/C (1.5 g, 20%) under N$_2$. The suspension was hydrogenated under H$_2$ (50 psi) at room temperature for 4.5 h. The catalyst was filtered, and the filtrate was concentrated under reduced pressure to give the deprotected spiroindolone product 16iv (8 g). $^1$H NMR (400 MHz, DMSO-d$_6$) δ 7.46 (d, J=7.2, 1H), 7.23-7.27 (m, 1H), 6.96-7.03 (m, 2H), 3.04-3.14 (m, 5H), 2.83-2.89 (m, 2H), 1.61-1.67 (m, 2H), 1.45-1.51 (m, 2H). MS (ESI) m/z 217.1 [M+H]$^+$.

1.0 eq of deprotected spiroindolone 16v (22 mg, 0.10 mmol) was dissolved in anhydrous 1,2-dichloroethane: 1,2-dimethoxyethane (1.0 mL, 1:1 v/v) and treated with 1.5 N-Carbethoxy-4-tropinone (30 mg, 0.15 mmol), followed by titanium tetraisopropoxide (88 μL, 85 mg, 0.30 mmol). The vial was flushed with nitrogen and stirred at room temperature ~70 h. The reaction was then diluted with methanol (1.0 mL), cooled in an ice water bath and treated with sodium borohydride (8 mg, 0.20 mmol). After warming to room temperature and stirring for 90 min, the reaction was further diluted with methanol (2.0 mL), quenched with 1.0 N NaOH (500 μL) and stirred vigorously at room temperature for 10 min. The suspension obtained was centrifuged (3K rpm, 10 min) and the supernatant concentrated under reduced pressure. The residue obtained was dissolved in MeOH:acetonitrile (1250 μL, 1:1 v/v), filtered, and purified by reverse-phase HPLC (2-40% CH$_3$CN/0.1% TFA gradient over 10 min) to yield ethyl 3-(1'-methyl-2'-oxospiro[cyclohexane-1,3'-indoline]-4-yl)-8-azabicyclo[3.2.1]octane-8-carboxylate (compound no. 149). LC/MS (10-99%) m/z [M+H]$^+$ 398.2, t$_R$ 1.93 min.

Example 17

Compound no. 364 was synthesized using known methods and those described above.

$^1$H NMR (400 MHz, CDCl$_3$) δ 1.27 (t, J=6.3 Hz, 3H), 1.56 (d, J=11.5 Hz, 2H), 1.67 (q, J=7.0 Hz, 4H), 1.82 (m, 2H), 1.97 (m, 6H), 2.29 (t, J=11.5 Hz, 2H), 2.82 (m, 1H), 2.89 (dd, J=13.7, 6.5 Hz, 2H), 4.13 (q, J=7.1 Hz, 2H), 4.35 (d, J=24.4 Hz, 2H), 7.17 (m, 4H).

Example 18

Compound no. 413 was synthesized using known methods and those described above.

$^1$H NMR (free base, 400 MHz, DMSO-d6) δ 7.20-7.10 (m, 4H), 4.02 (q, J=7.1 Hz, 2H), 3.99-3.96 (m, 2H), 2.84 (t, J=7.3 Hz, 2H), 2.81-2.77 (m, 4H), 2.16 (d, J=4.9 Hz, 2H), 2.06 (t, J=12.2 Hz, 2H), 1.94 (t, J=7.3 Hz, 2H), 1.80 (t, J=11.3 Hz, 2H), 1.74-1.70 (m, 3H), 1.43 (d, J=12.5 Hz, 2H), 1.18 (t, J=7.1 Hz, 3H), 1.02-0.93 (m, 2H).

Example 19

Compound no. 375 was synthesized using known methods and those described above.

$^1$H NMR (400 MHz, DMSO-d$_6$) δ 10.18 (s, 1H), 6.99 (dt, J=12.8, 4.5 Hz, 1H), 6.91 (dd, J=8.0, 2.7 Hz, 1H), 6.82 (dd, J=8.7, 4.1 Hz, 1H), 6.25 (q, J=2.9 Hz, 1H), 6.07 (q, J=2.7 Hz, 1H), 4.50 (s, 2H), 3.51 (t, J=13.2 Hz, 2H), 3.04-2.96 (m, 3H), 2.91-2.84 (m, 2H), 2.74-2.68 (m, 1H), 2.40-2.30 (m, 2H), 2.03-1.97 (m, 2H), 1.88 (d, J=14.2 Hz, 2H), 1.32 (dd, J=33.8, 7.1 Hz, 2H), 0.69 (d, J=11.4 Hz, 1H).

Example 20

Compound no. 181 was synthesized using known methods and those described above.

$^1$H-NMR (400 MHz, DMSO-d$_6$) δ 10.03 (br s, 1H), 7.21 (dd, J=8.5, 2.3 Hz, 1H), 7.08 (d, J=2.3 Hz, 1H), 6.85 (d, J=8.5 Hz, 1H), 4.52 (s, 2H), 3.41 (m, 2H), 3.25 (m, 1H), 3.01 (m, 2H), 2.63 (m, 2H), 2.44 (m, 1H), 2.27 (m, 1H), 1.86 (m, 4H), 1.51 (m, 3H), 1.39 (m, 2H), 1.24 (m, 1H).

Example 21

Compound no. 23 was synthesized using known methods and those described above.

$^1$H-NMR (400 MHz, DMSO-d$_6$) δ 10.27 (br s, 1H), 8.53 (br s, 1H), 6.93 (d, J=7.9 Hz, 1H), 6.88 (s, 1H), 6.72 (d, J=7.9 Hz, 1H), 3.48 (s, 2H), 3.40 (m, 3H), 3.04 (m, 2H), 2.64 (m, 1H), 2.57 (br s, 1H), 2.38 (m, 1H), 2.26 (m, 1H), 2.24 (s, 3H), 1.94 (m, 2H), 1.78 (m, 2H), 1.55 (m, 3H), 1.39 (m, 3H).

Example 22

Compound no. 367 was synthesized using known methods and those described above.

$^1$H-NMR (300 MHz, CDCl$_3$): δ 7.08 (m, 1H), 6.95 (m, 2H), 4.28 (br s, 2H), 4.09 (q, J=7.2 Hz, 2H), 3.80 (s, 2H), 3.62 (m, 2H), 3.00 (m, 2H), 2.91 (m, 2H), 2.49 (m, 3H), 1.95-2.02 (m, 6H), 1.69 (m, 2H), 1.48 (m, 2H), 1.25 (t, J=7.2 Hz, 3H).

Example 23

Compound no. 370 was synthesized using known methods and those described above.

$^1$H-NMR (400 MHz, DMSO-d$_6$) δ 10.65 (br s, 1H), 8.05 (dd, J=8.9, 4.9 Hz, 1H), 7.06 (td, J=9.0, 2.7 Hz, 1H), 6.92 (dd, J=8.3, 2.7 Hz, 1H), 4.27 (br s, 2H), 4.08 (m, 4H), 3.74 (m, 1H), 3.55 (br s, 2H), 3.06 (m, 2H), 2.30 (m, 2H), 2.20 (s, 3H), 2.07 (m, 2H), 1.86 (m, 6H), 1.67 (m, 2H), 1.22 (t, J=7.1 Hz, 3H).

Example 24

Compound no. 422 was synthesized using known methods and those described above.

$^1$H-NMR (400 MHz, DMSO-d$_6$) δ 10.61 (br s, 1H), 7.93 (d, J=8.1 Hz, 1H), 7.02 (d, J=8.2 Hz, 1H), 6.96 (s, 1H), 4.06 (s, 2H), 3.96 (m, 3H), 3.59 (s, 3H), 3.51 (m, 2H), 3.11 (m, 2H), 3.00 (t, J=6.0 Hz, 2H), 2.83 (br s, 2H), 2.47 (m, 1H), 2.28 (s, 3H), 2.18 (s, 3H), 2.11 (m, 1H), 1.88 (m, 2H), 1.77 (m, 2H), 1.13 (m, 2H).

Example 25

Compound no. 92 was synthesized using known methods and those described above.

$^1$H-NMR (400 MHz, DMSO-d$_6$) δ 10.97 (br s, 1H), 7.93 (d, J=8.1 Hz, 1H), 7.02 (d, J=8.2 Hz, 1H), 6.95 (s, 1H), 4.13 (m, 2H), 4.06 (m, 4H), 3.45 (m, 3H), 3.12 (m, 2H), 2.83 (br s, 2H), 2.43 (m, 2H), 2.28 (s, 3H), 2.19 (s, 3H), 2.17 (m, 2H), 1.82 (m, 2H), 1.64 (m, 2H), 1.20 (t, J=7.1 Hz, 3H).

Example 26

Compound no. 412 was synthesized using known methods and those described above.

$^1$H NMR (400 MHz, DMSO-d$_6$) δ 11.06 (s, 1H), 8.05 (q, J=4.6 Hz, 1H), 7.06 (dt, J=12.9, 4.5 Hz, 1H), 6.94 (dd, J=8.3, 2.6 Hz, 1H), 4.13-4.09 (m, 4H), 4.05 (q, J=7.1 Hz, 2H), 3.50-3.39 (m, 3H), 3.13 (q, J=11.4 Hz, 2H), 2.83 (bs, 2H), 2.46 (t, J=13.5 Hz, 2H), 2.20 (s, 3H), 2.16 (d, J=11.6 Hz, 2H), 1.88 (d, J=13.8 Hz, 2H), 1.67-1.59 (m, 2H), 1.20 (t, J=7.1 Hz, 3H).

Example 27

Compound no. 361 was synthesized using known methods and those described above.

$^1$H NMR (400 MHz, DMSO-d$_6$) δ 1.22 (t, J=7.2 Hz, 3H), 1.66 (d, J=6.5 Hz, 2H), 1.87 (m, 6H), 2.05 (s, 2H), 2.21 (t, J=12.3 Hz, 2H), 2.87 (s, 6H), 3.05 (m, 2H), 3.52 (d, J=11.6 Hz, 2H), 3.73 (m, 1H), 3.84 (s, 2H), 4.08 (q, J=7.1 Hz, 2H), 4.26 (s, 2H), 6.90 (dd, J=8.3, 2.4 Hz, 1H), 7.00 (m, 2H), 10.38 (br s, 1H).

Example 28

Compound no. 39 was synthesized using known methods and those described above.

$^1$H NMR (400 MHz, CD$_3$CN) δ 1.25 (t, J=7.1 Hz, 3H), 1.66 (qd, J=12.3, 4.5 Hz, 2H), 1.98 (s, 2H), 2.10 (d, J=11.8 Hz, 2H), 2.28 (td, J=14.2, 3.7 Hz, 2H), 2.81 (t, J=15.9 Hz, 2H), 2.92 (s, 6H), 3.08 (q, J=11.3 Hz, 2H), 3.38 (dd, J=13.4, 10.5 Hz, 1H), 3.52 (d, J=12.3 Hz, 2H), 3.87 (s, 2H), 4.11 (q, J=7.1 Hz, 2H), 4.26 (d, J=12.1 Hz, 2H), 6.97 (m, 3H).

Example 29

Compound no. 91 was synthesized using known methods and those described above.

$^1$H NMR (400 MHz, CD$_3$CN) δ 0.96 (t, J=7.4 Hz, 3H), 1.66 (m, 4H), 1.98 (s, 2H), 2.10 (d, J=11.3 Hz, 2H), 2.28 (dt, J=19.9, 7.2 Hz, 2H), 2.87 (br s, 2H), 2.92 (s, 6H), 3.08 (q, J=11.2 Hz, 2H), 3.38 (t, J=12.2 Hz, 1H), 3.52 (d, J=11.9 Hz, 2H), 3.87 (s, 2H), 4.02 (t, J=6.6 Hz, 2H), 4.27 (d, J=12.8 Hz, 2H), 6.97 (m, 3H).

Example 30

Compound no. 54 was synthesized using known methods and those described above.

$^1$H NMR (400 MHz, CD$_3$CN) δ 1.24 (d, J=6.2 Hz, 6H), 1.65 (dq, J=12.3, 4.5 Hz, 2H), 1.99 (s, 2H), 2.09 (d, J=11.9 Hz, 2H), 2.25 (td, J=14.2, 3.7 Hz, 2H), 2.81 (t, J=11.4 Hz, 2H), 2.93 (s, 6H), 3.09 (q, J=11.3 Hz, 2H), 3.39 (m, 1H), 3.52 (d, J=12.3 Hz, 2H), 3.87 (s, 2H), 4.26 (d, J=12.8 Hz, 2H), 4.86 (heptet, J=6.2 Hz, 1H), 6.98 (m, 3H).

Example 31

Compound no. 208 was synthesized using known methods and those described above.

$^1$H NMR (400 MHz, CD$_3$CN) δ 1.67 (dq, J=12.2, 4.2 Hz, 2H), 2.15 (m, 4H), 2.27 (t, J=14.2 Hz, 2H), 2.87 (br s, 2H), 2.92 (s, 6H), 3.09 (q, J=11.3 Hz, 2H), 3.39 (t, J=12.0 Hz, 1H), 3.52 (d, J=12.0 Hz, 2H), 3.82 (m, 6H), 3.87 (s, 2H), 4.25 (d, J=11.2 Hz, 2H), 5.19 (s, 1H), 6.96 (m, 3H).

Example 32

Compound no. 120 was synthesized using known methods and those described above.

$^1$H NMR (400 MHz, CD$_3$CN) δ 1.67 (dq, J=12.2, 4.2 Hz, 2H), 2.15 (m, 4H), 2.27 (t, J=14.2 Hz, 2H), 2.87 (br s, 2H), 2.92 (s, 6H), 3.09 (q, J=11.3 Hz, 2H), 3.39 (t, J=12.0 Hz, 1H), 3.52 (d, J=12.0 Hz, 2H), 3.82 (m, 6H), 3.87 (s, 2H), 4.25 (d, J=11.2 Hz, 2H), 5.19 (s, 1H), 6.96 (m, 3H).

Example 33

Compound no. 48 was synthesized using known methods and those described above.

$^1$H NMR (400 MHz, CD$_3$CN) δ 1.69 (dq, J=12.3, 4.1 Hz, 2H), 1.99 (s, 2H), 2.12 (d, J=11.5 Hz, 2H), 2.28 (t, J=14.1 Hz, 2H), 2.87 (brs, 2H), 2.92 (s, 6H), 3.09 (q, J=11.3 Hz, 2H), 3.40 (t, J=11.9 Hz, 1H), 3.52 (d, J=12.3 Hz, 2H), 3.87 (s, 2H), 4.27 (m, 3H), 4.34 (m, 1H), 4.56 (t, J=3.9 Hz, 1H), 4.68 (t, J=3.9 Hz, 1H), 6.97 (m, 3H).

Example 34

Compound no. 352 was synthesized using known methods and those described above.

$^1$H NMR (400 MHz, CD$_3$CN) δ 1.68 (qd, J=12.3, 4.5 Hz, 2H), 1.85 (t, J=2.3 Hz, 3H), 1.98 (s, 2H), 2.12 (d, J=12.1 Hz, 2H), 2.30 (td, J=14.1, 3.7 Hz, 2H), 2.87 (br s, 2H), 2.92 (s, 6H), 3.08 (q, J=11.0 Hz, 2H), 3.39 (t, J=12.1 Hz, 1H), 3.51 (d, J=11.8 Hz, 2H), 3.87 (s, 2H), 4.25 (br s, 2H), 4.65 (d, J=2.1 Hz, 2H), 6.98 (m, 3H).

Example 35

Compound no. 127 was synthesized using known methods and those described above.

$^1$H NMR (400 MHz, CD$_3$CN) δ 1.68 (qd, J=12.3, 4.4 Hz, 2H), 1.99 (s, 2H), 2.11 (d, J=12.3 Hz, 2H), 2.27 (m, 2H), 2.55 (td, J=6.6, 2.7 Hz, 2H), 2.85 (br s, 2H), 2.92 (s, 6H), 3.08 (q, J=11.1 Hz, 2H), 3.39 (t, J=11.9 Hz, 1H), 3.51 (d, J=12.4 Hz, 2H), 3.87 (s, 2H), 4.15 (t, J=6.6 Hz, 2H), 4.26 (d, J=13.2 Hz, 2H), 6.97 (m, 3H).

Example 36

Compound no. 264 was synthesized using known methods and those described above.

$^1$H NMR (400 MHz, CD$_3$CN) δ 1.67 (qd, J=12.3, 4.3 Hz, 2H), 1.99 (s, 2H), 2.11 (d, J=10.6 Hz, 2H), 2.29 (t, J=14.1 Hz, 2H), 2.87 (br s, 2H), 2.92 (s, 6H), 3.08 (q, J=10.9 Hz, 2H), 3.34 (s, 3H), 3.40 (t, J=6.6 Hz, 1H), 3.52 (d, J=6.3 Hz, 2H), 3.57 (t, J=4.6 Hz, 2H), 3.86 (s, 2H), 4.18 (dd, J=5.1, 4.0 Hz, 2H), 4.26 (d, J=12.7 Hz, 2H), 6.96 (m, 3H).

Example 37

Compound no. 172 was synthesized using known methods and those described above.

$^1$H NMR (400 MHz, CD$_3$CN) δ 1.71 (qd, J=12.3, 4.4 Hz, 2H), 1.99 (s, 2H), 2.14 (d, J=14.4 Hz, 2H), 2.22 (s, 3H), 2.35 (td, J=14.2, 3.4 Hz, 2H), 2.89 (br s, 2H), 3.10 (q, J=10.6 Hz, 2H), 3.41 (t, J=11.4 Hz, 1H), 3.53 (d, J=12.6 Hz, 2H), 4.06 (s, 2H), 4.28 (m, 2H), 4.35 (t, J=4.0 Hz, 1H), 4.57 (t, J=4.0 Hz, 1H), 4.69 (t, J=4.0 Hz, 1H), 7.01 (m, 2H), 8.14 (dd, J=8.8, 4.9 Hz, 1H).

Example 38

Compound no. 102 was synthesized using known methods and those described above.

$^1$H NMR (400 MHz, CD$_3$CN) δ 1.71 (qd, J=12.3, 4.4 Hz, 2H), 1.85 (t, J=2.4 Hz, 3H), 1.99 (s, 2H), 2.13 (d, J=12.2 Hz, 2H), 2.22 (s, 3H), 2.35 (td, J=14.1, 3.6 Hz, 2H), 2.88 (br s, 2H), 3.09 (q, J=11.2 Hz, 2H), 3.40 (t, J=12.0 Hz, 1H), 3.53 (d, J=12.7 Hz, 2H), 4.06 (s, 2H), 4.26 (br s, 2H), 4.66 (d, J=2.2 Hz, 2H), 6.99 (td, J=9.0, 2.7 Hz, 1H), 7.05 (dd, J=8.6, 2.6 Hz, 1H), 8.14 (dd, 8.7, 4.8, 1H).

Example 39

Compound no. 62 was synthesized using known methods and those described above.

$^1$H NMR (400 MHz, CD$_3$CN) δ 1.70 (qd, J=12.2, 4.3 Hz, 2H), 1.99 (s, 2H), 2.13 (d, J=11.1 Hz, 2H), 2.22 (s, 3H), 2.27

(t, J=2.6 Hz, 1H), 2.36 (td, J=14.0, 3.5 Hz, 2H), 2.55 (td, J=6.6, 2.7 Hz, 2H), 2.87 (br s, 2H), 3.09 (q, J=10.4 Hz, 2H), 3.40 (t, J=12.1 Hz, 1H), 3.53 (d, J=12.3 Hz, 2H), 4.06 (s, 2H), 4.16 (t, J=6.6 Hz, 2H), 4.28 (d, J=12.6 Hz, 2H), 6.99 (td, J=9.0, 2.6 Hz, 1H), 7.05 (dd, J=8.6, 2.6 Hz, 1H), 8.13 (dd, J=8.8, 4.9 Hz, 1H).

Example 40

Compound no. 32 was synthesized using known methods and those described above.

$^1$H NMR (400 MHz, CD$_3$CN) δ 1.72 (d, J=7.3 Hz, 2H), 1.91 (d, J=2.5 Hz, 2H), 1.99 (s, 2H), 2.10 (m, 2H), 2.31 (td, J=14.0, 3.7 Hz, 2H), 2.91 (s, 6H), 2.96 (m, 2H), 3.36 (m, 2H), 3.57 (d, J=12.4 Hz, 2H), 3.63 (br s, 1H), 3.84 (s, 2H), 4.29 (t, J=4.0 Hz, 1H), 4.37 (m, 3H), 4.58 (t, J=3.9 Hz, 1H), 4.70 (t, J=3.9 Hz, 1H), 6.96 (m, 3H).

Example 41

Compound no. 200 was synthesized using known methods and those described above.

$^1$H NMR (400 MHz, CD$_3$CN) δ 1.72 (d, J=7.2 Hz, 2H), 1.85 (t, J=2.4 Hz, 3H), 1.98 (m, 4H), 2.11 (m, 2H), 2.30 (td, J=14.0, 3.6 Hz, 2H), 2.91 (s, 6H), 2.96 (br s, 2H), 3.08-3.72 (m, 5H), 3.84 (s, 2H), 4.37 (s, 2H), 4.67 (d, J=16.6 Hz, 2H), 6.96 (m, 3H).

Example 42

Compound no. 229 was synthesized using known methods and those described above.

$^1$H NMR (400 MHz, CD$_3$CN) δ 1.66 (br s, 2H), 1.84 (br s, 2H), 1.92 (br s, 2H), 1.98 (br s, 2H), 2.23 (m, 3H), 2.50 (dd, J=6.4, 2.5 Hz, 2H), 2.84 (s, 6H), 2.93 (m, 2H), 3.08 (m, 2H), 3.50 (d, J=10.9 Hz, 2H), 3.65 (br s, 1H), 3.77 (s, 2H), 4.11 (s, 2H), 4.30 (s, 2H), 6.90 (m, 3H).

Example 43

Compound no. 165 was synthesized using known methods and those described above.

$^1$H NMR (400 MHz, DMSO-d$_6$) δ 9.73 (s, 1H), 8.08 (d, J=8.4 Hz, 1H), 7.74 (q, J=1.3 Hz, 1H), 7.65 (q, J=2.6 Hz, 1H), 7.60 (dd, J=8.4, 1.7 Hz, 1H), 7.49 (dd, J=5.0, 1.2 Hz, 1H), 7.45 (d, J=1.5 Hz, 1H), 4.16-4.10 (m, 4H), 4.06 (q, J=7.1 Hz, 2H), 3.56-3.49 (m, 3H), 3.19 (q, J=11.3 Hz, 2H), 2.85 (br s, 2H), 2.28-2.23 (m, 5H), 2.10 (d, J=12.9 Hz, 2H), 1.96 (d, J=13.9 Hz, 2H), 1.66-1.57 (m, 2H), 1.20 (t, J=7.1 Hz, 3H).

Example 44

Compound no. 406 was synthesized using known methods and those described above.

$^1$H NMR (400 MHz, DMSO-d$_6$) δ 9.62 (s, 1H), 8.03 (d, J=8.3 Hz, 1H), 7.18 (d, J=8.4 Hz, 1H), 7.10 (s, 1H), 6.39 (d, J=10.3 Hz, 1H), 5.78-5.69 (m, 1H), 4.15-4.10 (m, 4H), 4.06 (q, J=7.1 Hz, 2H), 3.58-3.49 (m, 3H), 3.16 (q, J=10.8 Hz, 2H), 2.84 (br s, 2H), 2.21 (s, 3H), 2.16-2.07 (m, 4H), 1.93 (d, J=13.9 Hz, 2H), 1.87 (d, J=7.2 Hz, 3H), 1.63-1.55 (m, 2H), 1.20 (t, J=7.1 Hz, 3H

Example 45

Compound no. 158 was synthesized using known methods and those described above.

$^1$H-NMR (400 MHz, DMSO-d$_6$) δ 10.40 (br s, 1H), 8.31 (d, J=8.2 Hz, 1H), 7.27 (m, 4H), 5.34 (m, 1H), 3.40 (m, 3H), 3.13 (m, 1H), 2.97 (m, 2H), 2.65 (m, 1H), 2.57 (br s, 1H), 2.30 (m, 2H), 1.97 (m, 2H), 1.88 (s, 3H), 1.65 (m, 4H), 1.46 (m, 5H).

Example 46

Compound no. 182 was synthesized using known methods and those described above.

$^1$H-NMR (400 MHz, DMSO-d$_6$) δ 10.43 (br s, 1H), 8.31 (d, J=8.2 Hz, 1H), 7.28 (m, 4H), 5.34 (m, 1H), 3.96 (br m, 2H), 3.59 (s, 3H), 3.50 (m, 2H), 3.07 (m, 4H), 2.72 (m, 4H), 2.28 (m, 1H), 2.08 (m, 1H), 1.88 (s, 3H), 1.85 (m, 2H), 1.66 (m, 3H), 1.12 (m, 2H).

Example 47

Compound no. 358 was synthesized using known methods and those described above.

$^1$H NMR (400 MHz, DMSO-d$_6$) δ 10.65 (s, 1H), 8.30 (d, J=8.1 Hz, 1H), 7.34-7.31 (m, 1H), 7.27 (dt, J=10.1, 3.7 Hz, 1H), 7.22 (d, J=7.3 Hz, 1H), 7.17 (d, J=7.3 Hz, 1H), 5.33 (q, J=7.8 Hz, 1H), 4.26 (m, 2H), 4.08 (q, J=7.0 Hz, 2H), 3.77-3.70 (m, 1H), 3.52 (t, J=13.0 Hz, 2H), 3.06 (q, J=11.5 Hz, 1H), 2.97 (q, J=11.8 Hz, 1H), 2.61 (dd, J=13.2, 8.0 Hz, 1H), 2.54-2.47 (m, 1H), 2.15-2.04 (m, 3H), 1.91-1.81 (m, 7H), 1.71-1.66 (m, 5H), 1.22 (t, J=7.1 Hz, 3H).

Example 48

Compound no. 191 was synthesized using known methods and those described above.

$^1$H NMR (free base, 400 MHz, DMSO-d$_6$) δ 10.34 (s, 1H), 7.43 (d, J=7.3 Hz, 1H), 7.18 (dt, J=10.6, 3.8 Hz, 1H), 6.94 (dt, J=10.4, 3.8 Hz, 1H), 6.84 (d, J=7.6 Hz, 1H), 4.03 (q, J=7.1 Hz, 4H), 2.94-2.88 (m, 2H), 2.79 (s, 2H), 2.72-2.66 (m, 2H), 2.58-2.51 (m, 1H), 1.82-1.75 (m, 4H), 1.64-1.59 (m, 2H), 1.43-1.33 (m, 2H), 1.18 (t, J=7.1 Hz, 3H).

Example 49

Compound no. 199 was synthesized using known methods and those described above.

$^1$H NMR ((free base, 400 MHz, DMSO-d$_6$) δ 10.35 (s, 1H), 7.42 (d, J=7.4 Hz, 1H), 7.17 (dt, J=10.5, 3.8 Hz, 1H), 6.94 (t, J=7.1 Hz, 1H), 6.83 (d, J=7.4 Hz, 1H), 4.18 (m, 2H), 4.05 (q, J=6.5 Hz, 2H), 2.94-2.84 (m, 3H), 2.63 (t, J=8.1 Hz, 2H), 1.97-1.83 (m, 3H), 1.78-1.70 (m, 5H), 1.62-1.58 (m, 4H), 1.19 (t, J=7.1 Hz, 3H).

Example 50

Compound no. 318 was synthesized using known methods and those described above. Compound was prepared using reductive amination conditions described above. $^1$H NMR ((free base, 400 MHz, DMSO-d$_6$) δ 10.35 (s, 1H), 7.46 (d, J=7.4 Hz, 1H), 7.18 (dt, J=10.6, 3.8 Hz, 1H), 6.94 (dt, J=10.4, 3.8 Hz, 1H), 6.85 (d, J=7.6 Hz, 1H), 4.02 (q, J=7.1 Hz, 2H), 3.97 (m, 2H), 2.82-2.77 (m, 4H), 2.56-2.52 (m, 1H), 2.27 (d, J=6.8 Hz, 2H), 1.84-1.72 (m, 5H), 1.63-1.59 (m, 2H), 1.18 (t, J=7.1 Hz, 3H), 1.04-0.94 (m, 2H).

Example 51

Compound no. 104 was synthesized using known methods and those described above.

¹H NMR (free base, 400 MHz, DMSO-d6) δ 7.74-7.68 (m, 2H), 7.61 (d, J=7.6 Hz, 1H), 7.46-7.42 (m, 1H), 6.17-6.15 (m, 1H), 5.97-5.95 (m, 1H), 2.95-2.76 (m, 4H), 2.55 (s, 2H), 2.36-2.28 (m, 1H), 2.09-1.99 (m, 6H), 1.87-1.81 (m, 1H), 1.45 (d, J=3.9 Hz, 2H), 1.34-1.20 (m, 2H), 0.55-0.51 (m, 1H)

Example 52

Compound no. 186 was synthesized using known methods and those described above.

¹H NMR (400 MHz, DMSO-d$_6$) δ 9.44 (br s, 1H), 7.07-6.95 (m, 2H), 6.85-6.82 (m, 1H), (tt, J=28.8, 18.1 Hz, 1H), 4.51 (s, 2H), 4.40-4.31 (m, 4H), 3.74 (q, J=5.5 Hz, 1H), 3.59-3.40 (m, 4H), 2.98 (q, J=10.8 Hz, 2H), 2.07-1.93 (m, 8H), 1.68 (d, J=5.5 Hz, 4H).

Example 53

Compound no. 275 was synthesized using known methods and those described above.

¹H NMR (400 MHz, DMSO-d$_6$) δ 9.25 (br s, 1H), 7.32 (d, J=2.6 Hz, 1H), 7.16 (dd, J=8.7, 2.5 Hz, 1H), 6.82 (d, J=8.7 Hz, 1H), 4.11 (t, J=5.1 Hz, 2H), 3.38-3.34 (m, 2H), 3.25-3.13 (m, 3H), 2.31-2.23 (m, 2H), 2.08-2.04 (m, 4H), 1.85 (d, J=13.7 Hz, 4H), 1.63 (d, J=12.6 Hz, 1H), 1.49-1.39 (m, 2H), 1.34-1.29 (m, 2H), 1.21 (m, 1H)

Example 54

Compound no. 258 was synthesized using known methods and those described above.

¹H NMR (400 MHz, DMSO-d$_6$) δ 10.60 (s, 1H), 9.20 (bs, 1H), 7.30-7.15 (m, 2H), 7.07-6.87 (m, 2H), 3.65-3.35 (m, 5H), 2.66-2.64 (m, 1H), 2.40-2.30 (m, 3H), 2.07-1.98 (m, 1H), 1.92 (d, J=14.7 Hz, 1H), 1.79 (d, J=14.3 Hz, 1H), 1.68-1.51 (m, 3H), 1.47-1.38 (m, 3H), 1.27-1.20 (m, 1H).

Example 55

Compound no. 152 was synthesized using known methods and those described above.

¹H NMR (400 MHz, DMSO-d$_6$) δ 9.41 (br s, 1H), 7.04-6.93 (m, 2H), 6.84-6.80 (m, 1H), 4.53 (s, 2H), 3.47 (d, J=12.1 Hz, 1H), 3.40-3.38 (m, 1H), 3.24-3.17 (m, 1H), 3.06 (q, J=11.3 Hz, 2H), 2.19-2.11 (m, 2H), 2.05 (d, J=10.2 Hz, 2H), 1.94 (d, J=14.1 Hz, 2H), 1.84 (d, J=12.9 Hz, 2H), 1.63 (d, J=12.5 Hz, 1H), 1.46-1.23 (m, 4H), 1.17-1.07 (m, 1H).

Example 56

Compound no. 288 was synthesized using known methods and those described above.

¹H NMR (400 MHz; DMSO-d$_6$) δ 9.33 (br s, 1H), 7.05-6.92 (m, 2H), 6.85-6.80 (m, 1H), 6.34-6.31 (m, 1H), 4.50 (s, 2H), 4.33 (d, J=13.4 Hz, 2H), 3.83-3.74 (m, 1H), 3.67-3.51 (m, 3H) 2.95 (q, J=11.0 Hz, 2H), 2.07-1.85 (m, 8H), 1.74-1.58 (m, 4H), 1.08 (d, J=6.6 Hz, 6H).

Example 57

Compound no. 211 was synthesized using known methods and those described above.

¹H NMR (400 MHz, DMSO-d$_6$) δ 7.65 (br s, 1H), 7.06-6.95 (m, 2H), 6.85-6.80 (m, 1H), 5.18 (s, 1H), 4.51 (s, 2H), 4.25 (s, 2H), 3.81-3.71 (m, 5H), 3.58 (d, J=12.1 Hz, 2H), 2.98-2.93 (m, 2H), 2.13-1.94 (m, 10H), 1.65 (d, J=7.4 Hz, 4H).

Example 58

Compound no. 156 was synthesized using known methods and those described above.

¹H NMR (400 MHz, DMSO-d$_6$) δ 9.56 (br s, 1H), 7.06-6.95 (m, 2H), 6.86-6.80 (m, 1H), 4.51 (s, 2H), 4.26 (s, 2H), 3.57-3.44 (m, 6H), 2.97 (q, J=11.1 Hz, 2H), 2.08-2.02 (m, 4H), 1.94 (d, J=13.5 Hz, 4H), 1.70-1.65 (m, 4H).

Example 59

Compound no. 181 was synthesized using known methods and those described above.

¹H NMR (400 MHz, DMSO-d$_6$) δ 10.06 (br s, 1H), 7.21 (dd, J=8.5, 2.2 Hz, 1H), 7.08 (d, J=22 Hz, 1H), 6.85 (d, J=8.5 Hz, 1H), 4.52 (s, 2H), 3.47-3.21 (m, 3H), 3.10-2.94 (m, 2H), 2.66-2.40 (m, 3H), 2.27 (s, 1H), 1.96-1.83 (m, 4H), 1.56-1.53 (m, 3H), 1.42-1.33 (m, 3H).

Example 60

Compound no. 178 was synthesized using known methods and those described above. ¹H NMR (400 MHz, DMSO-d$_6$) δ 9.42 (br s, 1H), 7.30 (d, J=2.6 Hz, 1H), 7.18-7.16 (m, 1H), 6.84-6.81 (m, 1H), 4.14-3.99 (m, 2H), 3.46 (d, J=12.1 Hz, 4H), 3.36-3.31 (m, 2H), 3.20-3.11 (m, 3H), 2.28-2.20 (m, 2H), 2.07-2.00 (m, 4H), 1.88 (d, J=14.4 Hz, 2H), 1.75-1.64 (m, 2H).

Example 61

Physical Characteristics of Compounds of Formulae (I and II)

Additional compounds having the structures shown in Table I were synthesized using known methods and those described above.

TABLE 2

Physical Characteristics of Compounds in Table 1

| Cmd No. | LCMS Plus | LCMS RT |
|---|---|---|
| 2 | 327.3 | 2.8 |
| 3 | 309 | 1.88 |
| 4 | 379.2 | 1.99 |
| 5 | 306.2 | 2.32 |
| 6 | 476.2 | 2.34 |
| 7 | 309.4 | 1.93 |
| 8 | 353.3 | 2.16 |
| 9 | 426.2 | 1.94 |
| 10 | 519.4 | 1.92 |
| 11 | 412.2 | 1.98 |
| 12 | 397.5 | 2.48 |
| 13 | 328.2 | 2.05 |
| 14 | 460.5 | 2.13 |
| 15 | 369.2 | 2.19 |
| 16 | 508.5 | 2.2 |
| 17 | 458.4 | 2.35 |
| 18 | 286 | 2.13 |
| 19 | 378.2 | 1.94 |
| 20 | 336.4 | 2.23 |
| 21 | 484.2 | 2.2 |
| 22 | 459.4 | 2.04 |
| 23 | 297.4 | 1.26 |
| 24 | 524.5 | 2.44 |
| 25 | 496.5 | 2.35 |

TABLE 2-continued

Physical Characteristics of Compounds in Table 1

| Cmd No. | LCMS Plus | LCMS RT |
|---|---|---|
| 26 | 448.5 | 2.18 |
| 27 | 359.2 | 2.09 |
| 28 | 502.2 | 2.15 |
| 29 | 367.2 | 2.31 |
| 30 | 462.4 | 2.53 |
| 31 | 372.2 | 1.83 |
| 32 | 477.2 | 2.2 |
| 33 | 476.5 | 2.29 |
| 35 | 357.2 | 1.99 |
| 36 | 428.2 | 2.08 |
| 37 | 307.2 | 1.01 |
| 38 | 464.2 | 2.1 |
| 39 | 433.2 | 2.14 |
| 40 | 546.4 | 2.53 |
| 41 | 496.4 | 2.28 |
| 42 | 389.2 | 2.22 |
| 43 | 411.4 | 2.31 |
| 44 | 496.5 | 2.31 |
| 45 | 496.4 | 2.29 |
| 46 | 414.5 | 2.26 |
| 47 | 472.3 | 2.08 |
| 48 | 451.2 | 2.1 |
| 49 | 476.2 | 2.08 |
| 50 | 510.5 | 2.12 |
| 51 | 365.2 | 2.11 |
| 52 | 345.2 | 1.91 |
| 53 | 480.2 | 2.35 |
| 54 | 447.2 | 2.22 |
| 55 | 381.2 | 2.21 |
| 56 | 398.2 | 2.07 |
| 57 | 498.5 | 2.28 |
| 59 | 514.4 | 2.2 |
| 60 | 418.3 | 2.22 |
| 61 | 400.5 | 1.89 |
| 62 | 428.2 | 2.12 |
| 63 | 476.4 | 2.63 |
| 65 | 448.2 | 1.77 |
| 66 | 550.4 | 2.6 |
| 67 | 472.3 | 2.06 |
| 68 | 395 | 2.6 |
| 69 | 512.5 | 2.41 |
| 70 | 387.2 | 2.02 |
| 71 | 414.2 | 1.98 |
| 72 | 325.5 | 1.94 |
| 73 | 510.3 | 2.4 |
| 74 | 428.2 | 2.19 |
| 75 | 347 | 1.57 |
| 76 | 460.5 | 2.11 |
| 77 | 484.2 | 2.3 |
| 78 | 476 | 2.34 |
| 79 | 418.3 | 2.24 |
| 80 | 532.5 | 2.33 |
| 81 | 410.3 | 2.27 |
| 82 | 460.5 | 2.12 |
| 83 | 526.6 | 2.09 |
| 84 | 480.2 | 2.28 |
| 85 | 331.3 | 1.98 |
| 87 | 498.5 | 2.29 |
| 88 | 483.3 | 2.15 |
| 89 | 547.4 | 2.49 |
| 90 | 490.4 | 2.16 |
| 91 | 447.2 | 2.23 |
| 92 | 400.3 | 2.16 |
| 93 | 544.5 | 2.29 |
| 94 | 444.5 | 2.29 |
| 95 | 399.2 | 2.31 |
| 96 | 488.7 | 2.25 |
| 97 | 460.5 | 2.95 |
| 98 | 432.5 | 2.33 |
| 99 | 405.2 | 2.36 |
| 100 | 467.4 | 2.41 |
| 101 | 351.2 | 2.11 |
| 102 | 428.2 | 2.18 |
| 103 | 466.4 | 2.09 |
| 104 | 308.2 | 2.08 |
| 105 | 463.4 | 1.45 |
| 106 | 516.5 | 2.61 |
| 107 | 377.4 | 2.29 |
| 108 | 473.4 | 2.35 |
| 109 | 384.3 | 1.72 |
| 110 | 297.5 | 1.7 |
| 111 | 315.3 | 1.65 |
| 112 | 544.5 | 2.3 |
| 113 | 390.2 | 1.76 |
| 114 | 448.4 | 2.37 |
| 115 | 516.5 | 2.51 |
| 116 | 397.3 | 2.59 |
| 117 | 520.5 | 2.33 |
| 118 | 353.4 | 2.62 |
| 120 | 475.2 | 2.05 |
| 122 | 492.5 | 2.53 |
| 123 | 415.2 | 2.29 |
| 124 | 443 | 2.33 |
| 125 | 528.3 | 2.6 |
| 126 | 462.4 | 2.23 |
| 127 | 457.4 | 2.19 |
| 128 | 452.2 | 2.06 |
| 129 | 404.5 | 2.09 |
| 130 | 501.3 | 2.21 |
| 131 | 373.2 | 2.31 |
| 132 | 404.4 | 1.76 |
| 133 | 429 | 2.39 |
| 134 | 399.2 | 2.02 |
| 135 | 333.2 | 1.47 |
| 136 | 430.2 | 2.07 |
| 137 | 414.4 | 1.99 |
| 138 | 339.3 | 1.97 |
| 139 | 398.2 | 2.21 |
| 140 | 430.5 | 2.29 |
| 141 | 420.2 | 1.95 |
| 142 | 432.4 | 2.08 |
| 143 | 341.2 | 1.78 |
| 144 | 467.4 | 1.78 |
| 145 | 448.2 | 2.36 |
| 146 | 480.2 | 2.24 |
| 148 | 494.5 | 2.56 |
| 150 | 492.4 | 2.25 |
| 151 | 426.3 | 2.32 |
| 152 | 290 | 2.16 |
| 153 | 370.3 | 1.6 |
| 154 | 419.2 | 2.03 |
| 155 | 305.2 | 1.88 |
| 156 | 375 | 1.92 |
| 157 | 319.2 | 2 |
| 158 | 339.3 | 1.92 |
| 159 | 341.3 | 2.96 |
| 160 | 417.5 | 2.35 |
| 161 | 353.3 | 2.25 |
| 162 | 532.5 | 2.33 |
| 163 | 343 | 2.03 |
| 164 | 344 | 2.56 |
| 165 | 468.2 | 1.16 |
| 166 | 500.5 | 2.78 |
| 167 | 446.4 | 2.12 |
| 168 | 436.2 | 1.84 |
| 169 | 495.4 | 2.27 |
| 170 | 480.3 | 2.93 |
| 171 | 339.3 | 1.92 |
| 172 | 422.2 | 2 |
| 173 | 420.2 | 2.07 |
| 174 | 456.5 | 2.4 |
| 175 | 302.3 | 2.16 |
| 176 | 393.2 | 2.42 |
| 177 | 540.4 | 2 |
| 178 | 322.4 | 2.17 |
| 179 | 470.5 | 2.51 |
| 180 | 351.3 | 2.22 |
| 181 | 318 | 2.38 |
| 182 | 400.2 | 1.86 |
| 183 | 313 | 1.46 |

TABLE 2-continued

Physical Characteristics of Compounds in Table 1

| Cmd No. | LCMS Plus | LCMS RT |
|---|---|---|
| 184 | 341.2 | 1.87 |
| 185 | 351.4 | 1.86 |
| 186 | 425 | 2.15 |
| 187 | 331 | 1.89 |
| 188 | 501.3 | 2.19 |
| 189 | 552.6 | 2.52 |
| 191 | 358 | 1.68 |
| 192 | 488.3 | 2.25 |
| 193 | 492.4 | 2.25 |
| 194 | 460.4 | 2.49 |
| 195 | 516.5 | 2.56 |
| 196 | 327.2 | 1.62 |
| 197 | 525.6 | 2.44 |
| 198 | 544.5 | 2.3 |
| 199 | 384.2 | 2.06 |
| 200 | 483.4 | 2.35 |
| 202 | 432.5 | 2.31 |
| 203 | 388.2 | 2.12 |
| 204 | 302.3 | 2.14 |
| 205 | 412 | 1.86 |
| 206 | 329.5 | 0.92 |
| 207 | 316.2 | 2.45 |
| 208 | 406.4 | 2.29 |
| 209 | 475.2 | 2.04 |
| 210 | 345.2 | 1.94 |
| 211 | 419.4 | 2.12 |
| 212 | 431.4 | 1.96 |
| 213 | 351.2 | 2.11 |
| 214 | 456.5 | 2.38 |
| 215 | 491.2 | 2.25 |
| 216 | 532.5 | 2.33 |
| 217 | 410.2 | 2.26 |
| 218 | 351.2 | 2.11 |
| 219 | 388.2 | 2.04 |
| 220 | 462.4 | 2.54 |
| 221 | 504.4 | 2.14 |
| 222 | 510.4 | 2.35 |
| 223 | 461.4 | 2.24 |
| 224 | 317 | 1.8 |
| 225 | 470.5 | 2.43 |
| 226 | 373 | 2.23 |
| 227 | 389.2 | 2.28 |
| 228 | 403.2 | 1.93 |
| 229 | 446.2 | 2.21 |
| 230 | 483.4 | 2.3 |
| 232 | 375 | 2.08 |
| 233 | 552.5 | 2.25 |
| 234 | 463.2 | 1.49 |
| 235 | 432.5 | 2.24 |
| 236 | 399.2 | 2.03 |
| 238 | 308.2 | 2.09 |
| 239 | 303.3 | 1.73 |
| 240 | 345.2 | 2.28 |
| 241 | NA | NA |
| 242 | 313.2 | 1.88 |
| 243 | 544.5 | 2.31 |
| 244 | 297.5 | 1.59 |
| 245 | 426.2 | 2.05 |
| 246 | 395.2 | 2.28 |
| 247 | 431.5 | 2.46 |
| 248 | 359.2 | 2.08 |
| 249 | 418.4 | 1.98 |
| 250 | 414.4 | 1.91 |
| 251 | 357.2 | 1.99 |
| 252 | 414.5 | 2.35 |
| 253 | 487.4 | 2.18 |
| 254 | 444.4 | 2.23 |
| 255 | 459.4 | 2.02 |
| 256 | 434.4 | 2.05 |
| 257 | 308.2 | 2.09 |
| 258 | 409.2 | 2.68 |
| 259 | 297.2 | 1.78 |
| 260 | 467.4 | 1.74 |
| 261 | 355.4 | 1.94 |
| 262 | 496.4 | 2.25 |
| 263 | 294.4 | 2.33 |
| 264 | 297.4 | 1.24 |
| 265 | 463.2 | 2.04 |
| 266 | 432.4 | 2.04 |
| 267 | 484.2 | 2.27 |
| 268 | 333.5 | 1.84 |
| 269 | 418.3 | 2.23 |
| 270 | 446.4 | 2.29 |
| 271 | 424.2 | 2.38 |
| 272 | 283.3 | 1.34 |
| 273 | 403.4 | 2.17 |
| 275 | 383 | 2.47 |
| 276 | 320.2 | 2.37 |
| 278 | 411.2 | 2.12 |
| 279 | 442.5 | 2.08 |
| 280 | 341.2 | 1.85 |
| 281 | 472.4 | 2.44 |
| 282 | 446.4 | 2.24 |
| 283 | 403.5 | 2.21 |
| 284 | 434.5 | 2.05 |
| 285 | 383.2 | 2.53 |
| 286 | 417.5 | 2.36 |
| 287 | 474.3 | 2.58 |
| 288 | 336.4 | 2.17 |
| 289 | 402.4 | 2.16 |
| 290 | 475.2 | 1.89 |
| 291 | 339.5 | 0.51 |
| 292 | 392.2 | 2.13 |
| 293 | 430.5 | 2.14 |
| 294 | 480.5 | 2.48 |
| 295 | 530.2 | 2.55 |
| 296 | 473.4 | 2.11 |
| 297 | 516.5 | 2.65 |
| 298 | 526.6 | 2.57 |
| 299 | 291 | 0.45 |
| 300 | 316.2 | 1.44 |
| 301 | 426.2 | 1.98 |
| 302 | 484.5 | 2.61 |
| 303 | 432.5 | 2.13 |
| 304 | 532.3 | 2.31 |
| 305 | 351.3 | 2.22 |
| 306 | 428.5 | 2.38 |
| 307 | 418.4 | 1.84 |
| 309 | 418.4 | 1.9 |
| 310 | 388.5 | 1.66 |
| 311 | 486.5 | 2.3 |
| 313 | 294 | 2.33 |
| 315 | 428 | 1.85 |
| 316 | 428.2 | 1.95 |
| 317 | 418.6 | 1.97 |
| 318 | 426.3 | 2.1 |
| 319 | 372.2 | 1.79 |
| 320 | 403.2 | 2.23 |
| 321 | 457.2 | 2.07 |
| 322 | 430.2 | 1.94 |
| 323 | 339.1 | 1.92 |
| 324 | 432.4 | 2.14 |
| 325 | 289.2 | 0.77 |
| 326 | 383.2 | 2.3 |
| 327 | 386 | 1.92 |
| 328 | 331.2 | 2.11 |
| 329 | 500.3 | 2.86 |
| 330 | 480.2 | 2.38 |
| 331 | 467.4 | 2.01 |
| 332 | 397.27 | 1.79 |
| 333 | 319.2 | 1.86 |
| 334 | 313 | 2.01 |
| 335 | 484.2 | 2.34 |
| 336 | 426 | 1.96 |
| 337 | 353.2 | 1.84 |
| 338 | 431.4 | 1.97 |
| 339 | 367.3 | 2.3 |
| 340 | 416.2 | 1.76 |
| 341 | 347 | 2.41 |
| 342 | 285.3 | 1.65 |

TABLE 2-continued

Physical Characteristics of Compounds in Table 1

| Cmd No. | LCMS Plus | LCMS RT |
|---|---|---|
| 343 | 316.8 | 1.64 |
| 344 | 502.4 | 2.17 |
| 345 | 470.5 | 2.48 |
| 346 | 458.4 | 2.35 |
| 347 | 397.2 | 2.47 |
| 348 | 331.3 | 1.96 |
| 349 | 494.3 | 2.3 |
| 350 | 297.3 | 1.04 |
| 351 | 404.5 | 1.9 |
| 352 | 344 | 0.7 |
| 353 | 457.4 | 2.22 |
| 354 | 437.2 | 2.48 |
| 355 | 411.4 | 2.31 |
| 356 | 417.4 | 1.94 |
| 357 | 403 | 2.19 |
| 358 | 341.2 | 1.77 |
| 359 | 426 | 1.79 |
| 360 | 473.4 | 2.35 |
| 361 | 516.5 | 2.5 |
| 362 | 459.2 | 1.96 |
| 363 | 445.3 | 2.08 |
| 364 | 424 | 1.8 |
| 365 | 369.2 | 2.41 |
| 366 | 369.2 | 2.14 |
| 367 | 355.2 | 2.02 |
| 368 | 401.25 | 1.75 |
| 369 | 332.2 | 2.4 |
| 370 | 452.2 | 2.19 |
| 371 | 430.2 | 1.94 |
| 372 | 313.1 | 1.55 |
| 373 | 487.4 | 2.19 |
| 374 | 390.3 | 1.98 |
| 375 | 271.2 | 0.59 |
| 376 | 314 | 2.39 |
| 377 | 315.3 | 1.66 |
| 378 | 419.2 | 1.97 |
| 379 | 482.5 | 2.55 |
| 380 | 414.5 | 2.28 |
| 381 | 404.4 | 1.75 |
| 382 | 411.4 | 2.75 |
| 383 | 452.3 | 2.17 |
| 384 | 466.4 | 2.23 |
| 385 | 369 | 2.19 |
| 386 | 460.5 | 2.51 |
| 387 | 331 | 1.78 |
| 388 | 508.5 | 2.21 |
| 389 | 470.5 | 2.5 |
| 390 | 458.5 | 2.12 |
| 391 | 420.3 | 2.08 |
| 392 | 351.2 | 2.11 |
| 393 | 345.2 | 2.03 |
| 394 | 408.2 | 1.72 |
| 395 | 432.4 | 2.01 |
| 396 | 502.2 | 2.34 |
| 397 | 311.3 | 1.72 |
| 398 | 442.5 | 2.08 |
| 399 | 428.2 | 2.06 |
| 400 | 368 | 1.97 |
| 401 | 510.4 | 2.27 |
| 402 | 516.5 | 2.51 |
| 403 | 456.5 | 2.17 |
| 404 | 428.3 | 2.36 |
| 405 | 504.5 | 2.53 |
| 406 | 505.4 | 1.81 |
| 407 | 426 | 2.1 |
| 408 | 351.2 | 2.11 |
| 409 | 486.5 | 2.7 |
| 410 | 484.2 | 2.3 |
| 411 | 552.5 | 2.25 |
| 412 | 444.4 | 1.81 |
| 413 | 404.5 | 2.11 |
| 414 | 357.2 | 2.39 |
| 415 | 322.4 | 2.15 |
| 416 | 301.2 | 1.23 |
| 417 | 446.2 | 2.04 |
| 418 | 446.3 | 2.02 |
| 419 | 444.5 | 2.18 |
| 420 | 297.5 | 1.61 |
| 421 | 351.2 | 2.11 |
| 422 | 504.5 | 2.51 |
| 423 | 400.5 | 2.16 |
| 424 | 446.3 | 2.01 |
| 425 | 399.2 | 2.31 |
| 426 | 452.4 | 2.28 |
| 427 | 434.4 | 2.21 |
| 428 | 476.2 | 2.09 |
| 429 | 316.2 | 1.4 |
| 430 | 400.3 | 1.88 |
| 431 | 392.2 | 1.62 |
| 432 | 415 | 1.43 |
| 433 | 400 | 1.7 |
| 434 | 430 | 1.71 |
| 435 | 467.4 | 1.87 |
| 436 | 467.4 | 1.96 |
| 437 | 455.2 | 2.15 |
| 438 | 455.2 | 2.19 |
| 439 | 455 | 2.02 |
| 440 | 467.4 | 1.76 |
| 441 | 467 | 2.05 |
| 442 | 467.4 | 1.73 |
| 443 | 485.4 | 2.12 |
| 444 | 439.4 | 1.76 |
| 445 | 439.4 | 1.75 |
| 446 | 439.4 | 1.66 |
| 447 | 444.4 | 1.53 |
| 448 | 439.2 | 1.74 |
| 449 | 439.4 | 1.73 |
| 450 | 444.4 | 1.5 |
| 451 | 444.4 | 1.5 |
| 452 | 438.2 | 1.44 |
| 453 | 438.4 | 1.46 |
| 454 | 443.2 | 1.93 |
| 455 | 469.5 | 2.21 |
| 456 | 456.2 | 1.92 |
| 457 | 435.3 | 2.05 |
| 458 | 441.4 | 1.76 |
| 459 | 463.4 | 2.26 |
| 460 | 489.2 | 2.03 |
| 461 | 463.4 | 2.13 |
| 462 | 453.4 | 1.4 |
| 463 | 406.4 | 1.58 |
| 464 | 421.2 | 1.7 |
| 465 | 435.2 | 2.04 |
| 466 | 449.4 | 2.13 |
| 467 | 498.4 | 1.9 |
| 468 | 435.4 | 2.04 |
| 469 | 455 | 2 |
| 470 | 406.4 | 1.65 |
| 471 | 420.2 | 2.09 |
| 472 | 467.4 | 2.21 |
| 473 | 495.4 | 1.92 |
| 474 | 455.5 | 2.09 |
| 475 | 411.2 | 2 |
| 476 | 455.4 | 1.88 |
| 477 | 494.4 | 1.97 |
| 478 | 435.2 | 1.71 |
| 479 | 440.6 | 2 |
| 480 | 464.4 | 1.92 |
| 481 | 513.4 | 2.2 |
| 482 | | |
| 483 | 425.2 | 2.01 |
| 484 | 454.7 | 2 |
| 485 | 420.2 | 1.81 |
| 486 | 461.4 | 1.78 |
| 487 | 449.2 | 2.16 |
| 488 | 469.4 | 1.5 |
| 489 | 440 | 1.75 |
| 490 | 537.7 | 2.52 |
| 491 | 397 | 1.99 |
| 492 | 426 | 1.62 |

TABLE 2-continued

Physical Characteristics of Compounds in Table 1

| Cmd No. | LCMS Plus | LCMS RT |
|---|---|---|
| 493 | 467.2 | 2.14 |
| 494 | 449.5 | 1.85 |
| 495 | 427.2 | 2.16 |
| 496 | 495.4 | 1.51 |
| 497 | 471.4 | 1.98 |
| 498 | | |
| 499 | 440.4 | 2.07 |
| 500 | 447.4 | 2.1 |
| 501 | 481.2 | 1.77 |
| 502 | 522.4 | 1.14 |
| 503 | 432.4 | 1.86 |
| 504 | 426.2 | 2.07 |
| 505 | 498.8 | 1.01 |
| 506 | 427.2 | 1.72 |
| 507 | 454.4 | 0.89 |
| 508 | 454.2 | 2.08 |
| 509 | 499.3 | 2.44 |

Example 62

Functional Mobilization of Intracellular Calcium to Determine Muscarinic Receptor Activity CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat#12430-054), containing 25 mM Hepes and supplemented with Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 µg/ml of Streptomycin (GIBCO Cat# 15140-122). The recombinant muscarinic receptor cell lines are grown under antibiotic pressure with media containing 25 µm/ml zeocin and 500 µg/ml G418 (M1-CHO), 4 µg/ml puromycin, 50 µg/ml zeocin and 2.5 µm/ml blasticidin (M2 and M4-CHO) or 50 µg/ml zeocin and 4 µg/ml puromycin (M3 and M5-CHO).

Cells are harvested at 80-90% confluence using Versene (GIBCO Cat# 15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath1 buffer (140-mM NaCl, 4.5-mM KCL, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 µl/well of Fluo-3 µM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 µl/well of this solution after the wash. Alternatively, cells can be loaded with the calcium indicator from Molecular Devices (Calcium 3 Assay Reagents, Cat # R7181) adding 5 µl of a 5× solution dye in Bath 1 containing 1 mM Probenecid (10 ml per dye flask cat# R7182 to generate a solution 20×) to 20 µl of the same buffer. After loading for 60 min, the experiment can be run without having to remove the dye.

Compounds are prepared at a 2× fold concentration in a 96-well plate (round bottom, Costar Corning cat# 3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 µl compound/well) to the cell assay plate (containing 25 µl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 µl compound/well) to the assay plate and pre-incubated for 15 min prior to adding 25 µl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on $M_4$ receptors.

The compounds of the present invention were found to modulate the $M_1$ and/or $M_4$ muscarinic receptors selectively over the other receptor types.

Examples of activities and efficacies of the muscarinic compounds of formulae (I and II) on modulating $M_1$ and $M_4$ receptors are shown below in Table 2. The compound activity for the $M_1$ receptor is illustrated with "+++" if activity was measured to be less than or equal to 0.7 µM, "++" if activity was measured to be between 0.7 µM and 3.0 µM, and "+" if activity was measured to be greater than or equal to 3.0 µM for compound nos. 1-454. For compounds 455-509, compound activity for the $M_1$ and $M_4$ receptors are illustrated with "+++" if activity was measured to be less than or equal to 2.0 µM, "++" if activity was measured to be between 2.0 µM and 5.0 µM, and "+" if activity was measured to be greater than or equal to 5.0 µM. The compound activity for the $M_4$ receptor is illustrated with "+++" if activity was measured to be less than or equal to 0.1 µM, "++" if activity was measured to be between 0.1 µM and 4.0 µM, and "+" if activity was measured to be greater than or equal to 4.0 µM for compound nos. 1-454.

The efficacy for $M_1$ modulation is illustrated with "+++" if efficacy was calculated to be 85% or more, "++" if efficacy was calculated to be between 85% and 65%, and "+" if efficacy was calculated to be 65% or less for compound nos. 1-454. The efficacy for $M_4$ modulation is illustrated with "+++" if efficacy was calculated to be 70% or more, "++" if efficacy was calculated to be between 70% and 55%, and "+" if efficacy was calculated to be 55% or less for compound nos. 1-454. For compound nos. 455-509, $M_1$ and $M_4$ receptor modulation is illustrated with "+++" if efficacy was calculated to be 100% or more, "++" if efficacy was calculated to be between 100% and 25%, and "+" if efficacy was calculated to be 25% or less. A "−" symbol indicates that no data was available at this time. It should be noted that 100% efficacy is the maximum response obtained with the Carbachol control.

TABLE 2

Compound activities and efficacies for modulating $M_1$ and $M_4$ receptors.

| Cmd No. | $M_1$ Activity | $M_4$ Activity | $M_1$ Efficacy | $M_4$ Efficacy |
|---|---|---|---|---|
| 1 | ++ | ++ | ++ | +++ |
| 2 | + | + | + | + |
| 3 | +++ | ++ | ++ | ++ |
| 4 | +++ | + | + | + |
| 5 | +++ | +++ | ++ | +++ |
| 6 | +++ | ++ | ++ | ++ |
| 7 | +++ | ++ | ++ | +++ |
| 8 | ++ | ++ | + | ++ |
| 9 | +++ | + | ++ | ++ |
| 10 | ++ | ++ | ++ | ++ |
| 11 | + | + | + | + |
| 12 | +++ | ++ | + | + |
| 13 | ++ | + | ++ | + |
| 14 | +++ | +++ | ++ | +++ |
| 15 | +++ | ++ | ++ | +++ |
| 16 | +++ | +++ | ++ | ++ |
| 17 | ++ | ++ | + | ++ |
| 18 | +++ | ++ | + | +++ |
| 19 | +++ | ++ | ++ | ++ |
| 20 | + | ++ | + | + |
| 21 | ++ | + | + | + |
| 22 | +++ | + | ++ | + |
| 23 | ++ | + | + | + |
| 24 | ++ | + | + | + |
| 25 | +++ | +++ | ++ | +++ |
| 26 | +++ | ++ | ++ | + |
| 27 | +++ | +++ | ++ | ++ |
| 28 | +++ | ++ | +++ | ++ |
| 29 | +++ | +++ | +++ | +++ |
| 30 | +++ | +++ | +++ | +++ |
| 31 | +++ | +++ | +++ | ++ |
| 32 | +++ | +++ | +++ | ++ |
| 33 | +++ | +++ | +++ | +++ |
| 34 | +++ | ++ | ++ | +++ |
| 35 | +++ | ++ | +++ | +++ |
| 36 | +++ | ++ | ++ | +++ |
| 37 | +++ | ++ | ++ | +++ |
| 38 | +++ | +++ | +++ | +++ |
| 39 | +++ | ++ | ++ | +++ |
| 40 | +++ | ++ | ++ | +++ |
| 41 | +++ | +++ | +++ | +++ |
| 42 | +++ | ++ | +++ | +++ |
| 43 | +++ | + | +++ | +++ |
| 44 | +++ | ++ | ++ | +++ |
| 45 | +++ | +++ | +++ | ++ |
| 46 | +++ | +++ | +++ | ++ |
| 47 | +++ | ++ | ++ | ++ |
| 48 | +++ | ++ | +++ | ++ |
| 49 | +++ | +++ | +++ | ++ |
| 50 | +++ | ++ | +++ | +++ |
| 51 | +++ | ++ | ++ | ++ |
| 52 | +++ | +++ | +++ | ++ |
| 53 | ++ | ++ | + | ++ |
| 54 | +++ | ++ | +++ | ++ |
| 55 | +++ | +++ | +++ | ++ |
| 56 | +++ | +++ | ++ | ++ |
| 57 | +++ | +++ | ++ | ++ |
| 58 | +++ | ++ | ++ | ++ |
| 59 | +++ | ++ | + | ++ |
| 60 | ++ | + | ++ | ++ |
| 61 | +++ | ++ | ++ | ++ |
| 62 | +++ | ++ | + | ++ |
| 63 | +++ | + | + | + |
| 64 | +++ | ++ | + | + |
| 65 | ++ | + | ++ | + |
| 66 | +++ | +++ | +++ | +++ |
| 67 | +++ | ++ | + | + |
| 68 | ++ | + | + | + |
| 69 | ++ | ++ | + | + |
| 70 | ++ | + | ++ | ++ |
| 71 | +++ | ++ | + | + |
| 72 | +++ | ++ | ++ | ++ |
| 73 | +++ | ++ | ++ | ++ |
| 74 | +++ | ++ | ++ | ++ |
| 75 | +++ | ++ | + | ++ |
| 76 | +++ | ++ | ++ | ++ |
| 77 | +++ | ++ | ++ | + |
| 78 | +++ | ++ | ++ | + |
| 79 | ++ | + | + | + |
| 80 | ++ | ++ | + | + |
| 81 | ++ | + | + | + |
| 82 | +++ | ++ | ++ | ++ |
| 83 | +++ | + | + | + |
| 84 | +++ | ++ | ++ | ++ |
| 85 | +++ | ++ | ++ | ++ |
| 86 | +++ | + | ++ | + |
| 87 | +++ | + | ++ | + |
| 88 | +++ | ++ | ++ | + |
| 89 | +++ | ++ | ++ | + |
| 90 | ++ | + | ++ | + |
| 91 | +++ | ++ | ++ | + |
| 92 | +++ | ++ | ++ | + |
| 93 | ++ | ++ | + | + |
| 94 | +++ | ++ | + | + |
| 95 | +++ | ++ | ++ | + |
| 96 | ++ | + | ++ | + |
| 97 | +++ | + | ++ | + |
| 98 | +++ | ++ | ++ | + |
| 99 | +++ | + | + | + |
| 100 | +++ | ++ | ++ | ++ |
| 101 | +++ | ++ | ++ | ++ |
| 102 | +++ | ++ | ++ | ++ |
| 103 | +++ | ++ | ++ | + |
| 104 | +++ | + | ++ | + |
| 105 | ++ | + | + | + |
| 106 | +++ | ++ | ++ | + |
| 107 | +++ | + | ++ | + |
| 108 | +++ | ++ | ++ | + |
| 109 | +++ | ++ | ++ | + |
| 110 | +++ | ++ | + | + |
| 111 | +++ | ++ | ++ | + |
| 112 | +++ | ++ | ++ | + |
| 113 | +++ | + | ++ | + |
| 114 | ++ | + | ++ | + |
| 115 | +++ | ++ | ++ | + |
| 116 | +++ | ++ | ++ | + |
| 117 | +++ | ++ | ++ | + |
| 118 | +++ | + | ++ | + |
| 119 | +++ | + | + | + |
| 120 | ++ | + | + | + |
| 122 | +++ | ++ | ++ | + |
| 123 | ++ | + | + | + |
| 124 | +++ | ++ | + | + |
| 125 | +++ | ++ | ++ | + |
| 126 | +++ | + | + | + |
| 127 | +++ | ++ | ++ | + |
| 128 | +++ | ++ | + | + |
| 129 | +++ | + | ++ | + |
| 130 | +++ | ++ | + | + |
| 131 | +++ | ++ | ++ | +++ |
| 132 | +++ | +++ | +++ | +++ |
| 133 | +++ | ++ | +++ | ++ |
| 134 | +++ | ++ | +++ | + |
| 135 | +++ | ++ | +++ | +++ |
| 136 | +++ | +++ | +++ | +++ |
| 137 | +++ | + | +++ | +++ |
| 138 | +++ | + | ++ | ++ |
| 139 | +++ | +++ | +++ | +++ |
| 140 | +++ | +++ | +++ | +++ |
| 141 | +++ | ++ | +++ | +++ |
| 142 | +++ | + | ++ | +++ |
| 143 | +++ | +++ | ++ | +++ |
| 144 | +++ | +++ | +++ | +++ |
| 145 | +++ | + | +++ | +++ |
| 146 | +++ | +++ | +++ | +++ |
| 147 | +++ | ++ | ++ | +++ |
| 148 | +++ | ++ | ++ | +++ |
| 149 | +++ | + | +++ | +++ |

TABLE 2-continued

Compound activities and efficacies for modulating $M_1$ and $M_4$ receptors.

| Cmd No. | $M_1$ Activity | $M_4$ Activity | $M_1$ Efficacy | $M_4$ Efficacy |
|---|---|---|---|---|
| 150 | +++ | + | ++ | +++ |
| 151 | +++ | +++ | +++ | +++ |
| 152 | ++ | + | ++ | +++ |
| 153 | +++ | +++ | +++ | +++ |
| 154 | +++ | +++ | ++ | +++ |
| 155 | +++ | + | +++ | +++ |
| 156 | +++ | +++ | ++ | +++ |
| 157 | +++ | + | ++ | +++ |
| 158 | +++ | + | +++ | +++ |
| 159 | ++ | + | +++ | +++ |
| 160 | +++ | ++ | +++ | +++ |
| 161 | ++ | + | +++ | +++ |
| 162 | +++ | + | ++ | +++ |
| 163 | +++ | ++ | ++ | +++ |
| 164 | ++ | + | +++ | +++ |
| 165 | + | + | ++ | +++ |
| 166 | +++ | + | +++ | +++ |
| 167 | +++ | ++ | ++ | +++ |
| 168 | ++ | ++ |  | +++ |
| 169 | +++ | + | ++ | +++ |
| 170 | ++ | + | ++ | +++ |
| 171 | ++ | + | +++ | ++ |
| 172 | + | + | +++ | ++ |
| 173 | +++ | ++ | ++ | +++ |
| 174 | +++ | + | +++ | ++ |
| 175 | +++ | ++ | ++ | ++ |
| 176 | ++ | ++ | +++ | ++ |
| 177 | +++ | ++ | ++ | ++ |
| 178 | ++ | + | +++ | ++ |
| 179 | ++ | + | +++ | ++ |
| 180 | +++ | +++ | ++ | ++ |
| 181 | ++ | + | ++ | ++ |
| 182 | + | + | ++ | ++ |
| 183 | ++ | + | ++ | ++ |
| 184 | ++ | + | +++ | ++ |
| 185 | + | + | ++ | ++ |
| 186 | +++ | + | +++ | ++ |
| 187 | ++ | + | ++ | ++ |
| 188 | + | + | + | ++ |
| 189 | +++ | + | ++ | ++ |
| 190 | + | + | +++ | ++ |
| 191 | +++ | + | ++ | ++ |
| 192 | +++ | + | ++ | ++ |
| 193 | + | + | + | + |
| 194 | +++ | + | +++ | ++ |
| 195 | ++ | + | + | + |
| 196 | +++ | + | ++ | + |
| 197 | ++ | + | + | + |
| 198 | ++ | + | ++ | + |
| 199 | ++ | + | ++ | + |
| 200 | ++ | + | ++ | + |
| 202 | ++ | + | ++ | + |
| 203 | +++ | ++ | ++ | + |
| 204 | +++ | + | ++ | + |
| 205 | + | + | + | + |
| 206 | +++ | + | ++ | + |
| 207 | ++ | + | ++ | + |
| 208 | ++ | + | + | + |
| 209 | ++ | + | +++ | + |
| 210 | ++ | + | ++ | + |
| 211 | + | + | + | + |
| 212 | + | + | + | + |
| 213 | ++ | + | ++ | + |
| 214 | + | + | + | + |
| 215 | ++ | + | + | + |
| 216 | +++ | + | +++ | + |
| 217 | ++ | + | + | + |
| 218 | ++ | + | + | + |
| 219 | + | + | ++ | + |
| 220 | + | + | ++ | + |
| 221 | ++ | + | ++ | + |
| 222 | + | + | + | + |
| 223 | + | + | + | + |
| 224 | + | + | ++ | + |
| 225 | + | + | + | + |
| 226 | + | + | + | + |
| 227 | +++ | +++ | +++ | +++ |
| 228 | + | + | + | + |
| 229 | ++ | +++ | + | +++ |
| 230 | + | ++ | + | +++ |
| 231 | + | + | ++ | +++ |
| 232 | ++ | +++ | + | +++ |
| 233 | +++ | +++ | ++ | +++ |
| 234 | +++ | +++ | ++ | ++ |
| 235 | ++ | + | ++ | ++ |
| 236 | +++ | ++ | ++ | ++ |
| 237 | +++ | ++ | + | + |
| 238 | + | + | + | + |
| 239 | + | + | ++ | ++ |
| 240 | ++ | + | ++ | +++ |
| 241 | ++ | + | + | +++ |
| 242 | +++ | ++ | ++ | +++ |
| 243 | +++ | + | ++ | ++ |
| 244 | ++ | + | ++ | ++ |
| 245 | ++ | ++ | + | +++ |
| 246 | ++ | ++ | + | +++ |
| 247 | ++ | + | ++ | +++ |
| 248 | ++ | + | ++ | + |
| 249 | + | + | ++ | ++ |
| 250 | ++ | + | ++ | ++ |
| 251 | ++ | + | ++ | ++ |
| 252 | + | + | + | ++ |
| 253 | ++ | + | ++ | ++ |
| 254 | + | + | ++ | ++ |
| 255 | + | + | + | + |
| 256 | ++ | ++ | + | + |
| 257 | + | + | +++ | + |
| 258 | + | + | ++ | + |
| 259 | + | + | ++ | + |
| 260 | +++ | + | ++ | + |
| 261 | ++ | + | + | + |
| 262 | + | + | + | + |
| 263 | +++ | +++ | + | + |
| 264 | + | + | + | + |
| 265 | ++ | ++ | + | + |
| 266 | + | + | + | + |
| 267 | + | + | + | + |
| 268 | + | + | + | + |
| 269 | +++ | +++ | ++ | +++ |
| 270 | +++ | +++ | ++ | +++ |
| 271 | +++ | +++ | ++ | + |
| 272 | +++ | +++ | ++ | +++ |
| 273 | +++ | ++ | +++ | +++ |
| 274 | +++ | + | ++ | +++ |
| 275 | +++ | ++ | ++ | +++ |
| 276 | +++ | + | ++ | ++ |
| 277 | +++ | + | ++ | + |
| 278 | ++ | ++ | ++ | ++ |
| 279 | ++ | ++ | + | + |
| 280 | + | + | ++ | ++ |
| 281 | ++ | ++ | + | ++ |
| 282 | +++ | ++ | + | ++ |
| 283 | ++ | + | ++ | ++ |
| 284 | ++ | ++ | + | + |
| 285 | ++ | + | + | + |
| 286 | ++ | + | + | + |
| 287 | ++ | + | + | + |
| 288 | + | + | + | + |
| 289 | +++ | + | + | + |
| 290 | +++ | + | + | + |
| 291 | ++ | + | ++ | ++ |
| 292 | ++ | + | ++ | ++ |
| 293 | ++ | +++ | +++ | +++ |
| 294 | ++ | ++ | +++ | ++ |
| 295 | +++ | +++ | ++ | ++ |
| 296 | + | + | ++ | ++ |
| 297 | + | + | ++ | ++ |
| 298 | + | + | + | ++ |

TABLE 2-continued

Compound activities and efficacies for modulating $M_1$ and $M_4$ receptors.

| Cmd No. | $M_1$ Activity | $M_4$ Activity | $M_1$ Efficacy | $M_4$ Efficacy |
|---|---|---|---|---|
| 299 | + | + | ++ | ++ |
| 300 | ++ | + | ++ | + |
| 301 | + | + | + | + |
| 302 | + | + | + | + |
| 303 | ++ | + | +++ | + |
| 304 | +++ | + | ++ | + |
| 305 | + | + | + | + |
| 306 | + | + | + | + |
| 307 | ++ | + | ++ | + |
| 308 | +++ | + | +++ | + |
| 309 | ++ | + | +++ | + |
| 310 | ++ | + | + | + |
| 311 | +++ | + | ++ | ++ |
| 312 | + | + | + | + |
| 313 | + | + | + | + |
| 314 | ++ | + | + | + |
| 315 | + | + | + | + |
| 316 | + | + | + | + |
| 317 | + | + | + | + |
| 318 | +++ | +++ | ++ | +++ |
| 319 | ++ | + | + | + |
| 320 | ++ | + | ++ | + |
| 321 | ++ | + | ++ | ++ |
| 322 | ++ | +++ | + | +++ |
| 323 | ++ | + | ++ | ++ |
| 324 | ++ | + | ++ | ++ |
| 325 | + | + | ++ | + |
| 326 | + | + | + | + |
| 327 | + | + | + | + |
| 328 | ++ | + | + | ++ |
| 329 | +++ | + | ++ | + |
| 330 | + | + | + | + |
| 331 | ++ | + | + | + |
| 332 | + | + | + | + |
| 333 | + | + | + | + |
| 334 | + | + | + | + |
| 335 | + | + | + | + |
| 336 | + | + | + | + |
| 337 | + | + | + | + |
| 338 | + | + | + | + |
| 339 | + | + | + | + |
| 340 | ++ | + | + | + |
| 341 | + | + | + | + |
| 342 | +++ | ++ | ++ | ++ |
| 343 | +++ | +++ | ++ | + |
| 344 | +++ | ++ | ++ | + |
| 345 | +++ | ++ | + | + |
| 346 | +++ | + | + | + |
| 347 | +++ | ++ | ++ | +++ |
| 348 | +++ | ++ | +++ | +++ |
| 349 | ++ | ++ | +++ | +++ |
| 350 | +++ | +++ | +++ | +++ |
| 351 | +++ | ++ | ++ | +++ |
| 352 | +++ | + | +++ | +++ |
| 353 | +++ | + | +++ | ++ |
| 354 | + | + | ++ | ++ |
| 355 | ++ | ++ | ++ | ++ |
| 356 | +++ | + | +++ | ++ |
| 357 | ++ | + | + | + |
| 358 | +++ | ++ | ++ | ++ |
| 359 | ++ | ++ | + | + |
| 360 | ++ | + | ++ | + |
| 361 | ++ | + | + | + |
| 362 | ++ | + | ++ | + |
| 363 | ++ | + | + | + |
| 364 | +++ | + | +++ | + |
| 365 | +++ | + | ++ | + |
| 366 | ++ | + | + | + |
| 367 | + | + | + | + |
| 368 | +++ | ++ | + | + |
| 369 | +++ | ++ | +++ | +++ |
| 370 | +++ | ++ | ++ | +++ |
| 371 | +++ | + | ++ | +++ |
| 372 | +++ | ++ | ++ | +++ |
| 373 | +++ | ++ | ++ | +++ |
| 374 | ++ | + | ++ | ++ |
| 375 | +++ | +++ | +++ | ++ |
| 376 | +++ | + | ++ | ++ |
| 377 | +++ | ++ | ++ | ++ |
| 378 | ++ | + | ++ | ++ |
| 379 | +++ | ++ | ++ | ++ |
| 380 | +++ | ++ | ++ | ++ |
| 381 | +++ | + | ++ | + |
| 382 | +++ | + | ++ | ++ |
| 383 | +++ | ++ | ++ | + |
| 384 | ++ | + | + | + |
| 385 | ++ | + | ++ | + |
| 386 | ++ | ++ | + | + |
| 387 | +++ | ++ | ++ | + |
| 388 | +++ | + | ++ | + |
| 389 | ++ | + | ++ | + |
| 390 | +++ | + | ++ | + |
| 391 | ++ | + | + | + |
| 392 | +++ | + | ++ | + |
| 393 | +++ | + | ++ | + |
| 394 | +++ | ++ | + | + |
| 395 | +++ | + | + | + |
| 396 | ++ | + | + | + |
| 397 | ++ | + | ++ | + |
| 398 | ++ | + | + | + |
| 399 | ++ | ++ | ++ | + |
| 400 | + | + | + | + |
| 401 | +++ | + | ++ | + |
| 402 | ++ | + | ++ | + |
| 403 | +++ | + | ++ | + |
| 404 | ++ | + | + | + |
| 405 | ++ | + | + | + |
| 406 | ++ | + | + | + |
| 407 | ++ | + | + | + |
| 408 | +++ | +++ | ++ | ++ |
| 409 | +++ | +++ | +++ | +++ |
| 410 | ++ | ++ | + | + |
| 411 | +++ | ++ | + | + |
| 412 | ++ | + | + | + |
| 413 | +++ | ++ | + | + |
| 414 | + | + | + | + |
| 415 | + | + | + | + |
| 416 | + | + | + | + |
| 417 | ++ | + | + | + |
| 418 | + | + | + | + |
| 419 | + | + | + | + |
| 420 | ++ | + | + | + |
| 421 | + | + | + | + |
| 422 | +++ | + | + | + |
| 423 | ++ | + | + | + |
| 424 | + | + | + | + |
| 425 | + | + | + | + |
| 426 | + | + | + | + |
| 427 | ++ | + | + | + |
| 428 | ++ | + | + | + |
| 429 | ++ | + | + | + |
| 430 | ++ | + | + | + |
| 431 | − | − | − | − |
| 432 | +++ | +++ | ++ | ++ |
| 433 | ++ | ++ | ++ | + |
| 434 | − | − | − | − |
| 435 | − | − | − | − |
| 436 | − | − | − | − |
| 437 | ++ | ++ | ++ | + |
| 438 | ++ | +++ | ++ | ++ |
| 439 | ++ | +++ | ++ | + |
| 440 | ++ | ++ | ++ | ++ |
| 441 | ++ | +++ | ++ | ++ |
| 442 | ++ | ++ | ++ | ++ |
| 443 | ++ | ++ | ++ | ++ |
| 444 | +++ | +++ | ++ | ++ |
| 445 | ++ | +++ | ++ | ++ |
| 446 | ++ | +++ | ++ | ++ |

TABLE 2-continued

Compound activities and efficacies for modulating $M_1$ and $M_4$ receptors.

| Cmd No. | $M_1$ Activity | $M_4$ Activity | $M_1$ Efficacy | $M_4$ Efficacy |
|---|---|---|---|---|
| 447 | +++ | +++ | ++ | ++ |
| 448 | +++ | +++ | +++ | ++ |
| 449 | +++ | +++ | ++ | ++ |
| 450 | ++ | +++ | ++ | ++ |
| 451 | ++ | +++ | ++ | ++ |
| 452 | ++ | +++ | ++ | ++ |
| 453 | +++ | +++ | ++ | ++ |
| 454 | ++ | ++ | ++ | ++ |
| 455 | +++ | ++ | +++ | ++ |
| 456 | ++ | ++ | +++ | ++ |
| 457 | +++ | ++ | +++ | ++ |
| 458 | +++ | ++ | +++ | +++ |
| 459 | ++ | ++ | +++ | ++ |
| 460 | +++ | ++ | +++ | ++ |
| 461 | ++ | ++ | +++ | ++ |
| 462 | + | ++ | ++ | + |
| 463 | +++ | ++ | +++ | ++ |
| 464 | +++ | ++ | +++ | +++ |
| 465 | ++ | ++ | +++ | ++ |
| 466 | ++ | ++ | +++ | ++ |
| 467 | +++ | + | +++ | ++ |
| 468 | + | ++ | +++ | ++ |
| 469 | +++ | ++ | +++ | ++ |
| 470 | +++ | ++ | +++ | ++ |
| 471 | ++ | ++ | +++ | ++ |
| 472 | +++ | ++ | +++ | ++ |
| 473 | +++ | ++ | +++ | ++ |
| 474 | +++ | ++ | +++ | ++ |
| 475 | ++ | ++ | ++ | ++ |
| 476 | +++ | +++ | +++ | +++ |
| 477 | +++ | ++ | +++ | ++ |
| 478 | +++ | ++ | +++ | ++ |
| 479 | +++ | ++ | +++ | ++ |
| 480 | ++ | ++ | ++ | ++ |
| 481 | +++ | ++ | + | + |
| 482 | +++ | ++ | +++ | ++ |
| 483 | ++ | ++ | ++ | ++ |
| 484 | +++ | ++ | +++ | ++ |
| 485 | +++ | ++ | +++ | ++ |
| 486 | +++ | ++ | +++ | ++ |
| 487 | +++ | ++ | +++ | ++ |
| 488 | + | ++ | +++ | ++ |
| 489 | +++ | ++ | +++ | ++ |
| 490 | ++ | ++ | +++ | ++ |
| 491 | + | ++ | + | + |
| 492 | +++ | ++ | +++ | ++ |
| 493 | +++ | ++ | +++ | ++ |
| 494 | +++ | ++ | +++ | ++ |
| 495 | + | + | ++ | ++ |
| 496 | + | ++ | +++ | ++ |
| 497 | +++ | ++ | +++ | ++ |
| 498 | +++ | ++ | +++ | ++ |
| 499 | + | ++ | +++ | ++ |
| 500 | +++ | ++ | +++ | ++ |
| 501 | +++ | ++ | +++ | ++ |
| 502 | ++ | ++ | ++ | ++ |
| 503 | +++ | ++ | + | + |
| 504 | + | ++ | ++ | ++ |
| 505 | +++ | ++ | +++ | ++ |
| 506 | ++ | ++ | +++ | ++ |
| 507 | +++ | ++ | +++ | ++ |
| 508 | ++ | ++ | ++ | ++ |
| 509 | ++ | ++ | +++ | ++ |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound formula (XX)

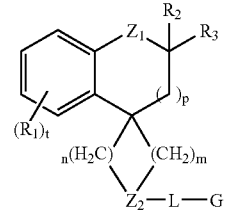

(XX)

or pharmaceutically acceptable salts thereof, wherein
Each of $R_1$, $R_2$, $R_3$ is independently $Q_1$ or $Q_2$;
$Z_1$ is —N($Q_1$)— or —N($Q_2$);
$Z_2$ is N;
L is a bond or —$CH_2$—;
G is

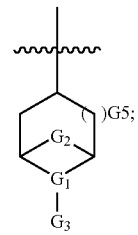

$G_1$ is —N—;
$G_2$ is absent or a $C_{1-3}$ alkyl;
$G_3$ is an aryl or heteroaryl, each optionally substituted with 1-3 substituents independently selected from $Q_2$ and $Q_3$; and
$G_5$ is 0 or 1 when $G_2$ is absent or 0 when $G_2$ is a $C_{1-3}$ alkyl;
Each $Q_1$ is independently halo, —CN, —$NO_2$, —$OQ_2$, —S(O)$_z$$Q_2$, —S(O)$_z$N($Q_2$)$_2$, —N($Q_2$)$_2$, —C(O)$OQ_2$, —C(O)-$Q_2$, —C(O)N($Q_2$)$_2$, —C(O)N($Q_2$)(O$Q_2$), —N($Q_2$)C(O)-$Q_2$, —N($Q_2$)C(O)N($Q_2$)$_2$, —N($Q_2$)C(O)O-$Q_2$, —N($Q_2$)S(O)$_z$-$Q_2$ or aliphatic optionally including 1-3 substituents independently selected from $Q_2$ or $Q_3$;
Each $Q_2$ is independently H, aliphatic, cycloaliphatic, aryl, arylalkyl, heterocyclic, or heteroaryl ring, each optionally including 1-3 substituents independently selected from $Q_3$;
Each $Q_3$ is halo, oxo, —CN, —$NO_2$, —$CF_3$, —$OCF_3$, —OH, —S(O)$_z$$Q_4$, —N($Q_4$)$_2$, —COO$Q_4$, —C(O)$Q_4$, —O$Q_4$, or $C_{1-4}$ alkyl optionally substituted with halo, oxo, —CN, —$NO_2$, —$CF_3$, —$OCF_3$, —OH, —SH, —S(O)$_z$H, —$NH_2$, or —COOH;
Each $Q_4$ is aliphatic, cycloaliphatic, aryl, aralkyl, heterocycloaliphatic, heteroaralky, or heteroaryl, each optionally including 1-3 substituents selected from halo, oxo, —CN, —$NO_2$, —$CF_3$, —$OCF_3$, —OH, —SH, —S(O)$_z$H, —$NH_2$, or —COOH;
Each $Q_5$ is a heterocyclic ring optionally including 1-3 substituents selected from halo, $C_{1-4}$ alkyl, oxo, —CN, —$NO_2$, —$CF_3$, —$OCF_3$, —OH, —SH, —S(O)$_z$H, —$NH_2$, —COOH;

Each i is independently 1, 2, or 3;

Each m and n is independently 2;

Each p is 0 or 1;

Each y is independently 0 or 1;

Each t is 1 to 4; and

Each z is independently 0, 1, or 2.

2. The compound of claim 1, wherein $G_2$ is absent.

3. The compound of claim 2, wherein $G_3$ is a heteroaryl optionally substituted with 1-3 of halo, cyano, $C_{1-4}$ alkoxy, $C_{1-4}$ alkyl, cyclopropyl or phenyl optionally substituted with 1-3 of halo, cyano, hydroxy, $C_{1-4}$ alkoxy, or $C_{1-4}$ alkyl.

4. The compound of claim 2, wherein G5 is 1.

5. The compound of claim 1, wherein G is one selected from

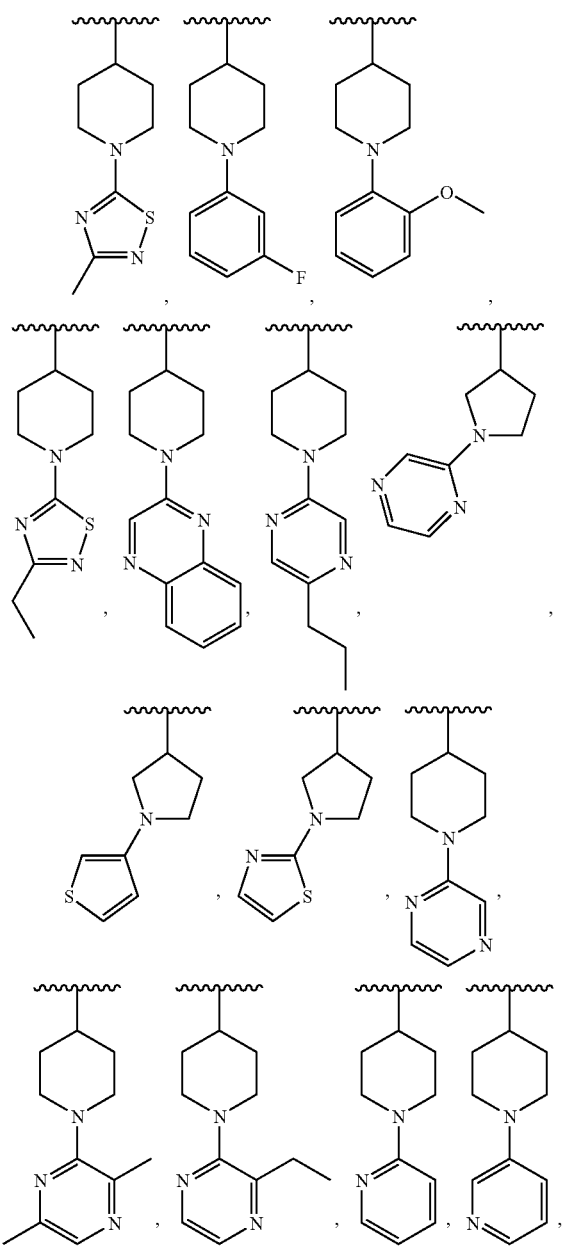

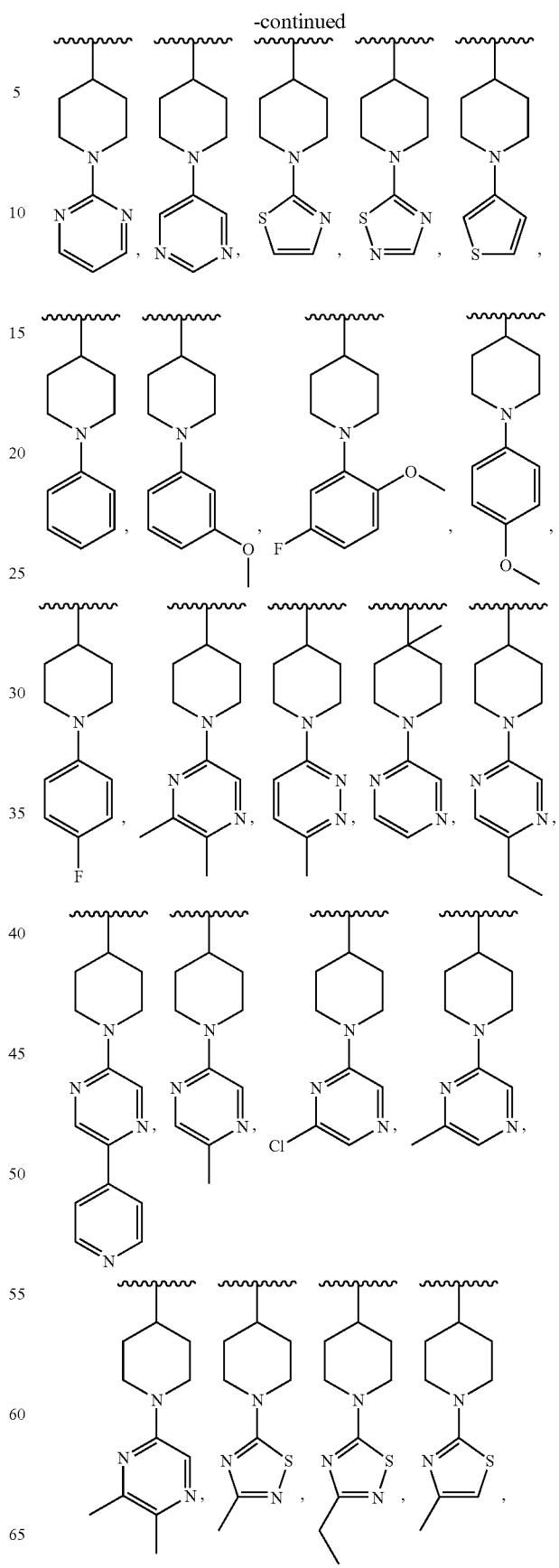

-continued

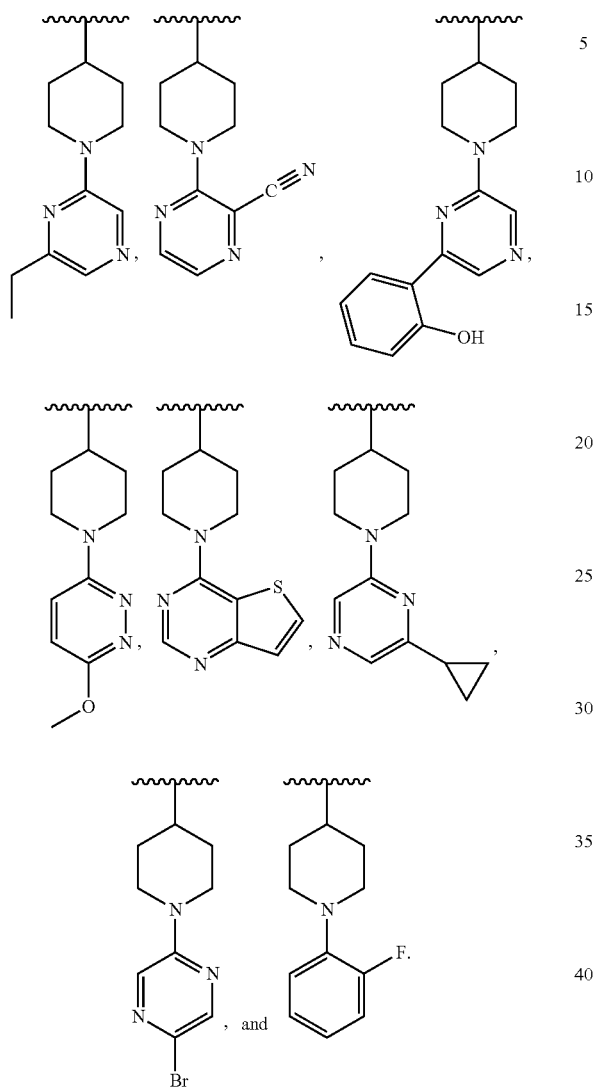

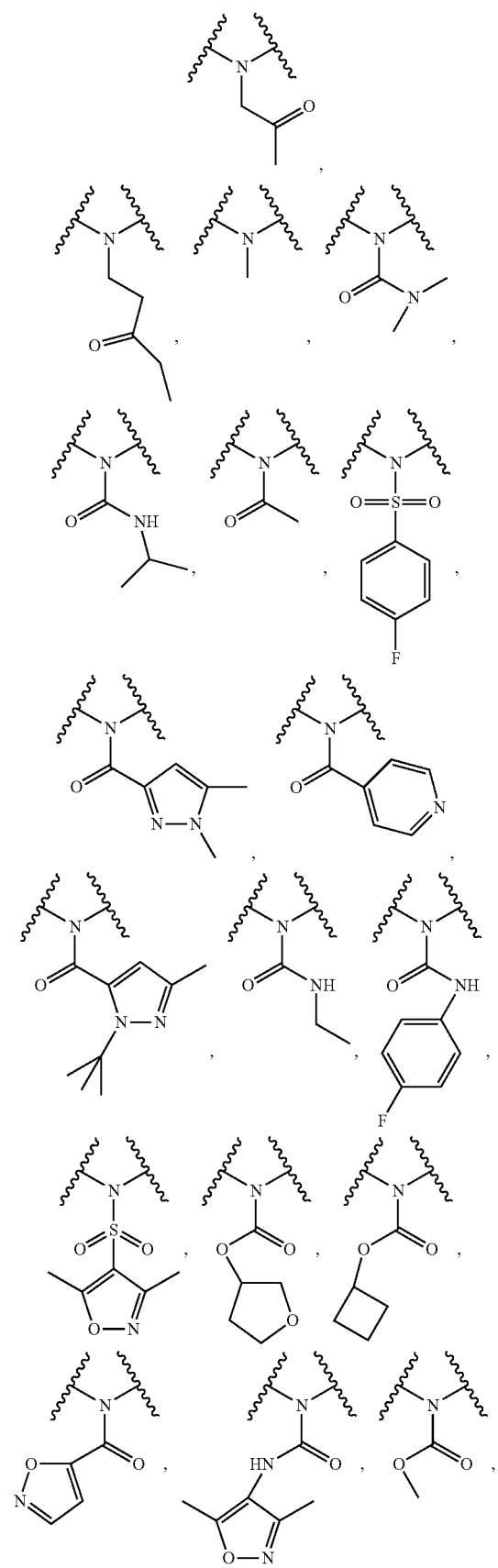

6. The compound of claim 1, wherein $Z_1$ is —NH—, or —N($Q_1$)-.

7. The compound of claim 6, wherein $Z_1$ is —N($Q_1$)- and $Q_1$ is alkylcarbonylamino, alkylsulfonylamino, alkoxycarbonylamino, aminocarbonyl, alkylcarbonylalkyl, alkoxyalkoxycarbonyl, alkoxyalkyl, alkylaminocarbonyl, alkoxycarbonyl, haloarylcarbonyl, haloarylsulfonyl, alkylheteroarylcarbonyl, heteroarylcarbonyl, heterocycloalkylcarbonyl, haloarylaminocarbonyl, alkylheteroarylsulfonyl, cyanoalkylarylcarbonyl, heterocycloalkoxycarbonyl, alkynyloxycarbonyl, cycloalkoxycarbonyl, heterobicycloarylcarbonyl, alkylheteroarylaminocarbonyl, alkylsulfonyl, alkylcarbonylalkyl, alkoxyarylcarbonyl, haloalkoxycarbonyl, alkylarylcarbonyl, haloalkoxyarylcarbonyl, alkylaminocarbonyl, alkylcarbonyl, or arylaminocarbonyl.

8. The compound of claim 6, wherein $Z_1$ is one selected from —NH—,

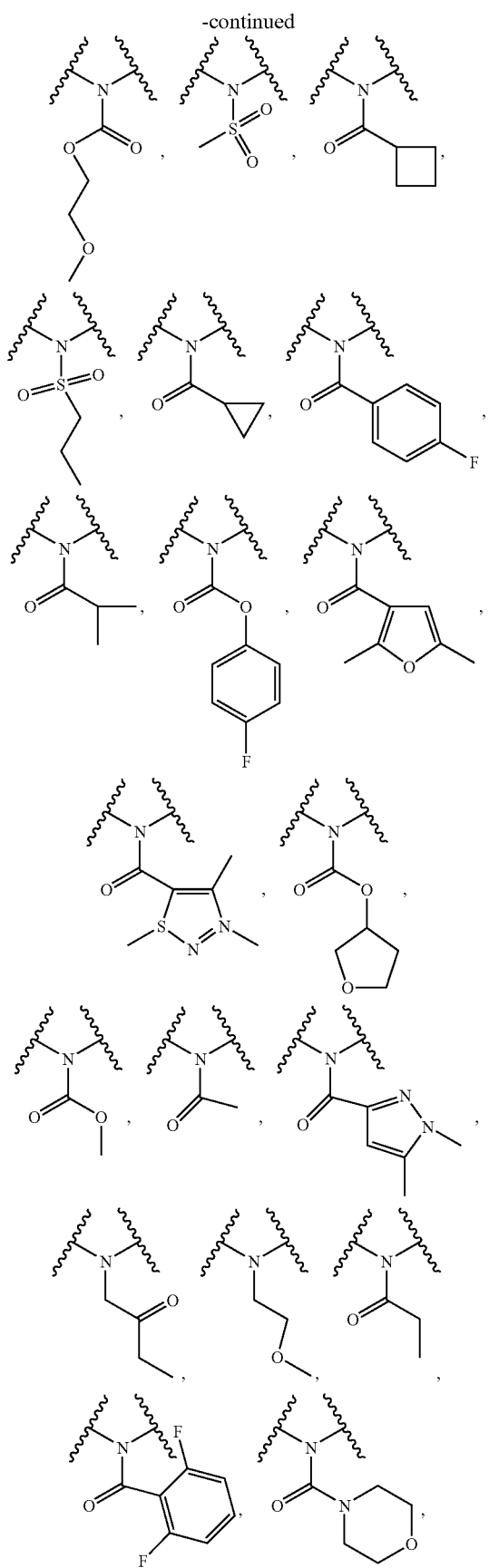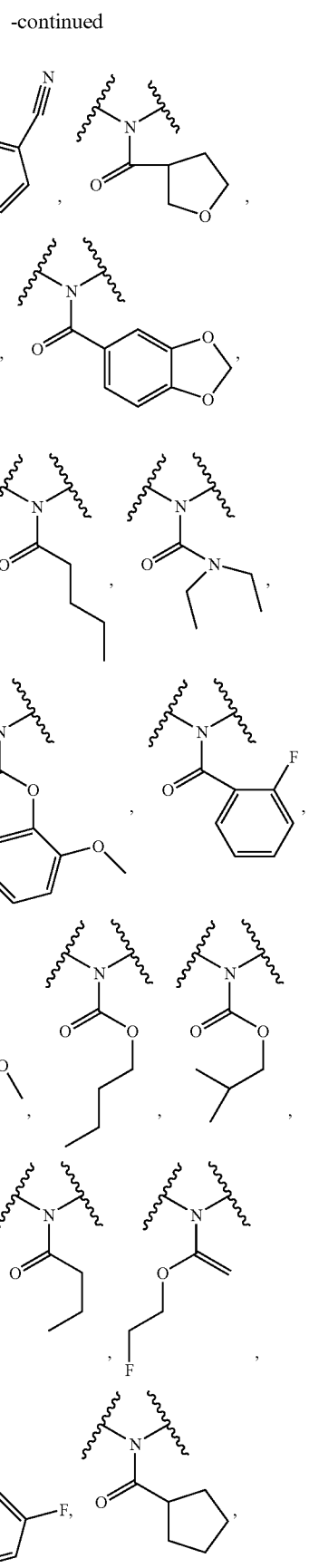

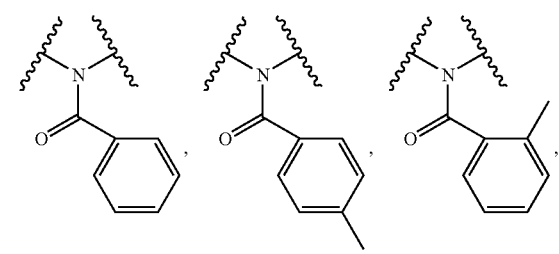
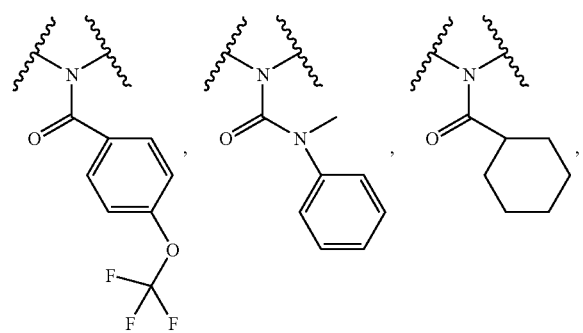
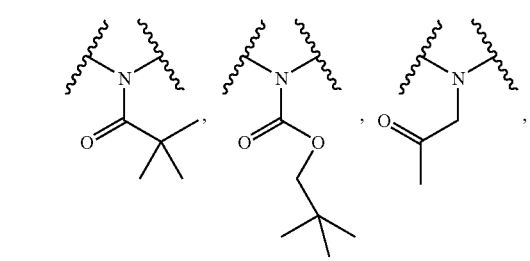
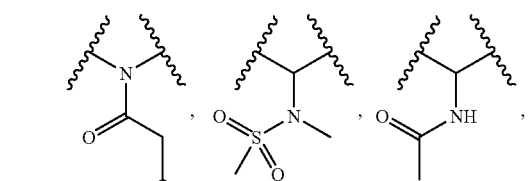
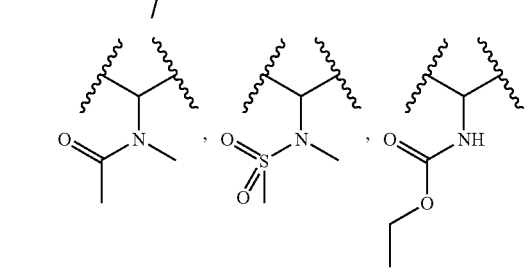
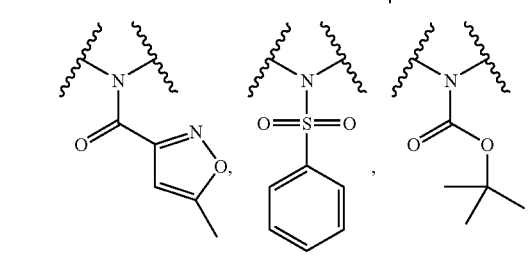

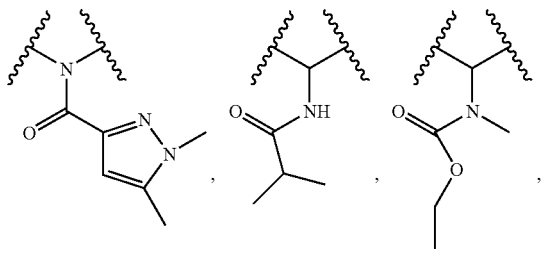
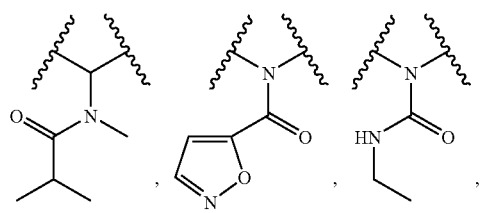
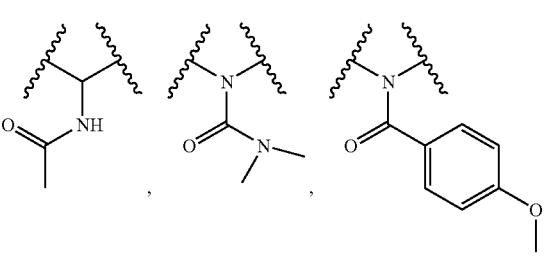
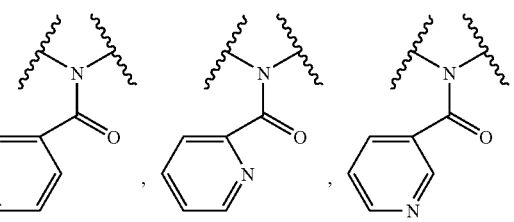
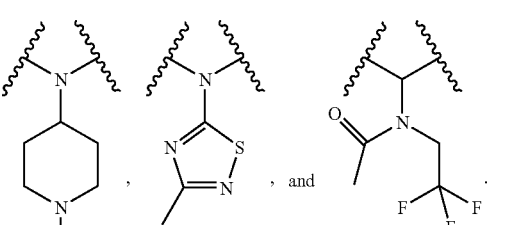

9. The compound of claim 1, wherein $R_1$ is selected from hydrogen, halo, or optionally substituted alkyl, heteroaryl, alkoxy, alkenyl, cycloalkyl, cyanoalkylaryl, alkylaryl, alkylsulfonylaryl, alkylcarbonylaryl, aryl, aminocarbonylaryl, alkylcarbonylaminoaryl, cycloalkenyl, and alkoxyaryl.

10. The compound of claim 9, wherein $R_1$ is selected from hydrogen, halo, methyl, —$OCH_3$

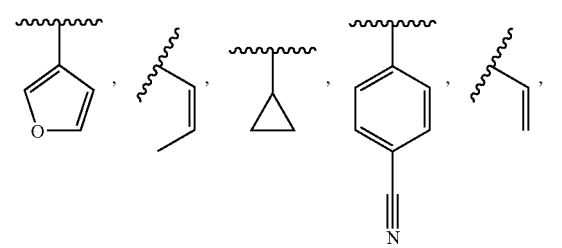
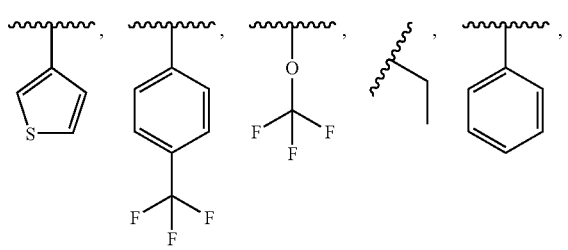
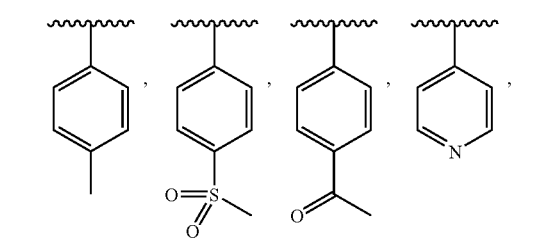
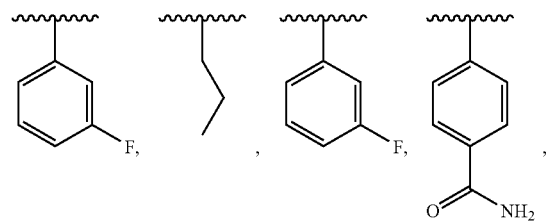
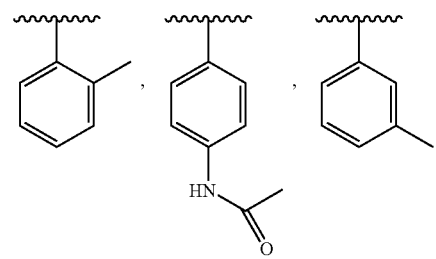
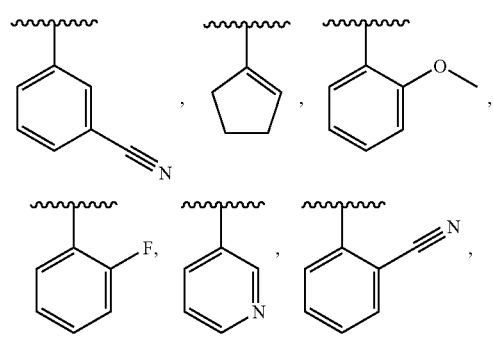
-continued
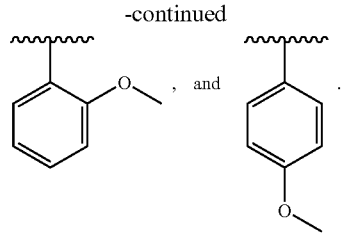, and
11. The compound of claim 1, wherein $R_2$ and $R_3$ are independently hydrogen or alkyl.
12. The compound of claim 11, wherein $R_2$ and $R_3$ are both hydrogen.
13. The compound of claim 1, wherein p is 0.
14. The compound of claim 1, wherein L is a bond.
15. A compound selected from
431
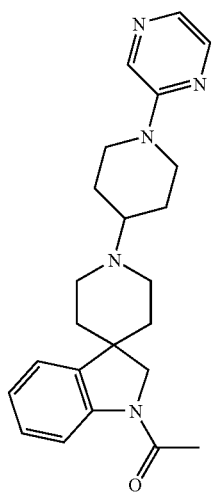
432
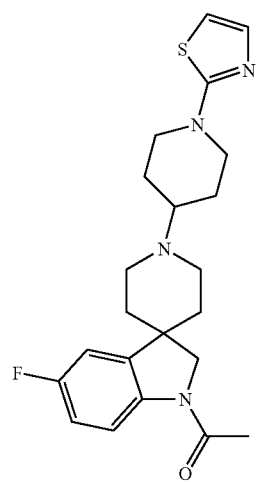

-continued
433
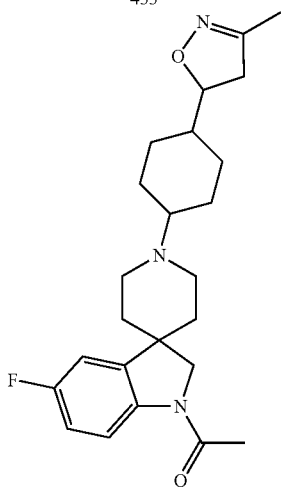
434
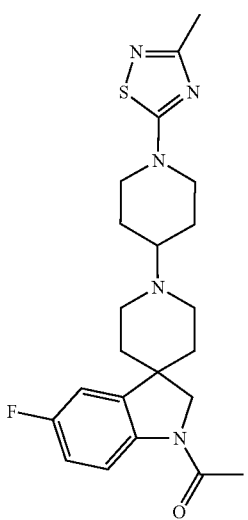
435
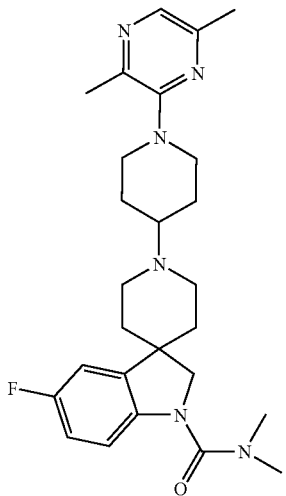
-continued
436
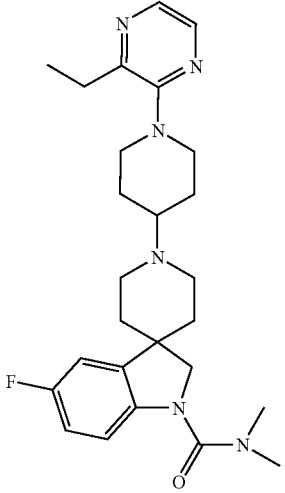
437
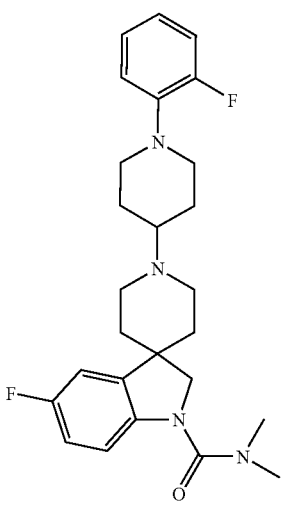
438
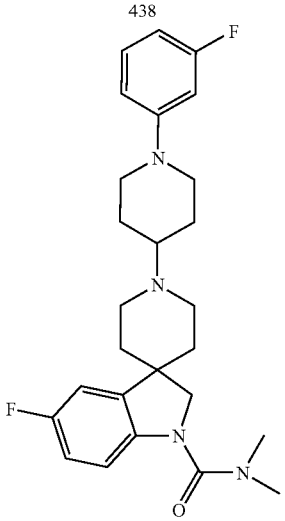

-continued
439
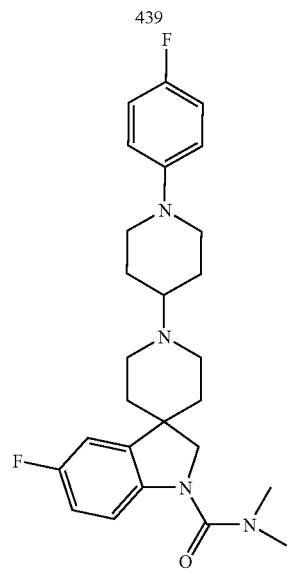
440
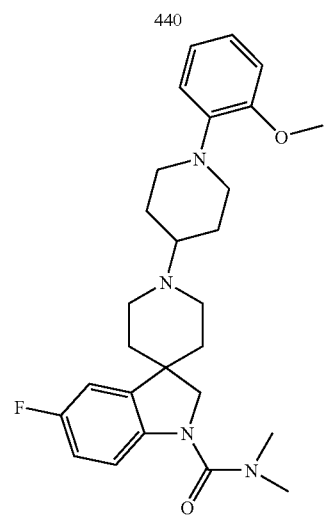
441
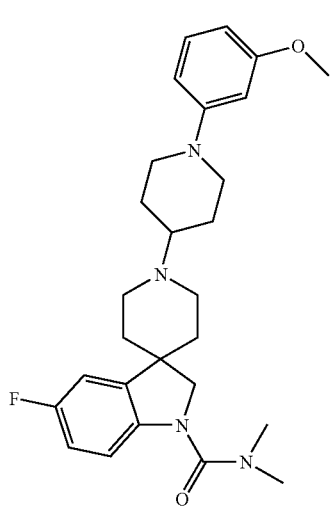
-continued
442
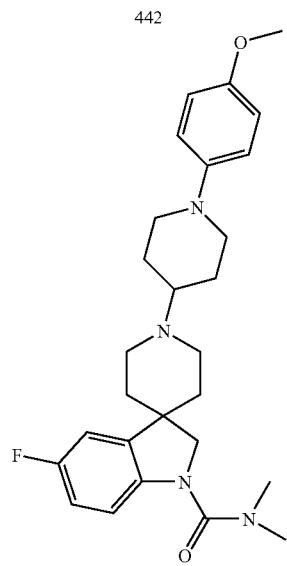
443
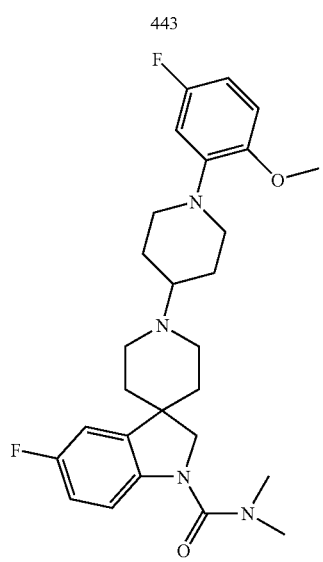
444
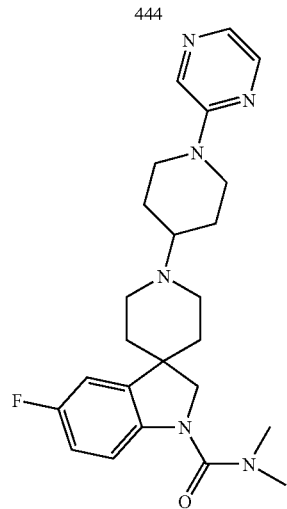

-continued
445
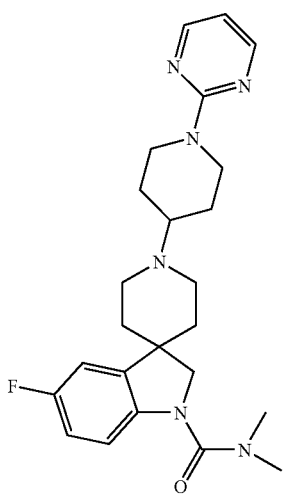
446
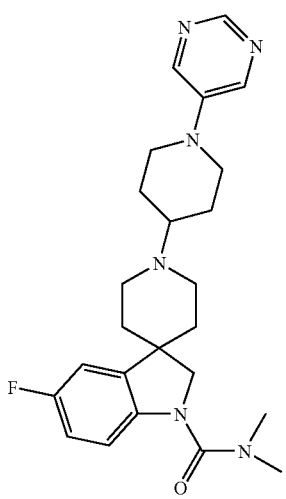
447
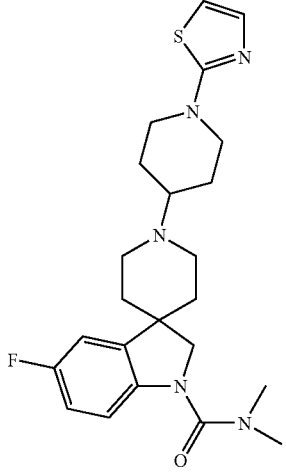
-continued
448
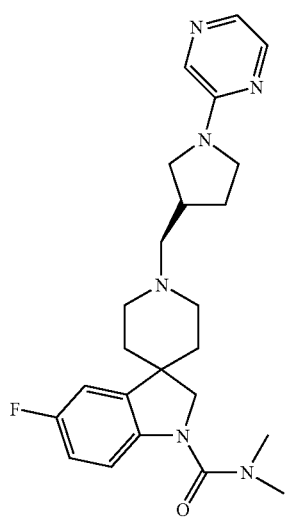
449
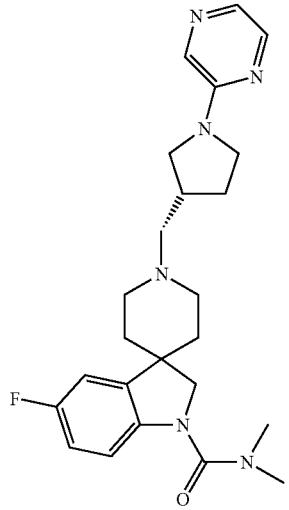
450
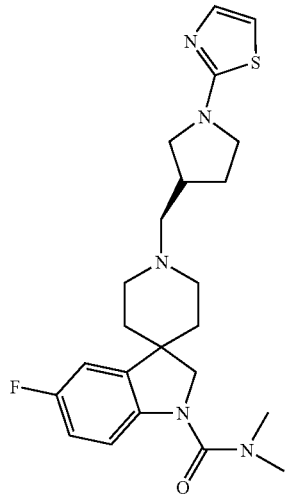

-continued
451
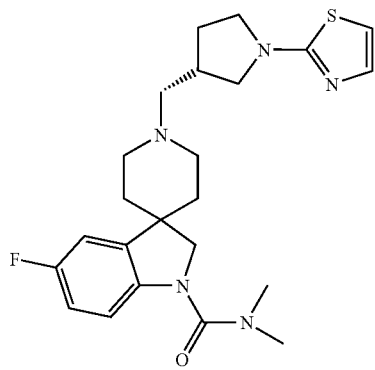
452
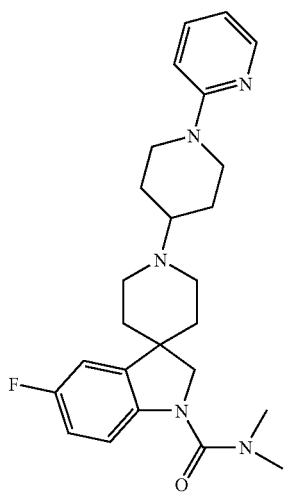
453
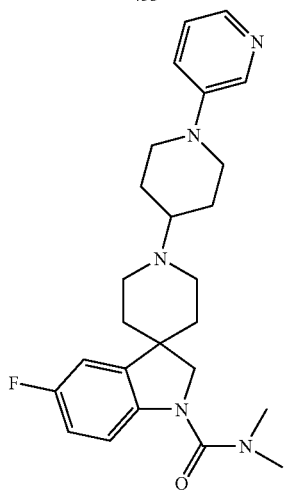
-continued
454
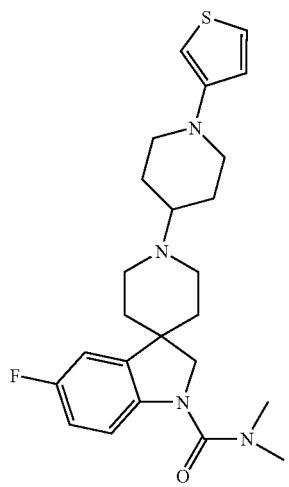
455
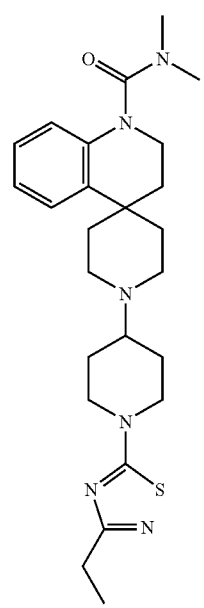

301
-continued
456
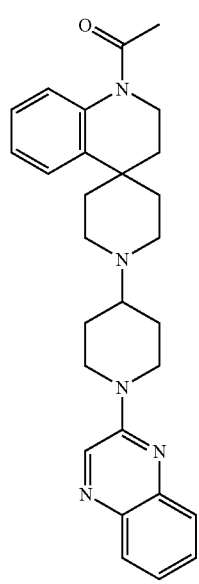
457
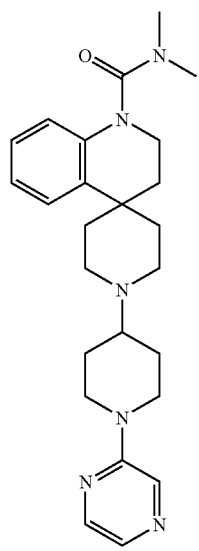
302
-continued
458
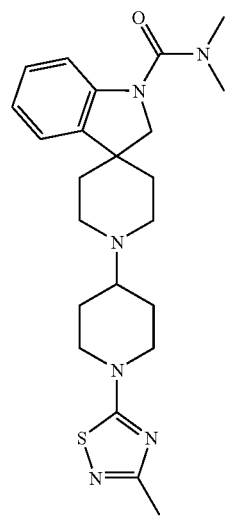
459
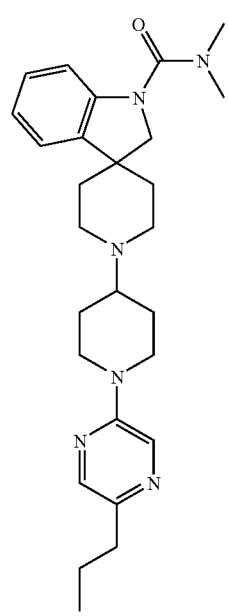

460
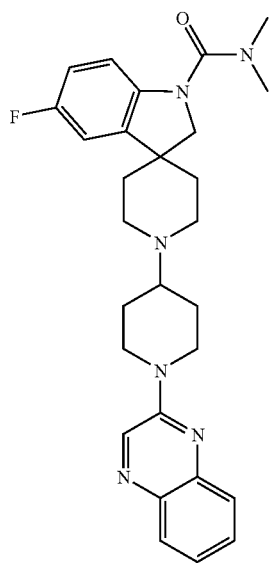
461
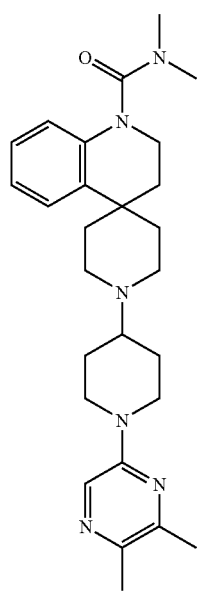
462
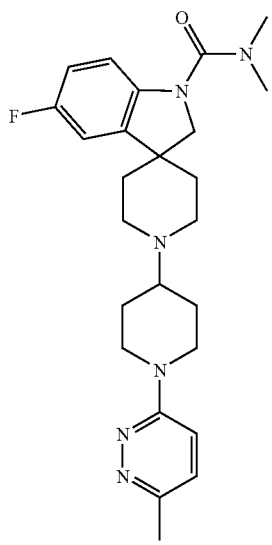
463
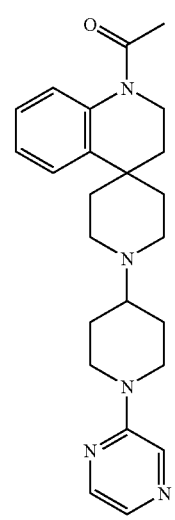

| 464 | 467 |
|---|---|
| 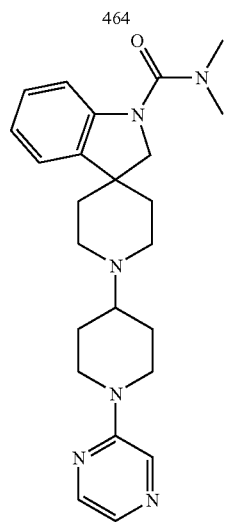 | 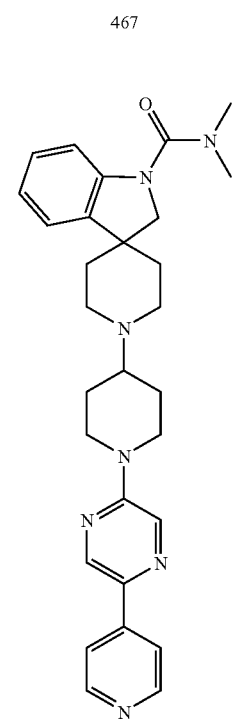 |
| 465 | |
| 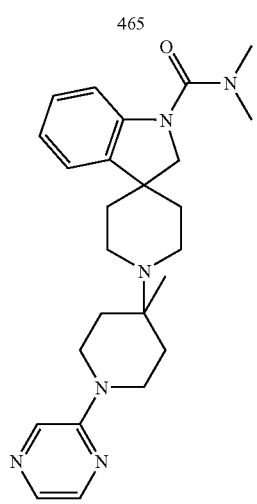 | 468 |
| 466 | |
| 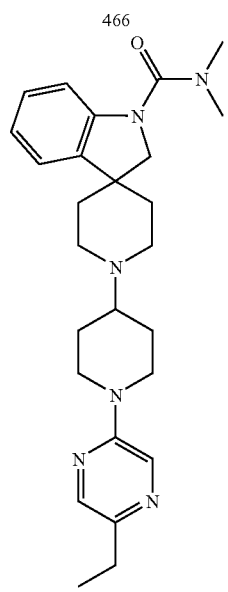 | 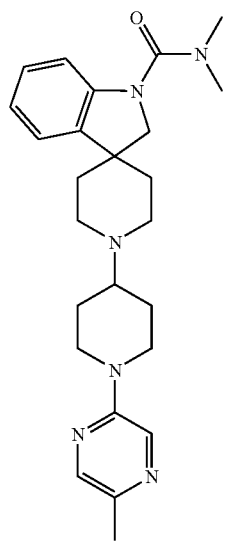 |

-continued
469
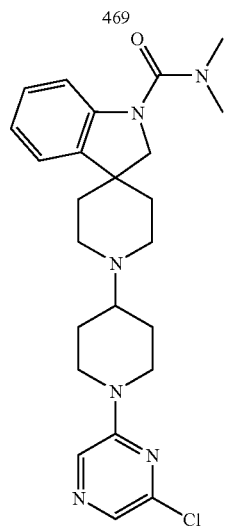
470
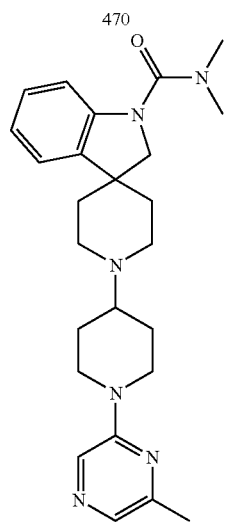
471
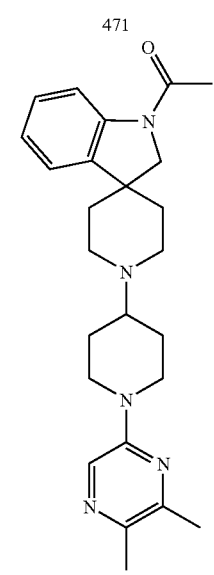
-continued
472
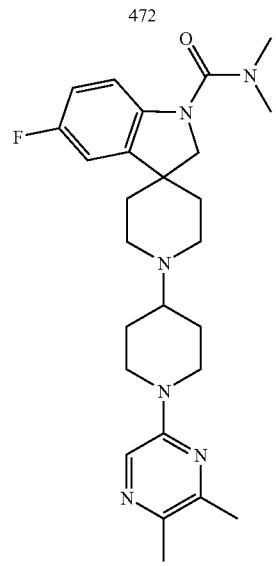
473
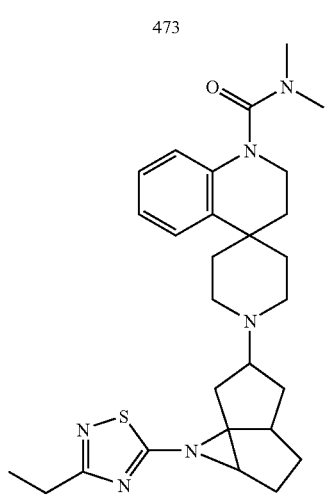
474
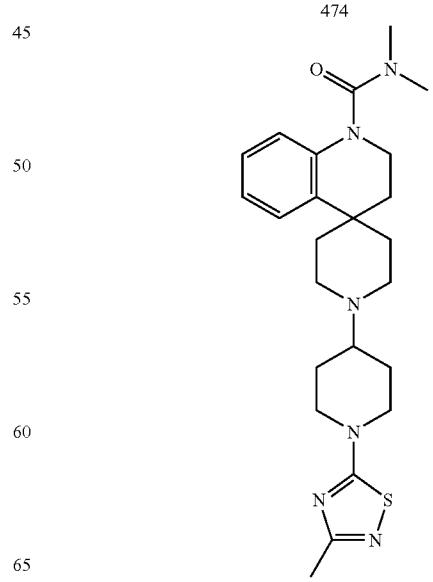

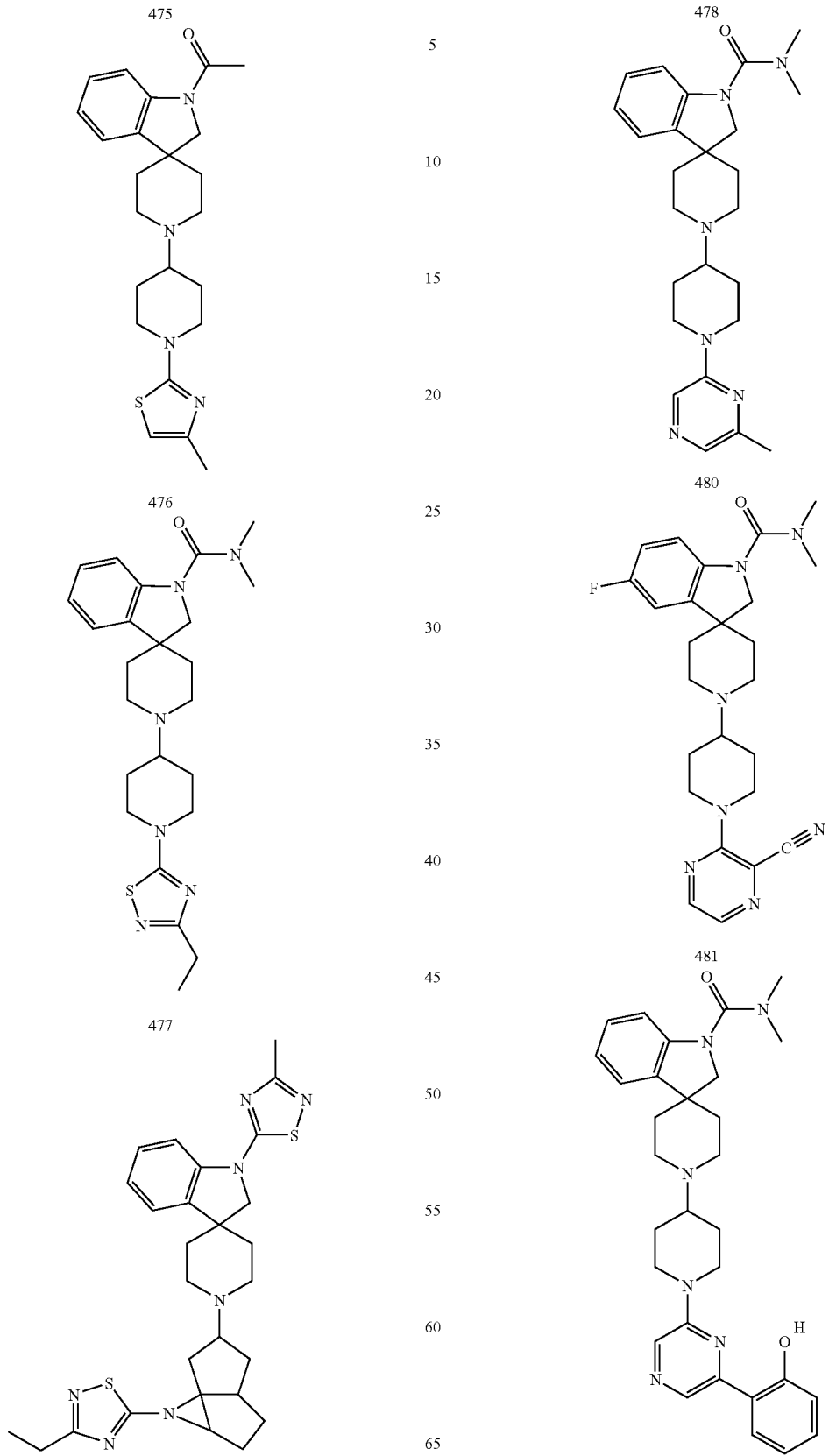

-continued
482
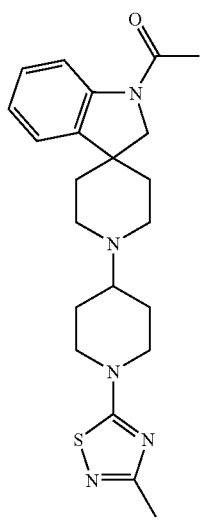
483
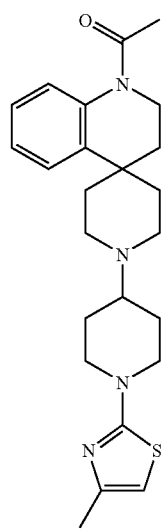
-continued
484
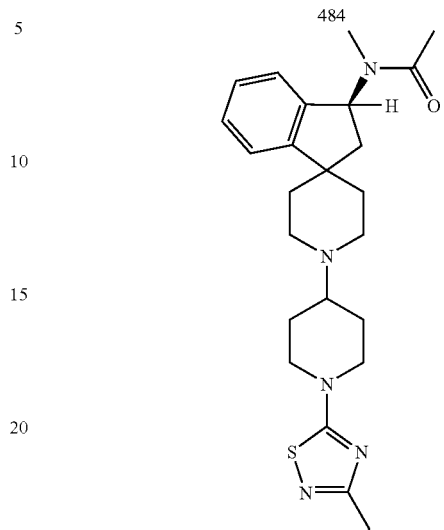
485
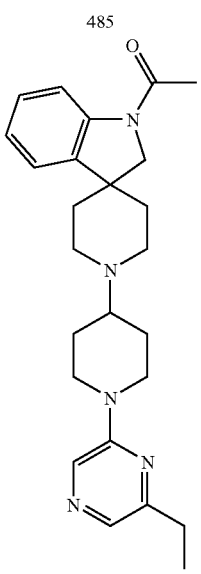
486
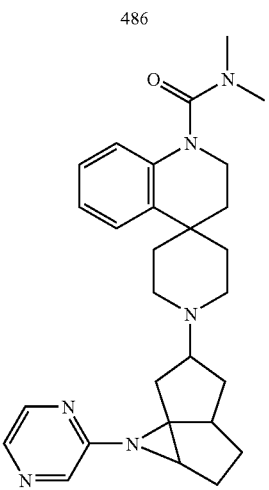

-continued
487
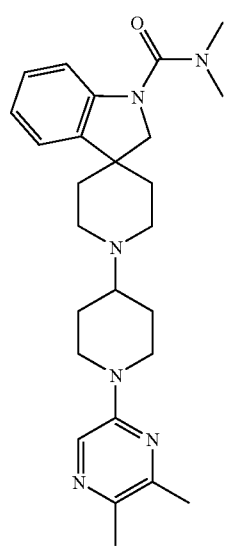
488
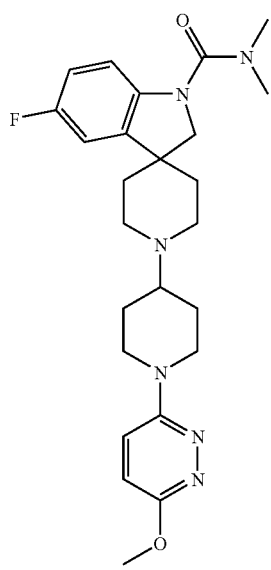
-continued
489
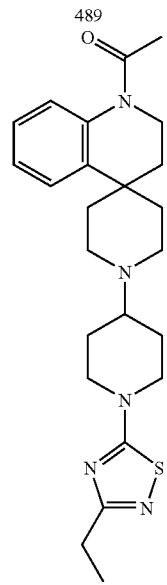
490
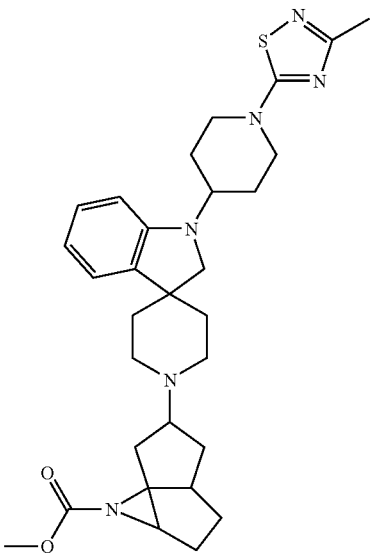
491
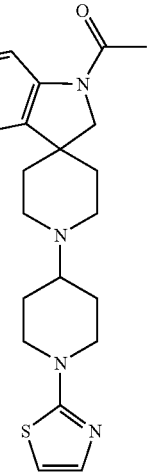

-continued
492
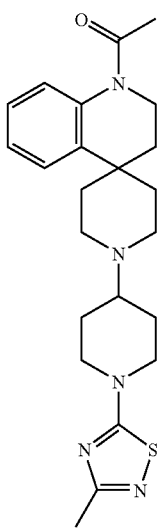
493
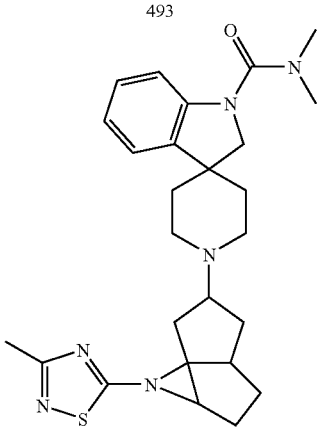
494
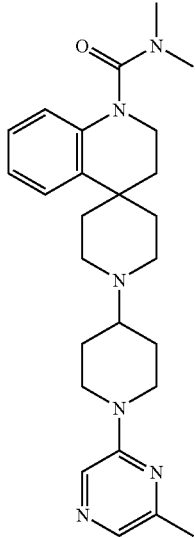
-continued
495
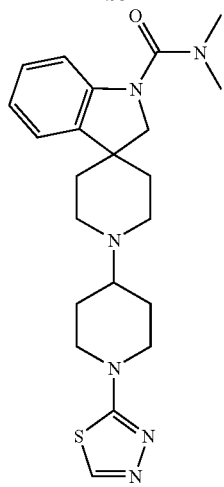
496
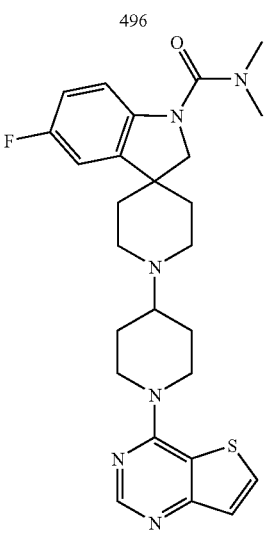
497
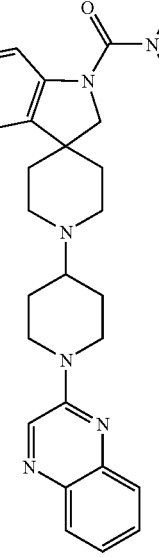

-continued
498
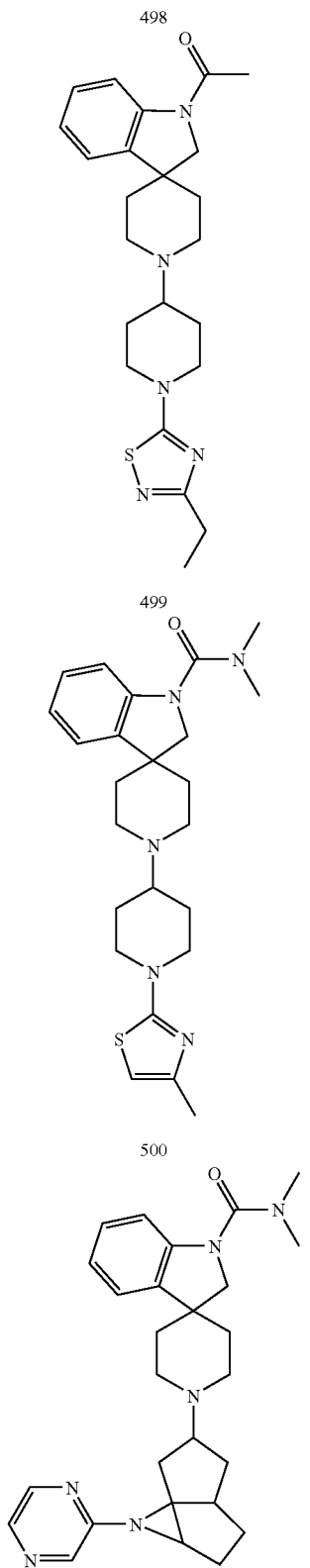
499
500
-continued
501
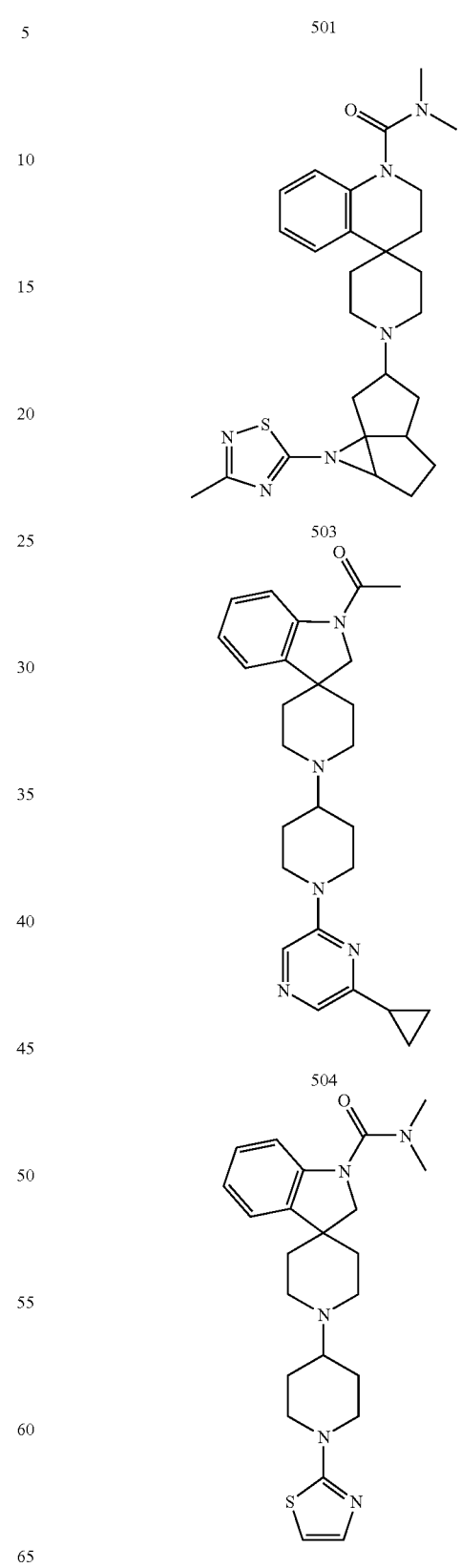
503
504

506

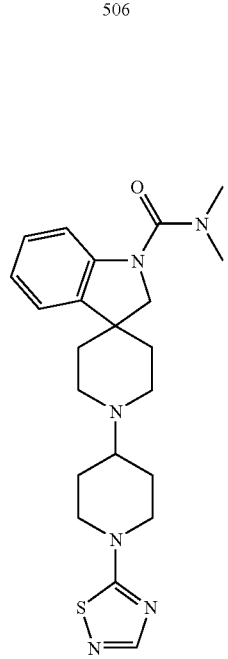

508

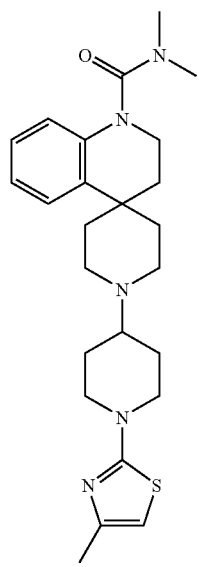

509

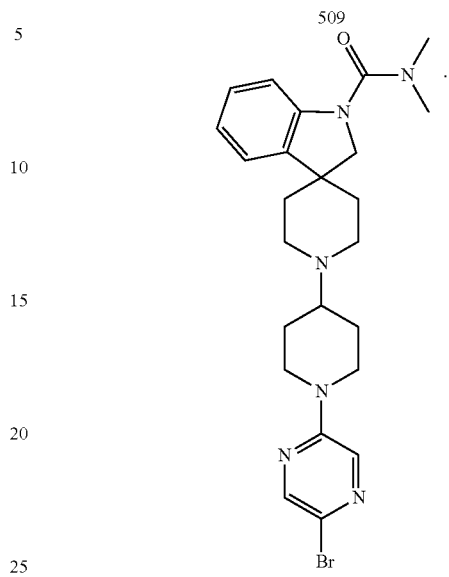

16. A pharmaceutical composition comprising a compound according to claim 1 and a pharmaceutical carrier.

17. A pharmaceutical composition comprising a compound according to claim 15 and a pharmaceutical carrier.

18. The compound of claim 1, wherein L is —CH$_2$—.

19. A compound formula (XX)

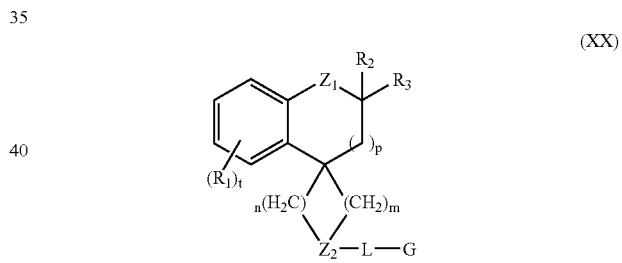

(XX)

or pharmaceutically acceptable salts thereof, wherein

Each of R$_1$, R$_2$, R$_3$ is independently Q$_1$ or Q$_2$;

Z$_1$ is —N(Q$_1$)- or —N(Q$_2$)-;

Z$_2$ is N;

L is a bond or —CH$_2$—;

G is

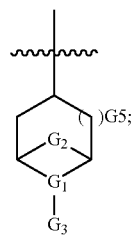

G$_1$ is —N—;

G$_2$ is absent or a C$_{1-3}$ alkyl;

$G_3$ is an aryl or heteroaryl, each optionally substituted with 1-3 substituents independently selected from $Q_2$ and $Q_3$; and $G5$ is 0 or 1 when $G_2$ is absent or 0 when $G_2$ is a $C_{1-3}$ alkyl;

Each $Q_1$ is independently halo, —CN, —NO$_2$, —OQ$_2$, —S(O)$_z$Q$_2$, —S(O)$_z$N(Q$_2$)$_2$, —N(Q$_2$)$_2$, —C(O)OQ$_2$, —C(O)-Q$_2$, —C(O)N(Q$_2$)$_2$, —C(O)N(Q$_2$)(OQ$_2$), —N(Q$_2$)C(O)-Q$_2$, —N(Q$_2$)C(O)N(Q$_2$)$_2$, —N(Q$_2$)C(O)O-Q$_2$, —N(Q$_2$)S(O)$_z$-Q$_2$ or aliphatic optionally including 1-3 substituents independently selected from $Q_2$ or $Q_3$;

Each $Q_2$ is independently H, aliphatic, cycloaliphatic, aryl, arylalkyl, heterocyclic, or heteroaryl ring, each optionally including 1-3 substituents independently selected from $Q_3$;

Each $Q_3$ is halo, oxo, —CN, —NO$_2$, —CF$_3$, —OCF$_3$, —OH, —S(O)$_z$Q$_4$, —N(Q$_4$)$_2$, —COOQ$_4$, —C(O)Q$_4$, —OQ$_4$, or $C_{1-4}$ alkyl optionally substituted with halo, oxo, —CN, —NO$_2$, —CF$_3$, —OCF$_3$, —OH, —SH, —S(O)$_z$H, —NH$_2$, or —COOH;

Each $Q_4$ is aliphatic, cycloaliphatic, aryl, aralkyl, heterocycloaliphatic, heteroaralky, or heteroaryl, each optionally including 1-3 substituents selected from halo, oxo, —CN, —NO$_2$, —CF$_3$, —OCF$_3$, —OH, —SH, —S(O)$_z$H, —NH$_2$, or —COOH;

Each Q5 is a heterocyclic ring optionally including 1-3 substituents selected from halo, $C_{1-4}$ alkyl, oxo, —CN, —NO$_2$, —CF$_3$, —OCF$_3$, —OH, —SH, —S(O)$_z$H, —NH$_2$, —COOH;

Each i is independently 1, 2, or 3;

Each m and n is independently 2;

Each p is 1;

Each y is independently 0 or 1;

Each t is 1 to 4; and

Each z is independently 0, 1, or 2.

* * * * *